(12) United States Patent
Hageman

(10) Patent No.: US 7,745,389 B2
(45) Date of Patent: Jun. 29, 2010

(54) METHODS FOR TREATMENT OF AGE-RELATED MACULAR DEGENERATION

(75) Inventor: Gregory S. Hageman, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 568 days.

(21) Appl. No.: 11/354,559

(22) Filed: Feb. 14, 2006

(65) Prior Publication Data

US 2007/0020647 A1    Jan. 25, 2007

Related U.S. Application Data

(60) Provisional application No. 60/735,697, filed on Nov. 9, 2005, provisional application No. 60/717,861, filed on Sep. 16, 2005, provisional application No. 60/715,503, filed on Sep. 9, 2005, provisional application No. 60/653,078, filed on Feb. 14, 2005.

(51) Int. Cl.
| | |
|---|---|
| *A61K 38/17* | (2006.01) |
| *A61K 38/00* | (2006.01) |
| *C07K 14/435* | (2006.01) |
| *C07H 21/02* | (2006.01) |
| *C07H 21/04* | (2006.01) |
| *C12Q 1/68* | (2006.01) |
| *G01N 33/53* | (2006.01) |

(52) U.S. Cl. ............................. 514/2; 514/12; 514/21; 530/350; 435/6; 435/7.1; 536/23.5

(58) Field of Classification Search ...................... None
See application file for complete search history.

(56) References Cited

U.S. PATENT DOCUMENTS

| | | | |
|---|---|---|---|
| 4,883,784 | A | 11/1989 | Kaneko |
| 6,248,365 | B1 | 6/2001 | Romisch |
| 7,011,952 | B2 | 3/2006 | Hageman et al. |
| 7,108,982 | B1 | 9/2006 | Hageman |
| 7,312,050 | B2 | 12/2007 | Hageman et al. |
| 7,344,846 | B2 | 3/2008 | Hageman et al. |
| 7,351,524 | B2 | 4/2008 | Hageman et al. |
| 2002/0015957 | A1 | 2/2002 | Hageman et al. |
| 2002/0102581 | A1 | 8/2002 | Hageman et al. |
| 2006/0281120 | A1 | 12/2006 | Gorin |
| 2007/0020647 | A1 | 1/2007 | Hageman et al. |
| 2007/0037183 | A1 | 2/2007 | Edwards |
| 2007/0059835 | A1 | 3/2007 | Chalberg |
| 2008/0146501 | A1 | 6/2008 | Hageman et al. |

FOREIGN PATENT DOCUMENTS

| | | | |
|---|---|---|---|
| WO | WO 2006/062716 A2 | 6/2006 | |
| WO | WO 2006/096561 A2 | 9/2006 | |
| WO | WO 2007/022590 A1 | 5/2007 | |

OTHER PUBLICATIONS

Edelhauser et al. Investigative Ophthalmology & Visual Science. Nov. 2008, 49: 4712-4720.*
Rudinger, J. Peptide Hormones. Edited by Parsons, University Park Press, Baltimore, 1976, p. 1-7.*
Skolnick et al. Trends in Biotechnology. 2000. 18(1): 34-39.*
Noris et al. Clinical and Experimental Immunology. 2008. 151: 199-209.*
Schmidt et al. Clinical and Experimental Immunology. 2008. 151: 14-24.*
Comer, G. et al., "Current and Future Treatment Options for Nonexudative and Exudative Age-Related Macular Degeneration," *Drugs Aging*, 2004; 21 (15): 967-992.
Conley, G. et al., "Candidate gene analysis suggests a role for fatty acid biosynthesis and regulation of the complement system in the etiology of age-related maculopathy," *Human Molecular Genetics*, 2005, vol. 14, No. 14, pp. 1991-2002.
Gotoh, N. et al., "No association between complement factor H gene polymorphism and exudative age-related macular degeneration in Japanese," *Human Genetics*, 2006, 120:139-143.
Goverdhan, S.V. et al., "Complement factor H Y402H gene polymorphism in coronary artery disease and atherosclerosis," *Atherosclerosis*, May 2006, 188:213-214.
Halushka, M. et al., "Patterns of single-nucleotide polymorphisms in candidate genes for blood-pressure homeostasis", *Nature Genetics*, Jul. 1999, 22:239-247.
Hirschhorn, J. et al.,"A comprehensive review of genetic association studies," *Genetics in Medicine*, Mar./Apr. 2002, vol. 4, No. 2, pp. 45-61.
Li, M. et al., "CFH haplotypes without the Y402H coding variant show strong association with susceptibility to age-related macular degeneration," *Nature Genetics*, Sep. 2006, vol. 38, No. 9, pp. 1049-1054.
Nicaud, V. et al., "Lack of association between complement factor H polymorphisms and coronary artery disease or myocardial infarction," *Journal of Molecular Medicine*, 2007, 85:771-775.
Sanchez-Corral, P. et al., "Molecular basis for factor H and FHL-1 deficiency in an Italian Family," *Immunogenetics*, 2000, 51:366-369.
Scholl, H.P.N. et al., "Y402H-Polymorphismus im Komplementfaktor H und altersabhängige Makuladegeneration (AMD)", *Ophthalmologe*, 2005, 102:1029-1035 (*English Abstract*).
Schultz, D. et al., "Analysis of the ARMD1 locus: evidence that a mutation in Hemicentin-1 is associated with age-related macular degeneration in a large family," *Human Molecular Genetics*, 2003, vol. 12, No. 24, pp. 3315-3323.

(Continued)

*Primary Examiner*—Carla Myers
(74) *Attorney, Agent, or Firm*—Townsend and Townsend and Crew LLP

(57) ABSTRACT

The invention relates to Factor H gene polymorphisms and haplotypes associated with an elevated or a reduced risk of AMD. The invention provides methods and reagents for diagnosis and treatment of AMD.

22 Claims, 19 Drawing Sheets

OTHER PUBLICATIONS

Sharma, A. et al., "Biologically active recombinant human complement factor H: synthesis and secretion by the baculovirus system," *Gene*, 1994, 143:301-302.
Sorbena, L.A. et al., "Ranibizumab," *Drugs of the Future*, 2003, 28(6): 541-545.
Souied, E. et al., "Y402H Complement factor H polymorphism associated with exudative age-related macular degeneration in the French population," *Molecular Vision*, 2005, 11:1135-40.
Tedeschi-Blok, N. et al., "Population-Based Study of Early Age-Related Macular Degeneration, Role of the Complement Factor H Y402H Polymorphism in Bilateral but Not Unilateral Disease," *Ophthalmology*, Jan. 2007, 114:99-103.
U.S. Appl. No. 60/653,078, filed Feb. 14, 2005, Hageman, et al.
U.S. Appl. No. 60/715,503, filed Sep. 9, 2005, Hageman, et al.
U.S. Appl. No. 60/717,861, filed Sep. 16, 2005, Hageman, et al.
U.S. Appl. No. 60/735,697, filed Nov. 9, 2005, Hageman, et al.
Ambati, J., et al., Age-related macular degeneration: etiology, pathogenesis, and therapeutic strategies, Surv Ophthalmol (2003) 48(3):257-293.
Anderson, D., et al., A role for local inflammation in the formation of drusen in the aging eye, Am J Ophthalmol (2002) 134:411-431.
Appel, G., et al., Membranoproliferative glomerulonephritis type II (Dense Deposit Disease): An update, J Am Soc Nephrol (2005) 16:1392-1403.
Ault, B., et al., Human factor H deficiency. Mutations in framework cysteine residues and block in H protein secretion and intracellular catabolism, J Biol Chem (1997) 272:25168-25175.
Caprioli, J., et al., Complement factor H mutations and gene polymorphisms in haemolytic uraemic syndrome: the C-257T, the A2089G and the G2881T polymorphisms are strongly associated with the disease, Hum Mol Genet (2003) 12:3385-3395.
de Jong, P., Risk Profiles for Ageing Macular Disease, Ophthalmologia (2004) 218 Suppl 1:5-16.
Dragon-Durey, M., et al., Heterozygous and Homozygous Factor H Deficiencies Associated with Hemolytic Uremic Syndrome or Membranoproliferative Glomerulonephritis: Report and Genetic Analysis of 16 Cases, J Am Soc Nephrol (2004) 15:787-795.
Edwards, A., et al., Complement Factor H Polymorphism and Age-Related Macular Degeneration, Science (2005) 308:421-424.
Esparza-Gordillo, J., et al., Predisposition to atypical hemolytic uremic syndrome involves the concurrence of different susceptibility alleles in the regulators of complement activation gene cluster in 1q32, Human Mol. Genetics (2005) 14:703-712.
Espinosa-Heidman, D., et al., Macrophage Depletion Diminishes Lesion Size and Severity in Experimental Choroidal Neovascularization, Invest. Ophthalmol. Vis. Sci. (2003) 44:3586-3592.
Fremeaux-Bacchi, V., et al., The development of atypical haemolytic-uraemic syndrome is influenced by susceptibility factors in factor H and membrane cofactor protein: evidence from two independent cohorts, J. Med Genet. (2005) 42(11):852-586.
Hageman, G., et al., A common haplotype in the complement regulatory gene factor H (HF1/CFH) predisposes individuals to age-related macular degeneration, Proc Natl Acad Sci USA (2005) 102:7227-7232.
Hageman, G., et al., Vitronectin is a constituent of ocular drusen and the vitronectin gene is expressed in human retinal pigmented epithelial cells, FASEB J. (1999) 13:477-484.
Hageman, G., et al., An integrated hypothesis that considers drusen as biomarkers of immune-mediated processes at the RPE-Bruch's membrane interface in aging and age-related macular degeneration, Prog Retin Eye Res (2001) 20:705-732.
Haines, J., et al., Complement Factor H Variant Increases the Risk of Age-Related Macular Degeneration, Science (2005) 308:419-421.
Holz, F., et al., Pathogenesis of Lesions in Late Age-related Macular Disease, Am J Ophthalmol (2004) 137(3):504-510.
Jansen, J., et al., In situ complement activation in porcine membranoproliferative glomerulonephritis type II, Kidney Int (1998) 53(2):331-349.
Klein, R., et al., Complement Factor H Polymorphism in Age-Related Macular Degeneration, Science (2005) 308:385-389.

Manuelian, T., et al., Mutations in factor H reduce binding affinity to C3b and heparin and surface attachment to endothelial cells in hemolytic uremic syndrome, J Clin Invest (2003) 111:1181-1190.
Meri, S., et al., Regulation of alternative pathway complement activation by glycosaminoglycans: specificity of the polyanion binding site on factor H, Biochem Biophys Res Commun (1994) 198:52-59.
Mullins, R., et al., Structure and composition of drusen associated with glomerulonephritis: Implications for the role of complement activation in drusen biogenesis, Eye (2001) 15:390-395.
Perez-Caballero, D., et al., Clustering of Missense Mutations in the C-Terminal Region of Factor H in Atypical Hemolytic Uremic Syndrome, Am. J. Hum. Genet. (2001) 68:478-484.
Pickering, M., et al., Uncontrolled C3 activation causes membranoproliferative glomerulonephritis in mice deficient in complement factor H, Nat Genet (2002) 31:424-428.
Richards, A., et al., Factor H Mutations in Hemolytic Uremic Syndrome Cluster in Exons 18-20, a Domain Important for Host Cell Recognition, Am. J. Hum. Genet. (2001) 68:485-490.
Rodriguez de Cordoba, S., et al., The human complement factor H: functional roles, genetic variations and disease associations, Mol Immunol (2004) 41:355-367.
Sanchez-Corral, P., et al., Structural and Functional Characterization of Factor H Mutations Associated with Atypical Hemolytic Uremic Syndrome, Am. J. Genet. (2002) 71:1285-1295.
Saunders, R., et al., An Interactive Web Database of Factor H-Associated Hemolytic Uremic Syndrome Mutations: Insights Into the Structural Consequences of Disease-Associated Mutations, Human Mutation (2006) 27:21-30.
van Leeuwen, R., et al., Epidemiology of age-related macular degeneration: a review, Eur J Epidemiol (2003) 18(9):845-854.
Zarbin, M., Age-related macular degeneration: review of pathogenesis, Eur J Ophthalmol (1998) 8:199-206.
Zarbin, M., Current Concepts in the Pathogenesis of Age-Related Macular Degeneration, Arch Ophthalmol (2004) 122(4):598-614.
Zipfel, P., et al., Complement factor H and hemolytic uremic syndrome, Int Immunopharmacol (2001) 1:461-468.
Zipfel, P., et al., Factor H family proteins: on complement, microbes and human diseases, Biochem Soc Trans (2002) 30:971-978.
Zipfel, P., et al., The role of complement in membranoproliferative glomerulonephritis, Complement and Kidney Disease (2006) 199-221.
Zipfel, P., Complement factor H: physiology and pathophysiology, Semin Thromb Hemost (2001) 27:191-199.
Zipfel, P., Hemolytic uremic syndrome: how do factor H mutants mediate endothelial damage?, Trends Immunol (2001) 22:345-348.
Zareparsi et al., "Strong Association of the Y402H Variant in Complement Factor H at 1q32 with Susceptibility to Age-Related Macular Degeneration," *Am J Hum Genet*, 77:149-153 (2005).
U.S. Appl No. 11/816,167, filed Aug. 20, 2008, Hageman.
U.S. Appl No. 11/894,667, filed Aug. 20, 2007, Hageman.
U.S. Appl No. 12/479,716, filed Jun. 5, 2009, Hageman.
U.S. Appl No. 12/480,588, filed Jun. 8, 2009, Hageman.
Bok, "Evidence for an inflammatory process in age-related macular degeneration gains new support", *Proc. Nat'l Acad Sci*, 102(20):7053-7054, (2005).
Marx, "A Clearer View of Macular Degeneration", *Science*, 311:1704-1705, (2006).
Skerka et al., "Defective Complement control of Factor H (Y402H) and FHL-1 in age-related macular degeneration", *Mol. Immunol.*, 44:3398-406, (2007).
Tortajada et al., "The disease-protective complement factor H allotypic variant Ile62 shows increased binding affinity for C3b and enhanced cofactor activity." *Hum Mol Genet*. Jun. 23, 2009. [Epub ahead of print].
Kühn et al., "Mapping of the Complement Regulatory Domains in the Human Factor H-Like Protein 1 and in Factor H", *Am Association of Immunologists*, 155:5663-5670, (1995).
*Ex parte Briskin*, Appeal No. 2008-2656, (Bd. Pat. App. Int. Dec. 23, 2008).
Busquets, "Intravitreal Injections: Technique and Infection Prophylaxis", *Retina Today*, 19-21, (2007).

Chen et al., "Association of complement factor H polymorphisms with exudative age-related macular degeneration", *Mol Vis.*, 12:1536-1542, (2006).

Okamoto et al., "Complement factor H polymorphisms in Japanese population with age-related macular degeneration", *Mol Vis.*, 12:156-158, (2006).

Kim et al., "Association between Complement Factor H Gene Polymorphisms and Neovascular Age-Related Macular Degeneration in Koreans", *Investigative Ophthalmology & Visual Science*, 49(5):2071-2076, (2008).

Kaur et al., "Analysis of *CFH, TLR4,* and *APOE* Polymorphism in India Suggests the Tyr402His Variant of *CFH* to be a Global Marker for Age-Related Macular Degeneration", *Investigative Ophthalmology & Visual Science*, 47(9):3729-3735, (2006).

"AEVR/NAEVR Networks Educate Capitol Hill in *AMD Awareness Week*; Vision Research Value Message Critical as Congress Considers NIH Funding, Reauthorization", NAEVR/AEVR 1 page, (2005).

Chowers et al., "Association of complement factor H Y402H polymorphism with phenotype of neovascular age related macular degeneration in Israel", *Molecular Vision*, 14:1829-1834, (2008).

Clark et al., "His-384 Allotypic Variant of Factor H Associated with Age-related Macular Degeneration Has Different Heparin Binding Properties from the Non-disease-associated Form," *J. Biol. Chem.*, 281:24713-720, (2006).

CFH Variation Viewer, downloaded from http://www.ncbi.nlm.nih.gov/sites/varvu on May 29, 2009, 34 pages.

Edwards et at "Molecular genetics of AMD and current animal models" *Angiogenesis* 2007, 10(2):119-32.

Fontaine et al., "Truncated forms of human complement Factor H", *Biochem. J.*, 258:927-930, (1089).

Hageman et al., "Extended haplotypes in the complement factor H (CFH) and CFH-related (CFHR) family of genes protect against age-related macular degeneration: characterization, ethnic distribution and evolutionary implications", *Ann Med.*, 38(8):592-604, (2006).

Hellwage et al., "Complement C3b/C3d and Cell Surface Polyanions Are Recognized by Overlapping Binding Sites on the Most Carboxyl-Terminal Domain of Complement Factor H", *J. of Immunology*, 169:6935-6944, (2002).

Jokiranta et al., "Each of the Three binding Sites on Complement Factor H Interacts with a Distinct Site on C3b", *J of Biological Chemistry*, 275(36):27657-27662, (2000).

Kurtz et al., "Management of membranoproliferative glomerulonephritis type II with plasmapheresis", *J Clin Apher*, 17(3):135-7, (2002).

Magnusson, et al., "CFH Y402H Confers Similar Risk of Soft Drusen and Both Forms of Advanced AMD", *PLoS Medicine*, 3(1)109-114, (2006).

Remuzzi et al., "Hemolytic Uremic Syndrome: A Fatal Outcome after Kidney and Liver Transplantation Performed to Correct Factor H Gene Mutation", *Am J of Transplantation*, 5:1146-1150, (2005).

Ripoche et al., "The complete amino acid sequence of human complement factor H", *Biochem. J.*, 249:593-602, (1988).

Saland et al., "Favorable Long-Term Outcome after Liver-Kidney Transplant for Recurrent Hemolytic Uremic Syndrome Associated with a Factor H Mutation", *Am J of Transplantation*, 6(8):1948-52, (2006).

Skerka et al., "A Novel Short Consensus Repeat-containing Molecule Is Related to Human Complement Factor H", *J. of Biological Chemistry*, 268(4):2904-2908, (1993).

*Written Description Training Materials*, Revision 1 (Mar. 2008).

* cited by examiner

FIGURE 6

```
AATTCTTGGAAGAGGAGAACTGGACGTTGTGAACAGAGTTAGCTGGTAAATGTCCTCTTAAAAGATCCAA
AAATGAGACTTCTAGCAAAGATTATTTGCCTTATGTTATGGGCTATTTGTGTAGCAGAAGATTGCAATG
AACTTCCTCCAAGAAGAAATACAGAAATTCTGACAGGTTCCTGGTCTGACCAAACATATCCAGAAGGCAC
CCAGGCTATCTATAAATGCCGCCCTGGATATAGATCTCTTGGAAATGTAATAATGGTATGCAGGAAGGGA
GAATGGGTTGCTCTTAATCCATTAAGGAAATGTCAGAAAAGGCCCTGTGGACATCCTGGAGATACTCCTT
TTGGTACTTTTACCCTTACAGGAGGAAATGTGTTTGAATATGGTGTAAAAGCTGTGTATACATGTAATGA
GGGGTATCAATTGCTAGGTGAGATTAATTACCGTGAATGTGACACAGATGGATGGACCAATGATATTCCT
ATATGTGAAGTTGTGAAGTGTTTACCAGTGACAGCACCAGAGAATGGAAAATTGTCAGTAGTGCAATGG
AACCAGATCGGGAATACCATTTTGGACAAGCAGTACGGTTTGTATGTAACTCAGGCTACAAGATTGAAGG
AGATGAAGAAATGCATTGTTCAGACGATGGTTTTTGGAGTAAAGAGAAACCAAAGTGTGTGGAAATTTCA
TGCAAATCCCCAGATGTTATAAATGGATCTCCTATATCTCAGAAGATTATTTATAAGGAGAATGAACGAT
TTCAATATAAATGTAACATGGGTTATGAATACAGTGAAAGAGGAGATGCTGTATGCACTGAATCTGGATG
GCGTCCGTTGCCTTCATGTGAAGAAAAATCATGTGATAATCCTTATATTCCAAATGGTGACTACTCACCT
TTAAGGATTAAACACAGAACTGGAGATGAAATCACGTACCAGTGTAGAAATGGTTTTTATCCTGCAACCC
GGGGAAATACAGCCAAATGCACAAGTACTGGCTGGATACCTGCTCCGAGATGTACCTTGAAACCTTGTGA
TTATCCAGACATTAAACATGGAGGTCTATATCATGAGAATATGCGTAGACATACTTTCCAGTAGCTGTA
GGAAAATATTACTCCTATTACTGTGATGAACATTTTGAGACTCCGTCAGGAAGTTACTGGGATCACATTC
ATTGCACACAAGATGGATGGTCGCCAGCAGTACCATGCCTCAGAAAATGTTATTTTCCTTATTTGGAAAA
TGGATATAATCAAAATCATGGAAGAAAGTTTGTACAGGGTAAATCTATAGACGTTGCCTGCCATCCTGGC
TACGCTCTTCCAAAAGCGCAGACCACAGTTACATGTATGGAGAATGGCTGGTCTCCTACTCCCAGATGCA
TCCGTGTCAAAACATGTTCCAAATCAAGTATAGATATTGAGAATGGGTTTATTTCTGAATCTCAGTATAC
ATATGCCTTAAAAGAAAAAGCGAAATATCAATGCAAACTAGGATATGTAACAGCAGATGGTGAAACATCA
GGATCAATTAGATGTGGGAAGATGGATGGTCAGCTCAACCCACGTGCATTAAATCTTGTGATATCCCAG
TATTTATGAATGCCAGAACTAAAAATGACTTCACATGGTTTAAGCTGAATGACACATTGGACTATGAATG
CCATGATGGTTATGAAAGCAATACTGGAAGCACCACTGGTTCCATAGTGTGTGGTTACAATGGTTGGTCT
GATTTACCCATATGTTATGAAAGAGAATGCGAACTTCCTAAAATAGATGTACACTTAGTTCCTGATCGCA
AGAAAGACCAGTATAAAGTTGGAGAGGTGTTGAAATTCTCCTGCAAACCAGGATTTACAATAGTTGGACC
TAATTCCGTTCAGTGCTACCACTTTGGATTGTCTCCTGACCTCCCAATATGTAAAGAGCAAGTACAATCA
TGTGGTCCACCTCCTGAACTCCTCAATGGGAATGTTAAGGAAAAAACGAAAGAAGAATATGGACACAGTG
AAGTGGTGGAATATTATTGCAATCCTAGATTTCTAATGAAGGGACCTAATAAAATTCAATGTGTTGATGG
AGAGTGGACAACTTTACCAGTGTGTATTGTGGAGGAGAGTACCTGTGGAGATATACCTGAACTTGAACAT
GGCTGGGCCCAGCTTTCTTCCCCTCCTTATTACTATGGAGATTCAGTGGAATTCAATTGCTCAGAATCAT
TTACAATGATTGGACACAGATCAATTACGTGTATTCATGGAGTATGGACCCAACTTCCCCAGTGTGTGGC
AATAGATAAACTTAAGAAGTGCAAATCATCAAATTTAATTATACTTGAGGAACATTTAAAAAACAAGAAG
GAATTCGATCATAATTCTAACATAAGGTACAGATGTAGAGGAAAAGAAGGATGGATACACACAGTCTGCA
TAAATGGAAGATGGGATCCAGAAGTGAACTGCTCAATGGCACAAATACAATTATGCCCACCTCCACCTCA
GATTCCCAATTCTCACAATATGACAACCACACTGAATTATCGGGATGGAGAAAAGTATCTGTTCTTTGC
CAAGAAAATTATCTAATTCAGGAAGGAGAAGAAATTACATGCAAAGATGGAAGATGGCAGTCAATACCAC
TCTGTGTTGAAAAAATTCCATGTTCACAACCACCTCAGATAGAACACGGAACCATTAATTCATCCAGGTC
TTCACAAGAAAGTTATGCACATGGGACTAAATTGAGTTATACTTGTGAGGGTGGTTTCAGGATATCTGAA
GAAAATGAAACAACATGCTACATGGGAAATGGAGTTCTCCACCTCAGTGTGAAGGCCTTCCTTGTAAAT
CTCCACCTGAGATTTCTCATGGTGTTGTAGCTCACATGTCAGACAGTTATCAGTATGGAGAAGAAGTTAC
GTACAAATGTTTTGAAGGTTTTGGAATTGATGGGCCTGCAATTGCAAATGCTTAGGAGAAAAATGGTCT
CACCCTCCATCATGCATAAAAACAGATTGTCTCAGTTTACCTAGCTTTGAAAATGCCATACCCATGGGAG
AGAAGAAGGATGTGTATAAGGCGGGTGAGCAAGTGACTTACACTTGTCAACATATTACAAAATGGATGG
AGCCAGTAATGTAACATGCATTAATAGCAGATGGACAGGAAGGCCAACATGCAGAGACACCTCCTGTGTG
AATCCGCCCACAGTACAAAATGCTTATATAGTGTCGAGACAGATGAGTAAATATCCATCTGGTGAGAGAG
TACGTTATCAATGTAGGAGCCCTTATGAAATGTTTGGGGATGAAGAAGTGATGTGTTTAAATGGAAACTG
GACGGAACCACCTCAATGCAAAGATTCTACAGGAAATGTGGGCCCCTCCACCTATTGACAATGGGGAC
ATTACTTCATTCCCGTTGTCAGTATATGCTCCAGCTTCATCAGTTGAGTACCAATGCCAGAACTTGTATC
AACTTGAGGGTAACAAGCGAATAACATGTAGAAATGGACAATGGTCAGAACCACCAAAATGCTTACATCC
```

FIGURE 6 (continued)

```
GTGTGTAATATCCCGAGAAATTATGGAAAATTATAACATAGCATTAAGGTGGACAGCCAAACAGAAGCTT
TATTCGAGAACAGGTGAATCAGTTGAATTTGTGTGTAAACGGGGATATCGTCTTTCATCACGTTCTCACA
CATTGCGAACAACATGTTGGGATGGGAAACTGGAGTATCCAACTTGTGCAAAAAGATAGAATCAATCATA
AAGTGCACACCTTTATTCAGAACTTTAGTATTAAATCAGTTCTCAATTTCATTTTTTATGTATTGTTTTA
CTCCTTTTTATTCATACGTAAAATTTTGGATTAATTTGTGAAAATGTAATTATAAGCTGAGACCGGTGGC
TCTCTT
```

FIGURE 7

```
MRLLAKIICLMLWAICVAEDCNELPPRRNTEILTGSWSDQTYPEGTQAIYKCRPGYRSLGNVIMVCRKGE
WVALNPLRKCQKRPCGHPGDTPFGTFTLTGGNVFEYGVKAVYTCNEGYQLLGEINYRECDTDGWTNDIPI
CEVVKCLPVTAPENGKIVSSAMEPDREYHFGQAVRFVCNSGYKIEGDEEMHCSDDGFWSKEKPKCVEISC
KSPDVINGSPISQKIIYKENERFQYKCNMGYEYSERGDAVCTESGWRPLPSCEEKSCDNPYIPNGDYSPL
RIKHRTGDEITYQCRNGFYPATRGNTAKCTSTGWIPAPRCTLKPCDYPDIKHGGLYHENMRRPYFPVAVG
KYYSYYCDEHFETPSGSYWDHIHCTQDGWSPAVPCLRKCYFPYLENGYNQNHGRKFVQGKSIDVACHPGY
ALPKAQTTVTCMENGWSPTPRCIRVKTCSKSSIDIENGFISESQYTYALKEKAKYQCKLGYVTADGETSG
SIRCGKDGWSAQPTCIKSCDIPVFMNARTKNDFTWFKLNDTLDYECHDGYESNTGSTTGSIVCGYNGWSD
LPICYERECELPKIDVHLVPDRKKDQYKVGEVLKFSCKPGFTIVGPNSVQCYHFGLSPDLPICKEQVQSC
GPPPELLNGNVKEKTKEEYGHSEVVEYYCNPRFLMKGPNKIQCVDGEWTTLPVCIVEESTCGDIPELEHG
WAQLSSPPYYYGDSVEFNCSESFTMIGHRSITCIHGVWTQLPQCVAIDKLKKCKSSNLIILEEHLKNKKE
FDHNSNIRYRCRGKEGWIHTVCINGRWDPEVNCSMAQIQLCPPPPQIPNSHNMTTTLNYRDGEKVSVLCQ
ENYLIQEGEEITCKDGRWQSIPLCVEKIPCSQPPQIEHGTINSSRSSQESYAHGTKLSYTCEGGFRISEE
NETTCYMGKWSSPPQCEGLPCKSPPEISHGVVAHMSDSYQYGEEVTYKCFEGFGIDGPAIAKCLGEKWSH
PPSCIKTDCLSLPSFENAIPMGEKKDVYKAGEQVTYTCATYYKMDGASNVTCINSRWTGRPTCRDTSCVN
PPTVQNAYIVSRQMSKYPSGERVRYQCRSPYEMFGDEEVMCLNGNWTEPPQCKDSTGKCGPPPPIDNGDI
TSFPLSVYAPASSVEYQCQNLYQLEGNKRITCRNGQWSEPPKCLHPCVISREIMENYNIALRWTAKQKLY
SRTGESVEFVCKRGYRLSSRSHTLRTTCWDGKLEYPTCAKR
```

FIGURE 8

```
AATTCTTGGAAGAGGAGAACTGGACGTTGTGAACAGAGTTAGCTGGTAAATGTCCTCTTAAAAGATCCAA
AAAATGAGACTTCTAGCAAAGATTATTTGCCTTATGTTATGGGCTATTTGTGTAGCAGAAGATTGCAATG
AACTTCCTCCAAGAAGAAATACAGAAATTCTGACAGGTTCCTGGTCTGACCAAACATATCCAGAAGGCAC
CCAGGCTATCTATAAATGCCGCCCTGGATATAGATCTCTTGGAAATGTAATAATGGTATGCAGGAAGGGA
GAATGGGTTGCTCTTAATCCATTAAGGAAATGTCAGAAAAGGCCCTGTGGACATCCTGGAGATACTCCTT
TTGGTACTTTTACCCTTACAGGAGGAAATGTGTTTGAATATGGTGTAAAAGCTGTGTATACATGTAATGA
GGGGTATCAATTGCTAGGTGAGATTAATTACCGTGAATGTGACACAGATGGATGGACCAATGATATTCCT
ATATGTGAAGTTGTGAAGTGTTTACCAGTGACAGCACCAGAGAATGGAAAAATTGTCAGTAGTGCAATGG
AACCAGATCGGGAATACCATTTTGGACAAGCAGTACGGTTTGTATGTAACTCAGGCTACAAGATTGAAGG
AGATGAAGAAATGCATTGTTCAGACGATGGTTTTTGGAGTAAAGAGAAACCAAAGTGTGTGGAAATTTCA
TGCAAATCCCCAGATGTTATAAATGGATCTCCTATATCTCAGAAGATTATTTATAAGGAGAATGAACGAT
TTCAATATAAATGTAACATGGGTTATGAATACAGTGAAAGAGGAGATGCTGTATGCACTGAATCTGGATG
GCGTCCGTTGCCTTCATGTGAAGAAAAATCATGTGATAATCCTTATATTCCAAATGGTGACTACTCACCT
TTAAGGATTAAACACAGAACTGGAGATGAAATCACGTACCAGTGTAGAAATGGTTTTTATCCTGCAACCC
GGGGAAATACAGCCAAATGCACAAGTACTGGCTGGATACCTGCTCCGAGATGTACCTTGAAACCTTGTGA
TTATCCAGACATTAAACATGGAGGTCTATATCATGAGAATATGCGTAGACCATACTTTCCAGTAGCTGTA
GGAAAATATTACTCCTATTACTGTGATGAACATTTTGAGACTCCGTCAGGAAGTTACTGGGATCACATTC
ATTGCACACAAGATGGATGGTCGCCAGCAGTACCATGCCTCAGAAAATGTTATTTTCCTTATTTGGAAAA
TGGATATAATCAAAATTATGGAAGAAAGTTTGTACAGGGTAAATCTATAGACGTTGCCTGCCATCCTGGC
TACGCTCTTCCAAAAGCGCAGACCACAGTTACATGTATGGAGAATGGCTGGTCTCCTACTCCCAGATGCA
TCCGTGTCAGCTTTACCCTCTGAACTTCTGATCGAAGGTCATCCCTCTCCAGCTTGAGTGGATCAAAGAT
GACAAGGGCCAATGGAACCAAGTTTGAGTCTTGCCAGGTCAATACTTGGGTCCTGAGTATGGTGACTAGT
ATCTGTTTTGTTATGTGTGTATTATTCCAGCCAGAATGGGAAATGCTAATTCAGCTCCTCCAGGCAGCCA
ATGGGGCTGGTGGCTTTGAGATTATTAAACTCTTCTGGATCCTCTACG
```

FIGURE 9

```
MRLLAKIICLMLWAICVAEDCNELPPRRNTEILTGSWSDQTYPEGTQAIYKCRPGYRSLGNVIMVCRKGE
WVALNPLRKCQKRPCGHPGDTPFGTFTLTGGNVFEYGVKAVYTCNEGYQLLGEINYRECDTDGWTNDIPI
CEVVKCLPVTAPENGKIVSSAMEPDREYHFGQAVRFVCNSGYKIEGDEEMHCSDDGFWSKEKPKCVEISC
KSPDVINGSPISQKIIYKENERFQYKCNMGYEYSERGDAVCTESGWRPLPSCEEKSCDNPYIPNGDYSPL
RIKHRTGDEITYQCRNGFYPATRGNTAKCTSTGWIPAPRCTLKPCDYPDIKHGGLYHENMRRPYFPVAVG
KYYSYYCDEHFETPSGSYWDHIHCTQDGWSPAVPCLRKCYFPYLENGYNQNYGRKFVQGKSIDVACHPGY
ALPKAQTTVTCMENGWSPTPRCIRVSFTL
```

FIGURE 10

MRLLAKIICLMLWAICVAEDCNELPPRRNTEILTGSWSDQTYPEGTQAIYKCRPGYRSLGNIIMVCRKGE
WVALNPLRKCQKRPCGHPGDTPFGTFTLTGGNVFEYGVKAVYTCNEGYQLLGEINYRECDTDGWTNDIPI
CEVVKCLPVTAPENGKIVSSAMEPDREYHFGQAVRFVCNSGYKIEGDEEMHCSDDGFWSKEKPKCVEISC
KSPDVINGSPISQKIIYKENERFQYKCNMGYEYSERGDAVCTESGWRPLPSCEEKSCDNPYIPNGDYSPL
RIKHRTGDEITYQCRNGFYPATRGNTAKCTSTGWIPAPRCTLKPCDYPDIKHGGLYHENMRRPYFPVAVG
KYYSYYCDEHFETPSGSYWDHIHCTQDGWSPAVPCLRKCYFPYLENGYNQNYGRKFVQGKSIDVACHPGY
ALPKAQTTVTCMENGWSPTPRCIRVKTCSKSSIDIENGFISESQYTYALKEKAKYQCKLGYVTADGETSG
SIRCGKDGWSAQPTCIKSCDIPVFMNARTKNDFTWFKLNDTLDYECHDGYESNTGSTTGSIVCGYNGWSD
LPICYERECELPKIDVHLVPDRKKDQYKVGEVLKFSCKPGFTIVGPNSVQCYHFGLSPDLPICKEQVQSC
GPPPELLNGNVKEKTKEEYGHSEVVEYYCNPRFLMKGPNKIQCVDGEWTTLPVCIVEESTCGDIPELEHG
WAQLSSPPYYYGDSVEFNCSESFTMIGHRSITCIHGVWTQLPQCVAIDKLKKCKSSNLIILEEHLKNKKE
FDHNSNIRYRCRGKEGWIHTVCINGRWDPEVNCSMAQIQLCPPPPQIPNSHNMTTTLNYRDGEKVSVLCQ
ENYLIQEGEEITCKDGRWQSIPLCVEKIPCSQPPQIEHGTINSSRSSQESYAHGTKLSYTCEGGFRISEE
NETTCYMGKWSSPPQCEGLPCKSPPEISHGVVAHMSDSYQYGEEVTYKCFEGFGIDGPAIAKCLGEKWSH
PPSCIKTDCLSLPSFENAIPMGEKKDVYKAGEQVTYTCATYYKMDGASNVTCINSRWTGRPTCRDTSCVN
PPTVQNAYIVSRQMSKYPSGERVRYQCRSPYEMFGDEEVMCLNGNWTEPPQCKDSTGKCGPPPPIDNGDI
TSFPLSVYAPASSVEYQCQNLYQLEGNKRITCRNGQWSEPPKCLHPCVISREIMENYNIALRWTAKQKLY
SRTGESVEFVCKRGYRLSSRSHTLRTTCWDGKLEYPTCAKR

FIGURE 11

```
MRLLAKIICLMLWAICVAEDCNELPPRRNTEILTGSWSDQTYPEGTQAIYKCRPGYRSLGNIIMVCRKGE
WVALNPLRKCQKRPCGHPGDTPFGTFTLTGGNVFEYGVKAVYTCNEGYQLLGEINYRECDTDGWTNDIPI
CEVVKCLPVTAPENGKIVSSAMEPDREYHFGQAVRFVCNSGYKIEGDEEMHCSDDGFWSKEKPKCVEISC
KSPDVINGSPISQKIIYKENERFQYKCNMGYEYSERGDAVCTESGWRPLPSCEEKSCDNPYIPNGDYSPL
RIKHRTGDEITYQCRNGFYPATRGNTAKCTSTGWIPAPRCTLKPCDYPDIKHGGLYHENMRRPYFPVAVG
KYYSYYCDEHFETPSGSYWDHIHCTQDGWSPAVPCLRKCYFPYLENGYNQNYGRKFVQGKSIDVACHPGY
ALPKAQTTVTCMENGWSPTPRCIRVSFTL
```

FIGURE 12
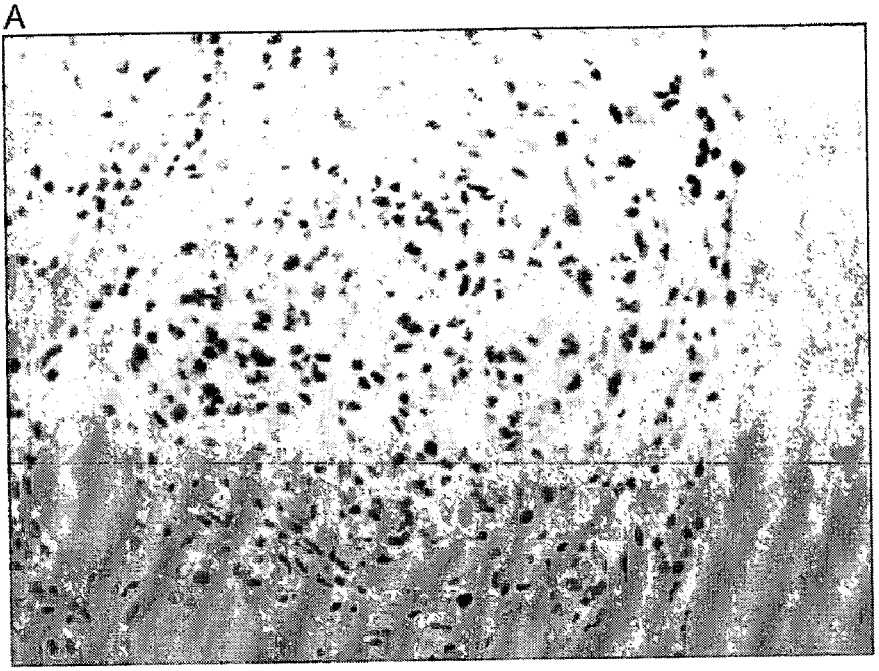
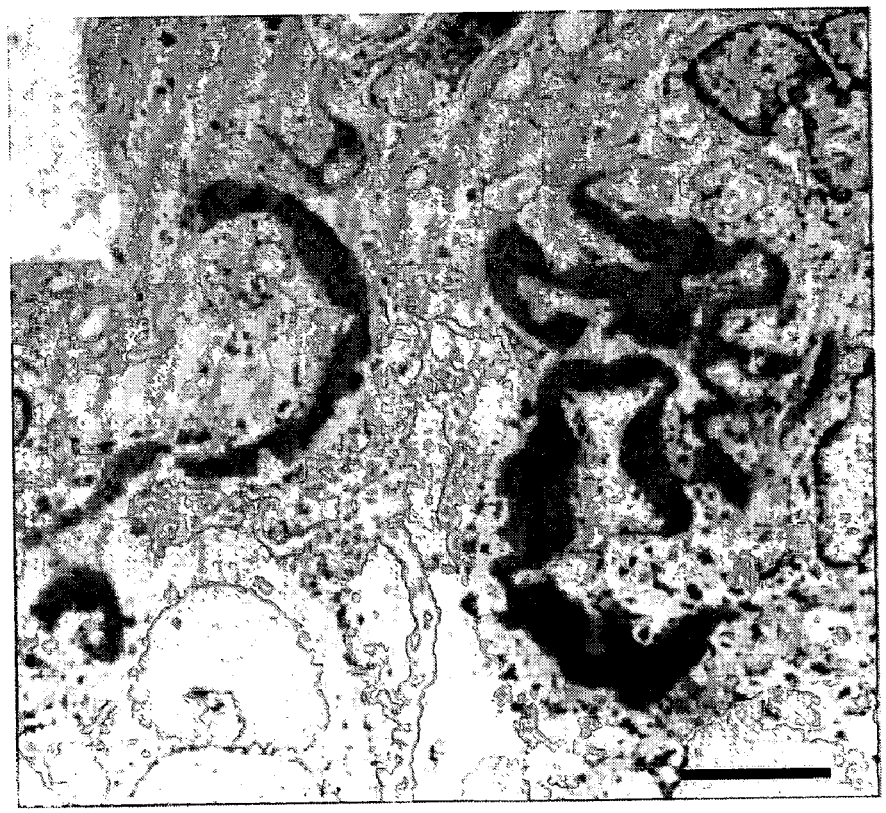

FIGURE 16

```
GGCAGGTGCTTGTTACTGTTAATGAAAGCAGATTTAAAGCAACACCACCATCACTGGAGTATTTTTAGTT
ATATACGATTGAGACTACCAAGCATGTTGCTCTTATTCAGTGTAATCCTAATCTCATGGGTATCCACTGT
TGGGGGAGAAGGAACACTTTGTGATTTTCCAAAAATACACCATGGATTTCTGTATGATGAAGAAGATTAT
AACCCTTTTTCCCAAGTTCCTACAGGGGAAGTTTTCTATTACTCCTGTGAATATAATTTTGTGTCTCCTT
CAAAATCCTTTTGGACTCGCATAACATGCACAGAAGAAGGATGGTCACCAACACCGAAGTGTCTCAGAAT
GTGTTCCTTTCCTTTTGTGAAAAATGGTCATTCTGAATCTTCAGGACTAATACATCTGGAAGGTGATACT
GTACAAATTATTTGCAACACAGGATACAGCCTTCAAAACAATGAGAAAAACATTTCGTGTGTAGAACGGG
GCTGGTCCACTCCTCCCATATGCAGCTTCACTAAAGGAGAATGTCATGTTCCAATTTTAGAAGCCAATGT
AGATGCTCAGCCAAAAAAAGAAAGCTACAAAGTTGGAGACGTGTTGAAATTCTCCTGCAGAAAAAATCTT
ATAAGAGTTGGATCAGACTCAGTTCAATGTTACCAATTTGGGTGGTCACCTAACTTTCCAACATGCAAAG
GACAAGTACGATCATGTGGTCCACCTCCTCAACTCTCCAATGGTGAAGTTAAGGAGATAAGAAAAGAGGA
ATATGGACACAATGAAGTAGTGGAATATGATTGCAATCCTAATTTTATAATAAACGGGCCTAAGAAAATA
CAATGTGTGGATGGAGAATGGACAACTTTACCCACTTGTGTTGAACAAGTGAAAACATGTGGATACATAC
CTGAACTCGAGTACGGTTATGTTCAGCCGTCTGTCCCTCCCTATCAACATGGAGTTTCAGTCGAGGTGAA
TTGCAGAAATGAATATGCAATGATTGGAAATAACATGATTACCTGTATTAATGGAATATGGACAGAGCTT
CCTATGTGTGTTGCAACACACCAACTTAAGAGGTGCAAAATAGCAGGAGTTAATATAAAAACATTACTCA
AGCTATCTGGGAAAGAATTTAATCATAATTCTAGAATACGTTACAGATGTTCAGACATCTTCAGATACAG
GCACTCAGTCTGTATAAACGGGAAATGGAATCCTGAAGTAGACTGCACAGAAAAAGGGAACAATTCTGC
CCACCGCCACCTCAGATACCTAATGCTCAGAATATGACAACCACAGTGAATTATCAGGATGGAGAAAAAG
TAGCTGTTCTCTGTAAAGAAAACTATCTACTTCCAGAAGCAAAAGAAATTGTATGTAAAGATGGACGATG
GCAATCATTACCACGCTGTGTTGAGTCTACTGCATATTGTGGGCCCCCTCCATCTATTAACAATGGAGAT
ACCACCTCATTCCCATTATCAGTATATCCTCCAGGGTCAACAGTGACGTACCGTTGCCAGTCCTTCTATA
AACTCCAGGGCTCTGTAACTGTAACATGCAGAAATAAACAGTGGTCAGAACCACCAAGATGCCTAGATCC
ATGTGTGGTATCTGAAGAAAACATGAACAAAAATAACATACAGTTAAAATGGAGAAACGATGGAAAACTC
TATGCAAAAACAGGGGATGCTGTTGAATTCCAGTGTAAATTCCACATAAAGCGATGATATCATCACCAC
CATTTCGAGCAATCTGTCAGGAAGGGAAATTTGAATATCCTATATGTGAATGAAGCAAGCATAATTTTCC
TGAATATATTCTTCAAACATCCATCTACGCTAAAAGTAGCCATTATGTAGCCAATTCTGTAGTTACTTCT
TTTATTCTTTCAGGTGTTGTTTAACTCAGTTTTATTTAGAACTCTGGATTTTTAGAGCTTTAGAAATTTG
TAAGCTGAGAGAACAATGTTTCACTTAATAGGAGGGTGTCTTAGTCCATATTACATTGTTATAACAGAGT
ATCACAGACTGGATAACTTCTAACCAATAGTTTATTTGTTTCATAAATCTAAAAGCTGAGAAGTCCAAGA
TGGTGGGGCTGCCTCTGGTGAGGGTCTTCTCGAAGCATCATAATATGCTGGAAGGCATCACAACATGGTG
GAAGGGATCACGTGGCAAAAGAGCATGTACATGGGAGTGAGAGAAAAGAGAGAGAGAGACAGAGTGGCG
GGGGCCGGGGAGGAGCGCAAACTCATCCTTTATAAAGACACCACTCCTGAGATAACAATCCAATCCCATG
ATAATGACATTAATCCATTCAAGAAGATAGAGCTCTCGTGACTTAATCACCTTCTAAAGATCTCACCTGA
CAACACTGTTGCATTGGCAGTTAAGTTTCCACGTAAACTTTCGGGGACACATTCAAACCACAGGAGAAAC
TCAAATTGTTCCTGGGCAAATCACAACATGGGGAATTTTATTCATAAATGTCCACAGAAACAGTAAATGT
TCTCGCTTCAGAACTTAATTCATCTAATCCCTCCTGTTTGTCTCAAATTATAGGATAACTTTGAAACTTT
CTGAATTAACGTTATTTAAAAGGAAATGTAGATGTTATTTTAGTCTCTATCTTCAGGTTATTATCACTTA
AAAACCTGCGAAAGCTGTCAACTTTTGTGGTTGTAGCAAGTATTAATAAATATTTATAAATCCTCTAATG
TAAGTCTAGCTACCTATCCAATACTAAATACCCCTTAAAGTATTAAATGCACTATCTGCTGTAAACGGAA
AAAAAAAAAAAAAAAAAAAAAA
```

FIGURE 17

```
MLLLFSVILISWVSTVGGEGTLCDFPKIHHGFLYDEEDYNPFSQVPTGEVFYYSCEYNFVSPSKSFWTRI
TCTEEGWSPTPKCLRMCSFPFVKNGHSESSGLIHLEGDTVQIICNTGYSLQNNEKNISCVERGWSTPPIC
SFTKGECHVPILEANVDAQPKKESYKVGDVLKFSCRKNLIRVGSDSVQCYQFGWSPNFPTCKGQVRSCGP
PPQLSNGEVKEIRKEEYGHNEVVEYDCNPNFIINGPKKIQCVDGEWTTLPTCVEQVKTCGYIPELEYGYV
QPSVPPYQHGVSVEVNCRNEYAMIGNNMITCINGIWTELPMCVATHQLKRCKIAGVNIKTLLKLSGKEFN
HNSRIRYRCSDIFRYRHSVCINGKWNPEVDCTEKREQFCPPPPQIPNAQNMTTTVNYQDGEKVAVLCKEN
YLLPEAKEIVCKDGRWQSLPRCVESTAYCGPPPSINNGDTTSFPLSVYPPGSTVTYRCQSFYKLQGSVTV
TCRNKQWSEPPRCLDPCVVSEENMNKNNIQLKWRNDGKLYAKTGDAVEFQCKFPHKAMISSPPFRAICQE
GKFEYPICE
```

METHODS FOR TREATMENT OF AGE-RELATED MACULAR DEGENERATION

CROSS-REFERENCE TO RELATED APPLICATIONS

This application claims benefit of U.S. Provisional Application Nos. 60/650,078 (filed Feb. 14, 2005), 60/717,861 (filed Sep. 16, 2005), 60/715,503 (filed Sep. 9, 2005), and 60/735,697 (filed Nov. 9, 2005), the entire contents of which are incorporated herein by reference.

STATEMENT AS TO RIGHTS TO INVENTIONS MADE UNDER FEDERALLY SPONSORED RESEARCH AND DEVELOPMENT

This invention was made with government support under NIH Eye Institute grant EY11515 awarded by the National Institutes of Health. The government has certain rights in the invention.

BACKGROUND OF THE INVENTION

Age-related macular degeneration (AMD) is the leading cause of irreversible vision loss in the developed world (for reviews see Zarbin, 1998, 2004; Klein et al., 2004; Ambati et al., 2003; de Jong, 2004; van Leeuwen et al., 2003) affecting approximately 15% of individuals over the age of 60. An estimated 600 million individuals are in this age demographic. The prevalence of AMD increases with age; mild, or early forms occur in nearly 30%, and advanced forms in about 7%, of the population that is 75 years and older (Klein et al., 1992; Vingerling et al., 1995a, 1995b). Clinically, AMD is characterized by a progressive loss of central vision attributable to degenerative changes that occur in the macula, a specialized region of the neural retina and underlying tissues. In the most severe, or exudative, form of the disease neovascular fronds derived from the choroidal vasculature breach Bruch's membrane and the retinal pigment epithelium (RPE) typically leading to detachment and subsequent degeneration of the retina.

AMD, a late-onset complex disorder, appears to be caused and/or modulated by a combination of genetic and environmental factors (Seddon and Chen, 2004; Tuo et al., 2004; Klein and Francis, 2003). Familial aggregation studies have estimated the genetic component to be primarily involved in as much as 25% of the disorder (Klaver et al., 1998a). According to the prevailing hypothesis, the majority of AMD cases is not a collection of multiple single-gene disorders, but instead represents a quantitative phenotype, an expression of interaction of multiple susceptibility loci. The number of loci involved, the attributable risk conferred, and the interactions between various loci remain obscure.

Linkage and candidate gene screening analyses have provided limited insight into the genetics of AMD. Reliable association of one gene with increased risk, ABCA4 (Allikmets et al., 1997) and one gene with decreased risk, ApoE4 (Klaver et al., 1998b, Souied et al., 1998) for AMD have been reported. In addition, several groups have reported results of genome-wide linkage analyses (reviewed in Tuo et al., 2004; Weeks et al., 2004). Linkage of one family with AMD phenotype to a specific chromosomal region, 1q25-q31 (ARMD1) has been documented (Klein et al., 1998). HEMICENTIN-1 has been suggested to be the causal gene (Schultz et al., 2003) although its role has not been reliably confirmed. The identification of overlapping loci on chromosome 1q in several studies (Weeks et al., 2001; Iyengar et al., 2003; Weeks et al., 2004) suggests that this locus may harbor AMD-associated gene(s).

Recent studies of drusen, the hallmark ocular lesions associated with the onset of AMD, have implicated a role for inflammation and other immune-mediated processes, in particular complement activation, in the etiology of early and late forms of AMD (Hageman et al., 1999, 2001; Mullins et al., 2000, 2001; Russell et al., 2000; Anderson et al., 2002, 2004; Johnson et al., 2000, 2001; Crabb et al., 2002; Ambati et al., 2003; Penfold et al., 2001; Espinosa-Heidman et al., 2003). These studies have revealed the terminal pathway complement components (C5, C6, C7, C8 and C9) and activation-specific complement protein fragments of the terminal pathway (C3b, iC3b, C3dg and C5b-9) as well as various complement pathway regulators and inhibitors (including Factor H, Factor I, Factor D, CD55 and CD59) within drusen, along Bruch's membrane (an extracellular layer comprised of elastin and collagen that separates the RPE and the choroid) and within RPE cells overlying drusen (Johnson et al., 2000, 2001; Mullins et al. 2000, 2001; Crabb et al., 2002). Many of these drusen-associated molecules are circulating plasma proteins previously thought to be synthesized primarily by the liver. Interestingly, many also appear to be synthesized locally by RPE and/or choroidal cells.

Activation of the complement system plays a key role in normal host defense and in the response to injury (Kinoshita, 1991). Inappropriate activation and/or control of this system, often caused by mutations in specific complement-associated genes, can contribute to autoimmune sequelae and local tissue destruction (Holers, 2003; Liszewski and Atkinson, 1991; Morgan and Walport, 1991; Shen and Meri, 2003), as has been shown in atherosclerosis (Torzewski et al., 1997; Niculescu et al., 1999), Alzheimer's disease (Akiyama et al., 2000) and glomerulonephritis (Schwertz et al., 2001).

Membranoproliferative glomerulonephritis type 2 (MPGN II) is a rare disease that is associated with uncontrolled systemic activation of the alternative pathway of the complement cascade. The disease is characterized by the deposition of abnormal electron-dense material comprised of C3 and C3c, proteins involved in the alternative pathway of complement, within the renal glomerular basement membrane, which eventually leads to renal failure. Interestingly, many patients with MPGNII develop macular drusen, RPE detachments and choroidal neovascular membranes that are clinically and compositionally indistinguishable from those that form in AMD, although they are often detected in the second decade of life (Mullins et al., 2001; O'Brien et al., 1993; Huang et al., 2003; Colville et al., 2003; Duvall-Young et al., 1989a, 1989b; Raines et al., 1989; Leys et al., 1990; McAvoy and Silvestri, 2004; Bennett et al., 1989; Orth and Ritz, 1998; Habib et al., 1975).

In most patients with MPGNII, the inability to regulate the complement cascade is mediated by an autoantibody directed against C3bBb. Other MPGN II patients, however, harbor mutations in Factor H (Ault et al., 1997; Dragon-Durey et al., 2004) a major inhibitor of the alternative complement pathway. A point mutation in Factor H (I1166R) causes MPGNII in the Yorkshire pig (Jansen et al., 1998) and Factor H deficient mice develop severe glomerulonephritis (Pickering et al., 2002). Moreover, affected individuals within some extended families with MPGNIII, a related disorder, show linkage to chromosome 1q31-32 (Neary et al., 2002) a region that overlaps a locus that has been identified in genome-wide linkage studies for AMD (see above). This particular locus contains a number of complement pathway-associated genes. One group of these genes, referred to as the regulators of complement activation (RCA) gene cluster, contains the genes that encode Factor H, five Factor H-related genes (CFHR1, CFHR2, CFHR3, CFHR4 and CFHR5), and the beta subunit of coagulation factor XIII. A second cluster of complement pathway-associated genes, including C4BPA, C4BPB, C4BPAL2, DAF (CD55) CR1, CR2, CR1L and MCP (CD46) lies immediately adjacent to the 1q25-31 locus.

BRIEF SUMMARY OF THE INVENTION

The invention relates to polymorphisms and haplotypes in the complement Factor H gene that are associated with development of age-related macular degeneration (AMD) and membranoproliferative glomerulonephritis type 2 (MPG-NII). The invention also relates to polymorphisms and haplotypes in the complement Factor H-related 5 (CFHR5) genes that are associated with development of AMD and MPGNII. The invention provides methods of diagnosing, monitoring, and treating these and other diseases.

In one aspect, the invention provides a diagnostic method for determining a subject's propensity to develop age-related macular degeneration (AMD), comprising detecting the presence or absence of a variation or variations at polymorphic site or polymorphic sites of the Factor H gene. In one embodiment, the invention provides methods of diagnosing an increased susceptibility to developing AMD involving detecting the presence or absence of a polymorphism in the Factor H gene of an individual. The methods may include obtaining the DNA from an individual and analyzing the DNA from the individual to determine whether the DNA contains a polymorphism in the Factor H gene. Certain polymorphisms indicate the individual has an increased susceptibility to developing AMD relative to a control population. Certain polymorphisms indicate the individual has a reduced likelihood of developing AMD. Certain polymorphisms indicate the individual has neither an increased nor a reduced likelihood of developing AMD.

In one embodiment, a method of diagnosing a propensity to develop age-related macular degeneration (AMD) in a subject involves obtaining a sample of DNA from the subject and detecting in the DNA of the patient the presence or absence of a polymorphism associated with development of AMD, the presence of the polymorphism being an indication that the subject has an increased propensity to develop AMD and the absence of the polymorphism being an indication that the subject has a reduced propensity to develop AMD.

In a related aspect, the invention provides methods of diagnosing susceptibility to developing AMD involving determining an individual's Factor H haplotype. The methods include obtaining the DNA from an individual and analyzing the DNA of the individual to determine their Factor H haplotype. Certain haplotypes (risk haplotypes) indicate the individual has an increased susceptibility to develop AMD. Certain haplotypes (protective haplotypes) indicate the individual has a decreased susceptibility to develop AMD. Certain haplotypes (neutral haplotypes) indicate the individual has neither an increased nor a reduced likelihood of developing AMD.

In a related embodiment the presence or absence of a variation at a polymorphic site of the Factor H gene is determined by analysis of a gene product, such as an RNA or a Factor H protein (e.g., protein isoform) encoded by the gene. Expression of a variant protein is an indication of a variation in the Factor H gene and can indicate an increased or reduced propensity to develop AMD. Proteins can be detected using immunoassays and other methods.

In another related aspect, the invention provides methods of diagnosing susceptibility to developing AMD or other diseases by detecting a variant Factor H polypeptide in a biological sample of an individual. In one embodiment, an antibody-based assay is used to diagnose AMD or other diseases in an individual by contacting a biological sample, e.g., a serum sample, of the individual with the antibody and detecting the presence or absence of the variant Factor H polypeptide. In an embodiment, the antibody specifically interacts with an epitope specific to a variant Factor H polypeptide (i.e., not found in the wild-type Factor H polypeptide). In an embodiment, a separation-based assay (e.g., PAGE) is used to diagnose AMD or other diseases in an individual by detecting the presence or absence of the variant Factor H polypeptide in a biological sample, e.g., a serum sample, of the individual.

In one aspect, the invention provides methods of treating an individual with AMD (e.g., an individual in whom a polymorphism or haplotype indicative of elevated risk of developing symptomatic AMD is detected) or other disease involving a variant Factor H gene by modulating the type and/or amount of systemic and/or ocular levels of Factor H. The Factor H polypeptide may be a wild-type Factor H polypeptide or a variant Factor H polypeptide. The Factor H polypeptide may be a Factor H polypeptide with a sequence encoded by neutral or protective alleles rather than alleles associated with a risk haplotype. In one embodiment, the method includes administering to the individual a Factor H polypeptide in an amount effective to reduce a symptom of the disease. In one embodiment, the method includes administering to an individual a Factor H polypeptide in an amount effective to reduce the propensity to develop symptoms of the disease and delay development or progression of the disease. In one embodiment, the method includes administering blood that contains Factor H. In one embodiment, the methods include administering a nucleic acid (e.g., transgene) including a nucleotide sequence encoding a Factor H polypeptide. In one embodiment, the methods include administering cells that express a Factor H polypeptide.

In one aspect, the invention provides methods of treating an individual with AMD (e.g., an individual in whom a polymorphism or haplotype indicative of elevated risk of developing symptomatic AMD is detected) or other disease involving a variant Factor H gene. In one embodiment, the method includes administering to the patient an agent that decreases the amount of a variant Factor H or expression of a gene encoding Factor H in an amount effective to reduce a symptom of the disease in the patient. In a related embodiment a therapeutic amount of an inhibitor (e.g., inactivator) of the variant Factor H polypeptide in the individual is administered.

In one embodiment an inhibitory nucleic acid (e.g., an RNA complementary to at least a portion of the nucleotide sequence of the variant Factor H polypeptide) in the individual is administered. In one embodiment, purified anti-sense RNA complementary to RNA encoding a variant Factor H polypeptide is administered.

In another embodiment a therapeutic amount of an anti-CFH antibody sufficient to partially inactivate the variant Factor H polypeptide in the individual is administered.

In another embodiment, the individual is treated to remove deleterious forms of Factor H from blood (e.g., by plasmaphoresis, antibody-directed plasmaphoresis, or complexing with a Factor H binding moiety, e.g., heparin).

In one aspect, the invention provides purified DNA encoding a variant Factor H polypeptide, purified RNA encoding a variant Factor H polypeptide, purified anti-sense RNA complementary to the RNA encoding a variant Factor H polypeptide, and purified variant Factor H polypeptide. In a related aspect, the invention provides nucleic acids for expressing wild-type or variant Factor H polypeptides or biologically active fragments of Factor H.

In one aspect, the invention provides gene therapy vectors comprising nucleic acid encoding the Factor H polypeptide. The vector may include a promoter that drives expression of the Factor H gene in multiple cell types. Alternatively, the vector may include a promoter that drives expression of the Factor H gene only in specific cell types, for example, in cells of the retina or in cells of the kidney. In an aspect, pharmaceutical compositions are provided containing a gene therapy vector encoding a Factor H protein and a pharmaceutically acceptable excipient, where the composition is free of pathogens and suitable for administration to a human patient. In one embodiment the encoded Factor H polypeptide is a protective variant.

In one aspect, the invention provides a composition containing recombinant or purified Factor H polypeptide, where the polypeptide is a protective variant.

In a related aspect, the invention provides a pharmaceutical composition containing recombinant or purified Factor H polypeptide and a pharmaceutically acceptable excipient, where the composition is free of pathogens and suitable for administration to a human patient. In one embodiment the encoded Factor H polypeptide has the wild-type sequence. In one embodiment the encoded Factor H polypeptide is a protective variant.

In one aspect, the invention provides antibodies that specifically interact with a variant Factor H polypeptide but not with a wild-type Factor H polypeptide. These antibodies may be polyclonal or monoclonal and may be obtained by subtractive techniques. These antibodies may be sufficient to inactivate a variant Factor H polypeptide. In a related aspect, the invention provides pharmaceutical compositions containing an anti-Factor H antibody and a pharmaceutically acceptable excipient, where the composition is free of pathogens and suitable for administration to a human patient.

In one aspect, the invention provides methods for identifying variant Factor H proteins associated with increased or reduced risk of developing AMD. In one embodiment, the invention provides a method of identifying a protective Factor H protein by (a) identifying an individual as having a protective haplotype and (b) determining the amino acid sequence(s) of Factor H encoded in the genome of the individual, where a protective Factor H protein is encoded by an allele having a protective haplotype. In one embodiment, the invention provides a method of identifying a neutral Factor H protein by (a) identifying an individual as having a neutral haplotype and (b) determining the amino acid sequence(s) of Factor H encoded in the genome of the individual, where a neutral Factor H protein is encoded by an allele having a neutral haplotype. In a related embodiment, the invention provides a method of identifying a variant form of Factor H associated with decreased risk of developing AMD comprising (a) identifying an individual as having a haplotype or diplotype associated with a decreased risk of developing AMD; (b) obtaining genomic DNA or RNA from the individual; and (c) determining the amino acid sequence(s) of the Factor H encoded in the individual's genome, where a protective Factor H protein is encoded by an allele having a haplotype associated with a decreased risk of developing AMD. In an embodiment, the protective or neutral Factor H proteins do not have the amino acid sequence of the wild-type Factor H polypeptide.

In a related method, a form of Factor H associated with increased risk of developing AMD is identified by (a) identifying an individual as having a risk haplotype and (b) determining the amino acid sequence(s) of Factor H encoded in the genome of the individual, where a risk Factor H protein is encoded by an allele having a risk haplotype. In a related embodiment, the invention provides as method of identifying a variant form of Factor H associated with increased risk of developing AMD comprising (a) identifying an individual as having a haplotype or diplotype associated with an increased risk of developing AMD; (b) obtaining genomic DNA or RNA from the individual; and (c) determining the amino acid sequence(s) of the Factor H encoded in the individual's genome, where a risk Factor H protein is encoded by an allele having a haplotype associated with an increased risk of developing AMD. In an embodiment, the risk Factor H proteins do not have the amino acid sequence of the wild-type Factor H polypeptide.

In one aspect, the invention provides methods of diagnosing a propensity or susceptibility to develop AMD or other diseases by detecting the ratio of full-length Factor H to truncated Factor H in a biological sample of a patient. In one embodiment, a method of diagnosing a propensity or susceptibility to develop AMD in a subject involves obtaining a sample of RNA from the subject and detecting in the RNA of the patient the ratio of expression of exon 10 (i.e., full-length Factor H) to exon 10A (i.e., truncated Factor H), the increase in ratio being an indication that the subject has an increased propensity or susceptibility to develop AMD and the decrease in ratio being an indication that the subject has a reduced propensity or susceptibility to develop AMD. In one embodiment, a method of diagnosing a propensity or susceptibility to develop AMD in a subject involves obtaining a sample of protein from the subject and detecting in the protein of the patient the ratio of expression of full-length Factor H to truncated Factor H, the increase in ratio being an indication that the subject has an increased propensity or susceptibility to develop AMD and the decrease in ratio being an indication that the subject has a reduced propensity or susceptibility to develop AMD.

In one aspect, the invention provides cells containing recombinant or purified nucleic acid encoding a Factor H protein or fragment thereof, e.g., a nucleic acid derived from the Factor H gene. The cells may be bacterial or yeast, or any other cell useful for research and drug development. Thus, the invention provides an isolated host cell or cell line expressing a recombinant variant human Factor H. In an embodiment, the variant is a risk variant and has a histidine at amino acid position 402. In an embodiment, the variant is a protective variant and has isoleucine at amino acid position 62. In an embodiment, the variant is a neutral variant. In an embodiment, the risk, protective or neutral variant Factor H proteins do not have the amino acid sequence of the wild-type Factor H polypeptide.

In one aspect, the invention provides transgenic non-human animals whose somatic and germ cells contain a transgene encoding a human variant Factor H polypeptide. Transgenic animals of the invention are used as models for AMD and for screening for agents useful in treating AMD. The animal may be a mouse, a worm, or any other animal useful for research and drug development (such as recombinant production of Factor H). In an embodiment, the Factor H is a variant human Factor H, wherein said variant has isoleucine amino acid 62 or has histidine at amino acid 402.

In one aspect, the invention provides methods of screening for polymorphic sites linked to polymorphic sites in the Factor H gene described in TABLES 1A, 1B and 1C. These methods involve identifying a polymorphic site in a gene that is linked to a polymorphic site in the Factor H gene, wherein the polymorphic form of the polymorphic site in the Factor H gene is associated AMD, and determining haplotypes in a population of individuals to indicate whether the linked polymorphic site has a polymorphic form in equilibrium disequilibrium with the polymorphic form of the Factor H gene that associates with the AMD phenotype.

In one aspect, the invention provides diagnostic, therapeutic and screening methods for MPGNII, carried out as described above for AMD.

In one aspect, the invention provides a diagnostic method for determining a subject's propensity to develop AMD or MPGNII, comprising detecting the presence or absence of a variation or variations at polymorphic site or polymorphic sites of the CFHR5 gene. In one embodiment, the invention provides methods of diagnosing an increased susceptibility to developing AMD or MPGNII involving detecting the presence or absence of a polymorphism in the CFHR5 gene of an individual. The methods may include obtaining the DNA from an individual and analyzing the DNA from the individual to determine whether the DNA contains a polymorphism in the CFHR5 gene. Certain polymorphisms indicate the individual has an increased susceptibility to developing AMD or MPGNII. Certain polymorphisms indicate the individual has a reduced likelihood of developing AMD or MPGNII. Certain polymorphisms indicate the individual has neither an increased nor a reduced likelihood of developing AMD or MPGNII.

In one embodiment, a method of diagnosing a propensity to develop AMD or MPGNII in a subject involves obtaining a sample of DNA from the subject and detecting in the DNA of the patient the presence or absence of a polymorphism associated with development of AMD or MPGNII, the presence of the polymorphism being an indication that the subject has an increased propensity to develop AMD or MPGNII and the absence of the polymorphism being an indication that the subject has a reduced propensity to develop AMD or MPGNII.

In a related embodiment the presence or absence of a variation at a polymorphic site of the CFHR5 gene is determined by analysis of a gene product, such as an RNA or a CFHR5 protein (e.g., protein isoform) encoded by the gene. Expression of a variant protein is an indication of a variation in the CFHR5 gene and can indicate an increased or reduced propensity to develop AMD or MPGNII. Proteins can be detected using immunoassays and other methods.

In a related, aspect, the invention provides methods of diagnosing susceptibility to developing AMD or MPGNII involving determining an individual's CFHR5 haplotype. The methods include obtaining the DNA from an individual and analyzing the DNA of the individual to determine their CFHR5 haplotype. Certain haplotypes (risk haplotypes) indicate the individual has an increased susceptibility to develop AMD or MPGNII relative to a control population. Certain haplotypes (protective haplotypes) indicate the individual has an decreased susceptibility to develop AMD or MPGNII. Certain haplotypes (neutral haplotypes) indicate the individual has neither an increased nor a reduced likelihood of developing AMD or MPGNII.

In another related, aspect, the invention provides methods of diagnosing susceptibility to developing AMD or MPGNII or other diseases by detecting a variant CFHR5 polypeptide in a biological sample of an individual. In one embodiment, an antibody-based assay is used to diagnose AMD or MPGNII or other diseases in an individual by contacting a biological sample, e.g., a serum sample, of the individual with the antibody and detecting the presence or absence of the variant CFHR5 polypeptide. In an embodiment, the antibody specifically interacts with an epitope specific to a variant CFHR5 polypeptide (i.e., not found in the wild-type CFHR5 polypeptide). In an embodiment, a separation-based assay (e.g., PAGE) is used to diagnose MPGNII or other diseases in an individual by detecting the presence or absence of the variant CFHR5 polypeptide in a biological sample, e.g., a serum sample, of the individual. Various types of immunoassay formats can be used to assay CFH or CFHR5 polypeptide or protein in a sample. These include sandwich ELISA, radioimmunoassay, fluoroimmunoassay, inmunohistochemistry assay, dot-blot, dip-stick and Western Blot.

In one aspect, the invention provides methods of treating an individual with or at risk for AMD or MPGNII (e.g., an individual in whom a polymorphism or haplotype indicative of elevated risk of developing symptomatic AMD or MPGNII is detected) or other disease involving a variant CFHR5 gene by modulating the type and/or amount of systemic and/or renal levels of CFHR5. The CFHR5 polypeptide may be a CFHR5 polypeptide encoded by neutral or protective alleles rather than alleles associated with a risk haplotype. In one embodiment, the method includes administering to the individual a CFHR5 polypeptide in an amount effective to reduce a symptom of the disease. In one embodiment, the method includes administering to an individual a CFHR5 polypeptide in an amount effective to reduce the propensity to develop symptoms of the disease and delay development or progression of the disease. In one embodiment, the method includes administering blood, which contains CFHR5. In one embodiment, the methods include administering a nucleic acid (e.g., transgene) including a nucleotide sequence encoding a CFHR5 polypeptide.

In one aspect, the invention provides methods of treating an individual with AMD or MPGNII (e.g., an individual in whom a polymorphism or haplotype indicative of elevated risk of developing symptomatic AMD or MPGNII is detected) or other disease involving a variant CFHR5 gene. In one embodiment, the method includes administering to the patient an agent that decreases the amount of a variant CFHR5 or expression of a gene encoding CFHR5 in an amount effective to reduce a symptom of the disease in the patient. The CFHR5 polypeptide may be a wild-type CFHR5 polypeptide or a variant CFHR5 polypeptide.

In one embodiment an inhibitory nucleic acid (e.g., an RNA complementary to at least a portion of the nucleotide sequence of the variant CFHR5 polypeptide) in the individual is administered. In one embodiment, purified anti-sense RNA complementary to RNA encoding a variant CFHR5 polypeptide is administered.

In another embodiment a therapeutic amount of an anti-CFHR5 antibody sufficient to partially inactivate the variant CFHR5 polypeptide in the individual is administered.

In a related embodiment a therapeutic amount of an inhibitor (e.g., inactivator) of the variant CFHR5 polypeptide in the individual is administered.

In another embodiment, the individual is treated to remove deleterious forms of CFHR5 from blood (e.g., by plasmaphoresis, antibody-directed plasmaphoresis, or complexing with a CFHR5 binding moiety, e.g., heparin).

In one aspect, the invention provides purified DNA encoding a variant CFHR5 polypeptide, purified RNA encoding a variant CFHR5 polypeptide, purified anti-sense RNA complementary to the RNA encoding a variant CFHR5 polypeptide, and purified variant CFHR5 polypeptide. In a related aspect, the invention provides nucleic acids for expressing wild-type or variant CFHR5 polypeptides or biologically active fragments of CFHR5.

In one aspect, the invention provides gene therapy vectors comprising nucleic acid encoding the CFHR5 polypeptide. The vector may include a promoter that drives expression of the CFHR5 gene in multiple cell types. Alternatively, the vector may include a promoter that drives expression of the CFHR5 gene only in specific cell types, for example, in cells of the retina or cells of the kidney (e.g., endothelial cells, mesangial cells, podocytes). In an aspect, pharmaceutical compositions are provided containing a gene therapy vector encoding a CFHR5 protein and a pharmaceutically acceptable excipient, where the composition is free of pathogens and suitable for administration to a human patient. In one embodiment the encoded CFHR5 polypeptide is a protective variant.

In one aspect, the invention provides a composition containing recombinant or purified CFHR5 polypeptide, where the polypeptide is a protective variant.

In a related aspect, the invention provides a pharmaceutical composition containing recombinant or purified CFHR5 polypeptide and a pharmaceutically acceptable excipient, where the composition is free of pathogens and suitable for administration to a human patient. In one embodiment the encoded CFHR5 polypeptide has the wild-type sequence. In one embodiment the encoded CFHR5 polypeptide is a protective variant.

In one aspect, the invention provides antibodies that specifically interact with a variant CFHR5 polypeptide but not with a wild-type CFHR5 polypeptide. These antibodies may be polyclonal or monoclonal and may be obtained by subtractive techniques. These antibodies may be sufficient to inactivate a variant CFHR5 polypeptide. In a related aspect, the invention provides pharmaceutical compositions containing an anti-CFHR5 antibody and a pharmaceutically acceptable excipient, where the composition is free of pathogens and suitable for administration to a human patient.

In one aspect, the invention provides methods for identifying variant CFHR5 proteins associated with increased or reduced risk of developing AMD or MPGNII. In one embodiment, the invention provides a method of identifying a protective CFHR5 protein by (a) identifying an individual as having a protective haplotype and (b) determining the amino acid sequence(s) of CFHR5 encoded in the genome of the individual, where a protective CFHR5 protein is encoded by an allele having a protective haplotype. In one embodiment, the invention provides a method of identifying a neutral CFHR5 protein by (a) identifying an individual as having a neutral haplotype and (b) determining the amino acid sequence(s) of CFHR5 encoded in the genome of the individual, where a neutral CFHR5 protein is encoded by an allele having a neutral haplotype. In a related embodiment, the invention provides as method of identifying a variant form of CFHR5 associated with decreased risk of developing AMD or MPGNII comprising (a) identifying an individual as having a haplotype or diplotype associated with a decreased risk of developing AMD or MPGNII; (b) obtaining genomic DNA, or RNA, from the individual; and (c) determining the amino acid sequence(s) of the CFHR5 encoded in the individual's genome, where a protective CFHR5 protein is encoded by an allele having a haplotype associated with a decreased risk of developing AMD or MPGNII. In an embodiment, the protective or neutral CFHR5 proteins do not have the amino acid sequence of the wild-type CFHR5 polypeptide.

In a related method, a form of CFHR5 associated with increased risk of developing AMD or MPGNII is identified by (a) identifying an individual as having a risk haplotype and (b) determining the amino acid sequence(s) of CFHR5 encoded in the genome of the individual, where a risk CFHR5 protein is encoded by an allele having a risk haplotype. In a related embodiment, the invention provides as method of identifying a variant form of CFHR5 associated with increased risk of developing AMD or MPGNII comprising (a) identifying an individual as having a haplotype or diplotype associated with an increased risk of developing AMD or MPGNII; (b) obtaining genomic DNA or RNA from the individual; and (c) determining the amino acid sequence(s) of the CFHR5 encoded in the individual's genome, where a risk CFHR5 protein is encoded by an allele having a haplotype associated with an increased risk of developing AMD or MPGNII. In an embodiment, the risk CFHR5 proteins do not have the amino acid sequence of the wild-type CFHR5 polypeptide.

In one aspect, the invention provides cells containing recombinant or purified nucleic acid derived from the CFHR5 gene. The cells may be bacterial or yeast, or any other cell useful for research and drug development. Thus, the invention provides an isolated host cell or cell line expressing a recombinant variant human CFHR5. In an embodiment, the CFHR5 variant is a risk variant and has a serine at amino acid position 46. In an embodiment, the CFHR5 variant is a neutral variant. In an embodiment, the risk, protective or neutral variant CFHR5 proteins does not have the amino acid sequence of the wild-type CFHR5 polypeptide.

In one aspect, the invention provides transgenic non-human animals whose somatic and germ cells contain a transgene encoding a human variant CFHR5 polypeptide. Transgenic animals of the invention are used as models for AMD or MPGNII and for screening for agents useful in treating AMD or MPGNII. The animal may be a mouse, a worm, or any other animal useful for research and drug development (such as recombinant production of CFHR5). In an embodiment, the CFHR5 is a variant human CFHR5, wherein said CFHR5 variant has serine at amino acid 46.

In one aspect, the invention provides methods of screening for polymorphic sites linked to polymorphic sites in the CFHR5 gene described in TABLE 14 or TABLE 15. These methods involve identifying a polymorphic site in a gene that is linked to a polymorphic site in the CFHR5 gene, wherein the polymorphic form of the polymorphic site in the CFHR5 gene is associated with AMD or MPGNII, and determining haplotypes in a population of individuals to indicate whether the linked polymorphic site has a polymorphic form in equilibrium disequilibrium with the polymorphic form of the CFHR5 gene that associates with the AMD or MPGNII phenotype.

In one aspect, the invention provides kits for analysis of a Factor H haplotype. The kits may be used for diagnosis of AMD in a patient. The kits may include one or more Factor H Factor H allele-specific oligonucleotides (e.g., allele-specific primers or probes), or antibodies that specifically recognize the Factor H polypeptide. The Factor H allele-specific oligonucleotides may include sequences derived from the coding (exons) or non-coding (promoter, 5' untranslated, introns or 3' untranslated) region of the Factor H gene. The Factor H-specific antibodies may recognize the normal or wild-type H polypeptide or variant Factor H polypeptides in which one or more non-synonymous single nucleotide polymorphisms (SNPs) are present in the Factor H coding region. The kits may be used to diagnose AMD, as well as other diseases associated with SNPs in the Factor H gene, such as MPGNII. The kits may include instead, or in addition, one or more Factor H-Related 5 (CFHR5) allele-specific oligonucleotides (e.g., primers and probes), or antibodies that specifically recognize the CFHR5 polypeptide. The CFHR5 allele-specific primers and Factor H-related 5 allele-specific oligonucleotides may include sequences derived from the coding (exons) or non-coding (promoter, 5' untranslated, introns or 3' untranslated) region of the Factor H-related 5 gene. The Factor H-related 5-specific antibodies may recognize the normal or wild-type H polypeptide or variant Factor H-related 5 polypeptides in which one or more non-synonymous single nucleotide polymorphisms (SNPs) are present in the Factor H-related 5 coding region.

In one embodiment the kit contains probes or primers that distinguish alleles at a polymorphic site listed in TABLE 1A, TABLE 1B and/or TABLE 1C. In an embodiment the probes are primers for nucleic acid amplification of a region spanning a Factor H gene polymorphic site listed in TABLE 1A, TABLE 1B and/or TABLE 1C. In an embodiment the kit has probes or primers that distinguish alleles at more than one polymorphic site listed in TABLE 1A, TABLE 1B and/or TABLE 1C. In an embodiment the kit has probes or primers that distinguish alleles at more than one polymorphic site, where the polymorphic site includes: (a) rs529825; (b) rs800292; (c) rs3766404; (d) rs1061147; (e) rs1061170; (f) rs203674; (g) at least one of rs529825 and rs800292; (h) at least one of rs1061147, rs1061170 and rs203674; (i) at least one of rs529825 and rs800292; and rs3766404; and at least one of rs1061147, rs1061170 and rs203674; or (j) at least rs529825, rs800292, rs3766404, rs1061170 and rs203674.

In a related embodiment the kit has probes or primers that distinguish alleles at more than one polymorphic site, where the polymorphic site includes: (a) rs529825; (b) rs800292; (c) intron 2 (IVS2 or insTT) (d) rs3766404; (e) rs1061147; (f) rs1061170; (g) exon 10A; (h) rs203674; (i) rs375046; (j) rs529825 and rs800292; (k) at least two or three of rs1061147, rs1061170 and rs203674; (l) at least one of rs529825 and rs800292; and intron 2; and rs3766404; and at least one of rs1061147, rs1061170 and rs203674; and exon 10A; and, rs375046; (m) at least rs529825; rs800292; intron 2; rs3766404; rs1061170; exon 10A; rs203674; and rs375046; (n) at least two, or at least three, or at least four of rs529825, rs800292, intron 2; rs3766404, rs1061170, exon 10A, rs203674, and rs375046; (o) exon 22 (1210); or (p) exon 22 (1210) in combination with any aforementioned variation or set of variations (a-o). In an embodiment the kit has probes or primers that distinguish alleles at one or both of rs460897 and rs460184. In an embodiment the kit has probes or primers that distinguish alleles at more than one polymorphic site, where the polymorphic sites are selected from: (a) rs3753394; (b) rs529825; (c) rs800292; (d) intron 2 (IVS2 or insTT); (e) rs3766404; (f) rs1061147; (g) rs1061170; (h) rs2274700; (i) rs203674; (j) rs3753396; and (k) rs1065489.

In one embodiment the kit contains, instead of, or in addition to, the probes described above, probes, primers, antibodies and the like that distinguish polymorphic sites in the CFHR5 gene. In a one aspect, the invention provides kits for the diagnosis of AMD or MPGNII in a patient based on variation in the CFHR5 gene. The kits may include one or more CFHR5-specific probes or CFHR5 allele-specific oligonucleotides, or antibodies that specifically recognize the CFHR5 polypeptide. The CFHR5-specific primers and CFHR5 allele-specific oligonucleotides may include sequences derived from the coding (exons) or non-coding (promoter, 5' untranslated, introns or 3' untranslated) region of the CFHR5 gene. The CFHR5-specific antibodies may recognize the normal or wild-type CFHR5 polypeptide or variant CFHR5 polypeptides in which one or more non-synonymous single nucleotide polymorphisms (SNPs) are present in the CFHR5 coding region. The kits may be used to diagnose AMD or MPGNII, as well as other diseases associated with SNPs in the CFHR5 gene.

In one embodiment the kit contains probes or primers that distinguish alleles at a polymorphic site listed in TABLE 14 or TABLE 15. In an embodiment the probes are primers for nucleic acid amplification of a region spanning a CFHR5 gene polymorphic site listed in TABLE 14 or TABLE 15. In an embodiment the kit has probes or primers that distinguish alleles at more than one polymorphic site listed in TABLE 14 or TABLE 15. In an embodiment the kit comprises probes or primers that distinguish alleles one, two or all of the following polymorphic sites: rs9427661 (−249T>C); rs9427662 (−20T>C); and rs12097550 (P46S).

In one embodiment the kit contains probes or primers that distinguish alleles at a polymorphic site in the CFH gene and at a polymorphic site in a CFHR gene, such as CFHR5.

In one aspect, the invention provides devices for determining a subject's haplotype. The devices are useful for, for example, the diagnosis of AMD or other diseases in a patient. In one embodiment the device contains probes or primers that distinguish alleles at a polymorphic site listed in TABLE 1A, 1B and/or 1C. In an embodiment the probes are primers for nucleic acid amplification of a region spanning a Factor H gene polymorphic site listed in TABLE 1A, 1B and/or 1C. In an embodiment the device has probes or primers that distinguish alleles at more than one polymorphic site listed in TABLE 1A, 1B and/or 1C. In an embodiment the device has probes or primers that distinguish alleles at more than one polymorphic site, where the polymorphic site includes (a) rs529825; (b) rs800292; (c) rs3766404; (d) rs1061147; (e) rs1061170; (f) rs203674; (g) at least one of rs529825 and rs800292; (h) at least one of rs1061147, rs1061170 and rs203674; (i) at least one of rs529825 and rs800292; and rs3766404; and at least one of rs1061147, rs1061170 and rs203674; or (j) at least rs529825, rs800292, rs3766404, rs1061170 and rs203674.

The kits described above and their contents may also be used to identity a propensity to develop MPGNII or to determine a Factor H haplotype for any purpose.

In a related embodiment the device has probes or primers that distinguish alleles at more than one polymorphic site, where the polymorphic site includes: (a) rs529825; (b) rs800292; (c) intron 2 (IVS2 or insTT) (d) rs3766404; (e) rs1061147; (f) rs1061170; (g) exon 10A; (h) rs203674; (i) rs375046; (j) rs529825 and rs800292; (k) at least two or three of rs1061147, rs1061170 and rs203674; (l) at least one of rs529825 and rs800292; and intron 2; and rs3766404; and at least one of rs1061147, rs1061170 and rs203674; and exon 10A; and rs375046; (m) at least rs529825; rs800292; intron 2; rs3766404; rs1061170; exon 10A; rs203674; and rs375046; (n) at least two, or at least three, or at least four of rs529825; rs800292; intron 2; rs3766404; rs1061170; exon 10A; rs203674; and rs375046; (o) exon 22 (1210); or (p) exon 22 (1210) in combination with any aforementioned variation or set of variations (a-o). In an embodiment the device has probes or primers that distinguish alleles at one or both of rs460897 and rs460184. In an embodiment the device has probes or primers that distinguish alleles at more than one polymorphic site, where the polymorphic sites are selected from: (a) rs3753394; (b) rs529825; (c) rs800292; (d) intron 2 (IVS2 or insTT); (e) rs3766404; (f) rs1061147; (g) rs1061170; (h) rs2274700; (i) rs203674; (j) rs3753396; and (k) rs1065489. In an embodiment the device has probes or primers that distinguish alleles at more than one polymorphic site, where the polymorphic sites are selected from: (a) rs3753394; (b) rs529825; (c) rs800292; (d) intron 2 (IVS2 or insTT); (e) rs3766404; (f) rs1061147; (g) rs1061170; (h) rs2274700; (i) rs203674; (j) rs3753396; and (k) rs1065489.

In a one aspect, the invention provides devices for the diagnosis of AMD or MPGNII in a patient. In one embodiment the device contains probes or primers that distinguish alleles at a polymorphic site listed in TABLE 14 or TABLE 15. In an embodiment the probes are primers for nucleic acid amplification of a region spanning a CFHR5 gene polymorphic site listed in TABLE 14 or TABLE 15. In an embodiment the device has probes or primers that distinguish alleles at more than one polymorphic site listed in TABLE 14 or TABLE 15. Devices of the invention may contain probes or primers that distinguish between both Factor H and CHFR5 variants, including any combination of the sites described above and elsewhere in this disclosure.

The devices described above and their contents may also be used to identity a propensity to develop MPGNII or to determine a Factor H haplotype for any purpose.

In one embodiment the device contains, instead of, or in addition to, the probes or primers described above, probes, primers, antibodies and the like that distinguish polymorphic sites in the CFHR5 gene. In a one aspect, the invention provides devices for the diagnosis of AMD or MPGNII in a patient based on variation in the CFHR5 gene. The devices may include one or more CFHR5-specific probes or CFHR5 allele-specific oligonucleotides, or antibodies that specifically recognize the CFHR5 polypeptide. The CFHR5-specific primers and CFHR5 allele-specific oligonucleotides may include sequences derived from the coding (exons) or non-coding (promoter, 5' untranslated, introns or 3' untranslated) region of the CFHR5 gene. The CFHR5-specific antibodies may recognize the normal or wild-type CFHR5 polypeptide or variant CFHR5 polypeptides in which one or more non-synonymous single nucleotide polymorphisms (SNPs) are present in the CFHR5 coding region. The devices may be used to diagnose AMD or MPGNII, as well as other diseases associated with SNPs in the CFHR5 gene.

In one embodiment the device contains probes or primers that distinguish alleles at a polymorphic site listed in TABLE 14 or TABLE 15. In an embodiment the probes are primers for nucleic acid amplification of a region spanning a CFHR5 gene polymorphic site listed in TABLE 14 or TABLE 15. In an embodiment the device has probes or primers that distinguish alleles at more than one polymorphic site listed in TABLE 14 or TABLE 15. In an embodiment the kit comprises probes or primers that distinguish alleles one, two or all of the following polymorphic sites: rs9427661 (−249T>C); rs9427662 (−20T>C); and rs12097550 (P46S).

In one embodiment the device contains probes or primers that distinguish alleles at a polymorphic site in the CFH gene and at a polymorphic site in a CFHR gene, such as CFHR5.

Additional aspects of the invention will be apparent upon reading the entire disclosure.

BRIEF DESCRIPTION OF THE FIGURES

FIG. 6 shows the 3926 base nucleotide sequence of the reference form of human Factor H cDNA (GenBank accession number Y00716 [SEQ ID NO:1]). The ATG initiation codon begins at nucleotide position 74 and the TAG termination codon ends at nucleotide position 3769.

FIG. 7 shows the polypeptide sequence encoded by SEQ ID NO:1 (GenBank accession number Y00716 [SEQ ID NO:2]). The 1231 amino acid Factor H polypeptide includes an 18 amino acid N-terminal signal peptide.

FIG. 8 shows the 1658 base nucleotide sequence of the reference form of HFL1, the truncated form of the human Factor H (GenBank accession number X07523 [SEQ ID NO:3]). The ATG initiation codon begins at nucleotide position 74 and the TGA termination codon ends at nucleotide position 1423.

FIG. 9 shows the polypeptide sequence of the reference form of HFL1 encoded by SEQ ID NO:3 (GenBank accession number X07523 [SEQ ID NO:4]). The 449 amino acid HFL1 polypeptide includes an 18 amino acid N-terminal signal peptide.

FIG. 10 shows the polypeptide sequence of an exemplary protective variant of human Factor H [SEQ ID NO:5]. This protective variant Factor H polypeptide has a isoleucine at amino acid position 62 and a tyrosine at amino acid position 402 (indicated in bold).

FIG. 11 shows the polypeptide sequence of an exemplary protective variant of HFL1, the truncated form of human Factor H (SEQ ID NO:6). This protective variant truncated Factor H polypeptide has a isoleucine at amino acid position 62 and tyrosine at amino acid position 402 (indicated in bold).

FIG. 12 shows marked glomerular hypercellularity with dense intramembranous deposits that cause capillary wall thickening in a patient with MPGNII, as viewed by (A) light microscopy and (B) electron microscopy. The deposits can form a segmental, discontinuous or diffuse pattern in the lamina densa of the glomerular basement membrane (GBM). By light microscopy, they are eosinophilic and refractile, stain brightly with periodic acid-Schiff and are highly osmophilic, which explains their electron-dense appearance (A). Even by electron microscopy the deposits lack substructure and appear as very dark homogeneous smudges (B). The exact composition of dense deposits remains unknown (bar, 5 μm).

FIG. 16 shows the 2821 base nucleotide sequence of the reference form of human CFHR5 (GenBank accession number AF295327 [SEQ ID NO:7]. The ATG initiation codon begins at nucleotide position 94 and the TGA termination codon ends at nucleotide position 1803.

FIG. 17 shows the polypeptide sequence encoded by SEQ ID NO:7 (GenBank accession number AAK15619 [SEQ ID NO:8]. The 569 amino acid CFHR5 polypeptide includes an 18 amino acid N-terminal signal peptide.

DETAILED DESCRIPTION OF THE INVENTION

I. Introduction

Figures 1A, 1B, 1C, 1D, 1E, 1F, 1G, 1H, 1I, 1J, 1K, 1L:
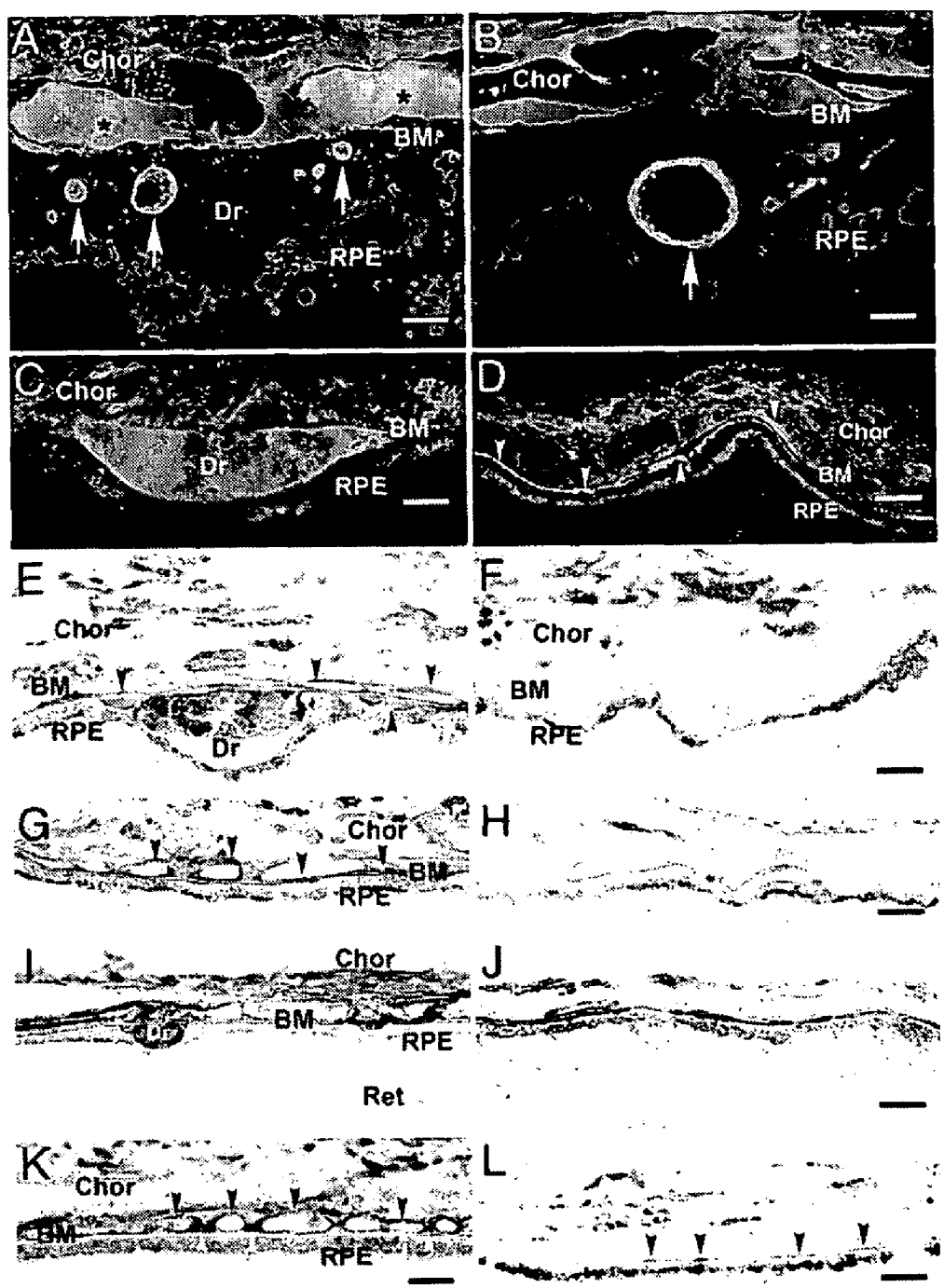
FIGS. 1A-1L show the immunolocalization of Factor H (FIGS. 1A-1H) and the terminal complement complex (C5b-9) (FIGS. 1I-1L) in the human retinal pigmented epithelium. Abbreviations: (RPE)-choroid (Chor) complex; Bruch's membrane (BM); Retina (Ret); Drusen (Dr).

The invention provides a collection of polymorphisms and haplotypes comprised of multiple variations in the Factor H gene, and in Factor H-related genes such as Factor H-Related 5 gene. These polymorphisms and haplotypes are associated with age related macular degeneration (AMD) and other Factor H-related conditions. Certain of these polymorphisms and haplotypes result in variant Factor H polypeptides. Detection of these and other polymorphisms and sets of polymorphisms (e.g., haplotypes) is useful in designing and performing diagnostic assays for AMD. Polymorphisms and sets of polymorphisms can be detected by analysis of nucleic acids, by analysis of polypeptides encoded by Factor H coding sequences (including polypeptides encoded by splice variants), or by other means known in the art. Analysis of such polymorphisms and haplotypes is also useful in designing prophylactic and therapeutic regimes for AMD.

Factor H is a multifunctional protein that functions as a key regulator of the complement system. See Zipfel, 2001, "Factor H and disease: a complement regulator affects vital body functions" Semin Thromb Hemost. 27:191-9. The Factor H protein activities include: (1) binding to C-reactive protein (CRP), (2) binding to C3b, (3) binding to heparin, (4) binding to sialic acid; (5) binding to endothelial cell surfaces, (6) binding to cellular integrin receptors (7) binding to pathogens, including microbes (see FIG. 3), and (8) C3b co-factor activity. The Factor H gene, known as HF1, CFH and HF, is located on human chromosome 1, at position 1q32. The 1q32 particular locus contains a number of complement pathway-associated genes. One group of these genes, referred to as the regulators of complement activation (RCA) gene cluster, contains the genes that encode Factor H, five Factor H-related genes (FHR-1, FHR-2, FHR-3, FHR-4 and FHR-5 or CFHR1, CFHR2, CFHR3, CFHR4 and CFHR5, respectively), and the gene encoding the beta subunit of coagulation factor XIII. The Factor H and Factor H related genes is composed almost entirely of short consensus repeats (SCRs). Factor H and FHL1 are composed of SCRs 1-20 and 1-7, respectively. FHR-1, FHR-2, FHR-3, FHR-4 and FHR-5 are composed of 5, 4, 5, 5 and 8 SCRs, respectively (see FIG. 14). The order of genes, from centromere to telomere is FH/FHL1, FHR-3, FHR-1, FHR-4, FHR-2 and FHR-5.

Factor H Gene

The reference form of human Factor H cDNA (SEQ ID NO:1) (see Ripoche et al., 1988, *Biochem J* 249:593-602) and genomic sequences have been determined. The Factor H cDNA encodes a polypeptide 1231 amino acids in length (SEQ ID NO:2) having an apparent molecular weight of 155 kDa. There is an alternatively spliced form of Factor H is known as FHL-1 (and also has been referred to as HFL1 or CFHT). FHL-1 (SEQ ID NO:3) corresponds essentially to exons 1 through 9 of Factor H (see Ripoche et al., 1988, *Biochem J* 249:593-602). The FHL1 cDNA encodes a polypeptide 449 amino acids in length (SEQ ID NO:4) having an apparent molecular weight of 45-50 kDA. The first 445 amino acids of FH1 and FHL1 are identical, with FHL1 having a unique C-terminal 4 amino acids (exon 10A). The alternative exon 10A is located in the intron between exon 9 and exon 10. cDNA and amino acid sequence data for human Factor H and FHL1 are found in the EMBL/GenBank Data Libraries under accession numbers Y00716 and X07523, respectively. The 3926 base nucleotide sequence of the reference form of human Factor H cDNA (GenBank accession number Y00716 [SEQ ID NO:1]) is shown in FIG. 6, and the polypeptide sequence encoded by SEQ ID NO:1 (GenBank accession number Y00716 [SEQ ID NO:2]) is shown in FIG. 7. The 1658 base nucleotide sequence of the reference form of HFL1, the truncated form of the human Factor H (GenBank accession number X07523 [SEQ ID NO:3]) is shown in FIG. 8, and the polypeptide sequence encoded by SEQ ID NO:3 (GenBank accession number X07523 [SEQ ID NO:4]) is shown in FIG. 9. The Factor H gene sequence (150626 bases in length) is found under GenBank accession number AL049744. The Factor H promoter is located 5' to the coding region of the Factor H gene.

FHR-1 Gene

The FHR-1 gene is also known as CHFR1, CFHL1, CFHL, FHR1 and HFL1. The reference form of human HFR-1 cDNA (see Estaller et al., 1991, *J. Immunol.* 146:3190-3196) and genomic sequences have been determined. The FHR-1 cDNA encodes a polypeptide 330 amino acids in length having an predicted molecular weight of 39 kDa. cDNA and amino acid sequence data for human FHR-1 are found in the EMBL/GenBank Data Libraries under accession number M65292. The FHR-1 gene sequence is found under GenBank accession number AL049741.

FHR-2 Gene

The FHR-2 gene is also known as CHFR2, CFHL2, FHR2 and HFL3. The reference form of human HFR-2 cDNA (see Strausberg et al., *Proc. Natl. Acad. Sci USA* 99:16899-16903) and genomic sequences have been determined. The FHR-2 cDNA encodes a polypeptide 270 amino acids in length having a predicted molecular weight of 31 kDa. cDNA and amino acid sequence data for human FHR-2 are found in the EMBL/GenBank Data Libraries under accession number BC022283. The FHR-2 gene sequence is found under GenBank accession number AL139418.

FHR-3 Gene

The FHR-3 gene is also known as CFHR3, CFHL3, FHR3 and HLF4. The reference form of human HFR-3 cDNA (see Strausberg et al., *Proc. Natl. Acad. Sci USA* 99:16899-16903) and genomic sequences have been determined. The FHR-3 cDNA encodes a polypeptide 330 amino acids in length having a predicted molecular weight of 38 kDa. cDNA and amino acid sequence data for human FHR-3 are found in the EMBL/GenBank Data Libraries under accession number BC058009. The FHR-3 gene sequence is found under GenBank accession number AL049741.

FHR-4 Gene

The FHR-4 gene is also known as CFHR4, CFHL4 and FHR4. The reference form of human HFR-4 cDNA (see Skerka et al., 1991, *J. Biol. Chem.* 272:5627-5634) and genomic sequences have been determined. The FHR-4 cDNA encodes a polypeptide 331 amino acids in length having a predicted molecular weight of 38 kDa. cDNA and amino acid sequence data for human FHR-4 are found in the EMBL/GenBank Data Libraries under accession number X98337. The FHR-4 gene sequence is found under GenBank accession numbers AF190816 (5' end), AL139418 (3' end) and BX248415.

FHR-5 Gene

The FHR-5 gene is also known as CFHR5, CFHL5 and FHR5. The reference form of human CFHR5 cDNA (SEQ ID NO:7) (see McRae et al., 2001, *J. Biol. Chem.* 276:6747-6754) and genomic sequences have been determined. The CFHR5 cDNA encodes a polypeptide 569 amino acids in length (SEQ ID NO:8) having an apparent molecular weight of 65 kDa. cDNA and amino acid sequence data for human CFHR5 are found in the EMBL/GenBank Data Libraries under accession number AF295327. The 2821 base nucleotide sequence of the reference form of human CFHR5 (GenBank accession number AF295327 [SEQ ID NO:7] is shown in FIG. 16, and the polypeptide sequence encoded by SEQ ID NO:7 (GenBank accession number AAK15619 [SEQ ID NO:8] is shown in FIG. 17. The CFHR5 gene sequence is found under GenBank accession numbers AL139418 (5' end) and AL353809 (3' end). The FHR-5 promoter is located 5' to the coding region of the CFHR5 gene.

II. Definitions

The following definitions are provided to aid in understanding the invention. Unless otherwise defined, all terms of art, notations and other scientific or medical terms or terminology used herein are intended to have the meanings commonly understood by those of skill in the arts of medicine and molecular biology. In some cases, terms with commonly understood meanings are defined herein for clarity and/or for ready reference, and the inclusion of such definitions herein should not be assumed to represent a substantial difference over what is generally understood in the art.

A "nucleic acid", "polynucleotide" or "oligonucleotide" is a polymeric form of nucleotides of any length, may be DNA or RNA, and may be single- or double-stranded. Nucleic acids may include promoters or other regulatory sequences. Oligonucleotides are usually prepared by synthetic means. Nucleic acids include segments of DNA, or their complements spanning or flanking any one of the polymorphic sites shown in TABLE 1A, TABLE 1B and/or TABLE 1C or otherwise known in the Factor H gene. The segments are usually between 5 and 100 contiguous bases, and often range from a lower limit of 5, 10, 12, 15, 20, or 25 nucleotides to an upper limit of 10, 15, 20, 25, 30, 50 or 100 nucleotides (where the upper limit is greater than the lower limit). Nucleic acids between 5-10, 5-20, 10-20, 12-30, 15-30, 10-50, 20-50 or 20-100 bases are common. The polymorphic site can occur within any position of the segment. A reference to the sequence of one strand of a double-stranded nucleic acid defines the complementary sequence and except where otherwise clear from context, a reference to one strand of a nucleic acid also refers to its complement. For certain applications, nucleic acid (e.g., RNA) molecules may be modified to increase intracellular stability and half-life. Possible modifications include, but are not limited to, the use of phosphorothioate or 2'-O-methyl rather than phosphodiesterase linkages within the backbone of the molecule. Modified nucleic acids include peptide nucleic acids (PNAs) and nucleic acids with nontraditional bases such as inosine, queosine and wybutosine and acetyl-, methyl-, thio- and similarly modified forms of adenine, cytidine, guanine, thymine, and uridine which are not as easily recognized by endogenous endonucleases.

"Hybridization probes" are nucleic acids capable of binding in a base-specific manner to a complementary strand of nucleic acid. Such probes include nucleic acids and peptide nucleic acids (Nielsen et al., 1991). Hybridization may be performed under stringent conditions which are known in the art. For example, see, e.g., Berger and Kimmel (1987) Methods In Enzymology, Vol. 152: Guide To Molecular Cloning Techniques, San Diego: Academic Press, Inc.; Sambrook et al. (1989) Molecular Cloning: A Laboratory Manual, 2nd Ed., Vols. 1-3, Cold Spring Harbor Laboratory; Sambook (2001) 3rd Edition; Rychlik, W. and Rhoads, R. E., 1989, Nucl. Acids Res. 17, 8543; Mueller, P. R. et al. (1993) In: Current Protocols in Molecular Biology 15.5, Greene Publishing Associates, Inc. and John Wiley and Sons, New York; and Anderson and Young, Quantitative Filter Hybridization in Nucleic Acid Hybridization (1985)). As used herein, the term "probe" includes primers. Probes and primers are sometimes referred to as "oligonucleotides."

The term "primer" refers to a single-stranded oligonucleotide capable of acting as a point of initiation of template-directed DNA synthesis under appropriate conditions, in an appropriate buffer and at a suitable temperature. The appropriate length of a primer depends on the intended use of the primer but typically ranges from 15 to 30 nucleotides. A primer sequence need not be exactly complementary to a template but must be sufficiently complementary to hybridize with a template. The term "primer site" refers to the area of the target DNA to which a primer hybridizes. The term "primer pair" means a set of primers including a 5' upstream primer, which hybridizes to the 5' end of the DNA sequence to be amplified and a 3' downstream primer, which hybridizes to the complement of the 3' end of the sequence to be amplified.

Exemplary hybridization conditions for short probes and primers is about 5 to 12 degrees C. below the calculated Tm. Formulas for calculating Tm are known and include: Tm=4° C.×(number of G's and C's in the primer)+2° C.×(number of A's and T's in the primer) for oligos<14 bases and assumes a reaction is carried out in the presence of 50 mM monovalent cations. For longer oligos, the following formula can be used: Tm=64.9° C.+41° C.×(number of G's and C's in the primer–16.4)/N, where N is the length of the primer. Another commonly used formula takes into account the salt concentration of the reaction (Rychlik, supra, Sambrook, supra, Mueller, supra.): Tm=81.5° C.+16.6° C.×(log10[Na+]+[K+])+0.41° C.×(% GC)−675/N, where N is the number of nucleotides in the oligo. The aforementioned formulae provide a starting point for certain applications; however, the design of particular probes and primers may take into account additional or different factors. Methods for design of probes and primers for use in the methods of the invention are well known in the art.

The terms "risk," "protective," and "neutral" are used to describe variations, SNPS, haplotypes, diplotypes, and proteins in a population encoded by genes characterized by such patterns of variations. A risk haplotype is an allelic form of a gene, herein Factor H or a Factor H-related gene, comprising at least one variant polymorphism, and preferably a set of variant polymorphisms, associated with increased risk for developing AMD. The term "variant" when used in reference to a Factor H or Factor H-related gene, refers to a nucleotide sequence in which the sequence differs from the sequence most prevalent in a population, herein humans of European-American descent. The variant polymorphisms can be in the coding or non-coding portions of the gene. An example of a risk Factor H haplotype is the allele of the Factor H gene encoding histidine at amino acid 402 and/or cysteine at amino acid 1210. The risk haplotype can be naturally occurring or can be synthesized by recombinant techniques. A protective haplotype is an allelic form of a gene, herein Factor H or a Factor H-related gene, comprising at least one variant polymorphism, and preferably a set of variant polymorphisms, associated with decreased risk of developing AMD. For example, one protective Factor H haplotype has an allele of the Factor H gene encoding isoleucine at amino acid 62. The protective haplotype can be naturally occurring or synthesized by recombinant techniques. A neutral haplotype is an allelic form of a gene, herein Factor H or a Factor H-related gene, that does not contain a variant polymorphism associated in a population or ethnic group with either increased or decreased risk of developing AMD. It will be clear from the following discussion that a protein encoded in a "neutral" haplotype may be protective when administered to a patient in need of treatment or prophylaxis for AMD or other conditions. That is, both "neutral" and "protective" forms of CFH or CFHR5 can provide therapeutic benefit when administered to, for example, a subject with AMD or risk for developing AMD, and thus can "protect" the subject from disease.

Figure 5:
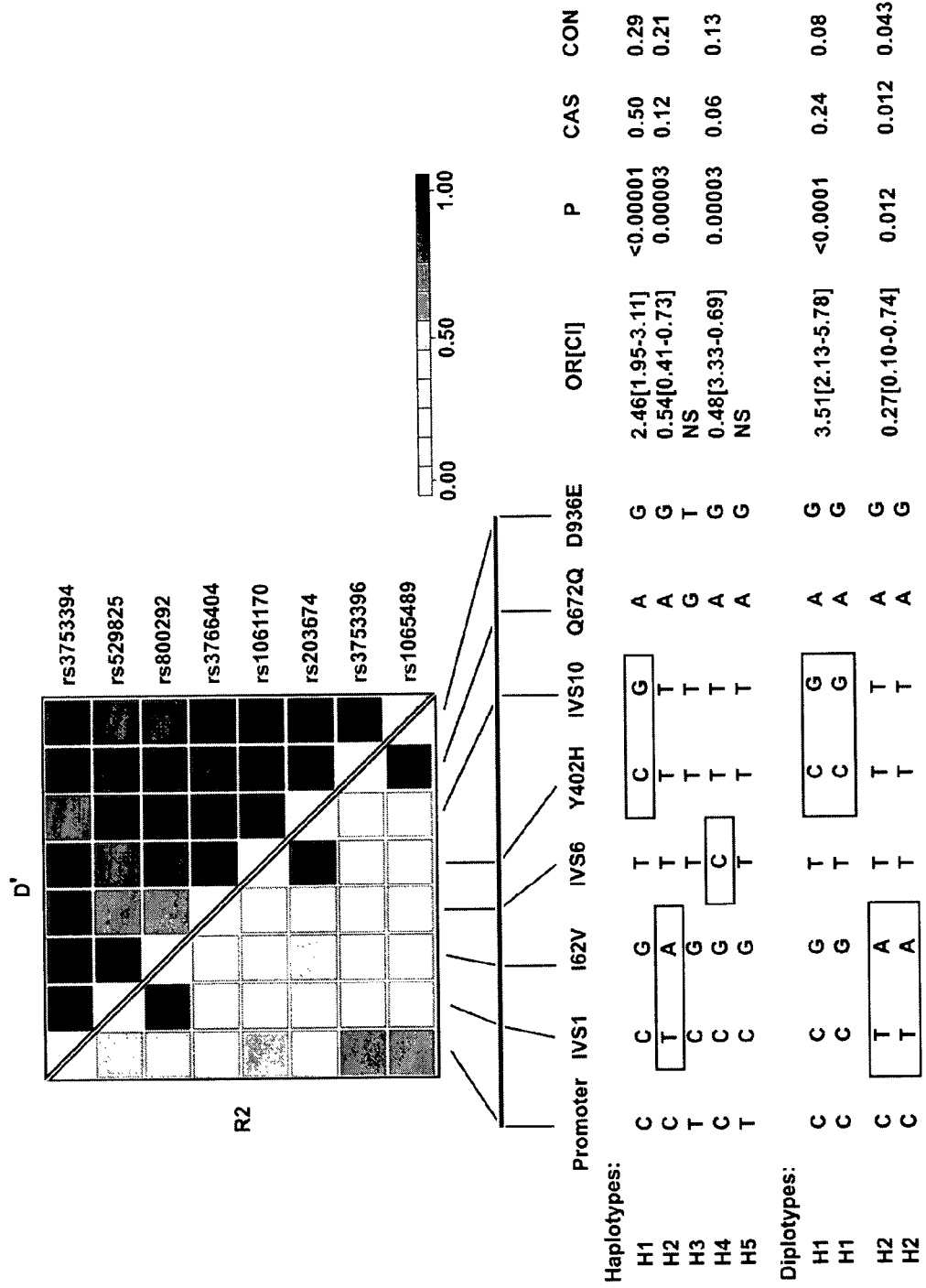
FIG. 5 shows an association analysis of human Factor H gene haplotypes and diplotypes. Eight informative SNPs were analyzed for pairwise linkage disequilibrium in AMD cases and controls. The nucleotide on the coding strand at the indicated polymorphic sites is shown, except for IVS1, where the nucleotide on the non-coding strand is shown.

The term "wild-type" refers to a nucleic acid or polypeptide in which the sequence is a form prevalent in a population, herein humans of European-American descent (approximately 40% prevalence; see FIG. 5). For purposes of this disclosure, a "wild-type" Factor H protein has the sequence of SEQ ID NO:2 (FIG. 7), except that the amino acid at position 402 is tyrosine (Y; [SEQ ID NO:337]). For purposes of this disclosure, a Factor H gene encoding a wild-type Factor H protein has the sequence of SEQ ID NO:1 (FIG. 6), except that the codon beginning at base 1277, corresponding to the amino acid at position 402 encodes tyrosine (TAT [SEQ ID NO:336]).

The term "variant" when used in reference to a Factor H or Factor H-related polypeptide, refers to a polypeptide in which the sequence differs from the normal or wild-type sequence at a position that changes the amino acid sequence of the encoded polypeptide. For example, some variations or substitutions in the nucleotide sequence of Factor H gene alter a codon so that a different amino acid is encoded (for example and not for limitation, having an alternative allele at one or more of I62V, Y402H, D936E) resulting in a variant polypeptide. Variant polypeptides can be associated with risk (e.g., having histidine at position 402), associated with protection (e.g., having isoleucine at position 62), or can be encoded by a neutral haplotype (e.g., having aspartic acid at position 936). Variant CFHR5 polypeptides can be associated with risk (e.g., having serine at position 46), associated with protection, or can be neutral.

The term "reference" when referring to a Factor H polypeptide means a polypeptide in which the amino acid sequence is identical to the sequence described by Ripoche et al., 1988, *Biochem J.* 249:593-602) for full-length (FH1, SEQ ID NO:2) or truncated (FHL1, SEQ ID NO:4) human Factor H. The term "reference" when referring to a CFHR5 polypeptide means a polypeptide in which the amino acid sequence is identical to the sequence described by McRae et al., 2001, *J. Biol. Chem.* 276:6747-6754) for full-length human CFHR5 (SEQ ID NO:8). The first identified allelic form is arbitrarily designated the reference form or allele; other allelic forms are designated as alternative or variant alleles. Wild-type and variant forms may have substantial sequence identity with the reference form (e.g., the wild-type or variant form may be identical to the reference form at at least 90% of the amino acid positions of the wild-type or variant, sometimes at least 95% of the positions and sometimes at least 98% or 99% of the positions). A variant may differ from a reference form in certain regions of the protein due to a frameshift mutation or splice variation.

The term "polymorphism" refers to the occurrence of two or more genetically determined alternative sequences or alleles in a population. A "polymorphic site" is the locus at which sequence divergence occurs. Polymorphic sites have at least two alleles. A diallelic polymorphism has two alleles. A triallelic polymorphism has three alleles. Diploid organisms may be homozygous or heterozygous for allelic forms. A polymorphic site may be as small as one base pair. Examples of polymorphic sites include: restriction fragment length polymorphisms (RFLPs); variable number of tandem repeats (VNTRs); hypervariable regions; minisatellites; dinucleotide repeats; trinucleotide repeats; tetranucleotide repeats; and simple sequence repeats. As used herein, reference to a "polymorphism" can encompass a set of polymorphisms (i.e., a haplotype).

A "single nucleotide polymorphism (SNP)" occurs at a polymorphic site occupied by a single nucleotide, which is the site of variation between allelic sequences. The site is usually preceded by and followed by highly conserved sequences of the allele. A SNP usually arises due to substitution of one nucleotide for another at the polymorphic site. Replacement of one purine by another purine or one pyrimidine by another pyrimidine is called a transition. Replacement of a purine by a pyrimidine or vice versa is called a transversion. A synonymous SNP refers to a substitution of one nucleotide for another in the coding region that does not change the amino acid sequence of the encoded polypeptide. A non-synonymous SNP refers to a substitution of one nucleotide for another in the coding region that changes the amino acid sequence of the encoded polypeptide. A SNP may also arise from a deletion or an insertion of a nucleotide or nucleotides relative to a reference allele.

A "set" of polymorphisms means more than one polymorphism, e.g., at least 2, at least 3, at least 4, at least 5, at least 6, or more than 6 of the polymorphisms shown in TABLE 1A, TABLE 1B and/or TABLE 1C or otherwise known in the Factor H gene or other gene.

The term "haplotype" refers to the designation of a set of polymorphisms or alleles of polymorphic sites within a gene of an individual. For example, a "112" Factor H haplotype refers to the Factor H gene comprising allele 1 at each of the first two polymorphic sites and allele 2 at the third polymorphic site. A "diplotype" is a haplotype pair.

An "isolated" nucleic acid means a nucleic acid species that is the predominant species present in a composition. Isolated means the nucleic acid is separated from at least one compound with which it is associated in nature. A purified nucleic acid comprises (on a molar basis) at least about 50, 80 or 90 percent of all macromolecular species present.

Two amino acid sequences are considered to have "substantial identity" when they are at least about 80% identical, preferably at least about 90% identical, more preferably at least about 95%, at least about 98% identical or at least about 99% identical. Percentage sequence identity is typically calculated by determining the optimal alignment between two sequences and comparing the two sequences. Optimal alignment of sequences may be conducted by inspection, or using the local homology algorithm of Smith and Waterman, 1981, *Adv. Appl. Math.* 2: 482, using the homology alignment algorithm of Needleman and Wunsch, 1970, *J. Mol. Biol.* 48: 443, using the search for similarity method of Pearson and Lipman, 1988, *Proc. Natl. Acad. Sci. U.S.A.* 85: 2444, by computerized implementations of these algorithms (e.g., in the Wisconsin Genetics Software Package, Genetics Computer Group, 575 Science Dr., Madison, Wis.) using default parameters for amino acid comparisons (e.g., for gap-scoring, etc.). It is sometimes desirable to describe sequence identity between two sequences in reference to a particular length or region (e.g., two sequences may be described as having at least 95% identity over a length of at least 500 basepairs). Usually the length will be at least about 50, 100, 200, 300, 400, 500, 600, 700, 800, 900 or 1000 amino acids, or the full length of the reference protein. Two amino acid sequences can also be considered to have substantial identity if they differ by 1, 2, or 3 residues, or by from 2-20 residues, 2-10 residues, 3-20 residues, or 3-10 residues.

"Linkage" describes the tendency of genes, alleles, loci or genetic markers to be inherited together as a result of their location on the same chromosome. Linkage can be measured by percent recombination between the two genes, alleles, loci or genetic markers. Typically, loci occurring within a 50 centimorgan (cM) distance of each other are linked. Linked markers may occur within the same gene or gene cluster. "Linkage disequilibrium" or "allelic association" means the preferential association of a particular allele or genetic marker with a specific allele or genetic marker at a nearby chromosomal location more frequently than expected by chance for any particular allele frequency in the population. A marker in linkage disequilibrium can be particularly useful in detecting susceptibility to disease, even if the marker itself does not cause the disease.

The terms "diagnose" and "diagnosis" refer to the ability to determine whether an individual has the propensity to develop disease (including with or without signs or symptoms). Diagnosis of propensity to develop disease can also be called "screening" and, as used herein, the terms diagnosis and screening are used interchangeably. It will be appreciated that having an increased or decreased propensity to developing a condition refers to the likelihood of developing the condition relative to individuals in the population without the condition.

III. Tables

Certain tables referred to herein are provided following the Examples, infra. The following descriptions are provided to assist the reader:

TABLES 1A-1C show human Factor H gene polymorphisms and their association with age-related macular degeneration. (1A) The dbSNP no., location, sequences of the coding (top, 5' to 3' direction) and non-coding (bottom) strands spanning the polymorphisms, amino acid changes, allele frequencies for the control and AMD cases, and $\chi^2$ and P-values for 1 SNPs in the human Factor H gene are shown. (1B) The dbSNP no., interrogated sequences, corresponding nucleotide in the chimp Factor H gene, location, amino acid changes, and sets of primers and probes for 11 SNPs in the human Factor H gene are shown. (1C) The location, sequences spanning the polymorphisms, amino acid position and amino acid change, if any, for 14 SNPs in the human Factor H gene that are not found in the dbSNP database are shown.

TABLE 2 shows a haplotype analysis of eight SNPs in the human Factor H gene in a cohort of AMD cases and controls.

TABLE 3 shows a haplotype analysis of six SNPs in the human Factor H gene and their association with AMD.

TABLE 4 shows the association of 11 human Factor H gene SNPs with age-related macular degeneration.

TABLE 5 shows the primers used for SSCP, DHPLC and DNA sequencing analysis for human Factor H.

TABLE 6 shows genotyping data of AMD patients and controls.

TABLE 7 shows the frequency of an at-risk haplotype in various ethnic groups.

TABLE 8 shows several Factor H diplotypes. Common risk and protective diplotypes are indicated.

TABLE 9 shows the sequences of primers used to amplify the Factor H coding sequence.

TABLE 10 shows the sequences of primers used to amplify the CFHR5 coding sequence.

TABLE 11 shows an analysis of Factor H SNPs in 22 MPGNII patients.

TABLE 12 shows a comparison of Factor H SNP frequencies in 22 MPGNII patients and AMD-negative, ethnically matched controls.

TABLE 13 lists Factor H SNPs associated with MPGNII and their related SCR.

TABLE 14 shows an analysis of CFHR5 SNPs in 22 MPGNII patients.

TABLE 15 shows a comparison of CFHR5 SNP frequencies in 22 MPGNII patients and AMD-negative, ethnically matched controls.

TABLE 16 shows exemplary allele-specific probes (16A) and primers (16B) useful for detecting polymorphisms in the Factor H gene.

IV. Complement Factor H Polymorphisms

In one aspect, the invention provides new diagnostic, treatment and drug screening methods related to the discovery that polymorphic sites in the Complement Factor H (HF1) gene are associated with susceptibility to and development of AMD.

Factor H polymorphisms associated with AMD were identified as described in Example 1, by examining the coding and adjacent intronic regions of Factor H (including exon 10A, which is transcribed for the Factor H isoform FHL1) for variants using SSCP analysis, DHPLC analysis, and direct sequencing, according to standard protocols. Remaining polymorphisms were typed by the 5' nuclease (Taqman, ABI) methodology. Taqman genotyping and association analysis were performed as described (Gold et al., 2004). Primers for SSCP and DNA sequencing analyses were designed to amplify each exon and its adjacent intronic regions using MacVector software. PCR-derived amplicons were screened for sequence variation by SSCP and DHPLC according to standard protocols. All changes detected by SSCP and DHPLC were confirmed by bidirectional sequencing according to standard protocols. Statistical analyses were performed using chi-square ($\chi^2$) and Fisher's exact tests (P values).

Two independent groups of AMD cases and age-matched controls were used. All participating individuals were of European-American descent, over the age of 60 and enrolled under IRB-approved protocols following informed consent. These groups were comprised of 352 unrelated patients with clinically documented AMD (mean age 79.5±7.8 years) and 113 unrelated, control patients (mean age 78.4±7.4 years; matched by age and ethnicity) from the University of Iowa, and 550 unrelated patients with clinically documented AMD (mean age 71.32±8.9 years) and 275 unrelated, matched by age and ethnicity, controls (mean age 68.84±8.6 years) from Columbia University. Patients were examined by indirect ophthalmoscopy and slit-lamp microscopy by retina fellowship-trained ophthalmologists.

Fundas photographs were graded according to a standardized, international classification system (Bird et al., 1995). Control patients were selected and included if they did not exhibit any distinguishing signs of macular disease or have a known family history of AMD. The AMD patients were subdivided into phenotypic categories: early AMD (ARM), geographic atrophy (GA), and exudative (CNV) AMD, based upon the classification of their most severe eye at the time of their entry into the study. The University of Iowa ARM and GA cases were further subdivided into distinct phenotypes (RPE changes alone, >10 macular hard drusen, macular soft drusen, BB (cuticular) drusen, PED, "Cherokee" atrophy, peninsular geographic atrophy and pattern geographic atrophy). The earliest documentable phenotype for all cases was also recorded and employed in the analyses.

As shown in TABLE 1A, a highly significant association of polymorphic sites in the Factor H gene with AMD was found in an examination of two independent cohorts that together included approximately 900 AMD cases and 400 matched controls. Sixteen (16) polymorphisms in the Factor H gene are listed in TABLES 1A-1B. Of these twelve (12) are found in the SNP database (dbSNP) which may be found in the National Center for Biotechnology Information (NCBI). The dbSNP is a collection of SNPs in the human Factor H gene which are dispersed among the 22 coding exons of the Factor H gene and among the promoter, the 5' untranslated region, the introns, and the 3' untranslated region of the Factor H gene. Listed below are the accession numbers for 379 SNPs in the human Factor H gene that are found in the dbSNP database. These SNPs can be used in carrying out methods of the invention.

TABLE A

| | | | | | | |
|---|---|---|---|---|---|---|
| rs17575212 | rs11582939 | rs7551203 | rs5014736 | rs2019724 | rs534479 | rs395963 |
| rs17573867 | rs11580821 | rs7546015 | rs5014735 | rs1984894 | rs534399 | rs395544 |
| rs16840522 | rs11579439 | rs7540032 | rs5014734 | rs1928433 | rs529825 | rs395129 |
| rs16840465 | rs11539862 | rs7539005 | rs5014733 | rs1928432 | rs528298 | rs393955 |
| rs16840462 | rs11398897 | rs7537967 | rs5003626 | rs1887973 | rs521605 | rs386258 |
| rs16840422 | rs11390840 | rs7535653 | rs5003625 | rs1831282 | rs520992 | rs385892 |
| rs16840419 | rs11340441 | rs7535263 | rs5003624 | rs1831281 | rs519839 | rs385543 |
| rs16840410 | rs11339120 | rs7529589 | rs5002880 | rs1831280r | rs518957 | rs383191 |
| rs16840401 | rs11318544 | rs7526622 | rs5002876 | rs1410997 | rs551397 | rs405306 |
| rs16840397 | rs11285593 | rs7524776 | rs5002875 | rs1410996 | rs544889 | rs403846 |
| rs16840394 | rs10922109 | rs7522681 | rs5002874 | rs1329429 | rs543879 | rs402991 |
| rs16840381 | rs10922108 | rs7519439 | rs4658046 | rs1329428 | rs536564 | rs402056 |
| rs16840379 | rs10922107 | rs7514261 | rs4657826 | rs1329427 | rs536539 | rs399469 |
| rs12756364 | rs10922106 | rs7513153 | rs4350148 | rs1329424 | rs515299 | rs398248 |
| rs12746361 | rs10922105 | rs7415913 | rs4044888 | rs1329423 | rs514756 | rs381974 |
| rs12740961 | rs10922104 | rs7413999 | rs4044884 | rs1329422 | rs514591 | rs380390 |
| rs12726401 | rs10922103 | rs7413137 | rs4044882 | rs1329421 | rs513699 | rs380060 |
| rs12566629 | rs10922102 | rs6695321 | rs3834020 | rs1299282 | rs512900 | rs379489 |
| rs12565418 | rs10922101 | rs6691749 | rs3766405 | rs1292487 | rs508505 | rs375046 |
| rs12406047 | rs10922100 | rs6690982 | rs3766404 | rs1292477 | rs499807 | rs374896 |
| rs12405238 | rs10922099 | rs6689826 | rs3766403 | rs1292476 | rs495968 | rs374231 |
| rs12402808 | rs10922098 | rs6689009 | rs3753397 | rs1292475 | rs495222 | rs371647 |
| rs12238983 | rs10922097 | rs6688272 | rs3753396 | rs1292474 | rs493367 | rs368465 |
| rs12144939 | rs10922096 | rs6685249 | rs3753395 | rs1292473 | rs491480 | rs364947 |
| rs12136675 | rs10922095 | rs6682138 | rs3753394 | rs1292472 | rs490864 | rs203688 |
| rs12134975 | rs10922094 | rs6680396 | rs3043115 | rs1292471 | rs488738 | rs203687 |
| rs12134598 | rs10922093 | rs6677604 | rs3043113 | rs1292466 | rs487114 | rs203686 |
| rs12127759 | rs10922092 | rs6677460 | rs3043112 | rs1156679 | rs482934 | rs203685 |
| rs12124794 | rs10801561 | rs6677089 | rs3043111 | rs1156678 | rs480266 | rs203684 |
| rs12116702 | rs10801560 | rs6675088 | rs2878649 | rs1089031 | rs466287 | rs203683r |
| rs12096637 | rs10801559 | rs6674960 | rs2878648 | rs1065489 | rs464798 | s203682 |
| rs12085209 | rs10801558 | rs6673106 | rs2878647 | rs1061171 | rs463726 | rs203681 |

TABLE A-continued

| | | | | | | |
|---|---|---|---|---|---|---|
| rs12081550 | rs10801557 | rs6664877 | rs2860102 | rs1061170 | rs460897 | rs203680 |
| rs12069060 | rs10801556 | rs6664705 | rs2746965 | rs1061147 | rs460787 | rs203679 |
| rs12047565 | rs10801555 | rs6660100 | rs2336225 | rs1061111 | rs460184 | rs203678 |
| rs12047106 | rs10801554 | rs6428357 | rs2336224 | rs1060821 | rs459598 | rs203677 |
| rs12047103 | rs10801553 | rs6428356 | rs2336223 | rs1048663 | rs454652 | rs203676 |
| rs12045503 | rs10754200 | rs5779848 | rs2336222 | rs1040597 | rs436337 | rs203675 |
| rs12042805 | rs10754199 | rs5779847 | rs2336221 | rs800295 | rs435628 | rs203674 |
| rs12041668 | rs10737680 | rs5779846 | rs2300430 | rs800293 | rs434536 | rs203673 |
| rs12040718 | rs10737679 | rs5779845 | rs2300429 | rs800292 | rs430173 | rs203672 |
| rs12039905 | rs10733086 | rs5779844 | rs2284664 | rs800291 | rs428060 | rs203671 |
| rs12038674 | rs10688557 | rs5022901 | rs2284663 | rs800290 | rs424535 | rs203670 |
| rs12038333 | rs10685027 | rs5022900 | rs2274700 | rs800280 | rs422851 | rs203669 |
| rs12033127 | rs10664537 | rs5022899 | rs2268343 | rs800271 | rs422404 | rs70621 |
| rs12032372 | rs10616982 | rs5022898 | rs2173383 | rs800269 | rs420922 | rs70620 |
| rs12030500 | rs10545544 | rs5022897 | rs2143912 | rs766001 | rs420921 | rs15809 |
| rs12029785 | rs10540668 | rs5016801 | rs2104714 | rs765774 | rs419137 | rs14473 |
| rs12025861 | rs10536523 | rs5014740 | rs2064456 | rs742855 | rs414539 | rs3645 |
| rs11809183 | rs10489456 | rs5014739 | rs2020130 | rs731557 | rs412852 | |
| rs11801630 | rs10465603 | rs5014738 | rs2019727 | rs572515 | rs410232 | |
| rs11799956 | rs10465586 | rs5014737 | rs1803696 | rs570618 | rs409953 | |
| rs11799595 | rs9970784 | rs5002879 | rs1587325 | rs569219 | rs409319 | |
| rs11799380 | rs9970075 | rs5002878 | rs1576340 | rs564657 | rs409308 | |
| rs11584505 | rs9427909 | rs5002877 | rs1474792 | rs559350 | rs407361 | |

Two frequent non-synonymous variants, I62V in exon 2 and Y420H in exon 9, and a less frequent variant, R1210C in exon 22, exhibited the most significant association with AMD.

Three additional polymorphisms in TABLES 1A-1B are not found in the SNP database: a polymorphism in the promoter (promoter 1 in TABLE 1A); a polymorphism in intron 2 in which two T nucleotides are inserted; and a polymorphism in Exon 10A.

The first column in TABLE 1A lists the dbSNP number for polymorphisms in the Factor H gene. For example, rs800292 is the dbSNP designation for a polymorphism in the Factor H gene. A description of this polymorphism, as well as the other Factor H gene polymorphisms in dbSNP, is available at the NCBI database (ncbi.nml.nih.gov/entrez/query.fcgi?db=snp&cmd=search&term=). The second column lists the location of the polymorphism. For example, the rs800292 polymorphism is located in exon 2 of the Factor H gene. Polymorphisms not identified by a database number can be referred to by location (e.g., "intron 2"). The third column lists the nucleic acid sequence of the coding (top, 5' to 3' direction) and non-coding (bottom) strands of DNA spanning the polymorphisms. For example, the rs800292 polymorphism, G or A as indicated in the brackets for the coding strand, is flanked by the 20 nucleotides shown 5' and 3' to the polymorphism. "N" in the sequence spanning the Exon 10A polymorphism indicates the insertion of a single nucleotide, either A, C, G or T, in the variant allele. The fourth column lists the SEQ ID NO: for the sequences. The fifth column lists the amino acid change, if any, associated with the polymorphism. For example, the rs800292 polymorphism results in a change in the amino acid sequence from valine (V) to isoleucine (I) at position 62 of the Factor H polypeptide. The sixth column lists the allele frequency of the polymorphism in a control population. The numbers 1 and 2 refer to the alleles that correspond to the first and second nucleotide, respectively, at the polymorphic site in the third column. For example, for the rs800292 polymorphism, G is present in 78% and A is present in 22% of the alleles sequenced from the control population. The seventh column lists the allele frequency of the polymorphism in an AMD population. For example, for the rs800292 polymorphism, G is present in 91% and A is present in 9% of the alleles sequenced from an AMD population. The eighth column lists the chi-square and Fisher's exact tests ($\chi^2$ and P values, respectively) for the comparison between the allele frequencies of the polymorphism in the control and AMD populations. For example, for the rs800292 polymorphism, the $\chi^2$ value is 16.19 and the P value is $5.74 \times 10^{-5}$, indicating that the G allele is associated with AMD.

The first column in TABLE 1B parts (1), (2) and (3) lists the dbSNP number for polymorphisms in the Factor H gene. For part (1), the second column lists the nucleic acid sequence spanning the polymorphisms (interrogated sequence). For the rs529825 (intron 1), rs800292 (exon 2), and rs203674 (intron 10) polymorphisms, the sequences of the non-coding strand of the human Factor H gene are shown. The third column lists the SEQ ID NOs: for the sequences. The fourth column lists the allele present in the chimp Factor H gene. The fifth column lists the location of the SNP. The sixth column lists the amino acid change, if any, associated with the polymorphism. For part (2), the second and fourth columns list the forward and reverse primers or AOD numbers for amplifying the polymorphisms. The third and fifth columns list the SEQ ID NOs: for the primers. For part (3), the second and fourth columns list probes used for detecting the polymorphisms. The third and fifth columns list the SEQ ID NOs: for the probes.

It should be understood that additional polymorphic sites in the Factor H gene, which are not listed in TABLES 1A-1B may be associated with AMD. Exemplary polymorphic sites in the Factor H gene are listed, for example and not limitation, above. TABLE 1C lists an additional 14 polymorphic sites in the Factor H gene, which are not found in the dbSNP database, that may be associated with AMD or other diseases. The first column lists the location of the SNP. The second column lists the nucleic acid sequence spanning the polymorphisms. "notG" in the sequence spanning the Exon 5 polymorphism indicates the presence of an A, C or T nucleotide in the variant allele. "not C" in the sequences spanning the Exon 6 polymorphisms indicates the presence of an A, G or T nucleotide in the variant allele. "N" in the sequences spanning the Exon 21 polymorphism indicates the insertion of a single nucleotide, either A, C, G or T, in the variant allele. The third column lists the amino acid change, if any associated with the polymorphism. The fourth column lists the SEQ ID NOs: for the sequences. These SNPs can also be used in carrying out methods of the invention. Moreover, it will be appreciated that these CFH polymorphisms are useful for linkage and association studies, genotyping clinical populations, correlation of genotype information to phenotype information, loss of heterozygosity analysis, and identification of the source of a cell sample.

TABLE 2 shows a haplotype analysis of eight SNPs in the human Factor H gene in AMD cases and controls. The at-risk haplotypes are shown in stippled boxes, with the haplotype determining SNPs (Y402H and IVS10) shown in denser stippling. The protective haplotypes are shown in diagonal-lined boxes, with the haplotype determining SNPs (IVS1, I62V and IVS6) shown indenser diagonal lines. The first column lists the allele of the polymorphism in the promoter (Prom). The second column lists the allele of the non-coding strand of the polymorphism in intron 1 (IVS1). The third column lists the allele of the non-coding strand of the polymorphism in exon 2 (I62V). The fourth column lists the allele of the polymorphism in intron 6 (IVS6). The fifth column lists the allele of the polymorphism in Exon 9 (Y402H). The sixth column lists the allele of the non-coding strand of the polymorphism in intron 10 (IVS10). The seventh column lists the allele of the polymorphism in Exon 13 (Q672Q). The eighth column lists the allele of the polymorphism in Exon 18 (D936E). The dbSNP designations for these eight SNPs are listed in TABLES 1A-1B. The ninth column lists the Odds Ratio (OR) for the haplotype. The tenth column lists the P value for the at-risk and two protective haplotypes. The eleventh and twelfth columns list the frequencies of the haplotype in AMD cases and controls.

TABLE 3 shows a haplotype analysis of six Factor H polymorphisms with AMD. The first column lists certain alleles of the polymorphism in the promoter (rs3753394). The second column lists the allele of the polymorphism in intron 1 (rs529825). The third column lists the allele of the polymorphism in intron 6 (rs3766404). The fourth column lists the polymorphism in intron 10 (rs203674). The fifth column lists the allele of the polymorphism in exon 13 (rs3753396). The sixth column lists the allele of the polymorphism in exon 18 (rs1065489). The numbers 1 and 2 in columns 1 to 6 refer to the alleles that correspond to the first and second nucleotide, respectively, at each of the polymorphic sites (see TABLE 1A). Thus, columns 1 to 6 list the alleles of polymorphisms from 5' to 3' in the Factor H gene. The seventh column lists the Factor H haplotype based on the polymorphisms listed in columns 1 to 6. The eighth column lists the frequency of the indicated Factor H haplotype in a control population. The ninth column lists the frequency of the indicated Factor H haplotype in the AMD population. As shown in TABLE 3, the haplotype analysis suggests that multiple variants contribute to the association and may confer either elevated or reduced risk of AMD.

TABLE 8 shows a diplotype analysis of seven Factor H polymorphisms. The first column indicates whether the diplotype is associated with increased (risk diplotype) or decreased (protective diplotype) risk of developing AMD. Common risk and protective diplotypes are indicated. The second column lists the alleles of the polymorpohism in exon 2 (I62V). The third column lists the alleles of the polymorphism in intron 2 (IVS2-18). The fourth column lists the alleles of the polymorphism in exon 9 (Y402H). The fifth column lists the alleles of the polymorphism in exon 18 (D936E). The sixth column lists the alleles of the polymorphism in intron 20 (IVS20).

Risk-Associated ("Risk") Polymorphisms and Haplotypes

Sites comprising polymorphisms associated with increased risk for AMD are shown in TABLE 1A and TABLE 2. Polymorphisms particularly associated with increased risk include a variant allele at: rs1061170 (402H; exon 9); rs203674 (intron 10) and the polymorphism at residue 1210 (R1210C; exon 22).

Certain haplotypes associated with increased risk for AMD are shown in TABLES 2 and 6 and FIG. 5. As shown in TABLE 2 and FIG. 5, one common at-risk haplotype is the H1 haplotype, which includes the variant allele at position 402 (encoding histidine) and the variant allele at IVS10 (intron 10, rs203674) and is found in 49% of AMD cases, but only in 26% of controls. Homozygotes for the risk diplotype (H1/H1) are significantly at risk. Other at-risk haplotypes and diplotypes are shown in TABLES 2 and 8. Similar data are presented in TABLE 3, which shows an at-risk haplotype (111211) found in 48% of AMD cases, but only in 28% of controls.

Notably, seventy percent of MPGN II (membranoproliferative glomerulonephritis type II) patients harbor this at-risk haplotype (see TABLE 7), indicating that propensity to develop MPGNII can be detected and treated as described herein for AMD.

Significant associations of these polymorphic sites were also found with various AMD subtypes, as disclosed in Example 1.

The non-synonymous polymorphism at amino acid position 1210 in exon 22 of the Factor H gene is strongly associated with AMD (see TABLE 1A). The variant allele, which encodes a cysteine instead of an arginine, is found in the heterozygous state in 5% of AMD cases, and no controls in a cohort comprised of 919 individuals ascertained at the University of Iowa. No 1210C homozygotes have been identified to date. The presence of cysteine at amino acid position 1210 of Factor H, therefore, provides a strong indication that the individual has AMD or is likely to develop AMD. Remarkably, 1210C is indicative of propensity to develop AMD or other complement mediated conditions even when detected on allele that is otherwise protective (e.g., Y402). Variation at CFH position 1210 (R1210C) is known to cause atypical hemolytic uremic syndrome (aHUS), a complement related disease with renal manifestations. By extension, other CFH variations or mutations known to cause aHUS may be associated with an increased risk for developing AMD. The most common established aHUS-causing variations include, but are not limited to, T956M, Q1076E, D1119G, W1183L, T1184R, L1189R, L1189F, S1191W, S1191L, V1197A, and R1215G (Esparza-Gordillo et al 2005; Perez-Caballero et al 2001; Richards et al 2001; Sanchez-Corral et al 2002); additional aHUS-causing mutations are described in Saunders (Saunders et al 2006). In one aspect of the present invention, a biological sample from a subject (e.g., protein or nucleic acid) is assayed for the presence of one or more aHUS-associated variations or mutations, the presence of which is indicative of a propensity to develop AMD.

It will be appreciated that additional polymorphic sites in the Factor H gene, which are not listed in TABLES 1A-1C, may further refine this haplotype analysis. A haplotype analysis using non-synonymous polymorphisms in the Factor H gene is useful to identify variant Factor H polypeptides. Other haplotypes associated with risk may encode a protein with the same sequence as a protein encoded by a neutral or protective haplotype, but contain an allele in a promoter or intron, for example, that changes the level or site of Factor H expression. It will also be appreciated that a polymorphism in the Factor H gene, or in a Factor H-related gene, may be linked to a variation in a neighboring gene. The variation in the neighboring gene may result in a change in expression or form of an encoded protein and have detrimental or protective effects in the carrier.

Protective Polymorphisms and Haplotypes

Unexpectedly, protective polymorphisms and haplotypes were also discovered. For example, as shown in TABLE 2 and FIG. 5, the protective H2 haplotype, including a variant allele in IVS6 (intron 6, rs3766404) occurs in 12% of controls, but only in 6% of AMD cases. The protective H4 haplotype includes the variant allele in IVS1 (intron 1, rs529825) and the variant allele (I62) (exon 2, rs800292) and occurs in 18% of controls, but only in 12% of AMD cases. Similar data is presented in TABLE 3, where the haplotype 121111 occurs in 21% of controls, but only in 13% of AMD cases and the haploptype 112111 occurs in 13% of controls, but only in 6% of AMD cases. As shown in FIG. 5, homozygotes with a protective haplotype are significantly protected.

In some cases the protein encoded by a gene characterized by a protective haplotype has a sequence different from risk haplotype proteins (e.g., due to the presence of a nonsynonymous SNP). For example, a protective form of Factor H protein generally does not have histidine at position 402. In some embodiments a protective form has isoleucine at position 62. Additional protective forms can be identified by (1) identifying an individual or individuals with a protective haplotype and (2) determining the sequence(s) of Factor H cDNA or protein from the individuals. Other protective forms are identified as described below in Section VIII.

Neutral Polymorphisms and Haplotypes

Certain haplotypes are associated in a population with neither increased risk nor decreased risk of developing AMD and are referred to as "neutral." Examples of neutral haplotypes identified in a Caucasian population are shown in FIG. 5 (H3 and H5). Additional or different neutral haplotypes may be identified in racially/ethnically different populations. Proteins encoded by a gene characterized by a neutral haplotype are "neutral" Factor H proteins. As explained supra, "neutral" Factor H proteins could provide therapeutic benefit when administered to patients having a risk haplotype or diagnosed with AMD. For example, exemplary proteins encoded by genes characterized by a neutral haplotype include proteins not having histidine at position 402 and/or not having isoleucine at position 62. A protein not having histidine at position 402 may have tyrosine at that position, or may have an amino acid other than histidine or tyrosine. A protein not having isoleucine at position 62 may have valine at that position, or may have an amino acid other than valine or isoleucine. A neutral form of Factor H protein generally does not have cysteine at position 1210.

V. Factor H Related 5 (CFHR5) Gene Polymorphisms

In one aspect, the invention provides new diagnostic, treatment and drug screening methods related to the discovery that polymorphic sites in the Factor H and CFHR5 genes are associated with susceptibility to and development of MPGNII.

Factor H and CFHR5 polymorphisms associated with MPGNII were identified as described in Example 2, by examining the coding and adjacent intronic regions of Factor H or CFHR5 for variants using PCR amplification, followed by agarose gel electrophoresis and bi-directional sequencing according to standard protocols to verify PCR products. Novel and reported SNPs were typed in the control population by denaturing high performance liquid chromatography (DHPLC). Primers used to amplify the Factor H and CFHR5 coding sequences are shown in TABLES 9 and 10, respectively.

The test group consisted of patients with biopsy-proven MPGNII were ascertained in nephrology divisions and enrolled in this study under IRB-approved guidelines. The control group consisted of ethnically-matched, but not age-matched, unrelated persons in whom AMD had been excluded by ophthalmologic examination.

As shown in TABLES 11 and 12, a significant association of polymorphic sites in the Factor H gene with MPGNII was found in an examination of 22 MPGNII cases and 131 ethnically-matched controls. Eleven (11) polymorphisms in the Factor H gene are listed in TABLES 11 and 12. Of these, six (6) are found in the SNP database (dbSNP) which may be found in the National Center for Biotechnology Information (NCBI). The dbSNP is a collection of SNPs in the human genome. The SNPs in the Factor H gene are dispersed among the 22 coding exons of the Factor H gene and among the promoter, the 5' untranslated region, the introns, and the 3' untranslated region of the Factor H gene. The accession numbers for 379 SNPs in the human Factor H gene that are found in the dbSNP database are listed above. These SNPs can be used in carrying out methods of the invention.

Five additional polymorphisms in TABLES 11 and 12 are not found in the SNP database: a polymorphism in intron 2 in which two T nucleotides are inserted (IVS2-18insTT); a polymorphism in intron 7 (IVS7-53G>T); a polymorphism in intron 15 (IVS15-30C>A); a polymorphism in intron 18 (IVS18-89T>C; and a polymorphism in Exon 20 (N1050Y). These polymorphisms are useful in the methods of the invention. Moreover, it will be appreciated that these CFHR5 polymorphisms are useful for linkage and association studies, genotyping clinical populations, correlation of genotype information to phenotype information, loss of heterozygosity analysis, and identification of the source of a cell sample.

The first row of TABLE 11 lists the exon or intron position of the SNP in the Factor H gene. For exon SNPs, the amino acid position and change, if any, is listed. For example the exon 2 SNP is at position 62 of the Factor H polypeptide and a change from valine (V) to isoleucine (I). For intron SNPs, the nature the SNP is indicated. For example, the intron 2 SNP is an insertion of two nucleotides, TT. The second row of TABLE 11 lists dbSNP number, if any, for the polymorphism. For example, rs800292 is the dbSNP designation for a polymorphism in exon 2 in the Factor H gene. A description of this polymorphism, as well as the other Factor H (CFH) gene polymorphisms in dbSNP, is available at the NCBI database (ncbi.nml.nih.gov/entrez/query.fcgi?db=snp&cmd=search&term=). The third to fifth rows of TABLE 11 lists number of times a particular diplotype is present among the 22 MPGNII patients. For example, for the exon 2 SNP, GG is present in 20 patients, GA is present in 2 patient, and AA is present in no patients, with MPGNII. The sixth and seventh rows of TABLE 11 list the frequency that a particular haplotype is present among the 22 MPGNII patients. For example, for the exon 2 SNP, G is present in 95%, and A is present in 5%, of the alleles of the 22 MPGNII patients. The eighth row lists the nucleotide of the common haplotype in the Factor H gene for the 22 MPGNII patients. For example, G is the more frequent nucleotide in the exon 2 SNP, and 9 T nucleotides is more frequently observed than 11 T nucleotides in the intron 2 SNP, in the Factor H gene for the 22 MPGNII patients. The remaining rows list the diplotype for the 11 SNPs in the Factor H gene for each of the 22 MPGNII patients.

It should be understood that additional polymorphic sites in the Factor H gene, which are not listed in TABLE 11 may be associated with MPGNII. Exemplary polymorphic sites in the Factor H gene are listed, for example and not limitation, above.

TABLE 12 shows a comparison of the SNP frequencies in patients with MPGNII versus AMD-negative, ethnically-matched control individuals. The first column of TABLE 12 lists the SNP in the Factor H gene. The second and third columns of TABLE 12 list the frequencies that a particular haplotype is present among the 22 MPGNII patients. The fourth and fifth columns of TABLE 12 list the frequencies that a particular haplotype is present among the 131 control individuals. The sixth column of TABLE 12 lists the P-value calculated for each data set.

As shown in TABLES 11 and 12, two frequent non-synonymous variants, I62V in exon 2 and Y420H in exon 9, a synonymous variant, A307A in exon 10, and a polymorphism in intron 2 exhibited significant association with MPGNII.

As shown in TABLES 14 and 15, a significant association of polymorphic sites in the FHR-5 gene with MPGNII was found in an examination of 22 MPGNII cases and 103 ethnically-matched controls. Five (5) polymorphisms in the CFHR5 gene are listed in TABLES 14 and 15; these are found in dbSNP in the NCBI. The SNPs in the CFHR5 gene are dispersed among the 10 coding exons of the CFHR5 gene and among the promoter, the 5' untranslated region, the introns, and the 3' untranslated region of the CFHR5 gene. Listed below are the accession numbers for 82 SNPs in the human CFHR5 gene that are found in the dbSNP database. These SNPs can be used in carrying out methods of the invention.

The first row of TABLE 14 lists the exon, promoter or intron position of the SNP in the CFHR5 gene. For exon SNPs, the amino acid position and change, if any, is listed. For example, the exon 2 SNP is at position 46 of the CFHR5 polypeptide and a change from proline (P) to serine (S). For promoter and intron SNPs, the nature of the SNP is indicated. For example, the promoter SNP at position −249 replaces T with C. The second row of TABLE 14 lists dbSNP number, if any, for the polymorphism. For example, rs9427661 is the dbSNP designation for a polymorphism in the promoter region of the CFHR5 gene. A description of this polymorphism, as well as the other CFHR5 gene polymorphisms in dbSNP, is available at the NCBI database (ncbi.nml.nih.gov/entrez/query.fcgi?db=snp&cmd=search&term=). The third to fifth rows of TABLE 14 lists number of times a particular diplotype is present among the 22 MPGNII patients. For example, for the exon 2 SNP, CC is present in 19 patients, CT is present in 3 patients, and TT is present in no patients, with MPGNII. The sixth and seventh rows of TABLE 14 list the frequency that a particular haplotype is present among the 22 MPGNII patients. For example, for the exon 2 SNP, C (encoding proline) is present in 93%, and T (encoding serine) is present in 7%, of the alleles of the 22 MPGNII patients. The eighth row lists the nucleotide of the common haplotype in the CFHR5 gene for the 22 MPGNII patients. For example, C is the more frequent nucleotide in the exon 2 SNP in the CFHR5 gene for the 22 MPGNII patients. The remaining rows list the diplotype for the 5 SNPs in the CFHR5 gene for each of the 22 MPGNII patients.

It should be understood that additional polymorphic sites in the CFHR5 gene, which are not listed in TABLE 14 may be associated with MPGNII. Exemplary polymorphic sites in the CFHR5 gene are listed, for example and not limitation, above.

TABLE 15 shows a comparison of the SNP frequencies in patients with MPGNII versus AMD-negative, ethnically-matched control individuals. The first column of TABLE 15 lists the SNP in the CFHR5 gene. The second and third columns of TABLE 15 list the frequencies that a particular haplotype is present among the 22 MPGNII patients. The fourth and fifth columns of TABLE 15 list the frequencies that a particular haplotype is present among the 103 control individuals. The sixth column of TABLE 15 lists the P-value calculated for each data set.

As shown in TABLES 14 and 15, one non-synonymous variant, P46S in exon 2, and two promoter polymorphisms, −249T>C and −2−T>C, exhibited significant association with MPGNII.

TABLE B

| rs16840956 | rs12116643 | rs10922151 | rs9427662 | rs7535993 | rs6694672 | rs1332664 |
| rs16840946 | rs12097879rs | rs10801584 | rs9427661 | rs7532441 | rs6692162 | rs1325926 |
| rs16840943 | 12097550 | rs10801583 | rs9427660 | rs7532068 | rs6657256 | rs1170883 |
| rs12755054 | rs12092294 | rs10622350 | rs9427659 | rs7528757 | rs6657171 | rs1170882 |
| rs12750576 | rs12091602 | rs10614978 | rs7555407 | rs7527910 | rs5779855 | rs1170881 |
| rs12745733 | rs12064805 | rs10613146 | rs7555391 | rs7522952 | rs3748557 | rs1170880 |
| rs12736097 | rs12049041 | rs10588279 | rs7554757 | rs7522197 | rs2151137 | rs1170879 |
| rs12736087 | rs12039272 | rs9727516 | rs7550970 | rs7419075 | rs2151136 | rs1170878 |
| rs12735776 | rs11583363 | rs9427942 | rs7550735 | rs7366339 | rs1855116 | rs928440 |
| rs12731848 | rs11306823 | rs9427941 | rs7550650 | rs6702632 | rs1759016 | rs928439 |
| rs12731209 | rs10922153 | rs9427664 | rs7547265 | rs6702340 | rs1750311 | |
| rs12142971 | rs10922152 | rs9427663 | rs7537588 | rs6674853 | rs1412636 | |

Risk-Associated ("Risk") Polymorphisms and Haplotypes Identified In MPGNII Patients Sites comprising polymorphisms in Factor H and CFHR5 associated with increased risk for MPGNII are shown in TABLES 11 and 12 and TABLES 14 and 15, respectively. Polymorphisms particularly associated with increased risk in Factor H and CFHR5 include a variant allele at rs1061170 (Y420H in exon 9) and rs12097550 (P46S in exon 2), respectively.

Certain haplotypes associated with increased risk for MPGNII are shown in TABLES 12 and 15. As shown in TABLE 12, one at-risk haplotype in the Factor H gene includes the variant allele (encoding histidine) at position 402 and is found in 64% of MPGNII cases, but only in 33% of controls. As shown in TABLE 15, one at-risk haplotype in the CFHR5 gene includes the variant allele (encoding serine) at position 46 and is found in 7% of MPGNII cases, but only in <1% of controls.

It will be appreciated that additional polymorphic sites in the Factor H and CFHR5 genes, which are not listed in TABLES 11-12 and 14-15, may further refine these haplotype analyses. A haplotype analysis using non-synonymous polymorphisms in the Factor H or CFHR5 gene is useful to identify variant Factor H or CFHR5 polypeptides. Other haplotypes associated with risk may encode a protein with the same sequence as a protein encoded by a neutral or protective haplotype, but contain an allele in a promoter or intron, for example, that changes the level or site of Factor H or CFHR5 expression.

Protective Polymorphisms and Haplotypes

Unexpectedly, protective polymorphisms and haplotypes were also discovered. For example, as shown in TABLE 12, the haplotype with the variant allele in exon 2 (rs800292, I62V) occurs in 23% of controls, but only in <3% of MPGNII cases and the haplotype with the variant allele in IVS2 (intron 2, −18insTT) occurs in 26% of controls, but only in <3% of MPGNII cases. The haplotype with the variant allele in exon 10 (rs2274700, A473A) occurs at higher frequency in controls than in MPGNII cases.

In some cases the protein encoded by a gene characterized by a protective haplotype has a sequence different from risk haplotype proteins. For example, a protective form of Factor H protein generally does not have histidine at position 402. In some embodiments a protective form has isoleucine at position 62. Additional protective forms can be identified by (1) identifying an individual or individuals with a protective haplotype and (2) determining the sequence(s) of Factor H cDNA or protein from the individuals. Some protective forms are less than full-length. Protective forms of CFHR5 protein may be similarly identified.

Neutral Polymorphisms and Haplotypes

Certain haplotypes are associated with neither increased risk or decreased risk of developing MPGNII and are referred to as "neutral." Proteins encoded by a gene characterized by a neutral haplotype are "neutral" Factor H or CFHR5 proteins. For example, exemplary proteins encoded by genes characterized by a neutral haplotype include Factor H proteins not having histidine at position 402 or isoleucine at position 62, and CFHR5 proteins not having serine at position 46.

Significance of Polymorphisms in MPGNII Patients

As shown in Example 2, it has been discovered that the same CFH polymorphisms associated with propensity to develop AMD are also associated with development of membranoproliferative glomerulonephritis type 2 (MPGN II). Indeed, the risk haplotypes originally found in AMD patients (Y402 H and IVS10) are also found in 70% of patients tested having membranoproliferative glomerulonephritis type 2 (MPGN II), indicating that the diagnostic methods of the invention are useful to detect this condition. In addition, variations and haplotypes in the CFHR5 gene were strongly associated with increased risk of having MPGNII. One conclusion that emerges from these data is that MPGNII and AMD are alternative manifestations of the same genetic lesion. Notably, patients with MPGNII develop drusen that are clinically and compositionally indistinguishable from drusen that form in AMD. The single feature that distinguishes these two fundus phenotypes is age of onset-drusen in MPGNII develop early, often in the second decade of life, while drusen in AMD develop later in life. We conclude that polymorphisms in the Factor H gene and CFHR5 gene identified in either population (AMD or MPGNII) are predictive of susceptibility to both diseases. There are likely other factors that contribute to MPGNII and account for the early manifestation. Because AMD is very common and MPGNII is rare, the haplotype analysis of both CFH and CFHR5 genes and other methods described herein will be useful for screening and treatment of patients with AMD, or with an increased likelihood of developing AMD.

Loss of Function

Loss of the normal or wild-type function of Factor H or CFHR5 may be associated with AMD. Non-synonymous polymorphisms in the Factor H gene, such as those shown in TABLES 1A, 1B, 1C, 11, 14 and 15, showing the strongest correlation with AMD and resulting in a variant Factor H polypeptide or variant CFHR5 polypeptide, are likely to have a causative role in AMD. Such a role can be confirmed by producing a transgenic non-human animal expressing human Factor H or CFHR5 bearing such a non-synonymous polymorphism(s) and determining whether the animal develops AMD. Polymorphisms in Factor H or CFHR5 coding regions that introduce stop codons may cause AMD by reducing or eliminating functional Factor H or CFHR5 protein. Stop codons may also cause production of a truncated Factor H or CFHR5 peptide with aberrant activities relative to the full-length protein. Polymorphisms in regulatory regions, such as promoters and introns, may cause AMD by decreasing Factor H or CFHR5 gene expression. Polymorphisms in introns (e.g., intron 2 of CFH) may also cause AMD by altering gene splicing patterns resulting in an altered Factor H or CFHR5 protein. CFH RNA or proteins can be assayed to detect changes in expression of splice variants, where said changes are indicative of a propensity to develop AMD. Alternative splice patterns have been reported for the Factor H gene itself.

The effect of polymorphisms in the Factor H gene or CFHR5 gene on AMD can be determined by several means. Alterations in expression levels of a variant Factor H or CFHR5 polypeptide can be determined by measuring protein levels in samples from groups of individuals having or not having AMD or various subtypes of AMD. Alterations in biological activity of variant Factor H or CFHR5 polypeptides can be detected by assaying for in vitro activities of Factor H or CFHR5, for example, binding to C3b or to heparin, in samples from the above groups of individuals.

VI. Polymorphisms at Sites of Genomic Duplication

Figure 18:
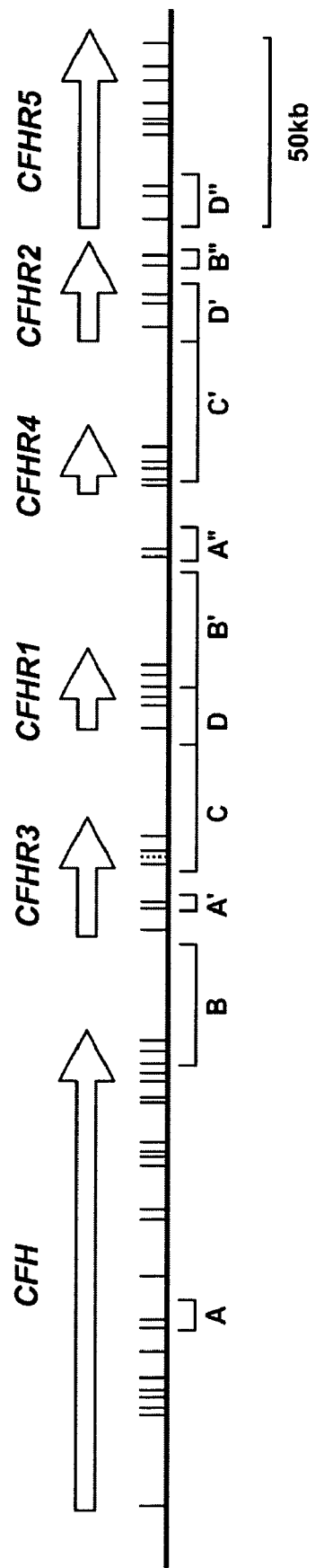
FIG. 18 shows genomic duplications in the genes for CFH and the Factor H-related proteins. Exons are indicated as vertical lines. Regions labeled with the same letter (e.g., A, A', and A") have substantially identical sequences.

As illustrated in FIG. 18, the genes for CFH and the factor H related (CFHR) 1-5 genes have regions of shared, highly conserved, sequence which likely arose from genomic duplications. Certain SNPs and variations found in CFH or CFHR5, such as those described herein, are also expected in the corresponding sequences of CFHR1, CFHR2, CFHR3, and CFHR4. For example, sequences corresponding to CFH exon 22 are found in CFH, CFHR1 and CFHR2, and it is possible that polymorphisms identified in exon 22 of CFH (e.g., R1210C) are also found in CFHR1 and/or CFHR2 and these variants might be linked to propensity to development of AMD, MPGNII, and other complement related conditions. Homologous blocks of sequence flanking the polymorphic sites identified in CFH and CFHR5 can be identified by alignment of the cDNA or genomic sequences in those regions. The conserved sequences flanking the polymorphic site usually comprise at least 10 bp (on either side of the polymorphic site) and more often at least 20 bp, or at least 50 bp, or at least 100 bp with at least 95% identity at the nucleotide level, and sometimes with at least 98% identity, at least 99% identity, or even 100% identity). Identity can be determined by inspection or using well know algorithms (Smith and Waterman, 1981 or Needleman and Wunsch, 1970, both supra). The invention therefore provides methods of determining a subject's propensity to develop age-related macular degeneration (AMD) or other conditions by detecting the presence or absence of a variation at a polymorphic site of a Factor H-related gene that corresponds to a homologous polymorphic site in the CFH or CFHR5 gene.

Sequences for CFH and the factor H related genes are known in the art (see sequences and accession numbers provided elsewhere herein). Also see Rodriquez de Cordoba, S., et al, 2004, *Mol Immunol* 41:355-67; Zipfel et al, 1999, *Immunopharmocology* 42:53-60; Zipfel et al., Factor H family proteins: on complement, microbes and human diseases, *Biochem Soc Trans.* 2002 November; 30(Pt 6):971-8; Diaz-Guillen M A, et al., A radiation hybrid map of complement factor H and factor H-related genes, *Immunogenetics,* 1999 June; 49(6):549-52; Skerka C, et al., A novel short consensus repeat-containing molecule is related to human complement factor H, *J Biol Chem.* 1993 Feb. 5; 268(4):2904-8; Skerka C, et al., The human factor H-related gene 2 (FHR2): structure and linkage to the coagulation factor XIIIb gene, *Immunogenetics,* 1995; 42(4):268-74; Male D A, et al., Complement factor H: sequence analysis of 221 kb of human genomic DNA containing the entire fH, fHR-1 and fHR-3 genes, *Mol Immunol.* 200 January-February; 37(1-2):41-52; Hellwage J, et al., Biochemical and functional characterization of the factor-H-related protein 4 (FHR-4), *Immunopharmacology.* 1997 December; 38(1-2):149-57; Skerka C, et al., The human factor H-related protein 4 (FHR-4). A novel short consensus repeat-containing protein is associated with human triglyceride-rich lipoproteins, *J Biol Chem.* 1997 Feb. 28; 272(9): 5627-34; Hellwage J, et al., Functional properties of complement factor H-related proteins FHR-3 and FHR-4: binding to the C3d region of C3b and differential regulation by heparin, *FEBS Lett.* 1999 Dec. 3; 462 (3):345-52; Jozsi M, et al., FHR-4A: a new factor H-related protein is encoded by the human FHR-4 gene, *Eur J Hum Genet.* 2005 March; 13(3): 321-9; McRae J L, et al., Location and structure of the human FHR-5 gene, *Genetica.* 2002 March; 114(2):157-61; McRae J L, et al., Human factor H-related protein 5 has cofactor activity, inhibits C3 convertase activity, binds heparin and C-reactive protein, and associates with lipoprotein, *J Immunol.* 2005 May 15; 174(10):6250-6; Murphy B, et al., Factor H-related protein-5: a novel component of human glomerular immune deposits, *Am J Kidney Dis.* 2002 January; 39(1):24-7.

VII. Detection and Analysis of Factor H Polymorphisms Associated with AMD

The discovery that polymorphic sites and haplotypes in the Factor H gene and CFHR5 gene are associated with AMD (and MPGNII) has a number of specific applications, including screening individuals to ascertain risk of developing AMD and identification of new and optimal therapeutic approaches for individuals afflicted with, or at increased risk of developing, AMD. Without intending to be limited to a specific mechanism, polymorphisms in the Factor H gene may contribute to the phenotype of an individual in different ways. Polymorphisms that occur within the protein coding region of Factor H may contribute to phenotype by affecting the protein structure and/or function. Polymorphisms that occur in the non-coding regions of Factor H may exert phenotypic effects indirectly via their influence on replication, transcription and/or translation. Certain polymorphisms in the Factor H gene may predispose an individual to a distinct mutation that is causally related to a particular AMD phenotype. Alternatively, as noted above, a polymorphism in the CFH gene, or in a CFHR5, may be linked to a variation in a neighboring gene (including but not limited to CFHR-1, 2, 3, or 4). The variation in the neighboring gene may result in a change in expression or form of an encoded protein and have detrimental or protective effects in the carrier.

A. Preparation of Samples for Analysis

Polymorphisms are detected in a target nucleic acid isolated from an individual being assessed. Typically genomic DNA is analyzed. For assay of genomic DNA, virtually any biological sample containing genomic DNA or RNA, e.g., nucleated cells, is suitable. For example, in the experiments described in Example 1, genomic DNA was obtained from peripheral blood leukocytes collected from case and control subjects (QIAamp DNA Blood Maxi kit, Qiagen, Valencia, Calif.). Other suitable samples include saliva, cheek scrapings, biopsies of retina, kidney or liver or other organs or tissues; skin biopsies; amniotic fluid or CVS samples; and the like. Alternatively RNA or cDNA can be assayed. Alternatively, as discussed below, the assay can detect variant Factor H proteins. Methods for purification or partial purification of nucleic acids or proteins from patient samples for use in diagnostic or other assays are well known.

B. Detection of Polymorphisms in Target Nucleic Acids

The identity of bases occupying the polymorphic sites in the Factor H gene and the Factor H-Related 5 gene shown in TABLES 1A, 1B, 1C, 11, 14 and 15, as well as others in the dbSNP collection that are located in or adjacent to the Factor H or CFHR5 genes (see lists above), can be determined in an individual, e.g., in a patient being analyzed, using any of several methods known in the art. Examples include: use of allele-specific probes; use of allele-specific primers; direct sequence analysis; denaturing gradient gel electropohoresis (DGGE) analysis; single-strand conformation polymorphism (SSCP) analysis; and denaturing high performance liquid chromatography (DHPLC) analysis. Other well known methods to detect polymorphisms in DNA include use of: Molecular Beacons technology (see, e.g., Piatek et al., 1998; *Nat. Biotechnol.* 16:359-63; Tyagi, and Kramer, 1996, *Nat. Biotechnology* 14:303-308; and Tyagi, et al., 1998, *Nat. Biotechnol.* 16:49-53), Invader technology (see, e.g., Neri et al., 2000, *Advances in Nucleic Acid and Protein Analysis* 3826: 117-125 and U.S. Pat. No. 6,706,471), nucleic acid sequence based amplification (Nasba) (Compton, 1991), Scorpion technology (Thelwell et al., 2000, *Nuc. Acids Res,* 28:3752-3761 and Solinas et al., 2001, "Duplex Scorpion primers in SNP analysis and FRET applications" *Nuc. Acids Res,* 29:20.), restriction fragment length polymorphism (RFLP) analysis, and the like. Additional methods will be apparent to the one of skill.

The design and use of allele-specific probes for analyzing polymorphisms are described by e.g., Saiki et al., 1986; Dattagupta, EP 235,726, Saiki, WO 89/11548. Briefly, allele-specific probes are designed to hybridize to a segment of target DNA from one individual but not to the corresponding segment from another individual, if the two segments represent different polymorphic forms. Hybridization conditions are chosen that are sufficiently stringent so that a given probe essentially hybridizes to only one of two alleles. Typically, allele-specific probes are designed to hybridize to a segment of target DNA such that the polymorphic site aligns with a central position of the probe.

Exemplary allele-specific probes for analyzing Factor H polymorphisms are shown in TABLE 16A. Using the polymorphism dbSNP No. rs1061170 as an illustration, examples of allele-specific probes include: 5'-TTTCTTCCAT-AATTTTG-3' [SEQ ID NO:234] (reference allele probe) and 5'-TTTCTTCCATGATTTTG-3' [SEQ ID NO:235] (variant allele probe); and 5'-TAATCAAAATTATGGAA-3' [SEQ ID NO:232] (reference allele probe) and 5'-TAATCAAAAT-CATGGAA-3' [SEQ ID NO:233] (variant allele probe). In this example, the first set of allele-specific probes hybridize to the non-coding strand of the Factor H gene spanning the exon 9 polymorphism. The second set of allele-specific probes hybridize to the coding strand of the Factor H spanning the exon 9 polymorphism. These probes are 17 bases in length. The optimum lengths of allele-specific probes can be readily determined using methods known in the art.

Allele-specific probes are often used in pairs, one member of a pair designed to hybridize to the reference allele of a target sequence and the other member designed to hybridize to the variant allele. Several pairs of probes can be immobilized on the same support for simultaneous analysis of multiple polymorphisms within the same target gene sequence.

The design and use of allele-specific primers for analyzing polymorphisms are described by, e.g., WO 93/22456 and Gibbs, 1989. Briefly, allele-specific primers are designed to hybridize to a site on target DNA overlapping a polymorphism and to prime DNA amplification according to standard PCR protocols only when the primer exhibits perfect complementarity to the particular allelic form. A single-base mismatch prevents DNA amplification and no detectable PCR product is formed. The method works best when the polymorphic site is at the extreme 3'-end of the primer, because this position is most destabilizing to elongation from the primer.

Exemplary allele-specific primers for analyzing Factor H polymorphisms are shown in TABLE 16B. Using the polymorphism dbSNP No. rs1061170 as an illustration, examples of allele-specific primers include: 5'-CAAACTTTCTTC-CATA-3' [SEQ ID NO:294] (reference allele primer) and 5'-CAAACTTTCTTCCATG-3' [SEQ ID NO:295] (variant allele primer); and 5'-GGATATAATCAAAATT-3' [SEQ ID NO:292] (reference allele primer) and 5'-GGATATAAT-CAAAATC-3' [SEQ ID NO:293] (variant allele primer). In this example, the first set of allele-specific primers hybridize to the non-coding strand of the Factor H gene directly adjacent to the polymorphism in exon 9, with the last nucleotide complementary to the reference or variant polymorphic allele as indicated. These primers are used in standard PCR protocols in conjunction with another common primer that hybridizes to the coding strand of the Factor H gene at a specified location downstream from the polymorphism. The second set of allele-specific primers hybridize to the coding strand of the Factor H gene directly adjacent to the polymorphic site in exon 9, with the last nucleotide complementary to the reference or variant polymorphic allele as indicated. These primers are used in standard PCR protocols in conjunction with another common primer that hybridizes to the non-coding strand of the Factor H gene at a specified location upstream from the polymorphism. The common primers are chosen such that the resulting PCR products can vary from about 100 to about 300 bases in length, or about 150 to about 250 bases in length, although smaller (about 50 to about 100 bases in length) or larger (about 300 to about 500 bases in length) PCR products are possible. The length of the primers can vary from about 10 to 30 bases in length, or about 15 to 25 bases in length. The sequences of the common primers can be determined by inspection of the Factor H genomic sequence, which is found under GenBank accession number AL049744.

Many of the methods for detecting polymorphisms involve amplifying DNA or RNA from target samples (e.g., amplifying the segments of the Factor H gene of an individual using Factor H-specific primers) and analyzing the amplified gene. This can be accomplished by standard polymerase chain reaction (PCR & RT-PCR) protocols or other methods known in the art. The amplifying may result in the generation of Factor H allele-specific oligonucleotides, which span the single nucleotide polymorphic sites in the Factor H gene. The Factor H-specific primer sequences and Factor H allele-specific oligonucleotides may be derived from the coding (exons) or non-coding (promoter, 5' untranslated, introns or 3' untranslated) regions of the Factor H gene.

Amplification products generated using PCR can be analyzed by the use of denaturing gradient gel electrophoresis (DGGE). Different alleles can be identified based on sequence-dependent melting properties and electrophoretic migration in solution. See Erlich, ed., PCR Technology, Principles and Applications for DNA Amplification, Chapter 7 (W.H. Freeman and Co, New York, 1992).

Alleles of target sequences can be differentiated using single-strand conformation polymorphism (SSCP) analysis. Different alleles can be identified based on sequence- and structure-dependent electrophoretic migration of single stranded PCR products (Orita et al., 1989). Amplified PCR products can be generated according to standard protocols, and heated or otherwise denatured to form single stranded products, which may refold or form secondary structures that are partially dependent on base sequence.

Alleles of target sequences can be differentiated using denaturing high performance liquid chromatography (DHPLC) analysis. Different alleles can be identified based on base differences by alteration in chromatographic migration of single stranded PCR products (Frueh and Noyer-Weidner, 2003). Amplified PCR products can be generated according to standard protocols, and heated or otherwise denatured to form single stranded products, which may refold or form secondary structures that are partially dependent on the base sequence.

Direct sequence analysis of polymorphisms can be accomplished using DNA sequencing procedures that are well-known in the art. See Sambrook et al., Molecular Cloning, A Laboratory Manual (2nd Ed., CSHP, New York 1989) and Zyskind et al., Recombinant DNA Laboratory Manual (Acad. Press, 1988).

A wide variety of other methods are known in the art for detecting polymorphisms in a biological sample. See, e.g., Ullman et al. "Methods for single nucleotide polymorphism detection" U.S. Pat. No. 6,632,606; Shi, 2002, "Technologies for individual genotyping: detection of genetic polymorphisms in drug targets and disease genes" *Am J Pharmacogenomics* 2:197-205; Kwok et al., 2003, "Detection of single nucleotide polymorphisms" *Curr Issues Biol.* 5:43-60).

It will be apparent to the skilled practitioner guided by this disclosure than various polymorphisms and haplotypes can be detected to assess the propensity of an individual to develop a Factor H related condition. The following examples and combinations, and others provided herein, are provided for illustration and not limitation. In one aspect of the invention, the allele of the patient at one of more of the following polymorphic sites in the Factor H gene is determined: rs529825; rs800292; rs3766404; rs1061147; rs1061170; and rs203674. In one embodiment the allele of the patient at rs529825 is determined. In one embodiment the allele of the patient at rs800292 is determined. In one embodiment the allele of the patient at rs3766404 is determined. In one embodiment the allele of the patient at rs1061147 is determined. In one embodiment the allele of the patient at rs1061170 is determined. In one embodiment the allele of the patient at rs203674 is determined. In one embodiment at least one of rs529825 and rs800292 is determined. In one embodiment at least one of rs1061147, rs1061170 and rs203674 is determined. In one embodiment at least one of rs529825 and rs800292 is determined, rs3766404 is determined, and at least one of rs1061147, rs1061170 and rs203674 is determined. In one embodiment alleles at rs529825, rs800292, rs3766404, rs1061170 and rs203674 are determined. The aforementioned polymorphisms and combinations of polymorphisms are provided herein for illustration and are not intended to limit the invention in any way. That is, other polymorphisms and haplotypes useful in practicing the invention will be apparent from this disclosure.

In a related aspect of the invention, the allele of the patient at one of more of the following polymorphic sites in the Factor H gene is determined: rs529825; rs800292; intron 2 (IVS2 or insTT); rs3766404; rs1061147; rs1061170; exon 10A; rs203674; rs375046; and exon 22 (1210). In one embodiment the allele of the patient at rs529825 is determined. In one embodiment the allele of the patient at rs800292 is determined. In one embodiment the allele of the patient at intron 2 is determined. In one embodiment the allele of the patient at rs3766404 is determined. In one embodiment the allele of the patient at rs1061147 is determined. In one embodiment the allele of the patient at rs1061170 is determined. In one embodiment the allele of the patient at exon 10A is determined. In one embodiment the allele of the patient at rs203674 is determined. In one embodiment the allele of the patient at rs375046 is determined. In one embodiment the allele of the patient at exon 22 (1210) is determined. In one embodiment at least one of rs529825 and rs800292 is determined; intron 2 is determined; rs3766404 is determined; at least one of rs1061147, rs1061170 and rs203674 is determined; exon 10A is determined; rs375046 is determined; and exon 22 (1210) is determined. In one embodiment alleles at rs529825, rs800292, intron 2; rs3766404, rs1061170, exon 10A, rs203674, rs375046, and exon 22 (1210) are determined. In one embodiment one, two, three, four five, or more than five of the following polymorphic sites in the Factor H gene is determined: rs529825; rs800292; intron 2 (IVS2 or insTT); rs3766404; rs1061147; rs1061170; rs2274700; exon 10A; rs203674; rs375046; and exon 22 (1210). The aforementioned polymorphisms and combinations of polymorphisms are provided for illustration and are not intended to limit the invention in any way.

As discussed above, the non-synonymous polymorphism at amino acid position 1210 in exon 22 of the Factor H gene is strongly associated with AMD, and the presence of cysteine at amino acid position 1210 of Factor H, therefore, provides a strong indication that the individual has AMD or is likely to develop AMD. Remarkably, 1210C is indicative of propensity to develop AMD or other complement mediated conditions even when detected on allele that is otherwise protective (e.g., Y402). Thus, the allele of the patient at exon 22 (1210) is highly informative with respect to risk of developing AMD or other Factor H-associated diseases.

In a related aspect of the invention, the allele of an individual at one of more of the following polymorphic sites in the CFHR5 gene is determined: rs9427661 (−249T>C); rs9427662 (−20T>C); and rs12097550 (P46S). In one embodiment the allele of the patient at rs9427661 is determined. In one embodiment the allele of the patient at rs9427662 is determined. In one embodiment the allele of the patient at rs12097550 is determined. In one embodiment at least one of rs9427661 and rs9427662 is determined. In one embodiment at least one of rs9427661 and rs9427662 is determined, and rs12097550 is determined. In one embodiment rs9427661, rs9427662 and rs12097550 is determined. The aforementioned polymorphisms and combinations of polymorphisms are provided for illustration and are not intended to limit the invention in any way. That is, other polymorphisms and haplotypes useful in practicing the invention will be apparent from this disclosure.

C. Detection of Protein Variants

In one embodiment of the invention, a protein assay is carried out to characterize polymorphisms in a subject's CFH or CFHR5 genes. Methods that can be adapted for detection of variant CFH, HFL1 and CFHR5 are well known. These methods include analytical biochemical methods such as electrophoresis (including capillary electrophoresis and two-dimensional electrophoresis), chromatographic methods such as high performance liquid chromatography (HPLC), thin layer chromatography (TLC), hyperdiffusion chromatography, mass spectrometry, and various immunological methods such as fluid or gel precipitin reactions, immunodiffusion (single or double), immunoelectrophoresis, radioimmnunoassay (RIA), enzyme-linked immunosorbent assays (ELISAs), immunofluorescent assays, western blotting and others.

For example, a number of well established immunological binding assay formats suitable for the practice of the invention are known (see, e.g., Harlow, E.; Lane, D. Antibodies: a laboratory manual. Cold Spring Harbor, N.Y.: Cold Spring Harbor Laboratory; 1988; and Ausubel et al., (2004) Current Protocols in Molecular Biology, John Wiley & Sons, New York N.Y. The assay may be, for example, competitive or non-conpetitive. Typically, immunological binding assays (or immunoassays) utilize a "capture agent" to specifically bind to and, often, immobilize the analyte. In one embodiment, the capture agent is a moiety that specifically binds to a variant CFH or CFHR5 polypeptide or subsequence. The bound protein may be detected using, for example, a detectably labeled anti-CFH/CFHR5 antibody. In one embodiment, at least one of the antibodies is specific for the variant form (e.g., does not bind to the wild-type CFH or CFHR5 polypeptide. In one embodiment, the variant polypeptide is detected using an immunoblot (Western blot) format.

D. Patient Screening/Diagnosis of AMD

Polymorphisms in the Factor H gene, such as those shown in TABLE 1A, TABLE 1B, TABLE 1C or identified as described herein, which correlate with AMD or with particular subtypes of AMD, are useful in diagnosing AMD or specific subtypes of AMD, or susceptibility thereto. Polymorphisms in the CFHR5 gene, such as those shown in TABLES 14 and 15 or identified as described herein, which correlate with AMD or with particular subtypes of AMD, are useful in diagnosing AMD or specific subtypes of AMD, or susceptibility thereto. These polymorphisms are also useful for screening for MPGNII and other Factor H-associated diseases.

Individuals identified as at high risk for developing AMD can take steps to reduce risk, including frequent ophthalmological examinations and treatments described below, known in the art, or developed in the future.

As described in Example 1, an at-risk CFH haplotype in combination with a triggering event (e.g., infection) appears to be sufficient for disease manifestation. Patients identified as at-risk for AMD can receive aggressive therapy (e.g., using antibiotics, anti-inflamatory agents, treatment with protective forms of CFH/CFHR5, or treatment with other modulators of CFH activity) at early signs of infection.

Combined detection of several such polymorphic forms (i.e., the presence or absence of polymorphisms at specified sited), for example, 1, 2, 3, 4, 5, 6, 7, 8, 9, 10, or all of the polymorphisms in the Factor H gene listed in TABLE 1A, TABLE 1B and/or TABLE 1C, alone or in combination with additional Factor H gene polymorphisms not included in TABLES 1A-1C, may increase the probability of an accurate diagnosis. Similarly, combined detection of several polymorphic forms in the CFHR5 gene, for example, 1, 2, 3, 4, 5, 6, 7, 8, 9, 10, or all of the polymorphisms in the CHFR5 gene listed in TABLES 14 and 15, alone or in combination with additional CFHR5 gene polymorphisms not included in TABLES 14 and 15, may increase the probability of an accurate diagnosis. In one embodiment, screening involves determining the presense or absense of at least one polymorphism in the Factor H gene and at least one polymorphism in the CFHR5 gene. In one embodiment, screening involves determining the presense or absense of at least 2, 3, or 4 polymorphisms in the Factor H gene in combination with and at least 2, 3, or 4 polymorphisms in the CFHR5 gene.

The polymorphisms in the Factor H and CFHR5 genes are useful in diagnosing AMD or specific subtypes of AMD, or susceptibility thereto, in family members of patients with AMD, as well as in the general population.

In diagnostic methods, analysis of Factor H polymorphisms and/or CFHR5 polymorphisms can be combined with analysis of polymorphisms in other genes associated with AMD, detection of protein markers of AMD (see, e.g., Hageman et al., patent publications US20030017501; US20020102581; WO0184149; and WO0106262), assessment of other risk factors of AMD (such as family history), with ophthalmological examination, and with other assays and procedures.

E. Identification of Patients for Drug Therapy

Polymorphisms in the Factor H gene and CFHR5 gene are also useful for identifying suitable patients for conducting clinical trials for drug candidates for AMD. Such trials are performed on treated or control populations having similar or identical polymorphic profiles at a defined collection of polymorphic sites in the Factor H gene and/or CFHR5 gene, or having similar or identical Factor H haplotypes and/or CFHR5 haplotypes. The use of genetically matched populations eliminates or reduces variation in treatment outcome due to genetic factors, leading to a more accurate assessment of the efficacy of a potential drug.

F. Screening Donor Tissue for Transplantation

Transplantation of organs (e.g., liver) and tissues (e.g., blood, hepatocytes) is increasingly common. It is desirable, in carrying out such transplantation, to avoid introducing into the recipient a deleterious form of Factor H or a Factor H-Related Protein and thereby increasing the recipient's risk of developing AMD. Thus, in one aspect of the invention, a donor tissue is tested to detect the presence or absence of a variation at a polymorphic site of a Factor H or CFHR5 gene to identify host tissues carrying risk haplotypes or other deleterious sequences. In addition or alternatively, organs and tissues can be tested for the expression of forms of Factor H or CFHR proteins, for example by using immunological assays as described herein. In one embodiment the transplanted tissue is blood or plasma (i.e., given in a blood transfusion or plasma replacement). Routine screening of donated blood to avoid administration of a protein associated with risk (e.g., the 1210C form of CFH) may avoid compromising the recipient.

G. Phenotypic Categories

Susceptibility to specific subtypes of AMD can be identified based on the association with particular haplotypes. Thus, the screening can be used to determine suitable therapies for groups of patients with different genetic subtypes of AMD.

The methods may be used for the diagnosis of AMD, which may be subdivided into phenotypic categories (for example, early AMD (ARM) geographic atrophy (GA) and exudative AMD (CNV)). The ARM and GA phenotypes may be further subdivided into distinct phenotypes (for example, RPE changes alone, >10 macular hard drusen, macular soft drusen, BB (cuticular) drusen, pigment epithelial detachment (PED), "Cherokee" atrophy, peninsular geographic atrophy and pattern geographic atrophy). For descriptions of these phenotypes see, e.g., Bird et al., 1995, Surv Ophthalmol 39, 367-74; and Klaver et al., 2001, Invest Ophthalmol Vis Sci 42, 2237-41.

H. Other Diseases

Polymorphisms in the Factor H and CFHR5 gene, such as those shown in TABLES 1A, 1B, 1C, 11, 14 and 15, can also be tested for association with other diseases, (for example, Alzheimer's disease, multiple sclerosis, lupus, and asthma) and conditions (for example, burn injuries, transplantation, and stroke) which involve dysregulation of the alternative complement pathway, that have known but hitherto unmapped genetic components. Without being limited to any particular mechanism of action, it is suggested herein that expression of variant Factor H and/or CFHR5 polypeptides is associated with dysregulation of the alternative complement pathway. The variant forms of Factor H and/or CHFR5 may have a causal effect on diseases involving a defect in the alternative complement pathway, or the presence of variant forms of Factor H and/or CFHR5 may indicate that another gene involved in the alternative complement pathway has a causal effect.

Polymorphisms in the Factor H gene may also be useful in mapping and treating diseases that map to chromosome 1q, in particular at or near 1q32 where the Factor H gene is located. This particular locus contains a number of complement pathway-associated genes. One group of these genes, referred to as the regulators of complement activation (RCA) gene cluster, contains the genes that encode Factor H, five Factor H-related genes and the beta subunit of coagulation factor XIII. A second cluster of complement-associated genes, including C4BPA, C4BPB, C4BPAL2, DAF (CD55) CR1, CR2, CR1L and MCP (CD46) lies immediately adjacent to the 1q25-31 locus.

VIII. Prevention and Treatment of AMD

A patient with a Factor H polymorphism can be treated by administering to a patient an antagonist of the variant Factor H polypeptide and/or variant CHFR5 polypeptide. An antagonist may include a therapeutic amount of an RNA complementary to the nucleotide sequence of a variant Factor H polypeptide and/or variant CHFR5 polypeptide or an antibody that specifically interacts with and neutralizes the activity of a variant Factor H polypeptide and/or variant CHFR5 polypeptide. Alternatively, AMD associated with the Factor H polymorphism and/or CFHR5 polymorphism can be treated by administering to a patient a form of Factor H and/or CHFR5 not associated with increased risk, such as the normal or wild-type Factor H protein and/or normal or wild-type CHFR5 polypeptide. In one method of the invention, a protective variant form of Factor H and/or protective variant form of CHFR5 is administered to a patient.

Therapeutic and prophylactic approaches in subjects identified as being at high risk for AMD include, but are not limited to, (1) increasing the amount or expression of neutral or protective forms of Factor H and/or neutral or protective forms of CHFR5; (2) decreasing the amount or expression of risk-associated forms of Factor H and/or risk-associated form of CHFR5; and (3) reducing activation of the complement alternative pathway. Examples of such therapeutic and prophylactic approaches include: (1) administration of neutral or protective forms of Factor H protein or therapeutically active fragments and/or neutral or protective forms of CHFR5 or therapeutically active fragments; (2) other wise increasing expression or activity of neutral and protective forms of Factor H; (3) interfering with expression of variant Factor H and/or variant CFHR5 proteins encoded by individuals with a risk haplotype by (e.g., by administration of antisense RNA); (4) reducing the amount of activity of a detrimental variant form.

Therapeutic agents (e.g., agents that increase or decrease levels of wild-type or variant Factor H or modulate its activity and/or agents that increase or decrease levels of wild-type or variant CFHR5 or modulate its activity) can be administered systemically (e.g., by i.v. injection or infusion) or locally (e.g., to the vicinity of the ocular RPE for treatment of AMD). Methods for administration of agents to the eye are well known in the medical arts and can be used to administer AMD therapeutics described herein. Exemplary methods include intraocular injection (e.g., retrobulbar, subretinal, intravitreal and intrachoridal), iontophoresis, eye drops, and intraocular implantation (e.g., intravitreal, sub-Tenons and sub-conjunctival). For examples, anti-VEGF antibody has been introduced into cynomolgus monkeys by intravitreal injection (see, e.g., Gaudreault et al., 2005, "Preclinical pharmacokinetics of Ranibizumab (rhuFabV2) after a single intravitreal administration" *Invest Ophthalmol Vis Sci.* 46:726-33), and bioactive VEGF and bFGF have been expressed in the eye via intravitreal implantation of sustained release pellets (Wong et al., 2001, "Intravitreal VEGF and bFGF produce florid retinal neovascularization and hemorrhage in the rabbit" *Curr Eye Res.* 22:140-7). Importantly, it has been discovered that Factor H is synthesized locally by the retinal pigment epithelium (see Example 1), indicating that local administration of agents has therapeutic benefit.

A) Administration of Therapeutic Factor H Polypeptides

Administration of neutral or protective forms of Factor H polypeptides and/or neutral or protective forms of CFHR5 polypeptides to subjects at risk for developing AMD (and/or with early stage disease) can be used to ameliorate the progression of the disease.

In one approach, recombinant Factor H polypeptide is administered to the patient. In one embodiment, the recombinant Factor H is encoded by a neutral haplotype sequence, which may be full-length (CFH/HF1), truncated (FHL1), or alternatively spliced form, or a biologically active fragment thereof. In another embodiment the recombinant Factor H has the sequence of a protective allele, either full-length or truncated form, or a protective biologically active fragment thereof. Methods for production of therapeutic recombinant proteins are well known and include methods described hereinbelow. The therapeutic polypeptide can be administered systemically (e.g., intravenously or by infusion) or locally (e.g., directly to an organ or tissue, such as the eye or the liver).

Some protective forms of Factor H and the CHFL1 protein are less than full-length. For example, fragments of neutral or protective forms of Factor H may be administered for treatment or prevention of AMD or MPGNII. In a particular embodiment, polypeptides encoded by CFH splice variants expressed in individuals with a protected phenotype are administered. These proteins can be identified by screening expression of CFH-related RNA in individuals homozygous for a protective or neutral haplotype.

In particular embodiments, the protective protein has a sequence corresponding to one or more exons of the CFH gene sequence. For example, the protective protein may have the sequence of full-length or truncated CFH protein, except that the amino acid residues encoded by 1, 2, 3 or more exons (which may or may not be contiguous) are deleted.

In one embodiment a protective Factor H protein of the invention has an amino acid sequence substantially identical to SEQ ID NO:2, with the proviso that the residue at position 402 is not histidine and the residue at position 1210 is not cysteine. In one embodiment the residue at position 62 is not valine. Preferably, the residue at position 62 is isoleucine. Preferably the residue at position 62 is isoleucine, the residue at position 402 is tyrosine and the residue at position 1210 is arginine. Preferably the protective Factor H protein has 95% amino acid identity to SEQ ID NO:2 or a fragment thereof; sometimes at least 95% amino acid identity, sometimes at least 98% amino acid identity, and sometimes at least 99% identity to the reference Factor H polypeptide of SEQ ID NO:2. The polypeptide sequence of an exemplary protective variant of human Factor H [SEQ ID NO:5] is shown in FIG. 10. This protective variant Factor H polypeptide has an isoleucine at amino acid position 62 and a tyrosine at amino acid position 402 (indicated in bold). The polypeptide sequence of an exemplary protective variant of HFL1, the truncated form of human Factor H (SEQ ID NO:6) is shown in FIG. 11. This protective variant truncated Factor H polypeptide has a isoleucine at amino acid position 62 and tyrosine at amino acid position 402 (indicated in bold).

In one embodiment a protective Factor H protein of the invention has an amino acid sequence substantially identical to SEQ ID NO:4 (FHL1). In one embodiment the residue at position 62 is not valine. Preferably, the residue at position 62 is isoleucine. Preferably the protective Factor H protein has 95% amino acid identity to SEQ ID NO:4 or a fragment thereof; sometimes at least 95% amino acid identity, sometimes at least 98% amino acid identity, and sometimes at least 99% identity to the reference Factor H polypeptide of SEQ ID NO:4.

In some embodiments the protective Factor H protein has one or more activities of the reference Factor H polypeptide. In one embodiment the activity is binding to heparin. In one embodiment the activity is binding to CRP. In one embodiment the activity is binding to C3b. In one embodiment the activity is binding to endothelial cell surfaces. In one embodiment the activity is C3b co-factor activity. In one embodiment, the protective Factor H protein has activity that is higher with respect to its normal function than the protein of SEQ ID NO:2. In one embodiment, the protective Factor H protein has activity with respect to its normal function that is higher than the protein of SEQ ID NO:4.

Assays for Factor H activities are well known and described in the scientific literature. For illustration and not limitation, examples of assays will be described briefly.

Binding of Protective Proteins (CFH Variants) to C3b or CRP

Interactions between C3b and CFH proteins can be analyzed by surface resonance using a Biacore 3000 system (Biacore AB, Uppsala, Sweden), as described previously (Manuelian et al., 2003, Mutations in factor H reduce binding affinity to C3b and heparin and surface attachment to endothelial cells in hemolytic uremic syndrome. *J Clin Invest* 111, 1181-90). In brief, C3b (CalBiochem, Inc), are coupled using standard amine-coupling to flow cells of a sensor chip (Carboxylated Dextran Chip CM5, Biacore AB, Uppsala, Sweden). Two cells are activated and C3b (50 µg/ml, dialyzed against 10 mM acetate buffer, pH 5.0) is injected into one flow cell until a level of coupling corresponding to 4000 resonance units is reached. Unreacted groups are inactivated using ethanolamine-HCl. The other cell is prepared as a reference cell by injecting the coupling buffer without C3b. Before each binding assay, flow cells will be washed thoroughly by two injections of 2 M NaCl in 10 mM acetate buffer, pH 4.6 and running buffer (PBS, pH 7.4). The Factor H protein is injected into the flow cell coupled with C3b or into the control cell at a flow rate of 5 ul/min at 25° C. Binding of Factor H to C3b is quantified by measuring resonance units over time, as described in Manuelian et al., 2003, supra.

Interactions between CRP and CHF proteins can be analyzed by surface resonance in an identical manner by substituting CRP for C3b in flow cells of a sensor chip Binding to Endothelial Cell Surface Binding of CHF proteins to endothelial cell surfaces is assayed by immunofluorescence staining of HUVECs and FACS analysis. HUVEC cells are kept in serum free DMEM (BioWhittaker) for 24 hrs prior to the assay. Cells are detached from the surface with DPBS/EDTA and washed twice with DPBS; $5 \times 10^5$ cells will be transferred into plastic tubes and unspecific binding sites will be blocked with 1% BSA/DPBS for 15 min prior to incubation with purified allele variants of factor H (5 µg). Controls are performed in the absence of the factor H isoform. Following binding of factor H, cells are thoroughly washed with DPBS. Polyclonal goat anti-human FH antiserum is used as a primary antibody (Cal-Biochem) (diluted 1:100), incubating cells at 4° C. for 15 minutes. Alexa-fluor 488-conjugated goat antiserum diluted 1:100 in blocking buffer is used as the secondary antibody. Cells are examined by flow cytometry (FACScalibur, Becton-Dickinson Immunocytometry, Mountain View, Calif., USA). Typically, 10,000 events are counted.

Cofactor Activity in Fluid Phase

For the fluid phase cofactor assay, C3b biotin (100 ng/reaction), Factor I (200 ng/reaction) and 100 ng of purified factor H are used in a total volume of 30 µl. Samples taken before and after addition of Factor I are separated by SDS-PAGE under reducing conditions and analyzed by Western blotting, detecting and quantitating C3b degradation products by Strepavidin-POD-conjugation (1:10000). C3b (40 µg) (CalBiochem) is biotinylated using the Biotin Labeling Kit (Roche Diagnostics, Mannheim, Germany), according to the manufacturer's instructions. In brief, 30 µg of C3b (CalBiochem) is labeled with D-biotinyl-epsilon-aminocaproic acid-N-hydroxysuccinimide ester for 2 hours at 25° C. Excess biotin is removed by gel filtration using a PBS equilibrated PD10 column (Amersham Biosciences). Also see Sanchez-Corral et al., 2002, *Am J. Hum. Genet.* 71:1285-95.

Heparin Binding Assay

Binding of purified CFH proteins (CFH402Y and CFH402H) to heparin is analyzed using heparin affinity chromatography in a high-performance liquid chromatograph (HPLC) system. 10 µg of CFH protein is diluted in ½×PBS and applied to a heparin-Sepharose affinity column (HiTrap, Amersham Biosciences) at a flow rate of 0.5 ml/min. The column is extensively washed with ½×PBS, and the bound CFH protein eluted using a linear salt gradient ranging from 75 to 500 mM NaCl, in a total volume of 10 ml and at a flow rate of 0.5 ml/min. Eluted fractions are assayed by SDS-PAGE and Western blot analysis. Elution of isoforms in different fractions is indicative that specific amino acid variations in the CFH protein can modulate binding of the protein to heparin. Also see, e.g., Pangburn et al., 1991, Localization of the heparin-binding site on complement Factor H, *J Biol Chem.* 266:16847-53.

CFHR5 Administration

In another approach, recombinant CFHR5 polypeptide is administered to the patient. In one embodiment, the recombinant CFHR5 has a neutral-type sequence, or a biologically active fragment thereof In another embodiment the recombinant CFHR5 has the sequence of a protective allele, or a protective biologically active fragment thereof. Methods for production of therapeutic recombinant proteins are well known and include methods described hereinbelow. The therapeutic polypeptide can be administered systemically (e.g., intravenously or by infusion) or locally (e.g., directly to an organ or tissue, such as the eye or the liver).

Therapeutic Compositions Containing CFH or CFHR5 Polypeptides

The invention provides therapeutic preparations of Factor H polypeptides, which may be wild-type or variants (e.g., neutral or protective variants), and may be full length forms, truncated forms, or biologically active fragments of the variant Factor H polypeptides. As described herein, protective Factor H proteins (and genes encoding them) can be identified by identifying an individual as having a protective haplotype and determining the amino acid sequence(s) of Factor H encoded in the genome of the individual, where a protective Factor H protein is encoded by an allele having a protective haplotype. Biologically active fragments may include any portion of the full-length Factor H polypeptide which confers a biological function on the variant protein. In some cases, a protective haplotype will be associated with expression of a less-than full length form of Factor H (i.e., in addition to FHL-1) due, for example, to the presense of a premature stop codon in the gene.

Therapeutically active fragments can also be identified by testing the effect of the protein on expression of AMD biomarkers. Exemplary AMD biomarkers include complement pathway components (for example, Factor I, Factor H, C1r, C3, C3a), C reactive protein, haptoglobin, apolipoprotein E, immunoglobulin heavy or light chain(s), alpha 1 antitrypsin, alpha 2 macroglobulin, transthyretin, creatinine, and others described in copending provisional application No. 60/715, 503 entitled "Biomarkers Associated With Age-Related Macular Degeneration."

The invention provides therapeutic preparations of CFHR5 polypeptides, which may be wild-type or variants (e.g., neutral or protective variants), and may be full length forms or biologically active fragments of the variant CFHR5 polypeptides. As described herein, protective CFHR5 proteins (and genes encoding them) can be identified by identifying an individual as having a protective haplotype and determining the amino acid sequence(s) of CFHR5 encoded in the genome of the individual, where a protective CFHR5 protein is encoded by an allele having a protective haplotype. Biologically active fragments may include any portion of the full-length CFHR5 polypeptide which confers a biological function on the variant protein. Therapeutically active fragments can also be identified by testing the effect of the protein on expression of AMD biomarkers as described above for Factor H.

Some forms of Factor H and CFHR5 can be isolated from the blood of genotyped donors, from cultured or transformed RPE cells derived from genotyped ocular donors, or from cell lines (e.g., glial or hepatic) that express endogenous Factor H. Alternatively, therapeutic proteins can be recombinantly produced (e.g., in cultured bacterial or eukaryotic cells) and purified using methods well known in the art and described herein. As noted above, some forms of Factor H and CFHR5 have been recombinantly expressed for research purposes. However, such research preparations are not suitable for therapeutic use. The present invention provides recombinant polypeptides suitable for administration to patients including polypeptides that are produced and tested in compliance with the Good Manufacturing Practice (GMP) requirements. For example, recombinant polypeptides subject to FDA approval must be tested for potency and identity, be sterile, be free of extraneous material, and all ingredients in a product (i.e., preservatives, diluents, adjuvants, and the like) must meet standards of purity, quality, and not be deleterious to the patient.

The invention provides a composition comprising a Factor H polypeptide or CFHR5 polypeptide, and a pharmaceutically acceptable excipient or carrier. The term "pharmaceutically acceptable excipient or carrier" refers to a medium that is used to prepare a desired dosage form of a compound. A pharmaceutically acceptable excipient or carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof. In one embodiment, the pharmaceutically acceptable excipient is not deleterious to a mammal (e.g., human patient) if administered to the eye (e.g., by intraocular injection). For intraocular administration, for example and not limitation, the therapeutic agent can be administered in a Balanced Salt Solution (BSS) or Balanced Salt Solution Plus (BSS Plus) (Alcon Laboratories, Fort Worth, Tex., USA). In a related aspect, the invention provides a sterile container, e.g. vial, containing a therapeutically acceptable Factor H protein, optionally a lyophilized preparation. Therapeutic Factor H proteins or CFHR5 polypeptides can be made recombinantly, as described above. Alternatively, Factor H protein or CFHR5 polypeptide can be isolated from cultured RPE cells (e.g., primary cultures) or other cells that express Factor H or CFHR5 endogenously.

The amount of neutral or protective forms of Factor H or truncated Factor H, or biologically active fragments thereof, or neutral or protective forms of CFHR5, or biologically active fragments thereof, to be administered to an individual can be determined. The normal plasma concentration of Factor H varies between 116 and 562 micrograms/ml and the half-life of Factor H in plasma is about 6½ days (for a recent review, see Esparza-Gordillo et al., 2004 "Genetic and environmental factors influencing the human factor H plasma levels" *Immunogenetics* 56:77-82). In one embodiment, exogenous Factor H can be administered to an individual in an amount sufficient to achieve a level similar to the plasma concentration of Factor H in a healthy individual, i.e., an amount sufficient to achieve a plasma level of from 50 to 600 mg/ml, such as from 100 to 560 mg/ml. The amount of Factor H to be administered to an individual (e.g., a 160 pound subject) can be, for example and not for limitation, from 10 milligrams to 5000 milligrams per dose, from 50 milligrams to 2000 milligrams per dose, from 100 milligrams to 1500 milligrams per dose, from 200 milligrams to 1000 milligrams per dose, or from 250 milligrams to 750 milligrams per dose. The frequency with which Factor H can be administered to an individual can be, for example and not for limitation, twice per day, once per day, twice per week, once per week, once every two weeks, once per month, once every two months, once every six months, or once per year. The amount and frequency of administration of Factor H to an individual can be readily determined by a physician by monitoring the course of treatment.

B) Gene Therapy Methods

In another approach, Factor H protein or CFHR5 polypeptide is administered by in vivo expression of protein encoded by exogenous polynucleotide (i.e., via gene therapy). In one example, gene therapy involves introducing into a cell a vector that expresses Factor H polypeptide or biologically active fragment or CFHR5 polypeptide or biologically active fragment.

Vectors can be viral or nonviral. A number of vectors derived from animal viruses are available, including those derived from adenovirus, adeno-associated virus, retroviruses, pox viruses, alpha viruses, rhadboviruses, and papillomaviruses. Usually the viruses have been attenuated to no longer replicate (see, e.g., Kay et al. 2001, *Nature Medicine* 7:33-40).

The nucleic acid encoding the Factor H polypeptide or CFHR5 polypeptide is typically linked to regulatory elements, such as a promoters and an enhancers, which drive transcription of the DNA in the target cells of an individual. The promoter may drive expression of the Factor H gene or CFHR5 gene in all cell types. Alternatively, the promoter may drive expression of the Factor H gene or CFHR5 gene only in specific cell types, for example, in cells of the retina or the kidney. The regulatory elements, operably linked to the nucleic acid encoding the Factor H polypeptide or CFHR5 polypeptide, are often cloned into a vector.

As will be understood by those of skill in the art, gene therapy vectors contain the necessary elements for the transcription and translation of the inserted coding sequence (and may include, for example, a promoter, an enhancer, other regulatory elements). Promoters can be constitutive or inducible. Promoters can be selected to target preferential gene expression in a target tissue, such as the RPE (for recent reviews see Sutanto et al., 2005, "Development and evaluation of the specificity of a cathepsin D proximal promoter in the eye" *Curr Eye Res.* 30:53-61; Zhang et al., 2004, "Concurrent enhancement of transcriptional activity and specificity of a retinal pigment epithelial cell-preferential promoter" *Mol Vis.* 10:208-14; Esumi et al., 2004, "Analysis of the VMD2 promoter and implication of E-box binding factors in its regulation" *J Biol Chem* 279:19064-73; Camacho-Hubner et al., 2000, "The Fugu rubripes tyrosinase gene promoter targets transgene expression to pigment cells in the mouse" *Genesis.* 28:99-105; and references therein).

Suitable viral vectors include DNA virus vectors (such as adenoviral vectors, adeno-associated virus vectors, lentivirus vectors, and vaccinia virus vectors), and RNA virus vectors (such as retroviral vectors). In one embodiment, an adeno-associated viral (AAV) vector is used. For recent reviews see Auricchio et al., 2005, "Adeno-associated viral vectors for retinal gene transfer and treatment of retinal diseases" *Curr Gene Ther.* 5:339-48; Martin et al., 2004, Gene therapy for optic nerve disease, *Eye* 18:1049-55; Ali, 2004, "Prospects for gene therapy" *Novartis Found Symp.* 255:165-72; Hennig et al., 2004, "AAV-mediated intravitreal gene therapy reduces lysosomal storage in the retinal pigmented epithelium and improves retinal function in adult MPS VII mice" *Mol Ther.* 10:106-16; Smith et al., 2003, "AAV-Mediated gene transfer slows photoreceptor loss in the RCS rat model of retinitis pigmentosa" *Mol Ther.* 8:188-95; Broderick et al., 2005, "Local administration of an adeno-associated viral vector expressing IL-10 reduces monocyte infiltration and subsequent photoreceptor damage during experimental autoimmune uveitis" *Mol Ther.* 12:369-73; Cheng et al., 2005, "Efficient gene transfer to retinal pigment epithelium cells with long-term expression. *Retina* 25:193-201; Rex et al., "Adenovirus-mediated delivery of catalase to retinal pigment epithelial cells protects neighboring photoreceptors from photo-oxidative stress. *Hum Gene Ther.* 15:960-7; and references cited therein).

Gene therapy vectors must be produced in compliance with the Good Manufacturing Practice (GMP) requirements rendering the product suitable for administration to patients. The present invention provides gene therapy vectors suitable for administration to patients including gene therapy vectors that are produced and tested in compliance with the GMP requirements. Gene therapy vectors subject to FDA approval must be tested for potency and identity, be sterile, be free of extraneous material, and all ingredients in a product (i.e., preservatives, diluents, adjuvants, and the like) must meet standards of purity, quality, and not be deleterious to the patient. For example, the nucleic acid preparation is demonstrated to be mycoplasma-free. See, e.g, Islam et al., 1997, An academic centre for gene therapy research and clinical grade manufacturing capability, *Ann Med* 29, 579-583.

Methods for administering gene therapy vectors are known. In one embodiment, Factor H or CFHR5 expression vectors are introduced systemically (e.g., intravenously or by infusion). In one embodiment, Factor H or CFHR5 expression vectors are introduced locally (i.e., directly to a particular tissue or organ, e.g., liver). In one preferred embodiment, Factor H or CFHR5 expression vectors are introduced directly into the eye (e.g., by ocular injection). For recent reviews see, e.g., Dinculescu et al., 2005, "Adeno-associated virus-vectored gene therapy for retinal disease" *Hum Gene Ther.* 16:649-63; Rex et al., 2004, "Adenovirus-mediated delivery of catalase to retinal pigment epithelial cells protects neighboring photoreceptors from photo-oxidative stress" *Hum Gene Ther.* 15:960-7; Bennett, 2004, "Gene therapy for Leber congenital amaurosis" *Novartis Found Symp.* 255:195-202; Hauswirth et al., "Range of retinal diseases potentially treatable by AAV-vectored gene therapy" *Novartis Found Symp.* 255:179-188, and references cited therein).

Thus in one aspect, the invention provides a preparation comprising a gene therapy vector encoding a Factor H protein or CFHR5 polypeptide, optionally a viral vector, where the gene therapy vector is suitable for administration to a human subject and in an excipient suitable for administration to a human subject (e.g., produced using GLP techniques). Optionally the gene therapy vector comprising a promoter that is expressed preferentially or specifically in retinal pigmented epithelium cells.

Nonviral methods for introduction of Factor H or CFHR5 sequences, such as encapsulation in biodegradable polymers (e.g., polylactic acid (PLA); polyglycolic acid (PGA); and co-polymers (PLGA) can also be used (for recent reviews see, e.g., Bejjani et al., 2005, "Nanoparticles for gene delivery to retinal pigment epithelial cells" *Mol Vis.* 11:124-32; Mannermaa et al., 2005, "Long-lasting secretion of transgene product from differentiated and filter-grown retinal pigment epithelial cells after nonviral gene transfer" *Curr Eye Res.* 2005 30:345-53; and references cited therein). Alternatively, the nucleic acid encoding a Factor H polypeptide or CFHR5 polypeptide may be packaged into liposomes, or the nucleic acid can be delivered to an individual without packaging without using a vector.

C) DNA Repair

In another approach, subjects at risk for developing AMD (and/or with early stage disease) can have a risk form of Factor H or CFHR5 replaced by a neutral or protective form of Factor H or CFHR5 by DNA repair. In one embodiment, triplex forming oligonucleotides designed to specifically bind to polymorphic sites in the Factor H or CFHR5 gene associated with a risk haplotype can be administered to an individual by viral or nonviral methods. Triplex-forming oligonucleotides bind to the major groove of duplex DNA in a sequence-specific manner and provoke DNA repair, resulting in the targeted modification of the genome (for a recent review see Kuan et al., 2004, "Targeted gene modification using triplex-forming oligonucleotides" *Methods Mol Biol.* 262:173-94). A triplex-forming oligonucleotide that binds to a sequence spanning a polymorphism associated with a risk haplotype provokes DNA repair, resulting in the modification of the sequence from a risk allele to a neutral or protective allele and can ameliorate the development or progression of disease.

D) Introduction of Cells, Tissues, or Organs Expressing a Neutral or Protective Form of Factor H Protein or CFHR5 Polypeptide In another approach, cells expressing neutral or protective forms of Factor H or Factor H-Related proteins (e.g., CFHR5) are administered to a patient. In an embodiment the recipient is heterozygous or, more often, homozygous for a risk haplotype. For example, hepatocyte transplantation has been used as an alternative to whole-organ transplantation to support many forms of hepatic insufficiency (see, e.g., Ohashi et al., Hepatocyte transplantation: clinical and experimental application, *J Mol Med.* 2001 79:617-30). According to this method, hepatocytes or other CFH or CFHR5-expressing cells are administered (e.g., infused) to a patient in need of treatment. These cells migrate to the liver or other organ, and produce the therapeutic protein. Also see, e.g., Alexandrova et al., 2005, "Large-scale isolation of human hepatocytes for therapeutic application" *Cell Transplant.* 14(10):845-53; Cheong et al., 2004, "Attempted treatment of factor H deficiency by liver transplantation" *Pediatr Nephrol.* 19:454-8; Ohashi et al., 2001, "Hepatocyte transplantation: clinical and experimental application" *J Mol Med.* 79:617-30; Serralta et al., 2005, "Influence of preservation solution on the isolation and culture of human hepatocytes from liver grafts" *Cell Transplant.* 14(10):837-43; Yokoyama et al., 2006, "In vivo engineering of metabolically active hepatic tissues in a neovascularized subcutaneous cavity" *Am. J. Transplant.* 6(1):50-9; Dhawan et al., 2005, "Hepatocyte transplantation for metabolic disorders, experience at King's College hospital and review of literature." *Acta Grastroenterol. Belg.* 68(4): 457-60; Bruns et al., 2005, "Injectable liver: a novel approach using fibrin gel as a matrix for culture and intrahepatic transplantation of hepatocytes" *Tissue Eng.* 11(11-12):1718-26. Other cell types that may be used include, for illustration and not limitation, kidney and pancreatic cells. In one embodiment, the administered cells are engineered to express a recombinant form of the protein.

In another, related approach, therapeutic organ transplantation is used. Most of the body's systemic Factor H is produced by the liver, making transplation of liver tissue the preferred method. See, Gerber et al., 2003, "Successful (?) therapy of hemolytic-uremic syndrome with factor H abnormality" *Pediatr Nephrol.* 18:952-5.

In another approach, a protective form of CFH protein is delivered to the back of the eye by injection into the eye (e.g. intravitreal) or via encapsulated cells. Neurotech's Encapsulated Cell Technology (ECT), as an example, is a unique technology that allows for the sustained, longterm delivery of therapeutic factors to the back of the eye. See (http://www-.neurotech.fr). ECT implants consist of cells that have been genetically modified to produce a specific therapeutic protein that are encapsulated in a semi-permeable hollow fiber membrane. The cells continuously produce the therapeutic protein that diffuses out of the implant and into the eye (Bush et al 2004). CNTF delivered to the human eye by ECT devices was recently shown to be completely successful and associated with minimal complications in 10 patients enrolled in a Phase I clinical trial (Sieving et al 2005). Also see Song et al., 2003; Tao 2002., and Hammang et al., U.S. Pat. No. 6,649,184. In one embodiment of the present invention, a protective form of Factor H (including the so-called neutral form) is expressed in cells and administered in an encapsulated form. In one embodiment, the cells used are the NTC-201 human RPE line (ATCC # CRL-2302) available from the American Type Culture Collection P.O. Box 1549, Manassas, Va. 20108.

E) Therapy to Decrease Levels of Risk Variant of Factor H or CFHR5

Loss of the normal or protective function of Factor H or CFHR5 may be associated with AMD. Non-synonymous polymorphisms in the Factor H and CFHR5 genes, such as those shown in TABLES 1A, 1B, 1C, 11, 14 and 15, showing the strongest correlation with AMD and resulting in a variant Factor H polypeptide or CFHR5 polypeptide, are likely to have a causative role in AMD. For example, the variant Factor H or CFHR5 may act as a so-called "dominant-negative" mutant interfering with normal Factor H or CFHR5 function.

Any method of reducing levels of the risk forms of Factor H or CFHR5 in the eye or systemically may be used for treatment including, for example, inhibiting transcription of a Factor H or CFHR5 gene, inhibiting translation of Factor H or CFHR5 RNA, increasing the amount or activity of a neutral or protective form of Factor H or truncated Factor H, or biologically active fragment thereof, increasing the amount or activity of a neutral or protective form of CFHR5 polypeptide, or biolgocially active fragment thereof, or decreasing the amount or activity of Factor H protein or CFHR5 polypeptides (e.g., by plasmaphoresis, antibody-directed plasmaphoresis, or complexing with a Factor H or CFHR5 binding moiety, e.g., heparin or variant specific antibody). In some embodiments levels of Factor H or CFHR5 are preferentially reduced in the eye (e.g., RPE) relative to other tissues. For illustration and not limitation, several methods are briefly described below.

In one approach, a subject identified as being at risk for AMD is treated by administration of heparin. Heparin and heparin derivatives (including heparinoids) may have promising therapeutic properties for the treatment various complement-associated diseases, including MPGNII (Floege et al., 1993; Girardi, 2005; Diamond and Karnovsky, 1986; Striker, 1999; Rops et al., 2004). In view of the association between AMD and MPGNII disclosed herein, heparin and heparin derivatives (including heparinoids) may be efficacious for the treatment of AMD. In a clinical trial of patients with chronic proliferative glomerulonephritis receiving daily subcutaneous injections of heparin for over one year, Cade and colleagues reported improved creatinine clearance and a regression of glomerular hypercellularity (Cade et al., 1971). Both heparin and low molecular weight heparin (Enoxaparin) have been shown to prevent the progression of antiphospholipid antibody syndrome in mice by blocking the alternative and classical pathways of the complement cascade (Girardi et al., 2004). The anti-complement activity of heparin includes blockade of the formation of C3bBb, the amplification convertase by the alternative pathway; fluid phase heparin prevents the generation of C3bBb by inhibiting the interaction of C3b with factor B and factor D (Weiler et al., 1976).

F) Administration of Inhibitory Nucleic Acids

Antisense nucleic acids—Antisense nucleic acids, such as purified anti-sense RNA complementary to the RNA encoding a variant Factor H polypeptide can be used to inhibit expression of a Factor H gene associated with a risk haplotype. For recent reviews see, e.g., Gomes et al., 2005, "Intraocular delivery of oligonucleotides" Curr Pharm Biotechnol. 6:7-15; and Henry et al., 2004, "Setting sights on the treatment of ocular angiogenesis using antisense oligonucleotides" Trends Pharmacol Sci 25:523-7; and references cited therein.

RNA Interference—Double stranded RNA (dsRNA) inhibition methods can also be used to inhibit expression of HF1. The RNA used in such methods is designed such that at least a region of the dsRNA is substantially identical to a region of the HF1 gene; in some instances, the region is 100% identical to the HF1 gene. For use in mammals, the dsRNA is typically about 19-30 nucleotides in length (i.e., short interfering RNAs are used (siRNA or RNAi)), and most often about 21 nucleotides in length. Methods and compositions useful for performing dsRNAi and siRNA are discussed, for example, in PCT Publications WO 98/53083; WO 99/32619; WO 99/53050; WO 00/44914; WO 01/36646; WO 01/75164; WO 02/44321; and U.S. Pat. No. 6,107,094. siRNA can be is synthesized in vitro and administered to a patient. Alternatively, RNAi strategies can be successfully combined with vector-based approaches to achieve synthesis in transfected cells of small RNAs from a DNA template (see, e.g., Sui et al., 2002, "A DNA vector-based RNAi technology to suppress gene expression in mammalian cells" Proc Natl Acad Sci USA 99:5515-20; and Kasahara and Aoki, 2005, "Gene silencing using adenoviral RNAi vector in vascular smooth muscle cells and cardiomyocytes" Methods Mol Med. 112:155-72; and references cited therein).

Ribozymes—Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding human Factor H. Specific ribozyme cleavage sites within any potential RNA target are initially identified by scanning the target molecule for ribozyme cleavage sites which include the sequences such as, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays. Properties of ribozymes are well known in the art; for a general description see patents by Cech (U.S. Pat. No. 6,180,399; U.S. Pat. No. 5,869,254; U.S. Pat. No. 6,025,167; U.S. Pat. No. 5,854,038; U.S. Pat. No. 5,591,610; U.S. Pat. No. 5,667,969; U.S. Pat. No. 5,354,855;U.S. Pat. No. 5,093,246; U.S. Pat. No. 5,180,818; U.S. Pat. No. 5,116,742; U.S. Pat. No. 5,037,746; and U.S. Pat. No. 4,987,071). Ribozymes and other inhibitory nucleic acids can be designed to preferentially inhibit expression of a gene having a sequence associated with a risk haplotype. Thus, a ribozyme that recognizes the sequence spanning the polymorphism and cleaving adjacent to GUA recognizes the risk form but not the neutral or protective form, allowing selective cleavage (Dawson et al., 2000, "Hammerhead ribozymes selectively suppress mutant type I collagen mRNA in osteogenesis imperfecta fibroblasts" Nucleic Acids Res. 28:4013-20; Blalock et al., 2004 "Hammerhead ribozyme targeting connective tissue growth factor mRNA blocks transforming growth factor-beta mediated cell proliferation" Exp Eye Res. 78:1127-36).

Triplex-Forming Oligonucleotides—Triplex-forming oligonucleotides bind to the major groove of duplex DNA in a sequence-specific manner and provoke DNA repair, resulting in the targeted modification of the genome (for a recent review see Kuan et al., 2004, "Targeted gene modification using triplex-forming oligonucleotides" *Methods Mol Biol.* 262:173-94). Oligonucleotides can be designed to specifically bind to polymorphic sites in the Factor H gene associated with a risk haplotype. A triplex-forming oligonucleotide that binds to a sequence spanning a polymorphism associated with a risk haplotype provokes DNA repair, resulting in the modification of the sequence from a risk allele to a neutral or protective allele.

Similar antisense nucleic acid, RNA interference, ribozyme and triplex-forming pliognucleotide methodologies as described above may be used to reduce levels of risk forms of CFHR5 in the eye or systemically for treatment of AMD.

It will be understood that inhibitory nucleic acids can be administered as a pharmaceutical composition or using gene therapy methods.

G) Antibody Therapy

In one aspect, an anti-HF1 antibody that specifically interacts with and neutralizes the activity of a variant Factor H polypeptide is administered to an individual with or at risk for AMD. In one embodiment, the antibody recognizes both wild-type and variant Factor H protein. In one embodiment, the antibody recognizes the variant but not the wild-type Factor H protein. In another aspect, an anti-CFHR5 antibody that specifically interacts with and neutralizes the activity of a variant CFHR5 polypeptide is administered to an individual with or at risk for AMD. In one embodiment, the antibody recognizes both wild-type and variant CFHR5 protein. In one embodiment, the antibody recognizes the variant but not the wild-type CFHR5 protein. The antibody can be administered systemically or locally (see, e.g., Gaudreault et al., 2005, "Preclinical pharmacokinetics of Ranibizumab (rhuFabV2) after a single intravitreal administration" *Invest Ophthalmol Vis Sci.* 46:726-33). Methods for making anti-HF1 and anti-CFHR5 antibodies are known in the art, and include methods described below. In a related aspect, an agent that preferentially interacts with and reduces the activity of a variant Factor H polypeptide and/or CFHR5 polypeptide is administered to an individual with or at risk for AMD.

H) Modulators of the Alternative Pathway

In one aspect the invention provides methods for treating AMD by administering an agent (e.g., native protein, recombinant protein, antibody, or small molecule) directed at modulating the alternative pathway (AP) of the complement cascade, either locally in the eye or at the systemic level. In one embodiment, the treatment comprises administering an agent that modulates the AP directly. In one embodiment, the treatment comprises administering an agent that modulates the triggering of the AP (e.g., microbes). In one embodiment, the treatment comprises administering an agent that modulates pathways downstream from the AP. Exemplary agents that modulate the AP are known in the art and include, but are not limited to, DFP, PR226, BCX-1470, FUT-175, sMCP, PS-oligo, Compstatin, Fucan, and GCRF (see, e.g., Makrides, 1998, "Therapeutic inhibition of the complement system" *Pharmacol Rev.* 50:59-87; Holland et al., 2004, "Synthetic small molecule complement inhibitors" *Curr Opin Investig Drugs* 5:1163-73; Holers et al., 2004, "The alternative pathway of complement in disease: opportunities for therapeutic targeting" *Mol Immunol.* 41:147-52). AP modulators can be administered systemically or by intraocular injection or other methods known for delivery of compounds to the eye.

I) Drug Screening/Antagonists of Risk Variant Factor H or Variant CFHR5

The invention provides a method of screening for an agent effective for treatment of AMD by contacting a variant protein, host cell or transgenic animal expressing a Factor H or CFHR5 variant, and monitoring binding, expression, processing or activity of the variant. In an embodiment, the Factor H variant has valine at amino acid 62 and/or has histidine at amino acid 402 and/or has cysteine at amino acid 1210. In an embodiment, the CFHR5 variant has a serine at amino acid 46.

Antagonists of variant Factor H polypeptides (e.g., variants associated with risk haplotypes) can be used to treat AMD. Antagonists may suppress expression of variant Factor H, suppress activity, or reduce RNA or protein stability. Antagonists can be obtained by producing and screening large combinatorial libraries, which can be produced for many types of compounds in a step-wise and high throughput fashion. Such compounds include peptides, polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates, and the like. Large combinatorial libraries of the compounds can be constructed by methods known in the art. See e.g., WO 95/12608; WO 93/06121; WO 94/08051; WO 95/35503; WO 95/30642 and WO 91/18980. Libraries of compounds are initially screened for specific binding to the variant Factor H polypeptide. Compounds with in vitro binding activity can also be assayed for their ability to interfere with a biological activity of the variant Factor H polypeptide, for example, binding to C3b or to heparin. Antagonist activity can be assayed in either a cell-based system or in a transgenic animal model in which exogenous variant Factor H polypeptide is expressed.

Antagonists of variant CFHR5 polypeptides (e.g., variants associated with risk haplotypes) can be used treat AMD and can be obtained as described above for variant Factor H antagonists.

J) Patient Specific Therapy

Customized therapies can be devised for groups of patients with different genetic subtypes of AMD, based upon the presence of certain polymorphisms in the Factor H gene or CFHR5 gene having causative roles in AMD and having elucidated the effect of these polymorphisms on the expression level and/or biological activity of variant Factor H polypeptides or CFHR5 polypeptides. For example, if a polymorphism in Factor H or CFHR5 causes AMD in an animal model by increasing the expression level and/or biological activity of a variant Factor H polypeptide or CFHR5 polypeptide, AMD associated with the Factor H or CFHR5 polymorphism can be treated by administering to a patient an antagonist of the variant Factor H polypeptide or variant CFHR5 polypeptide.

K) Assessing Therapeutic Efficacy Using AMD Biomarkers

As noted above, therapeutic efficacy of particular fragments of CFH or CFHR proteins can also be determined by testing the effect of the protein on expression of AMD biomarkers. Exemplary AMD biomarkers include those described hereinabove. These AMD-associated proteins (biomarkers) are present in individuals with AMD at different (elevated or reduced) levels compared to healthy individuals. The invention provides methods of assessing the efficacy of treatment of AMD and monitoring the progression of AMD by determining a level of a biomarker(s) in an individual with AMD being treated for the disease and comparing the level of the biomarker(s) to an earlier determined level or a reference level of the biomarker. As described in copending provisional application No. 60/715,503 the level of the biomarker(s) can be determined by any suitable method, such as conventional techniques known in the art, including, for example and not for limitation, separation-based methods (e.g., gel electrophoresis), immunoassay methods (e.g., antibody-based detection) and function-based methods (e.g., enzymatic or binding activity). In one embodiment, a method of assessing the efficacy of treatment of AMD in a individual involves obtaining a sample from the individual and determining the level of the biomarker(s) by separating proteins by 2-dimensional difference gel electrophoresis (DIGE).

VIII. Factor H and CFHR5 Nucleic Acids

A) Primers and Probes

The invention provides nucleic acids adjacent to or spanning the polymorphic sites. The nucleic acids can be used as probes or primers (including Invader, Molecular Beacon and other fluorescence resonance energy transfer (FRET) type probes) for detecting Factor H polymorphisms. In one embodiment, the probes or primers recognize the insertion in intron 2 but do not recognize the wild-type sequence. Exemplary nucleic acids comprise sequences that span at least one of the polymorphisms listed in TABLES 1A, 1B, 1C, 11, 14 and 15 in which the polymorphic position is occupied by an alternative base for that position. The base for that position, which is found more frequently in the control population, is denoted the normal or wild-type sequence, whereas the alternative base for that position, which is found less frequently in the control population, is denoted the variant sequence. The nucleic acids also comprise sequences that span other polymorphisms known in the Factor H and CFHR5 genes, such as polymorphisms identified in Tables A and B above.

B) Expression Vectors and Recombinant Production of Factor H and CFHR5 Polypeptides The invention provides vectors comprising nucleic acid encoding the Factor H polypeptide. The Factor H polypeptide may be wild-type or a variant (e.g., a protective variant) and may be a full-length form (e.g., HF1) or a truncated form. The nucleic acid may be DNA or RNA and may be single-stranded or double-stranded.

Some nucleic acids encode full-length, variant forms of Factor H polypeptides. The variant Factor H polypeptide may differ from normal or wild-type Factor H at an amino acid encoded by a codon including one of any non-synonymous polymorphic position known in the Factor H gene. In one embodiment, the variant Factor H polypeptides differ from normal or wild-type Factor H polypeptides at an amino acid encoded by a codon including one of the non-synonymous polymorphic positions shown in TABLE 1A, TABLE 1B and/or TABLE 1C, that position being occupied by the amino acid shown in TABLE 1A, TABLE 1B and/or TABLE 1C. It is understood that variant Factor H genes may be generated that encode variant Factor H polypeptides that have alternate amino acids at multiple polymorphic sites in the Factor H gene.

The invention provides vectors comprising nucleic acid encoding the CFHR5 polypeptide. The CFHR5 polypeptide may be wild-type or a variant (e.g., a protective variant). The nucleic acid may be DNA or RNA and may be single-stranded or double-stranded.

Some nucleic acids encode full-length, variant forms of CFHR5 polypeptides. The variant CFHR5 polypeptide may differ from normal or wild-type CFHR5 at an amino acid encoded by a codon including one of any non-synonymous polymorphic position known in the CFHR5 gene. In one embodiment, the variant CFHR5 polypeptides differ from normal or wild-type CFHR5 polypeptides at an amino acid encoded by a codon including one of the non-synonymous polymorphic positions shown in TABLES 14 and 15, that position being occupied by the amino acid shown in TABLES 14 and 15. It is understood that variant CFHR5 genes may be generated that encode variant CFHR5 polypeptides that have alternate amino acids at multiple polymorphic sites in the CFHR5 gene.

Expression vectors for production of recombinant proteins and peptides are well known (see Ausubel et al., 2004, Current Protocols In Molecular Biology, Greene Publishing and Wiley-Interscience, New York). Such expression vectors include the nucleic acid sequence encoding the Factor H polypeptide linked to regulatory elements, such a promoter, which drive transcription of the DNA and are adapted for expression in prokaryotic (e.g., $E.\ coli$) and eukaryotic (e.g., yeast, insect or mammalian cells) hosts. A variant Factor H or CFHR5 polypeptide can be expressed in an expression vector in which a variant Factor H or CFHR5 gene is operably linked to a promoter. Usually, the promoter is a eukaryotic promoter for expression in a mammalian cell. Usually, transcription regulatory sequences comprise a heterologous promoter and optionally an enhancer, which is recognized by the host cell. Commercially available expression vectors can be used. Expression vectors can include host-recognized replication systems, amplifiable genes, selectable markers, host sequences useful for insertion into the host genome, and the like.

Suitable host cells include bacteria such as $E.\ coli$, yeast, filamentous fungi, insect cells, and mammalian cells, which are typically immortalized, including mouse, hamster, human, and monkey cell lines, and derivatives thereof. Host cells may be able to process the variant Factor H or CFHR5 gene product to produce an appropriately processed, mature polypeptide. Such processing may include glycosylation, ubiquitination, disulfide bond formation, and the like.

Expression constructs containing a variant Factor H or CFHR5 gene are introduced into a host cell, depending upon the particular construction and the target host. Appropriate methods and host cells, both procarytic and eukaryotic, are well-known in the art. Recombinant full-length human Factor H has been expressed for research purposes in Sf9 insect cells (see Sharma and Pangburn, 1994, Biologically active recombinant human complement factor H: synthesis and secretion by the baculovirus system, *Gene* 143:301-2). Recombinant fragments of human Factor H have been expressed for research purposes in a variety of cell types (see, e.g., Cheng et al., 2005, "Complement factor H as a marker for detection of bladder cancer" *Clin Chem.* 5:856-63; Vaziri-Sani et al., 2005, "Factor H binds to washed human platelets" *J Thromb Haemost.* 3:154-62; Gordon et al., 1995, "Identification of complement regulatory domains in human factor H" *J Immunol.* 155:348-56). Recombinant full-length human CFHR5 has been expressed for research purposes in Sf9 insect cells (see McRae et al., 2001, Human Factor H-related Protein 5 (FHR-5), *J Biol. Chem.* 276:6747-6754).

A variant Factor H or CFHR5 polypeptide may be isolated by conventional means of protein biochemistry and purification to obtain a substantially pure product. For general methods see Jacoby, Methods in Enzymology Volume 104, Academic Press, New York (1984); Scopes, Protein Purification, Principles and Practice, 2nd Edition, Springer-Verlag, New York (1987); and Deutscher (ed) Guide to Protein Purification, Methods in Enzymology, Vol. 182 (1990). Secreted proteins, like Factor H or CFHR5, can be isolated from the medium in which the host cell is cultured. If the variant Factor H or CFHR5 polypeptide is not secreted, it can be isolated from a cell lysate.

In one embodiment the vector is an expression vector for production of a variant Factor H protein having a sequence having non-wildtype sequence at one or more of the polymorphic sites shown in TABLES 1A, 1B and/or 1C.

In one embodiment the vector is an expression vector for production of a variant Factor H protein having a sequence of a protective variant of Factor H.

In one embodiment the vector is an expression vector for production of a variant CFHR5 protein having a sequence having non-wildtype sequence at one or more of the polymorphic sites shown in TABLES 14 and 15.

In one embodiment the vector is an expression vector for production of a variant CFHR5 protein having a sequence of a protective variant of Factor H.

C) Gene Therapy Vectors

Methods for expression of Factor H polypeptides or CFHR5 polypeptides for gene therapy are known and are described in Section IV(A) above.

XI. Antibodies

The invention provides Factor H-specific antibodies that may recognize the normal or wild-type Factor H polypeptide or a variant Factor H polypeptide in which one or more non-synonymous single nucleotide polymorphisms (SNPS) are present in the Factor H coding region. In one embodiment, the invention provides antibodies that specifically recognize variant Factor H polypeptides or fragments thereof, but not Factor H polypeptides not having a variation at the polymorphic site.

The invention also provides CFHR5-specific antibodies that may recognize the normal or wild-type CFHR5 polypeptide or a variant CFHR5 polypeptide in which one or more non-synonymous single nucleotide polymorphisms (SNPs) are present in the CFHR5 coding region. In one embodiment, the invention provides antibodies that specifically recognize variant CFHR5 polypeptides or fragments thereof, but not CFHR5 polypeptides not having a variation at the polymorphic site.

The antibodies can be polyclonal or monoclonal, and are made according to standard protocols. Antibodies can be made by injecting a suitable animal with a variant Factor H or variant CFHR5 polypeptide, or fragment thereof, or synthetic peptide fragments thereof. Monoclonal antibodies are screened according to standard protocols (Koehler and Milstein 1975, *Nature* 256:495; Dower et al., WO 91/17271 and McCafferty et al., WO 92/01047; and Vaughan et al., 1996, *Nature Biotechnology*, 14: 309; and references provided below). In one embodiment, monoclonal antibodies are assayed for specific immunoreactivity with the variant Factor H or CFHR5 polypeptide, but not the corresponding wild-type Factor H or CFHR5 polypeptide, respectively. Methods to identify antibodies that specifically bind to a variant polypeptide, but not to the corresponding wild-type polypeptide, are well-known in the art. For methods, including antibody screening and subtraction methods; see Harlow & Lane, Antibodies, A Laboratory Manual, Cold Spring Harbor Press, New York (1988); Current Protocols in Immunology (J. E. Coligan et al., eds., 1999, including supplements through 2005); Goding, Monoclonal Antibodies, Principles and Practice (2d ed.) Academic Press, New York (1986); Burioni et al., 1998, "A new subtraction technique for molecular cloning of rare antiviral antibody specificities from phage display libraries" *Res Virol.* 149(5):327-30; Ames et al., 1994, Isolation of neutralizing anti-C5a monoclonal antibodies from a filamentous phage monovalent Fab display library. *J Immunol.* 152 (9):4572-81; Shinohara et al., 2002, Isolation of monoclonal antibodies recognizing rare and dominant epitopes in plant vascular cell walls by phage display subtraction. *J Immunol Methods* 264(1-2):187-94. Immunization or screening can be directed against a full-length variant protein or, alternatively (and often more conveniently), against a peptide or polypeptide fragment comprising an epitope known to differ between the variant and wild-type forms. Particular variants include the Y402H or I62V variants of CFH and HFL1, tha R1210C variant of CFH, the P46S variant of CFHR5, and truncated forms of CFH. In one embodiment the HF1 is measured. As discussed above, in one embodiment the ratio of HFL1 and CHF is measured. Monoclonal antibodies specific for variant Factor H or CFHR5 polypeptides (i.e., which do not bind wild-type proteins, or bind at a lower affinity) are useful in diagnostic assays for detection of the variant forms of Factor H or CFHR5, or as an active ingredient in a pharmaceutical composition.

The present invention provides recombinant polypeptides suitable for administration to patients including antibodies that are produced and tested in compliance with the Good Manufacturing Practice (GMP) requirements. For example, recombinant antibodies subject to FDA approval must be tested for potency and identity, be sterile, be free of extraneous material, and all ingredients in a product (i.e., preservatives, diluents, adjuvants, and the like) must meet standards of purity, quality, and not be deleterious to the patient.

The invention provides a composition comprising an antibody that specifically recognizes a Factor H or CFHR5 polypeptide (e.g., a normal or wild-type Factor H polypeptide or a variant Factor H polypeptide, or a normal or wild-type CFHR5 polypeptide or a variant CFHR5 polypeptide) and a pharmaceutically acceptable excipient or carrier.

In a related aspect, the invention provides a sterile container, e.g. vial, containing a therapeutically acceptable Factor H-specific or CFHR5-specific antibody. In one embodiment it is a lyophilized preparation.

In a related aspect, the invention provides pharmaceutical preparations of human or humanized anti-Factor H or anti-CFHR5 antibodies for administration to patients. Humanized antibodies have variable region framework residues substantially from a human antibody (termed an acceptor antibody) and complementarity determining regions substantially from a mouse-antibody, (referred to as the donor immunoglobulin). See, Peterson, 2005, Advances in monoclonal antibody technology: genetic engineering of mice, cells, and immunoglobulins, *ILAR J.* 46:314-9, Kashmiri et al., 2005, SDR grafting—a new approach to antibody humanization, *Methods* 356:25-34, Queen et al., *Proc. Natl: Acad. Sci. USA* 86:10029-10033 (1989), WO 90/07861, U.S. Pat. No. 5,693,762, U.S. Pat. No. 5,693,761, U.S. Pat. No. 5,585,089, U.S. Pat. No. 5,530,101, and Winter, U.S. Pat. No. 5,225,539. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly, (2) is adjacent to a CDR region, (3) otherwise interacts with a CDR region (e.g. is within about 6 Å of a CDR region), or (4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

IX. Identification of Risk, Protective, and Neutral Variations and Haplotypes The invention provides methods of screening for polymorphic sites linked to polymorphic sites in the Factor H gene and/or CFHR5 gene described in TABLES 1A, 1B, 1C, 11, 14 and 15. These methods involve identifying a polymorphic site in a gene that is linked to a polymorphic site in the Factor H gene or CFHR5 gene, wherein the polymorphic form of the polymorphic site in the Factor H gene or CFHR5 gene is associated AMD (e.g., increased or decreased risk), and determining haplotypes in a population of individuals to indicate whether the linked polymorphic site has a polymorphic form in equilibrium or disequilibrium with the polymorphic form of the Factor H gene or CFHR5 gene that correlates with the AMD phenotype.

Polymorphisms in the Factor H gene or CFHR5 gene, such as those shown in TABLES 1A, 1B, 1C, 11, 14 and 15, can be used to establish physical linkage between a genetic locus associated with a trait of interest and polymorphic markers that are not associated with the trait, but are in physical proximity with the genetic locus responsible for the trait and co-segregate with it. Mapping a genetic locus associated with a trait of interest facilitates cloning the gene(s) responsible for the trait following procedures that are well-known in the art.

Polymorphisms in the Factor H gene or CFHR5 gene, such as those shown in TABLES 1A, 1B, 1C, 11, 14 and 15, can be used in familial linkage studies to determine which polymorphisms co-segregate with a phenotypic trait, to determine individuals who require therapy, and to determine the effects of therapy.

Linkage is analyzed by calculation of a LOD (log of the odds) score, which is the $\log_{10}$ of the ratio of the likelihood of obtaining observed segregation data for a marker and a genetic locus when the two are located at a recombination fraction theta, versus the situation in which the two are not linked (segregating independently). See Thompson & Thompson, Genetics in Medicine (5th ed, W.B. Saunders Company, Philadelphia, 1991) and Strachan, "Mapping the human genome" in The Human Genome (BIOS Scientific Publishers Ltd, Oxford) Chapter 4). A LOD score of 3 indicates a 1000 to 1 odds against an apparent observed linkage being a coincidence. A LOD score of +3 or greater is considered definitive evidence that two loci are linked, whereas a LOD score of −2 or less is considered definitive evidence against linkage.

X. Transgenic Non-Human Animals

The invention provides transgenic non-human animals capable of expressing human variant Factor H or CFHR5 polypeptides. Transgenic non-human animals may have one or both of alleles of the endogenous Factor H or CFHR5 gene inactivated. Expression of an exogenous variant Factor H or CFHR5 gene is usually achieved by operably linking the gene to a promoter and optionally an enhancer, and then microinjecting the construct into a zygote following standard protocols. See Hogan et al., "Manipulating the Mouse Embryo, A Laboratory Manual," Cold Spring Harbor Laboratory. The endogenous Factor H or CFHR5 genes can be inactivated by methods known in the art (Capecchi, 1989). Factor H deficient mice are available for the introduction of exogenous human variant Factor H genes. Transgenic animals expressing human or non-human variant Factor H or CFHR5 polypeptides provide useful drug screening systems and as models of AMD and other complement related diseases. Transgenic animals may also be used for production of recombinant CFH and CFHR5 proteins of the invention (see, e.g. U.S. Pat. Nos. 6,066,725; 6,013,857; 5,994,616; and 5,959,171; Lillico et al., 2005; Houdebine, 2000).

XI. Kits

The invention provides reagents, devices and kits detecting Factor H or CFHR5 polymorphisms and haplotypes. Although particularly suited for screening for risk of developing AMD and/or for identifying appropriate therapy for preventing or ameliorating AMD in a subject, it will be understood that in certain embodiments these reagents, devices and kits can be used for analysis of Factor H and CFHR5 polymorphisms and haplotypes for any purpose, including but not limited to determining risk of developing MPGNII or any other complement associated condition.

A number of assay systems are known in the art, and it is within the skill of the art to arrive at means to determine the presence of variations associated with AMD. The kit reagents, such as multiple primers, multiple probes, combinations of primers, or combinations of probes, may be contained in separate containers prior to their use for diagnosis or screening. In an embodiment, the kit contains a first container containing a probe, primer, or primer pair for a first CFH or CFHR5 allele described herein, and a second container containing a probe, primer, or primer pair for a second CFH or CFHR5 allele described herein.

In one embodiment, the invention provides kits comprising at least one Factor H or CFHR5 allele-specific oligonucleotide that hybridizes to a specific polymorphism in the Factor H or CFHR5 gene. The kits may contain one or more pairs of Factor H or CFHR5 allele-specific oligonucleotides hybridizing to different forms of a polymorphism. The Factor H or CFHR5 allele-specific oligonucleotides may include sequences derived from the coding (exons) or non-coding (promoter, 5' untranslated, introns or 3' untranslated) region of the Factor H or CFHR5 gene. The Factor H or CFHR5 allele-specific oligonucleotides may be provided immobilized on a substrate. The substrate may comprise Factor H or CFHR5 allele-specific oligonucleotide probes for detecting at least 2, 3, 4, 5, more than 5, (e.g., at least 6, 7, or 8) or all of the polymorphisms shown in TABLES 1A, 1B, 1C, 11, 14 and 15 and/or other polymorphisms in the Factor H or CFHR5 gene (e.g., including polymorphisms listed above that are found in the SNP database). In one embodiment the kit is used to diagnose AMD. In a related embodiment, the kit is used to screen for another disease associated with variation in the Factor H or CFHR5 gene.

The kit may include at least one Factor H- or CFHR5-specific primer that hybridizes spanning or adjacent to a specific polymorphism in the Factor H or CFHR5 gene. The Factor H- or CFHR5-specific primers may include sequences derived from the coding (exons) or non-coding (promoter, 5' untranslated, introns or 3' untranslated) region of the Factor H or CFHR5 gene. Often, the kits contain one or more pairs of Factor H- or CFHR5-specific primers that hybridize to opposite strands of nucleic acid adjacent to a specific polymorphism in the Factor H or CFHR5 gene. In the presence of appropriate buffers and enzymes, the Factor H- or CFHR5-specific primer pairs are useful in amplifying specific polymorphisms in the Factor H or CFHR5 gene.

It will be apparent to the skilled practitioner guided by this disclosure that various polymorphisms and haplotypes can be detected to assess the propensity of an individual to develop a Factor H related condition. The following examples and combinations are provided for illustration and not limitation. In some cases, the assay identifies the allele at at least one, at least two, at least three, at least four, at least five or at least six polymorphic sites in the Factor H or CFHR5 gene. In some cases, the assay identifies the allele at 1, 2, 3, 4, 5, 6, 7, 8, 9, 10, or all of the polymorphisms in the Factor H or CFHR5 gene listed in TABLES 1A, 1B, 1C, 11, 14 and 15. In one embodiment, the sites are selected from: rs529825; rs800292; rs3766404; rs1061147; rs1061170; rs203674; and optionally including exon 22 (R120C). In one embodiment, the sites are selected from rs529825; rs800292; intron 2 (IVS2 or insTT); rs3766404; rs1061147; rs1061170; exon 10A; rs203674; rs375046; and optionally including exon 22 (R120C). In one embodiment, the sites are selected from: rs3753394; rs529825; rs800292; intron 2 (IVS2 or insTT); rs3766404; rs1061147; rs1061170; rs2274700; rs203674; rs3753396; rs1065489; and optionally including exon 22 (R1210C). In one embodiment, the sites are selected from: rs800292 (I62V); IVS 2 (−18insTT); rs1061170 (Y402H); and rs2274700 (A473A). In one embodiment, the sites are selected from: rs9427661 (−249T>C); rs9427662 (−20T>C); and rs12097550 (P46S). In a preferred embodiment, a diagnostic/screening assay of the invention identifies the allele at at least two polymorphic sites in the Factor H or CFHR5 gene. In a preferred embodiment, a diagnostic/screening assay of the invention identifies the allele at at least three polymorphic sites in the Factor H or CFHR5 gene. In a preferred embodiment, a diagnostic/screening assay of the invention identifies the allele at at least four polymorphic sites in the Factor H or CFHR5 gene.

In some cases, the kit includes primers or probes ("oligonucleotides") to identify the allele at 1, 2, 3, 4, 5, 6, 7, 8, 9, 10, or all of the polymorphisms in the Factor H or CFHR5 gene listed in TABLES 1A, 1B, 1C, 11, 14 and 15. In one embodiment the kit includes primers or probes to determine the allele at at least one of the following polymorphic sites: rs529825; rs800292; rs3766404; rs1061147; rs1061170; rs203674; and optionally including exon 22 (R120C). In one embodiment the kit includes primers or probes to determine the allele at at least one of the following polymorphic sites: rs529825; rs800292; intron 2 (IVS2 or insTT); rs3766404; rs1061147; rs1061170; exon 10A; rs203674; rs375046; and optionally including exon 22 (R120C). In one embodiment the kit includes primers or probes to determine the allele at at least one of the following polymorphic sites: rs3753394; rs529825; rs800292; intron 2 (IVS2 or insTT); rs3766404; rs1061147; rs1061170; rs2274700; rs203674; rs3753396; rs1065489; and optionally including exon 22 (R120C). In one embodiment, the sites are selected from: rs800292 (I62V); IVS 2 (−18insTT); rs1061170 (Y402H); and rs2274700 (A473A). In one embodiment, the sites are selected from: rs9427661 (−249T>C); rs9427662 (−20T>C); and rs12097550 (P46S).

The kit can include primers or probes to determine the allele at two of the above sites, at least three, at least four, at least five or at least six. In one embodiment the primers or probes distinguish alleles at rs529825. In one embodiment the primers or probes distinguish alleles at rs800292. In one embodiment the primers or probes distinguish alleles at rs3766404. In one embodiment the primers or probes distinguish alleles at rs1061147. In one embodiment the primers or probes distinguish alleles at rs1061170. In one embodiment the primers or probes distinguish alleles at rs203674. In one embodiment; the primers or probes distinguish alleles at exon 22 (R1210C). In one embodiment the primers or probes distinguish alleles at rs529825 and rs800292. In one embodiment the primers or probes distinguish alleles at two or three of rs1061147, rs1061170 and rs203674. In one embodiment the primers or probes distinguish alleles at at least one of rs529825 and rs800292; and rs3766404; and at least one of rs1061147, rs1061170 and rs203674. In one embodiment the primers or probes distinguish alleles at rs529825, rs800292, rs3766404, rs1061170 and rs203674. In one embodiment, the primers or probes distinguish alleles at exon 22 (R1210C) and at: (a) rs529825; rs800292; rs3766404; rs1061147; rs1061170; rs203674; rs529825 rs 800292; (b) at two or three of rs1061147, rs1061170 and rs203674; at rs529825 and rs800292, rs3766404, and two or three of rs1061147, rs1061170 and rs203674; or at rs529825, rs800292, rs3766404, rs1061170 and rs203674. In one embodiment the primers or probes distinguish alleles at at least one of rs529825 and rs800292; and rs3766404; and at least one of rs1061147, rs1061170 and rs203674. In one embodiment the primers or probes distinguish alleles at rs529825, rs800292, rs3766404, rs1061170 and rs203674.

The kit can include primers or probes to determine the allele at two of the above sites, or at least three of the above sites. In one embodiment, the primers or probes distinguish alleles at rs800292. In one embodiment, the primers or probes distinguish alleles at rs1061170. In one embodiment, the primers or probes distinguish alleles at exon 22 (R1210C). In one embodiment, the primers or probes distinguish alleles at exon 22 (R1210C) and rs800292 and/or exon 22 and rs1061170 and exon 22. In one embodiment, the primers or probes distinguish alleles at rs800292, rs1061170 and exon 22 (R1210C).

The kit can include primers or probes to determine the allele at two of the above sites, at least three, at least four, at least five or at least six. In one embodiment the primers or probes distinguish alleles at rs529825. In one embodiment the primers or probes distinguish alleles at rs800292. In one embodiment the primers or probes distinguish alleles at intron 2 (IVS2 or insTT). In one embodiment the primers or probes distinguish alleles at rs3766404. In one embodiment the primers or probes distinguish alleles at rs1061147. In one embodiment the primers or probes distinguish alleles at rs1061170. In one embodiment the primers or probes distinguish alleles at rs2274700. In one embodiment the primers or probes distinguish alleles at exon 10A. In one embodiment the primers or probes distinguish alleles at rs203674. In one embodiment the primers or probes distinguish alleles at rs375046. In one embodiment the primers or probes distinguish alleles at exon 22 (R1210C). In one embodiment the primers or probes distinguish alleles at rs529825 and rs800292. In one embodiment the primers or probes distinguish alleles at two or three of rs1061147, rs1061170 and rs203674. In one embodiment the primers or probes distinguish alleles at rs529825 and rs800292, at intron 2, at rs3766404, at two or three of rs1061147, rs1061170 and rs203674, at rs2274700, at exon 10A, and at rs375046. In one embodiment the primers or probes distinguish alleles at rs529825, rs800292, intron 2 (IVS2 or insTT), rs3766404, rs1061170, rs2274700, exon 10A, rs203674, and rs375046. In one embodiment, the primers or probes distinguish alleles at exon 22 (R1210C) and at any one or more of rs529825; rs800292; intron 2 (IVS2 or insTT); rs3766404; rs1061147; rs1061170; rs2274700, exon 1A; rs203674; rs375046; rs529825 and rs 800292. In one embodiment, the primers or probes distinguish alleles at exon 22 (R1210C) and at: (a) any two or three of rs1061147, rs1061170 and rs203674; (b) at rs529825 and rs800292, intron 2 (IVS2 or insTT), rs3766404, two or three of rs1061147, rs1061170 and rs203674, rs2274700, exon 10A, and rs375046; or at rs529825, rs800292, intron 2 (IVS2 or insTT), rs3766404, rs1061170, rs2274700, exon 10A, rs203674, and rs375046.

In one embodiment the kit contains probes or primers for detecting at least one variation in the Factor H gene as well as probes or primers for detecting at least one variation in the CHFR-5 gene. In this embodiment, the kit optionally contains probes or primers for detecting more than on variation in either or both of the Factor H and CHFR-5 genes, such as two, three or more than three variations.

A number of assay formats are known for determining haplotypes and can be adapted to the present invention. See, e.g., Görgens et al., 2004, One-Step Analysis of Ten Functional Haplotype Combinations of the Basic RET Promoter with a LightCycler Assay" Clinical Chemistry 50:1693-1695; Dawson, 1989, "Carrier identification of cystic fibrosis by recombinant DNA techniques." *Mayo Clin Proc* 64:325-34; Lee et al., 2005, "Gene SNPs and mutations in clinical genetic testing: haplotype-based testing and analysis." *Mutat Res.* 573:195-204.

In one embodiment, the primers or probes distinguish alleles at (a) any one or more of rs529825; rs800292; rs3766404; rs1061147; rs1061170; and rs203674; (b) any one of more of intron 2 (IVS2 or insTT); rs2274700; exon 10A; and rs375046; (c) one or both of rs529825 and rs800292; (d) one or more of rs1061147, rs1061170 and rs203674; (e) at least one of rs529825 and rs800292; and rs3766404; and at least one of rs1061147, rs1061170 and rs203674; (f) at least rs529825, rs800292, rs3766404, rs1061170, and rs203674; (g) exon 22 (R1210C); (h) exon 22 (R1210C) and any of (a)-(g); or (i) any one or more of rs529825; rs800292; rs3766404; rs1061147; rs1061170; rs203674; intron 2 (IVS2 or insTT); rs2274700; exon 10A; rs375046; and exon 22 (R1210C) and any one or more of rs9427661, rs9427662 and rs12097550. In one embodiment, the kits include oligonucleotide sufficient to distinguish any combination of alleles at the sites listed below in the context of devices.

The kits may include antibodies that specifically recognize the Factor H or CFHR5 polypeptide. The Factor H- or CFHR5-specific antibodies may recognize the normal, functional Factor H or CFHR5 polypeptide or variant Factor H or CFHR5 polypeptides in which one or more non-synonymous single nucleotide polymorphisms (SNPs) are present in the Factor H or CFHR5 coding region.

XII. Diagnostic Devices

Devices and reagents useful for diagnostic, prognostic, drug screening, and other methods are provided. In one aspect, a device comprising immobilized primer(s) or probe(s) specific for one or more Factor H and/or CFHR5 polymorphic sites is provided. In an embodiment the Factor H and/or CFHR5 polymorphic sites are those described herein as associated with AMD.

In one aspect, a device comprising immobilized primer(s) or probe(s) specific for one or more Factor H and/or CFHR5 gene products (polynucleotides or proteins) is provided. The primers or probes can bind polynucleotides (e.g., based on hybridization to specific polymorphic sites) or polypeptides (e.g., based on specific binding to a variant polypeptide).

In one embodiment, an array format is used in which a plurality (at least 2, usually at least 3 or more) of different primers or probes are immobilized. The term "array" is used in its usual sense and means that each of a plurality of primers or probes, usually immobilized on a substrate, has a defined location (address) e.g., on the substrate. The number of primers or probes on the array can vary depending on the nature and use of the device. For example, a dipstick format array can have as few as 2 distinct primers or probes, although usually more than 2 primers or probes, and often many more, will be present. One method for attaching the nucleic acids to a surface is by making high-density oligonucleotide arrays (see, Fodor et al., 1991, *Science* 251:767-73; Lockhart et al., 1996, *Nature Biotech* 14:1675; and U.S. Pat. Nos. 5,578,832; 5,556,752; and 5,510,270). It is also contemplated that, in some embodiments, a device comprising a single immobilized probe can be used.

In one embodiment, an array format is used in which a plurality (at least 2, usually at least 3 or more) of different primers or probes are immobilized. The term "array" is used in its usual sense and means that each of a plurality of primers or probes, usually immobilized on a substrate, has a defined location (address) e.g., on the substrate. The number of primers or probes on the array can vary depending on the nature and use of the device.

In one embodiment, the immobilized probe is an antibody or other Factor H or CFHR5 binding moiety.

It will be apparent to the skilled practitioner guided by this disclosure than various polymorphisms and haplotypes can be detected to assess the propensity of an individual to develop a Factor H related condition. The following examples and combinations are provided for illustration and not limitation. In some cases, the array includes primers or probes to identify the allele at 1, 2, 3, 4, 5, 6, 7, 8, 9, 10, or all of the polymorphisms in the Factor H or CFHR5 gene listed in TABLES 1A, 1B, 1C, 11, 14 and 15. In one embodiment the array includes primers or probes to determine the allele at at least one of the following polymorphic sites: rs529825; rs800292; rs3766404; rs1061147; rs1061170; rs203674; and optionally including exon 22 (R1210C). In one embodiment the array includes primers or probes to determine the allele at at least one of the following polymorphic sites: rs529825; rs800292; intron 2 (IVS2 or insTT); rs3766404; rs1061147; rs1061170; exon 10A; rs203674; rs375046; and optionally including exon 22 (R1210C). In an embodiment the array includes primers or probes to determine the allele at at least one of the following polymorphic sites: (a) rs3753394; (b) rs529825; (c) rs800292; (d) intron 2 (IVS2 or insTT); (e) rs3766404; (f) rs1061147; (g) rs1061170; (h) rs2274700; (i) rs203674; (j) rs3753396; (j) rs1065489; and optionally including exon 22 (R1210C). In one embodiment, the array includes primers or probes to determine the allele at at least one of the following polymorphic sites: rs800292 (I62V); IVS 2 (−18insTT); rs1061170 (Y402H); and rs2274700 (A473A). In one embodiment, the array includes primers or probes to determine the allele at at least one of the following polymorphic sites: rs9427661 (−249T>C); rs9427662 (−20T>C); and rs12097550 (P46S).

The array can include primers or probes to determine the allele at two of the above sites, at least three, at least four, at least five or at least six. In one embodiment the primers or probes distinguish alleles at rs529825. In one embodiment the primers or probes distinguish alleles at rs800292. In one embodiment the primers or probes distinguish alleles at rs3766404. In one embodiment the primers or probes distinguish alleles at rs1061147. In one embodiment the primers or probes distinguish alleles at rs1061170. In one embodiment the primers or probes distinguish alleles at rs203674. In one embodiment the primers or probes distinguish alleles at exon 22 (R1210C). In one embodiment the primers or probes distinguish alleles at rs529825 and rs800292. In one embodiment the primers or probes distinguish alleles at two or three of rs1061147, rs1061170 and rs203674. In one embodiment the primers or probes distinguish alleles at rs529825 and rs800292, at rs3766404, two or three of rs1061147, rs1061170 and rs203674. In one embodiment the primers or probes distinguish alleles at rs529825, rs800292, rs3766404, rs1061170 and rs203674. In one embodiment, the primers or probes distinguish alleles at exon 22 (R1210C) and at rs529825; at rs800292; at rs3766404; at rs1061147; at rs1061170; at rs203674; at rs529825 and rs 800292; at two or three of rs1061147, rs1061170 and rs203674; at rs529825 and rs800292, rs3766404, and two or three of rs1061147, rs1061170 and rs203674; or at rs529825, rs800292, rs3766404, rs1061170 and rs203674. In one embodiment, the primers or probes distinguish alleles at (a) any one or more of rs529825; rs800292; rs3766404; rs1061147; rs1061170; and rs203674; (b) any one of more of intron 2 (IVS2 or insTT); rs2274700; exon 10A; and rs375046; (c) one or both of rs529825 and rs800292; (d) one or more of rs1061147, rs1061170 and rs203674; (e) at least one of rs529825 and rs800292; and rs3766404; and at least one of rs1061147, rs1061170 and rs203674; (f) at least rs529825, rs800292, rs3766404, rs1061170, and rs203674; (g) exon 22 (R1210C); (h) exon 22 (R1210C) and any of (a)-(g); or (i) any one or more of rs529825; rs800292; rs3766404; rs1061147; rs1061170; rs203674; intron 2 (IVS2 or insTT); rs2274700; exon 10A; rs375046; and exon 22 (R1210C) and any one or more of rs9427661, rs9427662 and rs12097550.

The array can include primers or probes to determine the allele at two of the above sites, at least three, at least four, at least five or at least six. In one embodiment the primers or probes distinguish alleles at rs529825. In one embodiment the primers or probes distinguish alleles at rs800292. In one embodiment the primers or probes distinguish alleles at intron 2 (IVS2 or insTT). In one embodiment the primers or probes distinguish alleles at rs3766404. In one embodiment the primers or probes distinguish alleles at rs1061147. In one embodiment the primers or probes distinguish alleles at rs1061170. In one embodiment the primers or probes distinguish alleles at exon 10A. In one embodiment the primers or probes distinguish alleles at rs2274700. In one embodiment the primers or probes distinguish alleles at rs203674. In one embodiment the primers or probes distinguish alleles at rs375046. In one embodiment the primers or probes distinguish alleles at exon 22 (R1210C). In one embodiment the primers or probes distinguish alleles at rs529825 and rs800292. In one embodiment the primers or probes distinguish alleles at two or three of rs1061147, rs1061170 and rs203674. In one embodiment the primers or probes distinguish alleles at of rs529825 and rs800292, at intron 2, at rs3766404, at two or three of rs1061147, rs1061170 and rs203674, at exon 10A, at rs2274700, and at rs375046. In one embodiment the primers or probes distinguish alleles at rs529825, rs800292, intron 2 (IVS2 or insTT), rs3766404, rs1061170, exon 10A, rs2274700, rs203674, and rs375046. In one embodiment, the primers or probes distinguish alleles at exon 22 (R1210C) and at either at rs529825; at rs800292; at intron 2 (IVS2 or insTT); at rs3766404; at rs1061147; at rs1061170; at rs2274700, at exon 10A; at rs203674; at rs375046; at rs529825 and rs800292; at two or three of rs1061147, rs1061170 and rs203674; at rs529825 and rs800292, intron 2 (IVS2 or insTT), rs3766404, two or three of rs1061147, rs1061170 and rs203674, rs2274700, exon 10A, and rs375046; or at rs529825, rs800292, intron 2 (IVS2 or insTT), rs3766404, rs1061170, rs2274700, exon 10A, rs203674, and rs375046. In one embodiment, the device distinguishes any combination of alleles at the sites listed above in the context of kits.

In one embodiment, the substrate comprises fewer than about 1000 distinct primers or probes, often fewer than about 100 distinct primers or probes, fewer than about 50 distinct primers or probes, or fewer than about 10 distinct primers or probes. As used in this context, a primer is "distinct" from a second primer if the two primers do not specifically bind the same polynucleotide (i.e., such as cDNA primers for different genes). As used in this context, a probe is "distinct" from a second probe if the two probes do not specifically bind the same polypeptide or polynucleotide (i.e., such as cDNA probes for different genes). Primers or probes may also be described as distinct if they recognize different alleles of the same gene (i.e., CFH or CFHR5). Thus, in one embodiment diagnostic devices of the invention detect alleles of CFH only, CFHR5 only, CFH and CFHR5 only, or CFH, CFHR5 and up to 20, preferably up to 10, or preferably up to 5 genes other than CFH and/or CFHR5. That is, the device is particularly suited to screening for AMD and related complement-associated diseases. In one embodiment, the device comprises primers or probes that recognize CFH and/or one or more of CFHR1-5 only. In a related embodiment, the device contains primers and probes for up to 20, preferably up to 10, or preferably up to 5 other genes than CFH or CFHR1-5.

In one embodiment, the immobilized primer(s) is/are an allele-specific primer(s) that can distinguish between alleles at a polymorphic site in the Factor H or CHRF5 gene. Exemplary allele-specific primers to identify alleles at polymorphic sites in the Factor H gene are shown in TABLE 16A. The immobilized allele-specific primers hybridize preferentially to nucleic acids, either RNA or DNA, that have sequences complementary to the primers. The hybridization may be detected by various methods, including single-base extension with fluorescence detection, the oligonucleotide ligation assay, and the like (see Shi, M. M., 2001, Enabling large-scale pharmacogenetic studies by high-throughput mutation detection and genotyping technologies" *Clin. Chem.* 47(2):164-172). Microarray-based devices to detect polymorphic sites are commercially available, including Affymetrix (Santa Calar, Calif.), Protogene (Menlo Park, Calif.), Genometrix (The Woodland, Tex.), Motorola BioChip Systems (Northbrook, Ill.), and Perlegen Sciences (Mountain View, Calif.).

In one embodiment, the immobilized probe(s) is/are an allele-specific probe(s) that can distinguish between alleles at a polymorphic site in the Factor H or CFHR5 gene. Exemplary allele specific probes to identify alleles at polymorphic sites in the Factor H gene are shown in TABLE 16B. The immobilized allele-specific probes hybridize preferentially to nucleic acids, either RNA or DNA, that have sequences complementary to the probes. The hybridization may be detected by various methods, including fluorescence of hybridized nucleic acids (see Shi, M. M., 2001, Enabling large-scale pharmacogenetic studies by high-throughput mutation detection and genotyping technologies. *Clin. Chem.* 47(2):164-172). Microarray-based devices to detect polymorphic sites are commercially available, including Affymetrix (Santa Calar, Calif.), Protogene (Menlo Park, Calif.), Genometrix (The Woodland, Tex.), Motorola BioChip Systems (Northbrook, Ill.), and Perlegen Sciences (Mountain View, Calif.).

In certain embodiments probes or primers specific for particular SNPs and variations are excluded from a kit or a device of the invention. For example, in some embodiments, a kit or device does not include one or more of the following SNPs can be excluded: (i) rs529825; (ii) rs900292; (iii) intron 2 (IVS2 or insTT); (iv) rs3766404; (v) rs1061147; (vi) rs1061170; (vii) rs2274700; (viii) exon 10A; (ix) rs203674; (x) rs375046; (xi) rs3753396; (xii) rs1065489; or (xiii) exon 22 (R1210C).

XIII. Examples

Example 1

Common Haplotype in the Factor H Gene (HF1/CFH) Predisposes Individuals to Age-Related Macular Degeneration Age-related macular degeneration (AMD) is the most frequent cause of irreversible blindness in the elderly in developed countries, affecting more than 50 million individuals worldwide. Our previous studies implicated activation of the alternative complement pathway in the formation of ocular drusen, the hallmark lesion of AMD. We have also shown that macular drusen in AMD patients are indistinguishable from those that form at an early age in individuals with membranoproliferative glomerulonephritis type 2 (MPGNII), a disease characterized by uncontrolled activation of the alternative pathway of the complement cascade. Here we show that Factor H protein (HF1), the major inhibitor of the alternative complement pathway, accumulates within drusen, and is synthesized locally by the retinal pigment epithelium. Previous linkage analyses identified chromosome 1q25-32, which harbors the Factor H gene (HF1/CFH), as a major AMD susceptibility locus. We analyzed HF1 for genetic variation in two independent cohorts comprised of approximately 900 AMD cases and 400 matched controls. We find a highly significant association of 8 common HF1 SNPs with AMD in these cohorts; two common missense variants exhibit highly significant associations (I62V; $\chi^2=36.1$, $p=3.2\times10^{-7}$ and Y402H; $\chi^2=54.4$, $p=1.6\times10^{-13}$). Haplotype analysis suggests that multiple HF1 confer either an elevated or a reduced risk of AMD. One common at-risk haplotype is present at a frequency of 49% in AMD cases and 26% in controls (OR=2.67, 95% CI [1.80-2.85]). Homozygotes for this haplotype account for 22.1% of cases and 5.1% of controls (OR=5.26, 95% CI [2.84-9.76]). Several protective haplotypes are also identified (OR=0.44-0.55). Further strengthening these data is the finding of the risk haplotype in 70% of MPGNII patients. We propose that genetically pre-determined variation in regulators of the complement system, when combined with triggering events such as infection, underlie a major proportion of AMD in the human population.

Introduction

Age-related macular degeneration (AMD) is the leading cause of irreversible vision loss in the developed world (Klein et al., 2004; van Leeuwen et al., 2003), affecting 15% of individuals over the age of 60 or an estimated 600 million individuals. AMD is characterized by a progressive loss of central vision attributable to degenerative and neovascular changes which occur at the interface between the neural retina and the underlying choroid. At this location lie the photoreceptors, the adjacent retinal pigmented epithelium (RPE), a basement membrane complex known as Bruch's membrane BM), and a network of choroidal capillaries.

The prevailing view is that AMD is a complex disorder attributable to the interaction of multiple genetic and environmental risk factors (Klein et al., 2003; Tuo et al., 2004). Familial aggregation studies indicate that a genetic component can be identified in up to 25% of the cases (Klaver et al., 1998). As such, AMD appears to be a product of the interaction between multiple susceptibility loci rather than a collection of single-gene disorders. The number of loci involved, the attributable risk conferred, and the interactions between various loci remain obscure.

Linkage analyses and candidate gene screening have provided limited insight into the genetics of AMD. Reliable associations of one gene with increased risk, ABCA4 (Allikmets et al., 1997; Allikmets, 2000), and one gene with decreased risk, ApoE4 (Klaver et al., 1998; Souied et al., 1998), have been reported. Several groups have reported results from genome-wide linkage analyses (Tuo et al., 2004; Weeks et al., 2001). To date, linkage of one AMD phenotype (ARMD1; MIM 603075) to a specific chromosomal region, 1q25-q31, has been documented (Klein et al., 1998). HEMICENTIN-1, also known as Fibl6, has been tentatively identified as the causal gene (Schultz et al., 2003), although it does not account for a significant disease load (Abecasis et al., 2004; Hayashi et al., 2004). The identification of overlapping loci on chromosome 1q by several groups (Weeks et al., 2001; Iyengar et al., 2003) indicates that this locus is likely to harbor a major AMD-associated gene.

In AMD, as well as many other diseases such as Alzheimer's disease (Akiyama et al., 2000), atherosclerosis (Torzewski et al., 1997), and glomerulonephritis (Schwertz et al., 2001), characteristic lesions and deposits contribute to the pathogenesis and progression of the disease. Although the molecular pathogenesis of these diseases may be diverse, the deposits contain many shared molecular constituents that are attributable, in part, to local inflammation and activation of the complement cascade, a key element of host defense in the innate immune system. Drusen are the hallmark deposits associated with early AMD, and recent studies have implicated local inflammation and activation of the complement cascade in their formation as well (Hageman et al., 1999; Espinosa-Heidmann et al., 2003). Drusen contain a variety of complement activators, inhibitors, activation-specific complement fragments, and terminal pathway components including the membrane attack complex (MAC), the lytic complex formed as a consequence of complement activation. The MAC is potentially lethal to host cells and tissues as well as foreign pathogens.

Many individuals with membranoproliferative glomerulonephritis type II (MPGNII), a rare kidney disease characterized by uncontrolled systemic activation of the alternative activation pathway of complement, also develop ocular drusen in the macula that are indistinguishable in composition and appearance from those in AMD (Mullins et al., 2001; O'brien et al., 1993; McAvoy et al., 2004). Furthermore, one patient diagnosed with MPGNII harbors a mutation in HF1

(HF1), a major inhibitor of the alternative pathway of complement activation (Zipfel, personal communication). Additionally, individuals in a few extended families with MPGNIII, a related disorder, show linkage to a region of chromosome mapped in 1q31-32 (Neary et al., 2002) that overlaps the locus identified in genome-wide linkage studies for AMD. Collectively, these findings provided the impetus for examining whether HF1 is involved in the development of AMD and MPGNII.

In this investigation, we determined the frequencies of HF1 sequence variants in AMD and MPGNII patients and matched controls, and analyzed their association with disease phenotype. We also examined HF1 transcription and the distribution of HF1 protein in the macular RPE-choroid complex from normal and AMD donors.

Methods

Patients, Phenotyping and DNA—Two independent groups of AMD cases and age-matched controls were used for this study. All participating individuals were of European-American descent, over the age of 60, and enrolled under IRB approved protocols following informed consent. These groups were comprised of 404 unrelated patients with clinically documented AMD (mean age 79.5±7.8) and 131 unrelated, control individuals (mean age 78.4±7.4; matched by age and ethnicity) from the University of Iowa, and 550 unrelated patients with clinically documented AMD (mean age 71.32±8.9 years), and 275 unrelated, matched by age and ethnicity, controls (mean age 68.84±8.6 years) from the Columbia University. Patients were examined by indirect ophthalmoscopy and slit-lamp microscopy by retina fellowship-trained ophthalmologists.

Dr. Caroline Klaver, and later individuals trained by Dr. Klaver, graded fundus photographs at both institutions according to a standardized, international classification system (Bird et al., 1995). Control patients were selected and included if they did not exhibit any distinguishing signs of macular disease or have a known family history of AMD. The AMD patients were subdivided into phenotypic categories—early AMD (eAMD), geographic atrophy (GA) and exudative (CNV) AMD—based on the classification of their most severe eye at the time of their entry into the study. The University of Iowa eAMD and GA cases were further subdivided into distinct phenotypes (RPE changes alone, >10 macular hard drusen, macular soft drusen, BB (cuticular) drusen, PED, "Cherokee" atrophy, peninsular geographic atrophy and pattern geographic atrophy). The earliest documented phenotype for all cases was also recorded and employed in the analyses.

Genomic DNA was generated from peripheral blood leukocytes collected from case and control subjects using QIAamp DNA Blood Maxi kits (Qiagen, Valencia, Calif.).

Rapanui—Following an informed consent process approved by the Unidad de Bioetica, Ministerio de Salud (Santiago, Chile), 447 (66% female; 34% male) Easter Island inhabitants were provided a complete eye examination that included a dilated funduscopic examination. Medical, family and ophthalmic histories were taken and records and assistance from local physicians and community leaders were used to classify the ethnicity of the subjects. 49% of those patients examined were pure Rapanui, 9% were admixed (mixture of Rapanui and European, Chilean, Mapuchi and/or recent Polynesian), and 42% were continental (largely Chilean European). Peripheral venous blood and sera were collected from 201 of the older individuals; 114 of these individuals were pure Rapanui (108 were >50 years old; 89 were >60 years old). DNA from 60 of the pure Rapanui inhabitants and 13 of the Chilean residents over the age of 65 was used in this study.

Human Donor Eyes—Human donor eyes were obtained from the Iowa Lions Eye Bank (Iowa City, Iowa), the Oregon Lions Eye Bank (Portland, Oreg.) and the Central Florida Lions Eye and Tissue Bank (Tampa, Fla.) within five hours of death. Gross pathologic features of these eyes, as well as fundus photographs and angiograms, when available, were read and classified by retinal specialists. Fundi were graded according to a modified version of the International AMD grading system (Bird et al., 1995) by at least two individuals.

Total RNA was prepared from retina, RPE/choroid, and RPE cells derived from eyes using an RNeasy Mini Kit (Qiagen, Valencia, Calif.). Genomic DNA was sheared using a QiaShredder (Qiagen, Valencia, Calif.) and residual genomic DNA digested with DNAse (Promega). RNA integrity was assessed using an Agilent BioAnalyzer.

DNA derived from 38 unrelated donors with clinically documented AMD (mean age 81.5±8.6) and 19 unrelated, control donors (mean age 80.5±8.8; matched by age and ethnicity) were employed for SSCP analyses and to assess potential genotype-phenotype correlations.

Immunohistochemistry—Wedges of posterior poles, including the ora serrata and macula were fixed and processed as described previously (Hageman et al., 1999). Some posterior poles were embedded directly in OCT without prior fixation. Tissues were sectioned to a thickness of 6-8 µm on a cryostat and immunolabeling was performed as described previously (Hageman et al., 1999. Adjacent sections were incubated with secondary antibody alone, to serve as controls. Some immunolabeled specimens were prepared and viewed by confocal laser scanning microscopy, as described previously (Anderson et al., 2002).

Polymerase Chain Reaction (PCR)—First strand cDNA was synthesized from total RNA using Superscript reverse transcriptase (Gibco BRL) and random hexamers. PCR reactions were carried out using the following primer sets: FH1 (exon 8 to exon 10) 5'-GAACATTTTGAGACTCCGTC-3' [SEQ ID NO:324] and 5'-ACCATCCATCTTTCCCAC-3' [SEQ ID NO:325]; FH1 (exon 9 to exon 10) 5'-TCCTGGC-TACGCTCTTC-3' [SEQ ID NO:326] and 5'-ACCATC-CATCTTTCCCAC-3' [SEQ ID NO:325]; HFL1 (exon 8 to exon 10) 5'-TCCGTCAGGAAGTTACTGG-3' [SEQ ID NO:327] and 5'-AGTCACCATACTCAGGACCC-3' [SEQ ID NO:328]; HFL1 (exon 9 to exon 10), 5'-GGC-TACGCTCTTCCAAAAG-3' [SEQ ID NO:329] and 5'-AGT-CACCATACTCAGGACCC-3' [SEQ ID NO:330]. PCR primers (IDT, Coralville, Iowa) were designed using MacVector software (San Diego, Calif.). Reaction parameters were one cycle at 94° C. for 3 minutes, 40 cycles at 94° C. for 45 sec, 51.4° C. (FH1)/55° C. for 1 min, and one cycle at 72° C. for 3 min. The PCR products were run on 2% agarose gels and recorded using a Gel Doc 2000™ Documentation System accompanied by Quantity One® software (Bio-Rad, Hercules, Calif.).

Microarray Analyses: DNA microarray analyses were performed using total RNA extracted from native human RPE or the RPE-Choroid complex (RNeasy minikit, Qiagen, Valencia, Calif.) collected within <5 hours of death. Three different platforms were used: an 18,380 non-redundant DNA microarray (Incyte Pharmaceuticals; St. Louis, Mo.); the Affymetrix gene chip system; and a Whole Human Genome or Human 1A V2 oligo-microarray (Agilent Inc., Palo Alto, Calif.). The individual protocols followed each of the manufacturer's instructions. For the Incyte analyses, cDNA derived from 6 mm punches of macular and mid-peripheral regions was labeled with 33-P in a random-primed reaction, purified and hybridized to the Nylon-based arrays containing 18,380 non-redundant cDNAs. The membranes were phosphoimaged, signals were normalized and data were analyzed using the Genome Discovery Software package. For the Affymetrix analyses, RPE and RPE/choroid (from 6-8 mm macular and peripheral punches) cRNA was hybridized directly to Affymetrix GeneChips (HG-U133A) using standardized protocols. These procedures were conducted in the University of Iowa DNA core facility, which is equipped with a fluidics station and a GeneArray scanner. The Agilent data was obtained from punches of the macula and mid-periphery. CY3 and CY5 labeled amplified cRNA derived from macula and peripheral RPE/choroid was generated using an Agilent Low Input RNA Amplification Kit using the macular and peripheral RNA from the same donor. The Agilent array data were collected from 3 normal young donors, 3 AMD donors, and 3 age-matched non-AMD controls using a VersArray Scanner; data were quantified using the VersArray Analyzer Software (BioRad). The median net intensity of each spot was calculated using global background subtraction and the data was normalized using the local regression method.

Mutation Screening and Analysis—Coding and adjacent intronic regions of HF1 (including exon 10A that is transcribed to generate the truncated FHL1 isoform) were examined for variants using single-strand conformation polymorphism (SSCP) analyses, denaturing high performance liquid chromatography (DHPLC) and direct sequencing. The remaining SNPs were typed by the 5' nuclease (Taqman, ABI) methodology. Taqman genotyping and association analyses were performed as described (Gold et al., 2004). Primers for SSCP, DHPLC and DNA sequencing analyses (TABLE 5) were designed to amplify each exon and its adjacent intronic regions using MacVector software (San Diego, Calif.). PCR-derived amplicons were screened for sequence variation by SSCP and DHPLC, as described previously (Allikmets et al., 1997; Hayashi et al., 2004). All changes detected by SSCP and DHPLC were confirmed by bidirectional sequencing according to standard protocols. Statistical analyses were performed using chi-square and Fisher's exact tests.

Results

Factor H at the RPE-Choroid Interface

The distribution of Factor H protein in the RPE/choroid complex from the macula and extramacula was assessed in eyes obtained from six donors with a history of early AMD and three donors of similar age without AMD or drusen (FIGS. 1A-1L). In donors with AMD, intense HF1 immunoreactivity (IR) is present in drusen, beneath the RPE (i.e. the sub-RPE space), and around the choroidal capillaries (FIGS. 1A-1D, 1E, 1G). In the absence of the primary antibody, labeling in the RPE/choroid is absent (FIG. 1F). All of the Factor H antibodies labeled drusen to some degree, in a homogeneous fashion (FIGS. 1C and 1E). One antibody also labeled substructural elements within drusen (FIGS. 1A and 1B). Such structures are also labeled using antibodies to the activated complement component C3b/iC3b that binds HF1 (Anderson et al., 2004; Johnson et al., 2001). Factor H immunoreactivity is more robust in donors with AMD compared to age-matched controls; it is also more pronounced in the maculas of AMD donors than in the periphery (FIGS. 1G and 1H). The anti-HF1 pattern in the macula (FIG. 1G) is highly similar to the anti-C5b-9 pattern (FIGS. 1I and 1K); in both cases, labeling typically includes the choroidal capillaries. Extramacular locations show much less anti-C5b-9 immunoreactivity (FIG. 1J). Little or no C5b-9 immunoreactivity in the RPE-choroid is observed in donors under the age of 50 and without AMD (FIG. 1L).

Description of FIG. 1

(A-B) High magnification confocal immunofluorescence images from an 84 year old male donor diagnosed with atrophic AMD. Anti-HF1 (Advanced Research Technologies) labeling of substructural elements (white arrows) in drusen and the sub-RPE space is imaged on the Cy2/fluorescein channel. The sub-RPE space is the extracellular compartment between the basal RPE surface and the inner collagenous layer of Bruch's membrane. Such elements also display immunoreactivity (IR) using monoclonal antibodies directed against C3 fragments (iC3b, C3d, C3dg) that bind covalently to complement activating surfaces (Johnson et al, 2001; 2003). The intense anti-Factor H labeling in the lumens of choroidal capillaries (asterisks) from this donor most likely reflects the high circulating levels of HF1 in the bloodstream. Autofluorescent lipofuscin granules in the RPE cytoplasm are labeled on the Cy3/Texas Red channel. Magnification bars. A) 5 µm; B) 3 µm.

(C-D) Confocal immunofluorescence localization of HF1 in drusen and the sub-RPE space in an 83 year old male with AMD using a different HF1 polyclonal antibody (Quidel) (Cy2/fluorescein channel; green). C) In this donor eye, the drusen (Dr) labeling pattern is homogeneous. D) Low magnification image of the RPE-choroid. Anti-HF1 IR is present throughout the choroid and in the sub-RPE space (arrows), the anatomical compartment where drusen and other deposits associated with aging and AMD form. Lipofuscin autofluorescence (Cy3 channel; red). Magnification bars. C) 10 µm; D) 20 µm.

(E-F) Immunohistochemical localization of HF1 in drusen. E) Anti-HF1 monoclonal antibody (Quidel) labeling, signified by the purple alkaline phosphatase reaction product, is apparent in drusen, along Bruch's membrane, and on the choroidal capillary walls (arrows). F) Control section from the same eye. In the absence of the primary antibody, no labeling is present. Brown pigmentation in the RPE cytoplasm and choroid is melanin. Magnification bars=10 µm.

(G-H) Immunolocalization of HF1 in the macula. G) Extensive labeling is present along BM, the choroidal capillary walls, and the intercapillary pillars (arrows) in a donor with AMD. H) Control section from the macula of a donor without AMD; much less labeling is apparent in same structures. Magnification bars=20 µm.

(I-J) Immunohistochemical localization of the complement membrane attack complex (C5b-9) in the RPE-choroid underlying the macula (FIG. 1I) and extramacula (FIG. 1J) from the same AMD donor eye. In the macula, intense anti-C5b-9 labeling is associated with drusen, Bruch's membrane, and the choroidal capillary endothelium. Anti-C5b-9 labeling outside the macula is restricted to a narrow zone in the vicinity of Bruchs membrane. Brown pigment in the RPE cytoplasm and choroid represents melanin pigmentation. Magnification bars=20 µm.

(K-L) Immunohistochemical location of C5b-9 in the macula from a donor with AMD (FIG. 1K) and from a second donor without AMD (FIG. 1L). Brown pigmentation in the RPE cytoplasm and choroid represents melanin. The anti-C5b-9 labeling is associated primarily with the choroidal capillary walls (black arrows) and the intercapillary pillars (white arrows). Labeling is much more intense in the AMD eye. Note the strong similarity to the anti-HF1 labeling pattern in the macula from the same donor, as shown in FIG. G. Magnification bars. K=15 µm; L=20 µm.

The Retinal Pigment Epithelium is a Local Source of Factor H

Figure 2:
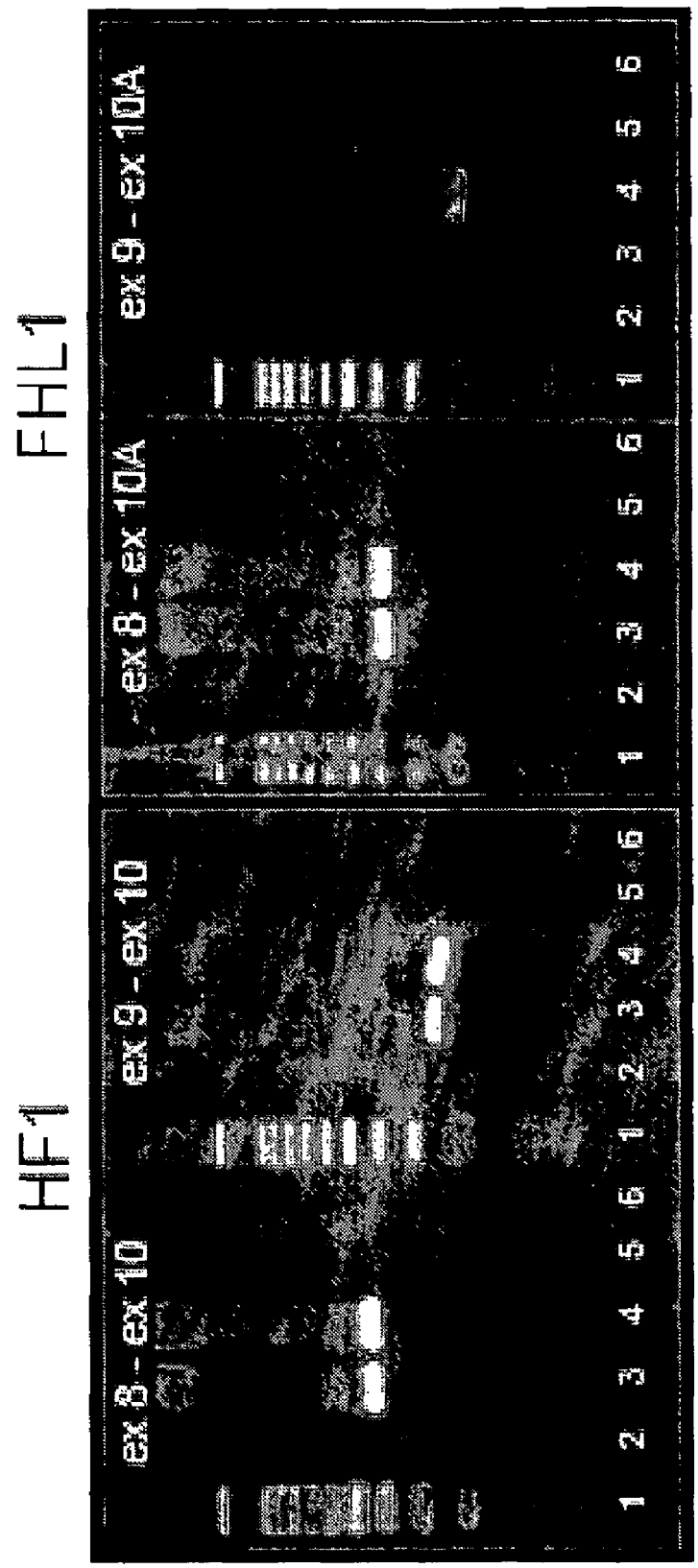
FIG. 2 shows RT-PCR analysis of Factor H gene expression (CFH and the truncated form HFL1) using RNA extracted from the human eye.

Expression of HF1 and FHL1 in the RPE, RPE/choroid and retina was assessed by RT-PCR and DNA microarray analysis. Appropriately sized PCR products for both gene products are present in freshly isolated RPE and the RPE/choroid complex, but not neural retina, in human eyes derived from donors with and without AMD (FIG. 2). Primers were chosen within exons 8, 9, 10A (the exon employed to generate the truncated isoform FHL1) and 10 of the HF1 coding sequence. The PCR reactions were performed with cDNA prepared from RNA extracted from human neurosensory retina (lanes 2), RPE and choroid (lanes 3), and freshly isolated RPE cells (lanes 4) derived from a donor with a clinically documented history of AMD. Genomic DNA was employed as a template for amplification (lanes 5); no template was added to the mixtures depicted in lanes 6. Lanes 1 contains the 100 bp ladder. Amplimers spanning from exon 8 to exon 10 (left panel), and from exon 9 to exon 10 (right panel), of HF1 and from exon 8 to exon 10A (left panel), and exon 8 to exon 10A (right panel), of FHL1 were of the expected sizes (376, 210, 424 and 248 bp, respectively). Transcripts for FHRs 1-5 are not detected in RPE or RPE/choroid, but FHRs 1-4 are detected in neural retina by RT-PCR (data not shown).

Gene expression array data derived from three platforms confirm that HF1 and FHL1 transcripts, but few if any of the HF1-related protein transcripts (FHR1 being the possible exception), are expressed locally by RPE and choroid cells. Data derived from Incyte arrays probed with RPE/choroid cDNA derived from nine donors with AMD and three age-matched controls show elevated levels that average 2-3 times that of HF1 mRNA in the donors with AMD. There is also a trend toward slightly higher levels in the macula regions as compared to the extramacular regions, although the difference is not statistically significant. The data generated from the examination of isolated RPE and adjacent RPE/choroid preparations from two donors with AMD and two age-matched control donors using Affymetrix arrays confirm the presence of HF1 transcripts in these tissues and shows that a significant proportion of the HF1 message is present within the RPE layer (data not shown).

Variants in HF1 are Associated with AMD and MPGNII

Figure 3:
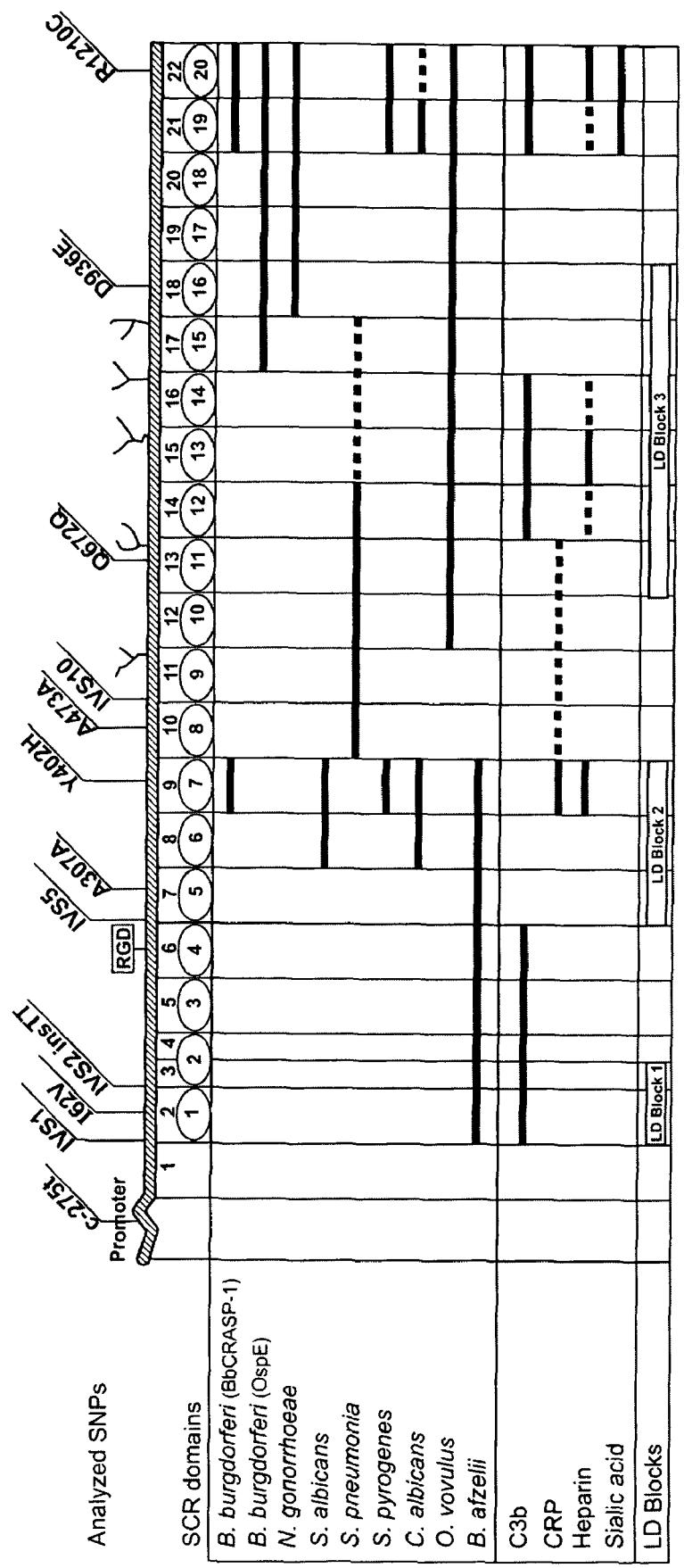
FIG. 3 is a diagram of the human Factor H gene showing the approximate locations of 12 SNPs used in the analysis, the 22 exons of the Factor H gene, the 20 short consensus repeats (SCRs), the binding sites for pathogens and other substrates, and the linkage disequilibrium (LD) blocks. The diagram, showing all 22 exons of CFH (but not introns) is not drawn to scale.

To test whether allele variants of HF1 gene are associated with AMD, all 22 coding exons and 50-100 bp flanking intronic sequences were screened, in a cohort of 404 AMD patients and 131 matched controls at the University of Iowa. A total of 26 sequence variants are detected; 17 SNPs in the coding region (cSNPs), including 5 synonymous and 12 non-synonymous substitutions, and 9 intronic SNPs (some of the variants shown in FIG. 3). FIG. 3 shows the approximate locations of 11 SNPs used in the analysis, the 20 short consensus repeats (SCRs), and the linkage disequilibrium (LD) blocks, and the approximate binding sites for pathogens and other substrates are depicted below the diagram based on previously published data (Zipfel et al., 2002; Rodriguez de Cordoba et al., 2004). cSNPs included previously described common non-synonymous variants, such as I62V in exon 2, Y402H in exon 9, and D936E in exon 18 (FIG. 3). An example of a common intronic SNP with a potentially functional effect is the IVS2-18insTT variant. Five rare (<0.5%) variants are also detected (data not shown) in both AMD patients and controls, excluding the possibility of the disease phenotype being caused by rare HF1 alleles (i.e., disease-causing mutations). Detailed genotyping data were obtained for 6 SNPs in some or all of the 404 patients and 131 controls (TABLES 4 and 6A-6C) and association analyses were performed using a case-control study design. Highly significant associations are found with several individual variants, including I62V ($\chi^2=15.0$, p=$1.1\times10^{-4}$) and Y402H ($\chi^2=49.4$, p=$2.1\times10^{-12}$). The strongest association with AMD in this cohort is observed with a synonymous A473A variant in exon 10, resulting in an odds ratio (OR) of 3.42 (95% confidence interval (CI) [2.27-5.15]).

These results were confirmed in an independent cohort of AMD patients (n=550) and matched controls (n=275) obtained at Columbia University, New York (TABLE 4). The same two non-synonymous SNPs are also highly associated with AMD in this second cohort (I62V; $\chi^2=36.1$, p=$3.2\times10^{-7}$ and Y402H; $\chi^2=54.4$, p=$1.6\times10^{-13}$). In addition, several other intronic SNPs were selected based on frequency and the availability of commercial assays (for a total of 11 SNPs). The strongest association in this cohort is observed with SNP rs203674 in intron 10 ($\chi^2=66.1$, p=$4.29\times10^{-16}$). This variant shows an OR of 2.44 with AMD (95% CI=1.97-3.03). Although the OR is modest, the variant is very common; 30.5% of the cases are homozygous for allele B, but only 12.9% of the controls. The Q672Q and D936E alleles in exon 13 and 18 show no statistically significant association, suggesting that variation in the N-terminal half of HF1, which includes domains involved in pathogen and substrate molecule recognition (FIG. 3, also see below), are associated with AMD. The two sets of data are strikingly similar, in that the genotyped SNPs are not only associated with AMD in a highly significant fashion, but the frequencies and extent of association are very similar in the two cohorts (TABLES 4 and 6).

The association is highly significant when the entire AMD patient cohorts are compared to controls (TABLE 4). When the major sub-phenotypes of AMD, such as the early AMD (eAMD, characterized by macular drusen and/or pigmentary abnormalities), CNV (neovascular membranes and/or disciform scars), and GA (geographic atrophy) are analyzed separately, the association is especially prominent in cases of eAMD and CNV. The GA group shows some deviation from the general trend in some cases, especially with the haplotype defined by exon 13 (Q672Q) and 18 (D936E) alleles (data not shown). While this deviation may be significant in terms of varying etiology, it did not reach statistical significance, most likely due to relatively small numbers of patients with GA.

Figure 4:
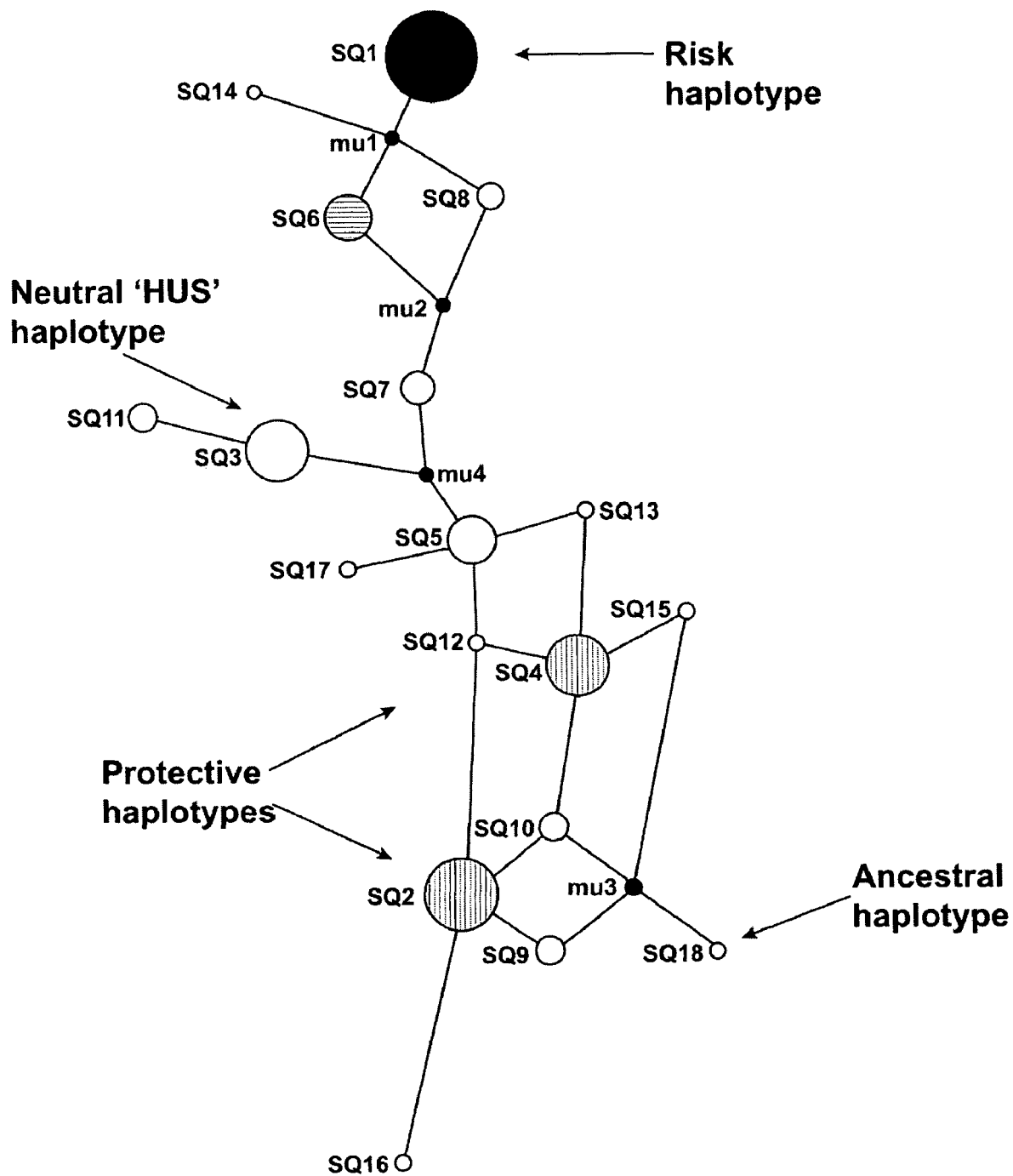
FIG. 4 is a haplotype network diagram of human Factor H gene SNPs showing the relationship between the risk (filled-in circles), protective (lined circles), neutral (open circles) and ancestral (indicated) haplotypes and the relative frequency of the haplotypes, as indicated by the sizes and positions of the circles.

Linkage disequilibrium (LD) analysis showed extensive LD across the entire HF1 gene (TABLE 2 and FIG. 3). Three SNPs in the exon 2-3 region are in virtually complete LD as are the A307A and Y402H variants in exons 7 and 9, and the Q672Q and D936E variants in exon 13 and 18 (TABLE 6 and FIG. 5). Haplotype estimation in cases and controls identified the most frequent at-risk haplotype in 49% of cases versus only in 26% of controls (OR=2.93 95% CI [2.29-3.74]). Homozygotes for this haplotype are present in 22.1% of the Columbia cases and 5.1% of the controls (OR=5.26, 95% CI [2.84-9.76]). Two common protective haplotypes are found in 30% of controls and 18% of cases (OR=0.476 95% CI [0.349-0.650] and OR=0.472, 95% CI [0.320-0.698]). These haplotypes differ only in the exon 2-3 locus SNPs and the intron 10 SNP. As shown in FIG. 4 and TABLE 2, these protective haplotypes are closely related to each other and are both at least five steps away from the risk haplotype. Interestingly, the 3 SNPs, (promoter −257C>T, A473A, and D936E) previously shown to be associated with HUS are all on one relatively common haplotype (12%) that is neutral for AMD risk (see the discussion below). For each SNP we identified the base present in the consensus chimpanzee genome. The haplotype generated represents the likely ancestral human haplotype and is closely related to the protective haplotypes (data not shown).

SNPs IVS2-18insTT and Y402H were also genotyped in 20 unrelated MPGNII patients, 52 Rapanui natives and small cohorts of Hispanic Americans, African Americans and European Americans (TABLE 7). The frequency of the at-risk haplotype was estimated in samples from different populations from genotypes of the Y402H variant and/or the IVS10 locus. These include Rapanui natives over the age of 65 (AMD is extremely rare, and most likely absent, in this Easter Island population), controls (>65 years of age) from Columbia University, Hispanics general population, controls (>65 years of age) from the University of Iowa, African Americans general population, AMD cases from Columbia University, European Americans general population, AMD cases from the University of Iowa and individuals with MPGNII. N=number of individuals. In the MPGNII cohort, the frequency of the risk haplotype is approximately 70%. In addition, the risk haplotype appears to be lower in frequency in Hispanic Americans and African Americans (35-45%), groups with lower incidences of AMD. However, the number of samples typed in these populations is small. The Rapa Nui population on Easter Island has a remarkably low level of AMD. From the analysis of 52 AMD-free Rapanui natives over the age of 65, we estimate the frequency of the risk haplotype to be only 19%.

Discussion

Factor H Polymorphisms and AMD

The data presented here links a major proportion of AMD cases in two independent cohorts to specific polymorphisms in the complement regulatory gene, Factor H (HF1/CFH) (Zipfel, 2001; Rodriguez de Cordoba et al., 2004). Haplotype analysis shows the most frequent at-risk haplotype to be present in almost half of individuals with AMD, compared to approximately 25% of controls. The frequencies and extent of SNP associations are very similar in the two cohorts and, genotyped SNPs show highly significant association with AMD in each. The associations are especially prominent in cases of early AMD or choroidal neovascularization, less so for geographic atrophy. The magnitude of the observed association of specific HF1 haplotypes with AMD is striking when compared to those genetic abnormalities previously linked to AMD.

Further support for the conclusion that specific HF1 haplotypes confer increased risk for an AMD disease phenotype was obtained by genotyping of SNPs IVS2-18insTT and Y402H in 20 unrelated patients with MPGNII, a renal disease associated with HF1 mutations in which patients develop early onset macular drusen, and in 52 Rapanui natives, a race with a remarkably low incidence of AMD, if any. Approximately 70% of MPGN II patients and 19% of Rapanui were found to harbor the HF1 at-risk haplotype in this study. Analysis of larger sample sets will be required to confirm these results, but the data do suggest that the HF1 association with AMD may not be restricted to European-derived populations. Protective haplotypes we also identified, further implicating HF1 function in the pathogenetic mechanisms underlying AMD.

Functional Implications of Factor H Polymorphisms

Factor H deficiencies in humans are associated with MPGN II and atypical hemolytic uremic syndrome (aHUS) (Zipfel et al., 2001). HF1 deficiency arises from mutations leading to protein truncations or amino acid substitutions that result in protein retention in the endoplasmic reticulum. Reduced levels of plasma HF1 ensue, leading to uncontrolled activation of the alternative complement pathway with concomitant consumption of C3 and other complement components. The HF1 mutations that lead to aHUS, in contrast, are typically missense mutations that limit the complement-inhibitory functions of FH1 at the cell surface. Recent studies have revealed an association between three common SNPs and aHUS in individuals both with and without FH1 mutations (Caprioli et al., 2003). Furthermore, insults such as infection have been documented to trigger the manifestation of aHUS.

Most of the genotyped SNPs of HF1 are located within important functional domains of the encoded protein (FIG. 3), which consists of 20 short consensus repeats (SCR) of 60 amino acids. The SCRs contain binding sites for C3b (SCR1-4, SCR12-14 and SCR19-20), heparin, sialic acid (SCR7, SCR13 and SCR19-20) and C-reactive protein (CRP) (SCR7). Therefore, SNPs located within the functional domains, although common, presumably affect protein function through variability in expression levels, binding efficiency, and other molecular properties. For example, the exon 2 I62V variant is located in SCR2, which is included in the first C3b binding site, and the exon 9 Y402H variant is within SCR7 domain, which binds both heparin and CRP. Intronic SNPs, such as the IVS2-18insTT variant, can affect splicing. For example, the analysis of the effect of the TT insertion (on the https://splice.cmh.edu/server) suggested a creation of a new cryptic splice acceptor 6 bp upstream of the natural acceptor site (data not shown). It is also possible that some of the studied SNPs affect the expression of HF1 isoforms. For example, I62V is present in a predicted exon splice enhancer (Wang et al., 2004) (data not shown).

The functional consequences of common SNPs may be modest, since they are involved in late-onset phenotypes and not subjected to (rigorous) evolutionary constraint. HF1 variants with more substantial effects, i.e., disease-causing mutations, are implicated in early-onset, severe (recessive) diseases, such as HF1 deficiency and aHUS (Zipfel et al., 2002; Rodriguez de Cordoba et al., 2004; Caprioli at al., 2003; Zipfel, 2001). Of interest is the fact that true disease-causing mutations have been identified in only about 25% to 35% of HUS patients after complete screening of the HF1 gene (Caprioli et al., 2003). At the same time, a disease-associated haplotype defined by variants −257C>T (promoter), A473A (exon 13) and D936E (exon 18) has been identified in HUS patients, predominantly in those persons with no disease-causing mutations (Caprioli et al., 2003). Moreover, the same study identified several families where affected probands had inherited a mutated allele from one parent and a susceptibility allele, from another. By contrast, healthy siblings of affected probands, carriers of the disease-causing mutation, had inherited a protective allele. In affected individuals from these families a disease-triggering effect, specified as bacterial or viral infection in >60% of cases, was identified in >80% of all cases and in >90% of cases with no apparent disease-associated mutation (Caprioli et al., 2003).

Together, these data strongly suggest that an at-risk HF1 haplotype in combination with an infectious triggering event is sufficient for disease manifestation. Interestingly, the at-risk HF1 haplotype in HUS (mainly C-terminal) does not overlap with that in AMD and/or MPGNII (TABLE 2), suggesting different triggers in HUS as opposed to MPGNII and AMD. Observation of early-onset drusen in MPGNII and those of the same composition in AMD, but not in HUS, support a different etiology for these diseases.

Disease-causing mutations in HF1 are rare in MPGN II and have not been reported in AMD, nor did we find them after extensive screening in this study. However, we observed the same at-risk haplotype at a frequency of 70% of patients with MPGN II and approximately 50% in patients with AMD. These data are consistent with an at-risk HF1 haplotype that, if triggered by an infectious agent, substantially increase one's susceptibility to disease. The combined effect of these factors determines the severity the resulting phenotype, ranging from AMD to MPGNII.

Evolutionary analysis of the HF1 haplotype indicates that the risk haplotype has evolved significantly from the ancestral haplotype found in the chimpanzee. FIG. 4 depicts a haplotype network diagram of HF1 SNPs which shows the relationship between the haplotypes and the size of the circles is proportional to the frequency of the haplotype. The large filled-in circle represents the major risk haplotype, the vertically-lined circles are the two significant protective haplotypes, and the large open circle is the haplotype that contains the three SNPs associated with atypical hemolytic uremic syndrome (HUS), which is neutral for AMD risk. The putative ancestral haplotype is also indicated. It is possible that different forms of the HF1 gene emerged in response to pathogens that activate the alternative complement pathway. Weakly acting HF1 haplotypes could provide reduced complement inhibition and stronger protection against bacterial infection. However, such weak alleles could have the consequence of predisposing individuals to the consequences of complement system dysfunction. It is interesting that the AMD risk haplotype is principally different in the 5' end of the gene that produces both the full length HF1 and the FHL1 protein. In contract the HUS mutations cluster in the 3' portion of the gene that is found only in HF1. Therefore, it will be important to determine the role of these two forms of the protein in disease.

Biological Model of Factor H Dysfunction in AMD

One of the primary functions of the complement system is to provide defense against such infectious agents. It mediates the opsonization and lysis of microorganisms, removal of foreign particles, recruitment of inflammatory cells, regulation of antibody production, and elimination of immune complexes (Morgan et al., 1991; Kinoshita, 1991). Activation of the system triggers a sequential, amplifying, proteolytic cascade that gives rise to modifications of activating surfaces, to the release of soluble anaphylatoxins that stimulate inflammatory cells, and ultimately, to formation of the membrane attack complex (MAC), a macromolecular complex that promotes cell lysis through the formation of transmembrane pores. Uncontrolled activation of complement can lead to bystander damage to host cells and tissues. As a result HF1, as well as other circulating and membrane-associated proteins, have evolved to modulate the system (Morgan, 1999).

A spectrum of complement components have been identified either within drusen (and/or the RPE cells that flank or overlie them), along Bruch's membrane, and/or on the choroidal endothelial cell membrane (Hageman et al., 2001; Mullins et al., 2000; Mullins et al., 2001; Anderson et al., 2002; Johnson, et al., 2000; Johnson et al., 2001; Crabb et al., 2002; Johnson et al., 2002; Mullins et al., 1997). These include terminal pathway complement components, activation-specific fragments of the terminal pathway, as well as various complement modulators. There is evidence that cell-mediated events may also contribute to this process (Penfold et al., 2001; Seddon et al., 2004; Miller et al., 2004).

We now show that HF1 is also a constituent of drusen in human donors with a prior history of AMD. Secondly, we show that HF1 co-localizes with its ligand C3b in amyloid-containing substructural elements within drusen, further implicating these structures as candidate complement activators (Anderson et al., 2004; Johnson et al., 2002). We also demonstrate that HF1 and the MAC, as shown by C5b-9 immunoreactivity, co-distribute at the RPE-choroid interface and that these deposits are more robust in eyes from donors with prior histories of AMD. Finally, HF1 and C5b-9 immunoreactivities are more intense in the macula compared to more peripheral locations from the same eye. All of these findings are consistent with the fact that AMD pathology is manifested primarily in the macula and with the conclusion that complement activation at the level of Bruch's membrane is a key element in the process of drusen formation as well as a contributing factor in the pathogenesis of AMD Hageman et al., 2001; Anderson et al., 2002).

The distribution of HF1 at the RPE-choroid interface is strikingly similar to that of C5b-9, implying that significant amounts of the MAC are generated and deposited at the RPE-choroid interface. This suggests that the protein associated with the at-risk HF1 haplotype(s) may undergo a reduction in its normal ability to attenuate complement activation. Thus, the HF1 variants associated with AMD may put RPE and choroidal cells at sustained risk for alternative pathway-mediated complement attack, drusen formation and the disruption of Bruch's membrane integrity that is associated with late-stage neovascular AMD. Since Bruch's membrane is significantly thinner in the macula than elsewhere (Chong et al., 2005), it may be more susceptible to subsequent neovascular invasion. Because Bruch's membrane is significantly thinner in the macula than in the periphery, it may be more likely to become degraded to an extent that it is susceptible to neovascular invasion.

In summary, the results of this investigation provide strong evidence that common haplotypes in HF1 predispose individuals to AMD. We propose that alterations in genes that regulate the alternative pathway of the complement cascade, in combination with events that activate the system, underlie a major proportion of AMD in the human population.

Example 2

Variations in the Complement Regulatory Genes Factor H (CFH) and Factor H Related 5 (CFHR5) are Associated with Membranoproliferative Glomerulonephritis Type II (Dense Deposit Disease)

Introduction

The membranoproliferative glomerulonephritides are diseases of diverse and often obscure etiology that account for 4% and 7% of primary renal causes of nephrotic syndrome in children and adults, respectively (Orth et al., 1998). Based on renal immunopathology and ultrastructural studies, three subtypes are recognized. Membranoproliferative glomerulonephritis (MPGN) types I and III are variants of immune complex-mediated disease; MPGNII, in contrast, has no known association with immune complexes (Appel et al., 2005).

MPGNII accounts for less than 20% of cases of MPGN in children and only a fractional percentage of cases in adults (Orth et al., 1998; Habib et al., 1975; Habib et al., 1987). Both sexes are affected equally, with the diagnosis usually made in children between the ages of 5-15 years who present with non-specific findings like hematuria, proteinuria, acute nephritic syndrome or nephrotic syndrome (Appel et al., 2005). More than 80% of patients with MPGNII are also positive for serum C3 nephritic factor (C3NeF), an autoantibody directed against C3bBb, the convertase of the alternative pathway of the complement cascade (Schwertz et al., 2001). C3NeF is found in up to one-half of persons with MPGN types I and III and also in healthy individuals, making the electron microscopic demonstration of dense deposits in the glomerular basement membrane (GBM) necessary for a definitive diagnosis of MPGN II (Appel et al., 2005). This morphological hallmark is so characteristic of MPGN II that the disease is more accurately referred to as Dense Deposit Disease (MPGNII/DDD) (FIG. 12).

Spontaneous remissions of MPGNII/DDD are uncommon (Habib et al., 1975; Habib et al., 1987; Cameron et al., 1983; Barbiano di Belgiojoso et al., 1977). The more common outcome is chronic deterioration of renal function leading to end-stage renal disease (ESRD) in about half of patients within 10 years of diagnosis (Barbiano di Belgiojoso et al., 1977; Swainson et al., 1983). In some patients, rapid fluctuations in proteinuria occur with episodes of acute renal deterioration in the absence of obvious triggering events; in other patients, the disease remains stable for years despite persistent proteinuria.

Figure 13:
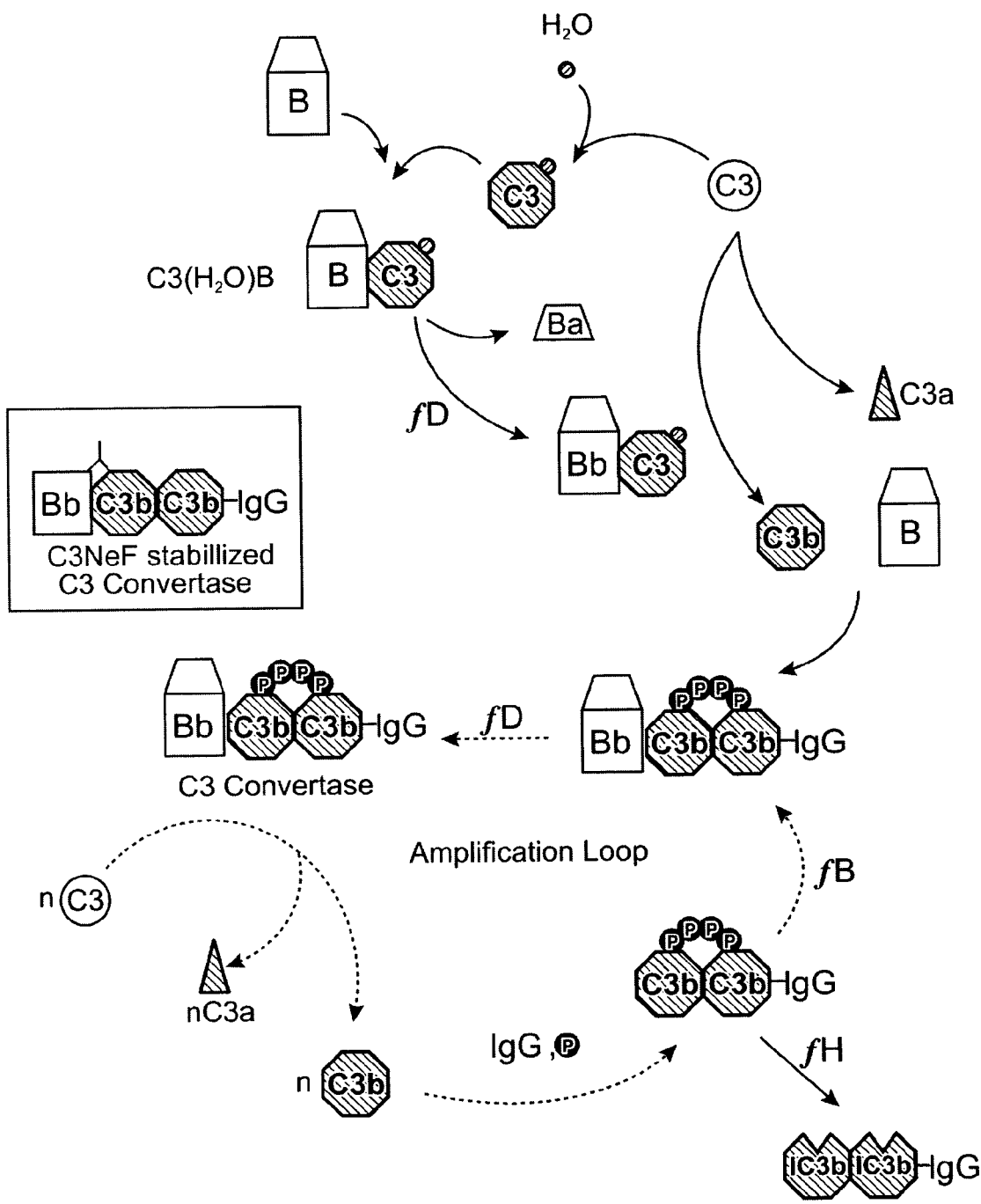
FIG. 13 is a diagram showing the activation and regulation of the alternative pathway of the complement cascade, which is systematically activated at a high level in patients with AMD and MPGNII. The alternative pathway of the complement cascade is systematically activated at a high level in patients with MPGN II/DDD. Normally, continuous low-level activation of C3 occurs by a process of spontaneous hydrolysis known as tick-over. C3 hydrolysis is associated with a large conformational protein change shown at the top of the diagram. The conformational change makes C3(H20) similar to C3b, a C3 cleavage product. The initial convertase, C3(H2O)Bb, activates C3 to form C3b. Although C3b has a fleeting half-life, if it binds to IgG, cells or basement membranes, it is protected from immediate inactivation. (C3b)2-IgG complexes form in the fluid phase and bind properdin (P), which facilitates factor B binding and the generation of C3bBb, the convertase of the alternative pathway, shown here as a Bb(C3b)2-IgG-properdin complex. The amplification loop is depicted by the arrows. C3NeF prolongs the half-life of C3 convertase and is shown in the inset. One mechanism to degrade C3 convertase is through its interaction with complement Factor H (CFH), shown at the bottom right as fH. Deficiency of and mutations in Factor H are associated with MPGN II/DDD.

C3NeF persists throughout the disease course in more than 50% of patients with MPGNII/DDD (Schwertz et al., 2001). Its presence is typically associated with evidence of complement activation, such as a reduction in CH50, decrease in C3, increase in C3dg/C3d and persistently high levels of activation of the alternative pathway of the complement cascade. C3, the most abundant complement protein in serum (~1.2 mg/ml), normally undergoes low levels of continuous autoactivation by hydrolysis of its thioester in a process known as tick-over. C3 hydrolysis induces a large conformational protein change, making $C3(H_2O)$ similar to C3b, a cleavage product of C3. $C3(H_2O)$ associates with factor B to form $C3(H_2O)$Bb, which cleaves C3 to C3b in an amplification loop that consumes C3 and produces C3bBb$^2$ (FIG. 13).

In MPGNII/DDD, C3NeF binds to C3bBb (or to the assembled convertase) to prolong the half-life of this enzyme, resulting in persistent C3 consumption that overwhelms the normal regulatory mechanisms to control levels of C3bBb and complement activation (Appel et al., 2005). Normal control involves at least seven proteins, four of which are present in serum (complement Factor H (CFH), complement factor H-like protein 1 (CFHL1), complement factor I (CFI) and C4 binding protein (C4BP)) and three of which are cell membrane-associated (membrane co-factor protein (MCP, CD46), decay accelerating factor (DAF, CD55) and complement receptor 1 (CR1, CD35)) (Appel et al., 2005; Meri et al., 1994; Pascual et al., 1994).

Figure 14:
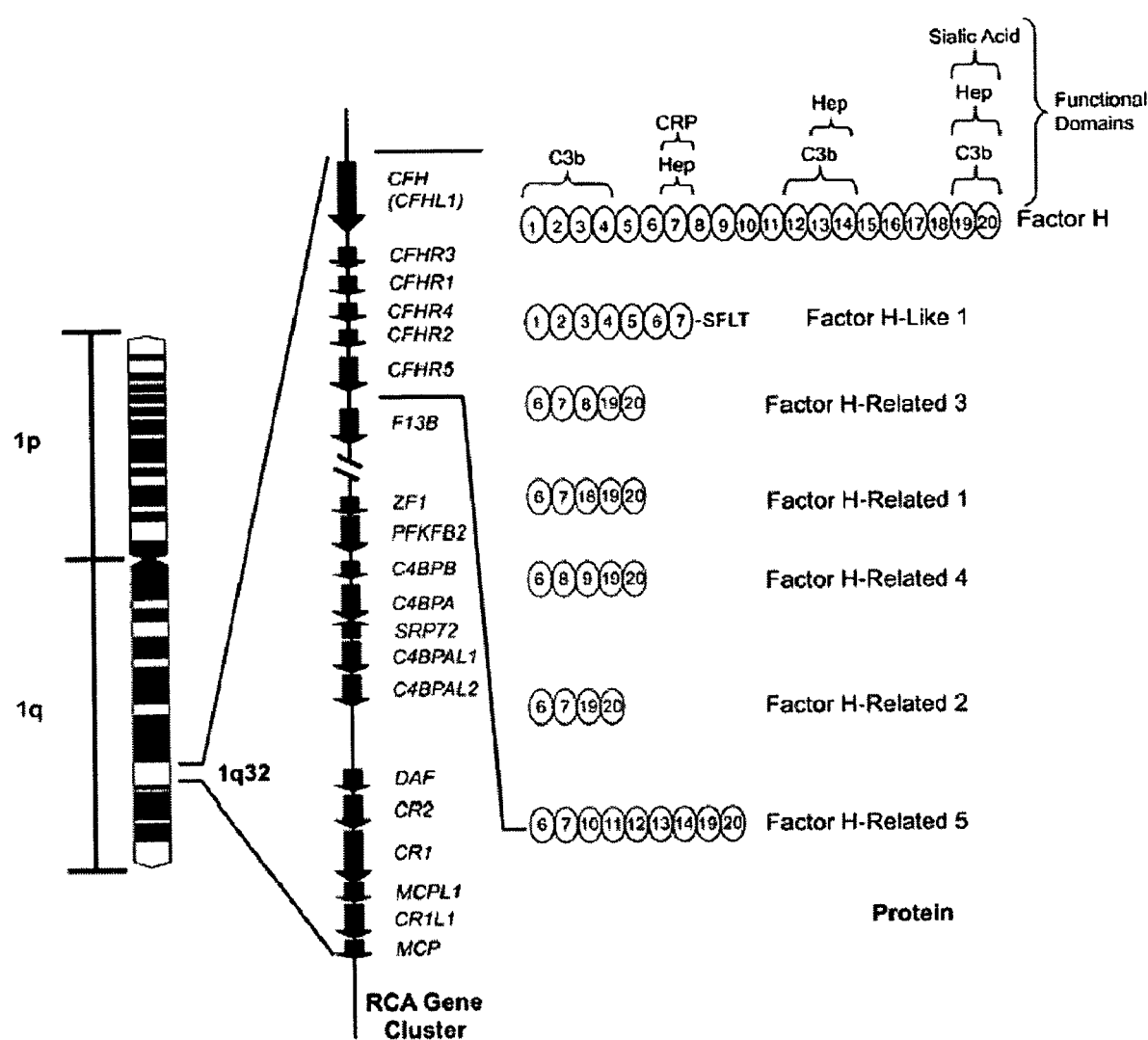
FIG. 14 is a diagram showing the organization of the regulators-of-complement-activation (RCA) gene cluster on chromosome 1q32 and the arrangement of approximately 60-amino acid domains known as short consensus repeats (SCRs) in complement Factor H (CFH), Factor H-Like 1 (CFHL1) and Factor H-Related 1, 2, 3, 4 and 5 (CFHR1, CFHR2, CFHR3, CFHR4 and CFHR5). CFH has 20 SCRs. The interacting partners with some of these SCRs has been determined and is shown on the top right (CRP, C reactive protein; Hep, heparin). Complement factor H-like 1 (CFHL1) is a splice isoform of CFH, while complement factor H-related proteins 1-5 (CFHR1-5) are each encoded by a unique gene (CFHR1-5). The SCRs of CFHR1-5 are similar to some of the SCRs in CFH, as denoted by the numbers in the ovals. For example, CFHR5 has 9 SCRs, with the first two being similar to SCRs 6 and 7 of Factor H and therefore having CRP and heparin binding properties. SCRs5-7 of CFHR5 have the numbers 12-14 within the corresponding ovals because these SCRs are similar to SCRs 12-14 of Factor H and have C3b and heparin binding properties.

Of particular relevance to MPGNII/DDD is Factor H, one of 7 proteins in the Factor H family. In pigs and mice, its deficiency is associated with the development of renal disease that is similar at the light and electron microscopic level to MPGNII/DDD, and in humans its deficiency as well as mutations in the Factor H gene have been reported in patients with MPGNII/DDD (Meri et al., 1994; Dragen-Durey et al., 2004; Zipfel et al., 2005) (FIG. 14).

The other 6 members of the Factor H family include FHL1, which is a splice isoform of Factor H, and five CFH-related proteins encoded by distinct genes (CFHR1-5). There is little known about the latter five proteins, although they do show varying degrees of structural similarity to Factor H (Appel et al., 2005). Most interesting in this group with respect to MPGNII/DDD is CFHR5, because it shows the highest similarity to Factor H and has been demonstrated in renal biopsies of patients with other types of glomerulonephritis (Appel et al., 2005; Murphy et al., 2002). In vitro studies have also shown that V is present on surfaces exposed to complement attack, suggesting a possible role in the complement cascade (Murphy et al., 2002).

A possible relationship between Factor H/CFHR5 and MPGNII/DDD is further strengthened by the observation that patients with MPGNII/DDD develop an ocular phenotype called drusen. Drusen result from the deposition of abnormal extracellular deposits in the retina within the ocular Bruch's membrane beneath the retinal pigment epithelium. The drusen of MPGNII/DDD are clinically and compositionally indistinguishable from drusen that form in age-related macular degeneration (AMD) (Mullins et al., 2001; Anderson et al., 2002), which is the most common form of visual impairment in the elderly (Klein et al., 2004; van Leeuwen et al., 2003). The single feature that distinguishes these two types of drusen is age of onset-drusen in MPGNII/DDD develop early, often in the second decade of life, while drusen in AMD are found in the elderly.

Four recent studies have implicated specific allele variants of Factor with AMD, suggesting that subtle differences in Factor H-mediated regulation of the alternative pathway of complement may play a role in a substantial proportion of AMD cases (Hageman et al., 2005; Edwards et al., 2005; Haines et al., 2005; Klein et al., 2005). One of these studies also showed that MPGNII/DDD and AMD patients segregate several of the same Factor H risk alleles (Hageman et al., 2005). In this study, we sought to refine the association of allele variations of Factor H and CFHR5 with MPGNII/DDD.

Materials and Methods

Patients and Controls. Patients with biopsy-proven MPGNII/DDD were ascertained in nephrology divisions and enrolled in this study under IRB-approved guidelines. The control group was ascertained from ethnically-matched but not age-matched unrelated persons in whom AMD had been excluded by ophthalmologic examination.

Mutation Screening and Analysis. Coding and adjacent intronic regions of Factor H and CFHR5 were PCR amplified for 35 cycles of 30 seconds each at 94° C. denaturing, 61° C. annealing and 70° C. extension. The sequences of primers used to amplify the Factor H and CFHR5 coding sequences are shown in TABLES 10 and 11, respectively. Product generation was verified by agarose gel electrophoresis and amplicons were then bi-directionally sequenced in patients with MPGNII/DDD. All novel and reported SNPs identified through data mining (Ensemble database, dbSNP, Applied Biosystems) were typed in the control population by denaturing high performance liquid chromatography (DHPLC) (Tables 9 and 10). In brief, DHPLC analysis of each amplicon was performed at three different temperatures. Amplicons were analyzed using Wavemaker software to estimate optimal temperature, run time and acetonitrile gradient. Predicted temperatures were bracketed by ±2° C. to optimize sensitivity and maximize the likelihood that novel mutations would be detected (Prasad et al., 2004).

Haplotype Analysis. Construction of block structures with distribution of haplotypes was completed using Haploview, a publicly available software program developed at the Whitehead Institute (http://www.broad.mit.edu/mpg/haploview/) (see Barrett et al.). Two datasets, one consisting of each control's sex and genotype, and the other describing marker information including SNP identification and chromosomal location, were assimilated in Excel files, which were uploaded into the Haploview program. The output consisted of linkage disequilibrium (LD) plots and the corresponding population frequencies with crossover percentages.

Statistical Analysis. The chi-square test of independence was used to detect differences in SNP frequencies between patients with MPGNII/DDD and controls. P-values≦0.05 were considered significant. The LD plots for Factor H and CFHR5 were created using the control population.

Results

Patients and Controls. Twenty-two patients with biopsy-proven MPGNII/DDD and 131 persons without AMD participated in this study. Mean age of the control group was 78.4 years, reflecting our ascertainment criterion to exclude AMD.

Factor H, CFHR5 and MPGNII/DDD. Allele frequencies of four of seven Factor H SNPs genotyped in the MPGNII/DDD patient group and the control population showed a significant association with the MPGNII/DDD disease phenotype at p<0.05. These SNPs included exon 2 I62V, IVS 2-18insTT, exon 9 Y402H and exon 10 A473A. Allele frequencies for exon 7 A307A, exon 13 Q672Q and exon 18 D936E were not significantly different between groups (TABLES 11 to 13).

Five CFHR5 SNPs were genotyped in the MPGNII/DDD patient group and control population, including one non-synonymous SNP (exon 2 P46S), two promoter SNPs (−249T>C, −20 T>C) and two intronic SNPs (IVS1+75T>A, IVS2+58C>T). Allele frequencies of three SNPs—exon 2 P46S, −249T>C and −20 T>C—were significantly different between groups at p<0.05 (TABLES 14 and 15).

Figure 15:
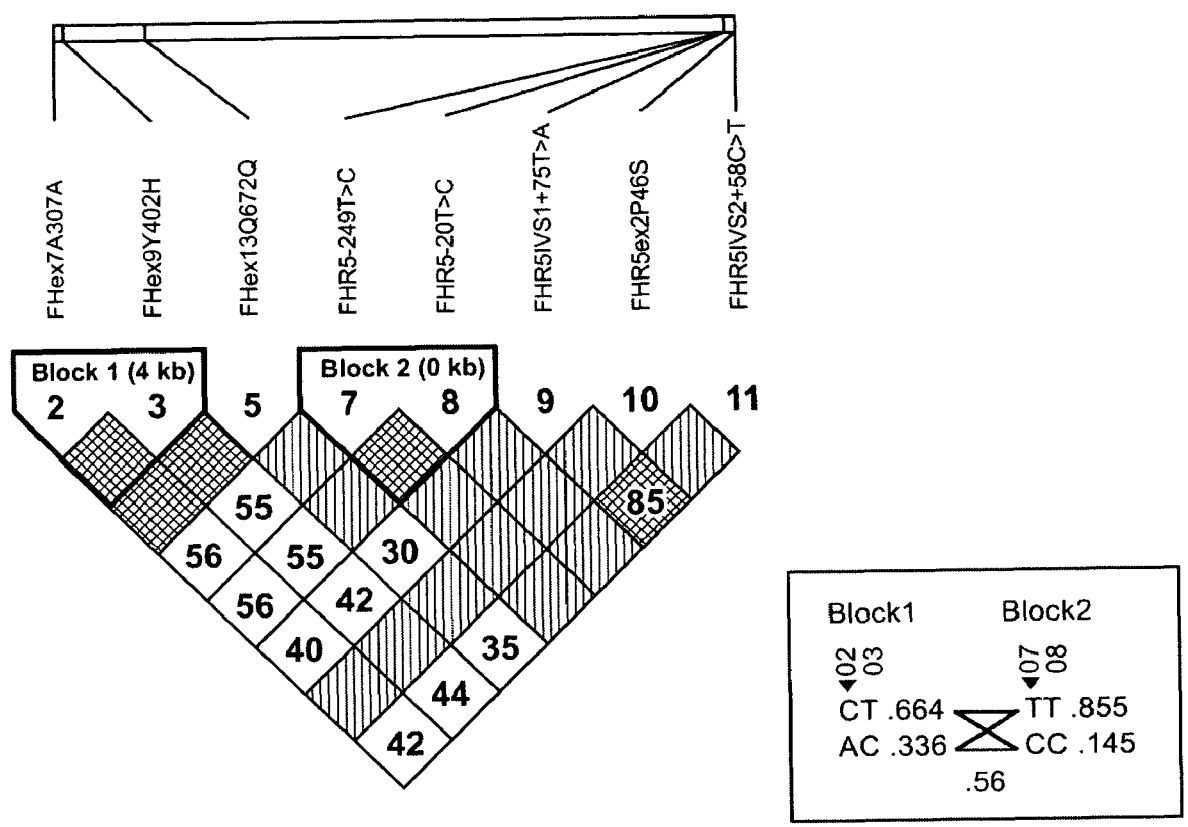
FIG. 15 shows a linkage disequilibrium plot indicating that A307A and Y402H are in linkage disequilibrium in Factor H and −249T>C and −20T>C are in linkage disequilibrium in CFHR5.

Haploblocks. Haplotype blocks showed that A307A and Y402H are in linkage disequilibrium in Factor H while −249T>C and −20T>C are in linkage disequilibrium in CFHR5 (FIG. 15).

Discussion

The alternative pathway of complement represents an elegant system to protect humans from pathogens. Its central component, C3, circulates at a high concentration in plasma and is distributed throughout body fluids (Walport; 2001). Its activation creates a toxic local environment that damages foreign surfaces and results in the elimination of microbes. To prevent unrestricted complement activation, host cells and tissue surfaces down-regulate the amplification loop using a combination of surface-attached and membrane-bound regulators of complement. Some host cells express a single membrane-bound regulator of complement in high copy number, while other cells express several membrane-bound regulators and also attach soluble fluid-phase regulators. A few tissues lack membrane-bound regulators and depend exclusively on the attachment of soluble regulators (Appel et al., 2005).

In the kidney, endothelial and mesangial cells express two membrane-bound regulators of complement, MCP and DAF (van den Dobbelsteen et al., 1994; Timmerman et al., 1996). Podocytes express four: MCP, DAF, CR1 and CD59. Both mesangial cells and podocytes also secrete the soluble regulator, Factor H, which is up-regulated in membranous nephropathy in response to complement activation and inflammation (Angaku et al., 1998; Bao et al., 2002). Factor H acts in an autocrine fashion by binding directly to the secreting mesangial cells and podocytes.

The GBM, in contrast, is unique. It lacks endogenous membrane-bound regulators to protect it from complement-mediated injury, however its highly negatively charged surface binds and absorbs Factor H (Zipfel et al., 2005). The dependency of the GBM on Factor H for local complement control is consistent with the finding of pathologic mutations in Factor H in a few persons with MPGNII/DDD (Ault et al., 1997; Dragen-Durey et al., 2004).

Our data identifying several allele variants of Factor H and CFHR5 associated with MPGNII/DDD is consistent with the hypothesis that complement control plays a role in the pathogenesis of this disease. A comparison of our data with reported AMD data adds additional support, as the allele frequency for each of the identified at-risk SNP variants we observed in Factor H is higher in the MPGNII/DDD patient cohort than in the AMD patient cohort, and strong evidence implicates Factor H in AMD (Hageman et al., 2005; Edwards et al., 2005; Haines et al., 2005; Klein et al., 2005). Although it is not known whether the amino acid changes in exons 2 and 9 of Factor H impact function, these changes are found in domains that interact with C3b and heparin, and differences in C3b/C3d and heparin binding have been demonstrated with several amino acid changes in Factor H that are associated with another renal disease, atypical hemolytic uremic syndrome (Manuelian et al., 2003) (TABLES 12 and 13).

With the exception of Factor H, the function of other members of the Factor H-related family is largely unknown and their expression patterns have not been explored, however studies of CFHR5 have shown that it has properties similar to Factor H, including heparin, CRP and C3b binding (Murphy et al., 2002) (FIG. 14). This similarity suggests that like Factor H, CFHR5 plays a role in MPGNII/DDD. Consistent with this is our finding of CFHR5 expression in renal biopsies from two patients with MPGNII/DDD (data not shown).

Our genotyping data show that some allele variants of CFHR5 preferentially associate with the MPGNII/DDD disease phenotype. Included are two SNPs in the promoter region of CFHR5 which could affect transcription, one by removing a binding site for C/EBPbeta and the other by adding a GATA-1 binding site. The other significant association changes a proline to serine in exon 2. Since exons 1 and 2 of CFHR5 encode a domain homologous to short consensus repeat 6 (SCR6) of Factor H, which is integral to heparin and CRP binding, this change could affect complement activation and control.

Example 3

Production of Protective Form of Factor H Protein

An exemplary protective form of human complement factor H (CFH) was prepared based on haplotype H2 (FIG. 5). Briefly, RNA was isolated from ocular tissues (RPE/choroid complexes) of four donors. The RNA was amplified by reverse transcription-polymerase chain reaction using the following primers:

```
5'-GAAGATTGCAATGAACTTCCTCCAAG-3'    [SEQ ID NO:331]

5'-AAGTTCTGAATAAAGGTGTGC-3'.        [SEQ ID NO:332]
```

RT-PCR reactions were performed using Superscript III One-Step High Fidelity with Platinum Taq, as described by the manufacturer (Invitrogen, Carlsbad, Calif.). The appropriate sized products (3,769 bp) were excised from agarose gels and isolated using spin columns.

The PCR products were cloned using the TOPO-TA cloning system, as recommended by the manufacturer (Invitrogen) in the vector pCR2.1-TOPO. The complete genetic sequences of the clones derived from each of the four patients were determined by direct sequencing. The DNA derived from one patient (patient #498-01) had the fewest number of nucleotide polymorphisms relative to that of an exemplary protective reference sequence (H2), although this DNA encoded the risk sequence at amino acid position 402 (histidine) and encoded valine at amino acid position 62. To prepare a gene encoding a protective form of CFH we changed the bases encoding amino acid 62 such that it coded for isoleucine and those at position 402 such that they encoded a tyrosine, using the QuikChange Mutagenesis system (Stratagene, La Jolla, Calif.), resulting in SEQ ID NO:335. The amino acid at position 1210 of this protein is arginine. The oligonucleotides employed were as follows (plus the appropriate antisense version):

62: [SEQ ID NO:333]
5'-TATAGATCTCTTGGAAATATAATAATGGTATGCAGG-3'

402: [SEQ ID NO:334]
5'-ATGGATATAATCAAAATTATGGAAGAAAGTTTGTAC-3'

The fidelity of the introduced mutations were confirmed by direct sequencing of the entire gene. The resulting protective gene was cloned into the eukaryotic expression vector pcDNA3.1 (Invitrogen) under control of the cytomegalovirus promoter. This expression vector was transfected into the human lung carcinoma cell line A549 (ATCC, Manassas, Va.) using the Exgen 500 transfection reagent (Fermentas, Hanover, Md.). Subsequent to transfection, cells were grown in serum-free media (Hybridoma-SFM, Invitrogen).

Supernatants were collected 48 hours after transfection and subjected to Western blot analyses. The presence of the appropriate-sized product (approximately 150 kDa) was confirmed using monoclonal and polyclonal antibodies directed against human CFH (Quidel, San Diego, Calif.).

Patient #498-01 (62I, 402Y) CFH Gene [SEQ ID NO:335]

AGTTAGCTGGTAAATGTCCTCTTAAAAGATCCAAAAAATGAGACTTCTAG

CAAAGATTATTTGCCTTATGTTATGGGCTATTTGTGTAGCAGAAGATTGC

AATGAACTTCCTCCAAGAAGAAATACAGAAATTCTGACAGGTTCCTGGTC

TGACCAAACATATCCAGAAGGCACCCAGGCTATCTATAAATGCCGCCCTG

GATATAGATCTCTTGGAAATATAATAATGGTATGCAGGAAGGGAGAATGG

GTTGCTCTTAATCCATTAAGGAAATGTCAGAAAAGGCCCTGTGGACATCC

TGGAGATACTCCTTTTGGTACTTTTACCCTTACAGGAGGAAATGTGTTTG

AATATGGTGTAAAAGCTGTGTATACATGTAATGAGGGGTATCAATTGCTA

GGTGAGATTAATTACCGTGAATGTGACACAGATGGATGGACCAATGATAT

TCCTATATGTGAAGTTGTGAAGTGTTTACCAGTGACAGCACCAGAGAATG

GAAAAATTGTCAGTAGTGCAATGGAACCAGATCGGGAATACCATTTTGGA

CAAGCAGTACGGTTTGTATGTAACTCAGGCTACAAGATTGAAGGAGATGA

AGAAATGCATTGTTCAGACGATGGTTTTTGGAGTAAAGAGAAACCAAAGT

GTGTGGAAATTTCATGCAAATCCCCAGATGTTATAAATGGATCTCCTATA

TCTCAGAAGATTATTTATAAGGAGAATGAACGATTTCAATATAAATGTAA

CATGGGTTATGAATACAGTGAAAGAGGAGATGCTGTATGCACTGAATCTG

GATGGCGTCCGTTGCCTTCATGTGAAGAAAATCATGTGATAATCCTTAT

ATTCCAAATGGTGACTACTCACCTTTAAGGATTAAACACAGAACTGGAGA

TGAAATCACGTACCAGTGTAGAAATGGTTTTTATCCTGCAACCCGGGGAA

ATACAGCAAAATGCACAAGTACTGGCTGGATACCTGCTCCGAGATGTACC

TTGAAACCTTGTGATTATCCAGACATTAAACATGGAGGTCTATATCATGA

GAATATGCGTAGACCATACTTTCCAGTAGCTGTAGGAAAATATTACTCCT

ATTACTGTGATGAACATTTTGAGACTCCGTCAGGAAGTTACTGGGATCAC

ATTCATTGCACACAAGATGGATGGTCGCCAGCAGTACCATGCCTCAGAAA

ATGTTATTTTCCTTATTTGGAAAATGGATATAATCAAAATTATGGAAGAA

AGTTTGTACAGGGTAAATCTATAGACGTTGCCTGCCATCCTGGCTACGCT

CTTCCAAAAGCGCAGACCACAGTTACATGTATGGAGAATGGCTGGTCTCC

TACTCCCAGATGCATCCGTGTCAAAACATGTTCCAAATCAAGTATAGATA

TTGAGAATGGGTTTATTTCTGAATCTCAGTATACATATGCCTTAAAAGAA

AAAGCGAAATATCAATGCAAACTAGGATATGTAACAGCAGATGGTGAAAC

ATCAGGATCAATTACATGTGGGAAAGATGGATGGTCAGCTCAACCCACGT

GCATTAAATCTTGTGATATCCCAGTATTTATGAATGCCAGAACTAAAAAT

GACTTCACATGGTTTAAGCTGAATGACACATTGGACTATGAATGCCATGA

TGGTTATGAAAGCAATACTGGAAGCACCACTGGTTCCATAGTGTGTGGTT

ACAATGGTTGGTCTGATTTACCCATATGTTATGAAAGAGAATGCGAACTT

CCTAAAATAGATGTACACTTAGTTCCTGATCGCAAGAAAGACCAGTATAA

AGTTGGAGAGGTGTTGAAATTCTCCTGCAAACCAGGATTTACAATAGTTG

GACCTAATTCCGTTCAGTGCTACCACTTTGGATTGTCTCCTGACCTCCCA

ATATGTAAAGAGCAAGTACAATCATGTGGTCCACCTCCTGAACTCCTCAA

TGGGAATGTTAAGGAAAAAACGAAAGAAGAATATGGACACAGTGAAGTGG

TGGAATATTATTGCAATCCTAGATTTCTAATGAAGGGACCTAATAAAATT

CAATGTGTTGATGGAGAGTGGACAACTTTACCAGTGTGTATTGTGGAGGA

GAGTACCTGTGGAGATATACCTGAACTTGAACATGGCTGGCCCCAGCTTT

CTTCCCCTCCTTATTACTATGGAGATTCAGTGGAATTCAATTGCTCAGAA

TCATTTACAATGATTGGACACAGATCAATTACGTGTATTCATGGAGTATG

GACCCAACTTCCCCAGTGTGTGGCAATAGATAAACTTAAGAAGTGCAAAT

CATCAAATTTAATTATACTTGAGGAACATTTAAAAAACAAGAAGGAATTC

GATCATAATTCTAACATAAGGTACAGATGTAGAGGAAAAGAAGGATGGAT

ACACACAGTCTGCATAAATGGAAGATGGGATCCAGAAGTGAACTGCTCAA

TGGCACAAATACAATTATGCCCACCTCCACCTCAGATTCCCAATTCTCAC

AATATGACAACCACACTGAATTATCGGGATGGAGAAAAAGTATCTGTTCT

TTGCCAAGAAAATTATCTAATTCAGGAAGGAGAAGAAATTACATGCAAAG

ATGGAAGATGGCAGTCAATACCACTCTGTGTTGAAAAAATTCCATGTTCA

CAACCACCTCAGATAGAACACGGAACCATTAATTCATCCAGGTCTTCACA

AGAAAGTTATGCACATGGGACTAAATTGAGTTATACTTGTGAGGGTGGTT

TCAGGATATCTGAAGAAAATGAAACAACATGCTACATGGGAAAATGGAGT

TCTCCACCTCAGTGTGAAGGCCTTCCTTGTAAATCTCCACCTGAGATTTC

TCATGGTGTTGTAGCTCACATGTCAGACAGTTATCAGTATGGAGAAGAAG

TTACGTACAAATGTTTTGAAGGTTTTGGAATTGATGGGCCTGCAATTGCA

AAATGCTTAGGAGAAAAATGGTCTCACCCTCCATCATGCATAAAAACAGA

TTGTCTCAGTTTACCTAGCTTTGAAAATGCCATACCCATGGGAGAGAAGA

-continued
AGGATGTGTATAAGGCGGGTGAGCAAGTGACTTACACTTGTGCAACATAT
TACAAAATGGATGGAGCCAGTAATGTAACATGCATTAATAGCAGATGGAC
AGGAAGGCCAACATGCAGAGACACCTCCTGTGTGAATCCGCCCACAGTAC
AAAATGCTTATATAGTGTCGAGACAGATGAGTAAATATCCATCTGGTGAG
AGAGTACGTTATCAATGTAGGAGCCCTTATGAAATGTTTGGGGATGAAGA
AGTGATGTGTTTAAATGGAAACTGGACGGAACCACCTCAATGCAAAGATT
CTACAGGAAAATGTGGGCCCCCTCCACCTATTGACAATGGGGACATTACT
TCATTCCCGTTGTCAGTATATGCTCCAGCTTCATCAGTTGAGTATCAATG -continued
CCAGAACTTGTATCAACTTGAGGGTAACAAGCGAATAACATGTAGAAATG
GACAATGGTCAGAACCACCAAAATGCTTACATCCGTGTGTAATATCCCGA
GAAATTATGGAAAATTATAACATAGCATTAAGGTGGACAGCCAAACAGAA
GCTTTATTCGAGAACAGGTGAATCAGTTGAATTTGTGTGTAAACGGGGAT
ATCGTCTTTCATCACGTTCTCACACATTGCGAACAACATGTTGGGATGGG
AAACTGGAGTATCCAACTTGTGCAAAAGATAGAATCAATCATAAAGTGC
ACACCTTTATTCAGAACTT

TABLE 1A

| dbSNP No. | Location | Sequence Spanning Polymorphism | SEQ ID No: | AA Change |
|---|---|---|---|---|
|  | Promoter 1 | GGGGTTTTCTGGGATGTAAT[A/G]ATGTTCAGTGTTTTGACCTT CCCCAAAAGACCCTACATTA[T/C]TACAAGTCACAAAACTGGAA | 9 |  |
| rs3753394 | Promoter 4 | TTATGAAATCCAGAGGATAT[C/T]ACCAGCTGCTGATTTGCACA AATACTTTAGGTCTCCTATA[G/A]TGGTCGACGACTAAACGTGT | 10 |  |
| rs529825 | Intron 1 | AGTCCAAGTTTACACAGTAC[G/A]ATAGACTTACCCATTGCCAA TCAGGTTCAAATGTGTCATG[C/T]TATCTGAATGGGTAACGGTT | 11 |  |
| rs800292 | Exon 2 | GATATAGATCTCTTGGAAAT[G/A]TAATAATGGTATGCAGGAAG CTATATCTAGAGAACCTTTA[C/T]ATTATTACCATACGTCCTTC | 12 | I62V |
|  | Intron 2 | TAATTCATAACTTTTTTTTT[-/TT]CGTTTTAGAAAGGCCCTGTG ATTAAGTATTGAAAAAAAAA[-/AA]GCAAAATCTTTCCGGGACAC | 13 |  |
| rs3766404 | Intron 6 | AAAGGAATACATTTAGGACT[C/T]ATTTGAAGTTAGTGTCAACA TTTCCTTATGTAAATCCTGA[G/A]TAAACTTCAATCACAGTTGT | 14 |  |
| rs1061147 | Exon 7 | CAACCCGGGGAAATACAGC[A/C]AAATGCACAAGTACTGGCTG GTTGGGCCCCTTTATGTCG[T/G]TTTACGTGTTCATGACCGAC | 15 | A307A |
| rs1061170 | Exon 9 | AAAATGGATATAATCAAAAT[T/C]ATGGAAGAAAGTTTGTACAG TTTTACCTATATTAGTTTTA[A/G]TACCTTCTTTCAAACATGTC | 16 | Y402H |
| rs2274700 | Exon 10 | TATGCCTTAAAAGAAAAAGC[G/A]AAATATCAATGCAAACTAGG ATACGGAATTTTCTTTTTCG[C/T]TTTATAGTTACGTTTGATCC | 17 | A473A |
|  | Exon 10A | CAGCTTGAGTGGATCAAAGA[-/N]TGACAAGGGCCAATGGAACC GTCGAACTCACCTAGTTTCT[-/N]ACTGTTCCCGGTTACCTTGG | 18 |  |
| rs203674 | Intron 10 | ACGGTACCTATTTATTAGTA[G/T]ATCTAATCAATAAAGCTTTT TGCCATGGATAAATAATCAT[C/A]TAGATTAGTTATTTCGAAAA | 19 |  |
| rs203674 | Intron 10* | AAAAGCTTTATTGATTAGAT[A/C]TACTAATAAATAGGTACCGT | 63 |  |
| rs3753396 | Exon 13 | AAGGGACCTAATAAAATTCA[A/G]TGTGTTGATGGAGAGTGGAC TTCCCTGGATTATTTTAAGT[T/C]ACACAACTACCTCTCACCTG | 20 | Q672Q |
| rs375046 | Intron 15 | TTTTTTATTTTTTATTATAA[C/A]ATTAATTATATTTTTAATAT AAAAAATAAAAAATAATATT[G/T]TAATTAATATAAAAATTATA | 21 |  |
| rs1065489 | Exon 18 | CCTTGTAAATCTCCACCTGA[G/T]ATTTCTCATGGTGTTGTAGC GGAACATTTAGAGGTGGACT[C/A]TAAAGAGTACCACAACATCG | 22 | D936E |
|  | Exon 22 | GGGGATATCGTCTTTCATCA[C/T]GTTCTCACACATTGCGAACA CCCCTATAGCAGAAAGTAGT[G/A]CAAGAGTGTGTAACGCTTGT | 23 | R1210C |

| dbSNP No. | Location | Allele Freq. CTL | Allele Freq. AMD | Chi2 & P Value |
|---|---|---|---|---|
|  | Promoter 1 | 1-0.944:2-0.056 | 1-0.96:2-0.04 |  |
| rs3753394 | Promoter 4 | 1-0.31:2-0.69 | 1-0.25:2-0.75 | 6.485:0.039 |
| rs529825 | Intron 1 | 1-0.74:2-0.26 | 1-0.84:2-0.16 | 26.07:2.18E-06 |

TABLE 1A-continued

| | | | | | |
|---|---|---|---|---|---|
| | rs800292 | Exon 2 | 1-0.78:2-0.22 | 1-0.91:2-0.09 | 16.19:5.74E-05 |
| | | Intron 2 | 1-0.77:2-0.23 | 1-0.89:2-0.11 | 22.19:2.47E-06 |
| | rs3766404 | Intron 6 | 1-0.83:2-0.17 | 1-0.91:2-0.09 | 23.82:6.71E-06 |
| | rs1061147 | Exon 7 | 1-0.34:2-0.66 | 1-0.59:2-0.41 | 50.39:1.26E-12 |
| | rs1061170 | Exon 9 | 1-0.66:2-0.34 | 1-0.46:2-0.54 | 55.20:1.03E-12 |
| | rs2274700 | Exon 10 | 1-0.54:2-0.46 | 1-0.80:2-0.20 | 36.48:1.55E-09 |
| | | Exon 10A | 1-1.00:2-0.00 | 1-0.933:2-0.067 | |
| | rs203674 | Intron 10 | 1-0.66:2:0.34 | 1-0.44:2-0.56 | 66.97:2.86E-15 |
| | rs203674 | Intron 10* | 1-0.66:2:0.34 | 1-0.44:2-0.56 | 66.97:2.86E-15 |
| | rs3753396 | Exon 13 | 1-0.84:2-0.16 | 1-0.86:2-0.14 | 0.308:0.579 |
| | rs375046 | Intron 15 | 1-0.67:2-0.31 | 1-0.85:2-0.14 | |
| | rs1065489 | Exon 18 | 1-0.87:2-0.13 | 1-0.85:2-0.15 | 0.155:0.694 |
| | | Exon 22 | 1-1.00:2-0.00 | 1-0.95:2-0.05 | |

*Shows the non-coding strand of the genomic sequence.

TABLE 1B (1)

| SNP name | Interrogated Sequence | SEQ ID NO: | Chimp | Location | AA |
|---|---|---|---|---|---|
| rs3753394 | AAATCCAGAGGATAT[C/T]ACCAGCTGCTGATTT | 24 | C | Promoter | |
| rs529825 | AATGGGTAAGTCTAT[C/T]GTACTGTGTAAACTT | 25 | T | Intron 1 | |
| rsa800292 | TGCATACCATTATTA[C/T]ATTTCCAAGAGATCT | 26 | T | Exon 2 | I 62V |
| Intron 2 insTT | ACATACTAATTCATAAC[—/TT]TTTTTTTTTCGTTTTAGG | 27 | | Intron 2 | |
| rs3766404 | AATACATTTAGGACT[T/C]ATTTGAAGTTAGTGT | 28 | C | Intron 6 | |
| rs1061147 | CCGGGGAAATACAGC[C/A]AAATGCACAAGTACT | 29 | A | Exon 7 | A307A |
| rs1061170 | GGATATAATCAAAAT[T/C]ATGGAAGAAAGTTTG | 30 | T | Exon 9 | Y402H |
| rs2274700 | CTTAAAAGAAAAAGC[G/A]AAATATCAATGCAAA | 31 | G | Exon 10 | A473A |
| rs203674 | CTTTATTGATTAGAT[A/C]TACTAATAAATAGGT | 32 | A | Intron 10 | |
| rs3753396 | ACCTAATAAAATTCA[A/G]TGTGTTGATGGAGAG | 33 | A | Exon 13 | Q672Q |
| rs1065489 | TAAATCTCCACCTGA[G/T]ATTTCTCATGGTGTT | 34 | G | Exon 18 | D936E |

(2)

| SNP name | Forward Primer or AOD number | SEQ ID NO: | Reverse Primer | SEQ ID NO: |
|---|---|---|---|---|
| rs3753394 | C_2530387_10 | | | |
| rs529825 | C_2550476_10 | | | |
| rsa800292 | C_2530382_10 | | | |
| Intron 2 insTT | ACTTGTTCCCCCACTCCTAC | 35 | CCTCTTTTCGTATGGACTAC | 36 |
| rs3766404 | C_11890065_10 | | | |
| rs1061147 | TGAAATCACGTACCAGTGTAGAAATGG | 37 | CAGGTATCCAGCCAGTACTTGT | 38 |
| rs1061170 | CTTTATTTATTTATCATTGTTATGGTCCTTAGGAAAATGTTATTT | 39 | GGCAGGCAACGTCTATAGATTTACC | 40 |
| rs2274700 | TCACCATCTGCTGTTACATATCCTAGT | 41 | TGGGTTTATTTCTGAATCTCAGTATACATATGC | 42 |
| rs203674 | C_2530311_10 | | | |
| rs3753396 | C_2530296_10 | | | |
| rs1065489 | C_2530274_10 | | | |

(3)

| SNP name | VIC Probe | SEQ ID NO: | FAM Probe | SEQ ID NO: |
|---|---|---|---|---|
| rs1061147 | AATACAGCAAAATGC | 43 | ATACAGCCAAATGC | 46 |
| rs1061170 | TTTCTTCCATGATTTTG | 44 | TTCTTCCATAATTTTG | 47 |
| rs2274700 | AAGAAAAAGCGAAATAT | 45 | AAGAAAAAGCAAAATAT | 48 |

TABLE 1C

| Location | Sequence Spanning Polymorphism | AA Position | SEQ ID NO: |
|---|---|---|---|
| Exon 2 | CCAGGCTATCTATAAATGCC [G/A] CCCTGGATATAGATCTCTTG | R53H | 49 |
| Exon 3 | TTGGTACTTTTACCCTTACA [G/T] GAGGAAATGTGTTTGAATAT | G100R | 50 |
| Exon 5 | ACGATGGTTTTTGGAGTAAA [G/notG] AGAAACCAAAGTGTGTGGGT | 201 | 51 |
| Exon 6 | TTATTTATAAGGAGAATGAA [C/notC] GATTTCAATATAAATGTAAC | R232X | 52 |
| Exon 6 | CACTGAATCTGGATGGCGTC [C/notC] GTTGCCTTCATGTGAAG (end Exon 6) | 258 | 53 |
| Exon 8 | AAGATGGATGGTCGCCAGCA [G/C] [—/C] TACCATGCCTCA (end Exon 8) | V383L | 54 |
| Exon 16 | ACAATTATGCCCACCTCCAC [C/G] TCAGATTCCCAATTCTCACA | 815 | 55 |
| Exon 17 | CAACCACCTCAGATAGAACA [C/T] GGAACCATTAATTCATCCAG | H878H | 56 |
| Exon 17 | GTCTTCACAAGAAAGTTATG [C/T] ACATGGGACTAAATTGAGTT | A892V | 57 |
| Exon 18 | CACATGTCAGACAGTTATCA [G/T] TATGGAGAAGAAGTTACGTA | Q950H | 58 |
| Exon 18 | TCAGTATGGAGAAGAAGTTA [C/T] GTACAAATGTTTTGAAGGTT | S956L | 59 |
| Intron 18 | (begin IVS18) GTATGG [G/T] GCATTGAATTTTATTATATG | | 60 |
| Exon 20 | (begin Exon 20) ACACCTCCTGTGTG [A/T] ATCCGCCCACAGTACAAAAT | N1050Y | 61 |
| Exon 21 | CTTGTATCAACTTGAGGGTA [—/N] A [—/N] CAAGCGAATAACATGTAGAAA | 1147 | 62 |

TABLE 2

Haplotype Analysis of HF1 SNPs in AMD Cases and Controls

| Prom | IVS1 | I62V | IVS6 | Y402H | IVS10 | Q672Q | D936E | OR est | P | Cases | Con |
|---|---|---|---|---|---|---|---|---|---|---|---|
| | | | | | | | | 2.67 | <0.000001 | 0.49 | 0.26 |
| | | | | | | | | 0.48 | <0.000011 | 0.06 | 0.12 |
| | | | | | | | | 0.63 | 0.00035 | 0.12 | 0.18 |
| | | | | | | | | 2.68 | | 0.48 | 0.26 |
| | | | | | | | | 0.50 | | 0.06 | 0.12 |
| | | | | | | | | 0.62 | | 0.12 | 0.18 |
| | | | | | | | | 2.65 | | 0.49 | 0.26 |
| | | | | | | | | 0.50 | | 0.06 | 0.12 |
| | | | | | | | | 0.6 | | 0.12 | 0.19 |
| | | | | | | | | 2.56 | | 0.49 | 0.27 |
| | | | | | | | | 0.49 | | 0.06 | 0.12 |
| | | | | | | | | 0.6 | | 0.12 | 0.19 |
| | | | | | | | | 2.33 | | 0.51 | 0.31 |
| | | | | | | | | 0.51 | | 0.06 | 0.12 |
| | | | | | | | | 0.56 | | 0.13 | 0.21 |
| | | | | | | | | 2.54 | | 0.51 | 0.29 |
| | | | | | | | | 0.48 | | 0.07 | 0.14 |
| | | | | | | | | 0.58 | | 0.12 | 0.19 |
| | | | | | | | | 2.55 | | 0.51 | 0.29 |
| | | | | | | | | 0.48 | | 0.07 | 0.14 |
| | | | | | | | | 0.58 | | 0.12 | 0.19 |
| | | | | | | | | 2.46 | | 0.51 | 0.30 |
| | | | | | | | | 0.47 | | 0.07 | 0.14 |
| | | | | | | | | 0.56 | | 0.12 | 0.20 |
| | | | | | | | | 2.47 | | 0.51 | 0.30 |
| | | | | | | | | 0.48 | | 0.07 | 0.14 |
| | | | | | | | | 0.55 | | 0.12 | 0.20 |
| | | | | | | | | 2.12 | | 0.76 | 0.60 |
| | | | | | | | | 0.51 | | 0.08 | 0.14 |
| | | | | | | | | 0.53 | | 0.13 | 0.21 |
| | | | | | | | | 2.49 | | 0.52 | 0.30 |
| | | | | | | | | 0.45 | | 0.29 | 0.47 |
| | | | | | | | | 0.58 | | 0.12 | 0.19 |

TABLE 3

| rs3753394 Promoter | rs529825 Intron 1 | rs3766404 Intron 6 | rs203674 Intron 10 | rs3753396 Exon 13 | rs1065489 Exon 18 | Haplotype | Freq. CTL | Freq. AMD |
|---|---|---|---|---|---|---|---|---|
| 1 | 1 | 1 | 2 | 1 | 1 | 111211 | 0.28436 | 0.478059 |
| 1 | 2 | 1 | 1 | 1 | 1 | 121111 | 0.210856 | 0.131313 |
| 2 | 1 | 1 | 1 | 2 | 2 | 211122 | 0.149247 | 0.126697 |

TABLE 3-continued

| rs3753394 Promoter | rs529825 Intron 1 | rs3766404 Intron 6 | rs203674 Intron 10 | rs3753396 Exon 13 | rs1065489 Exon 18 | Haplotype | Freq. CTL | Freq. AMD |
|---|---|---|---|---|---|---|---|---|
| 1 | 1 | 2 | 1 | 1 | 1 | 112111 | 0.129893 | 0.061917 |
| 2 | 1 | 1 | 1 | 1 | 1 | 211111 | 0.094861 | 0.07125 |
| 2 | 1 | 1 | 2 | 1 | 1 | 211211 | 0.046438 | 0.06834 |
| 1 | 2 | 2 | 1 | 1 | 1 | 122111 | 0.026677 | 0.014859 |
| 2 | 1 | 2 | 1 | 1 | 1 | 212111 | 0.012731 | 0.01473 |
| 1 | 1 | 1 | 1 | 1 | 1 | 111111 | 0.012686 | 0.007305 |
| 1 | 2 | 1 | 2 | 1 | 1 | 121211 | 0.012684 | 0.004723 |
| 1 | 2 | 1 | 1 | 2 | 2 | 121122 | 0.009249 | 0.000945 |
| 1 | 1 | 1 | 1 | 2 | 2 | 111122 | 0.007487 | 0.008705 |
| 2 | 1 | 2 | 1 | 2 | 1 | 212121 | 0.002049 | |
| 1 | 2 | 2 | 2 | 1 | 1 | 122211 | 0.00078 | 0.000488 |
| 2 | 1 | 2 | 1 | 2 | 2 | 212122 | 0.000001 | |
| 2 | 1 | 1 | 2 | 1 | 2 | 211212 | | 0.002175 |
| 2 | 1 | 1 | 1 | 1 | 2 | 211112 | | 0.001869 |
| 2 | 2 | 1 | 1 | 1 | 1 | 221111 | | 0.00169 |
| 2 | 1 | 2 | 2 | 1 | 1 | 212211 | | 0.001061 |
| 1 | 2 | 1 | 2 | 2 | 2 | 121222 | | 0.00096 |
| 1 | 1 | 2 | 1 | 1 | 2 | 112112 | | 0.00095 |
| 2 | 1 | 1 | 1 | 2 | 1 | 211121 | | 0.00095 |
| 2 | 1 | 2 | 2 | 1 | 2 | 212212 | | 0.00069 |
| 2 | 2 | 1 | 2 | 1 | 1 | 221211 | | 0.000322 |
| 1 | 2 | 2 | 1 | 1 | 2 | 122112 | | 0.000001 |

TABLE 4

HF1 SNP Association with Age-related Macular Degeneration

| | | Promoter rs3753394 | IVS1 rs529825 | Exon 2 I62V | IVS2 insTT | IVS6 rs3766404 | Exon 7/9 A307A/Y402H | Exon 10 A473A | IVS10 rs203674 | Exon 13 Q672Q | Exon 18 D936E |
|---|---|---|---|---|---|---|---|---|---|---|---|
| Iowa | # Controls | | | 68 | 126 | | 131 | 68 | | 129 | 67 |
| | # Cases | | | 228 | 390 | | 404 | 221 | | 404 | 223 |
| | X2 | | | 15 | 22.21 | | 49.4 | 35.14 | | 0.21 | 0.64 |
| | P | | | 0.000108 | $2.44 \times 10^{-06}$ | | $2.09 \times 10^{-12}$ | $3.07 \times 10^{-09}$ | | 0.65 | 0.8 |
| | OR | | | 2.79 | 2.38 | | 2.82 | 3.42 | | 1.12 | 0.89 |
| | 95% CI | | | 1.67-4.65 | 1.65-3.44 | | 2.11-3.78 | 2.27-5.15 | | 0.76-1.64 | 0.51-1.56 |
| Columbia | # Controls | 126 | 266 | 261 | 273 | 271 | 272 | 264 | 264 | 265 | 264 |
| | # Cases | 329 | 547 | 546 | 549 | 546 | 549 | 542 | 545 | 545 | 536 |
| | X2 | 8.61 | 25.4 | 36.12 | 28.4 | 23.04 | 54.4 | 66.1 | 66.1 | 2.05 | 0.53 |
| | P | 0.00334 | $4.66 \times 10^{-07}$ | $3.21 \times 10^{-07}$ | $9.87 \times 10^{-08}$ | $1.59 \times 10^{-06}$ | $1.64 \times 10^{-13}$ | $1.60 \times 10^{-11}$ | $4.29 \times 10^{-16}$ | 0.15 | 0.46 |
| | OR | 0.70 | 1.92 | 1.95 | 2.042 | 2.105 | 2.25 | 2.10 | 2.44 | 1.24 | 1.12 |
| | 95% CI | 0.56-0.89 | 1.49-2.48 | 1.51-2.52 | 1.57-2.63 | 1.56-2.85 | 1.79-2.75 | 1.69-2.61 | 1.97-3.03 | 0.937-1.65 | 0.846-1.49 |

The frequency of allele 1 and allele 2 from each SNP was compared between cases and controls and the Yates Chi squared (X2) and P values were calculated along with the Odds Ratio (OR) and 95% confidence interval (95% CI). The actual counts of each genotype are given in Tables 6A-6C.

TABLE 5

SSCP, DHPLC and Sequencing Primers

| Exon | Region | Forward Primer (5'-3') | SEQ ID NO: | Reverse Primer (5'-3') | SEQ ID NO: |
|---|---|---|---|---|---|
| 1 | 5'upstream-int1 | GCAAAAGTTTCTGATAGGC | 64 | AATCTTACCTTCTGCTACAC | 65 |
| 2 | int-int2 | TTAGATAGACCTGTGACTG | 66 | TCAGGCATAATTGCTAC | 67 |
| 3 | int2-int3 | ACTTGTTCCCCCACTC | 68 | CCTCTTTTCGTATGGACTAC | 69 |
| | int2-ex3 | TTGTTCCCCCACTCCTAC | 70 | ACACATTTCCTCCTGTAAGG | 71 |
| | ex3-int3 | CCCTGTGGACATCCTGG | 72 | AACCTCTTTTCGTATGGACTAC | 73 |

TABLE 5-continued

SSCP, DHPLC and Sequencing Primers

| Exon | Region | Forward Primer (5'-3') | SEQ ID NO: | Reverse Primer (5'-3') | SEQ ID NO: |
|---|---|---|---|---|---|
| 4 | int3-ex4 | ATGCTGTTCATTTTCC | 74 | CCATCCATCTGTGTCAC | 75 |
|   | ex4-int4 | ATTACCGTGAATGTGAC | 76 | TTGTATGAGAAAAAAAAC | 77 |
| 5 | int4-int5 | TCCAATCTTATCCTGAGG | 78 | TCTTACCCACACACTTTG | 79 |
| 6 | int5-ex6 | GTCCTGGTCACAGTCC | 80 | GCATACAGCATCTCCTC | 81 |
|   | ex6-int6 | GCACTGAATCTGGATG | 82 | ATGAACCTTGAACACAG | 83 |
| 7 | int6-ex7 | CGGATACTTATTTCTGC | 84 | CGTGATTTCATCTCCAG | 85 |
|   | ex7-int7 | AGAACTGGAGATGAAATC | 86 | TGAATGGAACTTACAGG | 87 |
| 8 | int7-ex8 | GTGAAACCTTGTGATTATC | 88 | TCCCAGTAACTTCCTG | 89 |
|   | ex8-int8 | CTGTGATGAACATTTTGAG | 90 | TGCTCTCCTTTCTTCG | 91 |
| 9 | int8-int9 | CATTGTTATGGTCCTTAGG | 92 | ACATGCTAGGATTTCAGAG | 93 |
| 10 | int9-ex9 | CTTTTTCTTATTCTCTTCCC | 94 | TCACCATCTGCTGTTAC | 95 |
|   | ex9-int10 | TGTAACAGCAGATGGTG | 96 | CCCACAAAAAGACTAAAG | 97 |
| 11 | int10-ex11 | GGGAAATACTCAGATTG | 98 | ATGGCATTCATAGTCC | 99 |
|   | ex11-ex11 | CCAGAACTAAAAATGACTTC | 100 | GGTAAATCAGACCAACC | 101 |
|   | ex11-int11 | ATAGTGTGTGGTTACAATG | 102 | GTTTATGTCAAATCAGGAG | 103 |
| 12 | int11-int12 | CAAGAAAGAGAATGCGAAC | 104 | AGATTACAGGCAATGGG | 105 |
| 13 | int12-ex13 | TTGATTGTTTAGGATGC | 106 | TTGAGGAGTTCAGGAGGTGG | 107 |
|   | ex13-int13 | CTGAACTCCTCAATGG | 108 | ATTACCAATACACACTGG | 109 |
| 14 | int13-int14 | TTACATAGTGGAGGAGAG | 110 | TGGAAATGTTGAGGC | 111 |
| 15 | int14-int15 | AGTTGGTTTGATTCCTATC | 112 | TTGAGCAGTTCACTTCTG | 113 |
| 16 | int15-ex16 | TTATGCCCACCTCCAC | 114 | ATACACTACTGACCAACAC | 115 |
|   | ex16-int16 | GTCTATGAGAATACAAGCC | 116 | GAATCTGAGGTGGAGG | 117 |
| 17 | int16-ex17 | CCCTTTGATTTTCATTC | 118 | AGAACTCCATTTTCCC | 119 |
|   | ex17-int17 | CACAACCACCTCAGATAG | 120 | GCCTAACCTTCACACTG | 121 |
| 18 | int17-ex18 | GTCATAGTAGCTCCTGTATTG | 122 | ACGTAACTTCTTCTCCATAC | 123 |
|   | ex18-int18 | CTTCCTTGTAAATCTCCAC | 124 | CAATGCACCATACTTATGC | 125 |
| 19 | int18-ex19 | TAAAGATTTGCGGAAC | 126 | GGCTCCATCCATTTTG | 127 |
|   | ex19-int19 | TTACAAAATGGATGGAG | 128 | AAGTGCTGGGATTACAGGCG | 129 |
| 20 | int19-ex20 | CTACTCAAAATGAACACTAGG | 130 | TTTAACCCTGCTATACTCC | 131 |
|   | ex20-int20 | TAAATGGAAACTGGACG | 132 | ACCCTATTACTTGTGTTCTG | 133 |
| 21 | int20-int21 | GTGTTTGCGTTTGCC | 134 | GAGATTTTCCAGCCAC | 135 |
| 22 | int21-ex22 | TCTCACACATTGCGAAC | 136 | ACCGTTAGTTTTCCAGG | 137 |
|   | ex22-3'downstream | GGTTTGGATAGTGTTTTGAG | 138 | ATGTTGTTCGCAATGTG | 139 |

TABLE 6

| | Promoter | Promoter | rs3753394 | Intron 1 | IVS1 | rs529825 | Exon 2 | I62V | rs800292 | Intron 2 | IVS2 |
|---|---|---|---|---|---|---|---|---|---|---|---|
| Cohort 1 | | | | | | | | | | | |
| | | | | | | | GG | CON 44 | AMD 190 | SS | CON 78 |
| | | | | | | | GA | 18 | 34 | SL | 38 |
| | | | | | | | AA | 6 | 4 | LL | 10 |
| Sum | | | | | | | | 68 | 228 | | 126 |
| freq allele 1 | | | | | | | G | 0.78 | 0.91 | S | 0.77 |
| freq allele 2 | | | | | | | A | 0.22 | 0.09 | L | 0.23 |
| AMD association | | | | | | | | | | | |
| Chi square | | | | | | | | X2 16.19 | P 5.73703E−05 | | X2 22.19 |
| | | | | | | | | 2.79 | | | 2.38 |
| Count Allele 1 | | | | | | | Allele 1 | 106 | 414 | | 194 |
| Count Allele 2 | | | | | | | Allele 2 | 30 | 42 | | 58 |
| Yates $\chi^2$/P value | | | | | | | | 15 | 0.000107511 | | 22.21 |
| OR/95% CI | | | | | | | | 2.79 | 1.67-4.65 | | 2.38 |
| Cohort 2 | | | | | | | | | | | |
| | | | CON | All AMD | | CON | All AMD | | CON | All AMD | | CON |
| | 11 CC | 126 | 291 | 11 GG | 149 | 392 | GG | 148 | 395 | SS | 160 |
| | 12 CT | 114 | 225 | 12 GA | 95 | 140 | GA | 90 | 135 | SL | 95 |
| | 22 TT | 24 | 33 | 22 AA | 22 | 15 | AA | 23 | 16 | LL | 18 |
| Sum | | 264 | 549 | | 266 | 547 | | 261 | 546 | | 273 |
| freq allele 1 | T | 0.31 | 0.25 | G | 0.74 | 0.84 | G | 0.74 | 0.85 | S | 0.76 |
| freq allele 2 | C | 0.69 | 0.75 | A | 0.26 | 0.16 | A | 0.26 | 0.15 | L | 0.24 |
| | | 0 | 0.095 | | 26.1 | 2.18E−06 | | | | | 29.18756 |
| Count allele 1 | | 366 | 807 | | 393 | 924 | | 386 | 925 | | 415 |
| Count allele 2 | | 162 | 291 | | 139 | 170 | | 136 | 167 | | 131 |
| Yates $\chi^2$/P value | | 2.84 | 0.089 | | 25.4 | 4.65918E−07 | | 26.12 | 3.20843E−07 | | 28.4 |
| OR/95% CI | | 1.23 | 0.977-1.52 | | 1.922 | 1.49-2.48 | | 1.95 | 1.51-2.52 | | 2.042 |

| | insTT | Intron 6 | IVS6 | rs376644 | Exon 7/9 | A307A/ Y402H | rs1061147/ rs1061170 | Exon 7 | A307A | rs1061147 |
|---|---|---|---|---|---|---|---|---|---|---|
| Cohort 1 | | | | | | | | | | |
| | AMD | | | | | CON | AMD | | CON | AMD |
| | 310 | | | | AA/CC | 16 | 146 | AA | 16 | 146 |
| | 73 | | | | AC/CT | 56 | 183 | AC | 56 | 183 |
| | 7 | | | | CC/TT | 59 | 75 | CC | 59 | 75 |
| Sum | 390 | | | | | 131 | 404 | | 131 | 404 |
| freq allele 1 | 0.89 | | | | A/C | 0.34 | 0.59 | A | 0.34 | 0.59 |
| freq allele 2 | 0.11 | | | | C/T | 0.66 | 0.41 | C | 0.66 | 0.41 |
| AMD association | | | | | | | | | | |
| Chi square | P 2.4667E−06 | | | | | X2 50.4 | P 1.2593E−12 | | X2 50.4 | P 1.2593E−12 |
| | | | | | | 2.82 | | | 2.82 | |
| Count Allele 1 | 693 | | | | | 88 | 475 | | 88 | 475 |
| Count Allele 2 | 87 | | | | | 174 | 333 | | 174 | 333 |
| Yates $\chi^2$/P value | 2.44398E−06 | | | | | 49.4 | 2.08746E−12 | | 49.4 | 2.08746E−12 |
| OR/95% CI | 1.65-3.44 | | | | | 2.82 | 2.11-3.78 | | 2.82 | 2.11-3.78 |
| Cohort 2 | | | | | | | | | | |
| | All AMD | | CON | All AMD | | | | | CON | All AMD |
| | 409 | 11 TT | 186 | 452 | | | | CC | 120 | 114 |
| | 133 | 12 CT | 76 | 89 | | | | AC | 109 | 275 |
| | 7 | 22 CC | 9 | 5 | | | | AA | 33 | 158 |
| Sum | 549 | | 271 | 546 | | | | | 262 | 547 |
| freq allele 1 | 0.87 | T | 0.83 | 0.91 | | | | C | 0.67 | 0.46 |
| freq allele 2 | 0.13 | C | 0.17 | 0.09 | | | | A | 0.33 | 0.54 |
| | 4.59201E−07 | | 23.82449569 | 6.70774E−06 | | | | | | |
| Count allele 1 | 951 | | 448 | 993 | | | | | 349 | 503 |
| Count allele 2 | 147 | | 94 | 99 | | | | | 175 | 591 |
| Yates $\chi^2$/P value | 9.86653E−08 | | 23.04 | 1.58666E−06 | | | | | 59.6 | 1.16235E−14 |
| OR/95% CI | 1.57-2.63 | | 2.105 | 1.56-2.85 | | | | | 2.34 | 1.89-2.91 |

TABLE 6-continued

| | | Exon 9 | Y402H rs1061170 | Exon 10 | A473A rs2274700 | Intron 10 | IVS10 rs203674 | Exon 13 |
|---|---|---|---|---|---|---|---|---|
| Cohort 1 | | | | | | | | |
| | | | CON AMD | | CON AMD | | | |
| | CC | | 16 146 | GG | 22 145 | | | AA |
| | CT | | 56 183 | GA | 30 65 | | | GA |
| | TT | | 59 74 | AA | 16 11 | | | GG |
| Sum | | | 131 403 | | 68 221 | | | |
| freq allele 1 | C | | 0.34 0.59 | G | 0.54 0.80 | | | A |
| freq allele 2 | T | | 0.66 0.41 | A | 0.46 0.20 | | | G |
| AMD association | | | | | | | | |
| | | | X2 P | | X2 P | | | |
| Chi square | | | 50.4 1.2593E−12 | | 36.5 1.54526E−09 | | | |
| | | | 2.82 | | 3.42 | | | |
| Count Allele 1 | | | 88 475 | | 74 355 | | | |
| Count Allele 2 | | | 174 333 | | 62 87 | | | |
| Yates $\chi^2$/P value | | | 49.4 2.08746E−12 | | 35.14 3.06833E−09 | | | |
| OR/95% CI | | | 2.82 2.11-3.78 | | 3.42 2.27-5.15 | | | |
| Cohort 2 | | | | | | | | |
| | | | CON All AMD | | CON All AMD | | CON All AMD | |
| | TT | | 122 118 | GG | 77 269 | 11 | TT 118 103 | GG |
| | CT | | 113 271 | GA | 131 233 | 12 | GT 112 276 | GA |
| | CC | | 37 160 | AA | 56 40 | 22 | GG 34 166 | AA |
| Sum | | | 272 549 | | 264 542 | | 264 545 | |
| freq allele 1 | T | | 0.66 0.46 | G | 0.54 0.71 | T | 0.66 0.44 | G |
| freq allele 2 | C | | 0.34 0.54 | A | 0.46 0.29 | G | 0.34 0.56 | A |
| | | | 55.19838 1.03234E−12 | | 46.2 9.24391E−11 | | 66.97458 2.86191E−15 | |
| Count allele 1 | | | 357 507 | | 285 771 | | 348 482 | |
| Count allele 2 | | | 187 591 | | 243 313 | | 180 608 | |
| Yates $\chi^2$/P value | | | 54.4 1.63563E−13 | | 45.4 1.60634E−11 | | 66.1 4.28616E−16 | |
| OR/95% CI | | | 2.25 1.79-2.75 | | 2.10 1.69-2.61 | | 2.44 1.97-3.03 | |

| | | Q672Q rs3753396 | Exon 18 | D936E rs1065489 |
|---|---|---|---|---|
| Cohort 1 | | | | |
| | | CON AMD | | CON AMD |
| | | 92 295 | GG | 51 162 |
| | | 33 101 | GT | 14 56 |
| | | 4 8 | TT | 2 5 |
| Sum | | 129 404 | | 67 223 |
| freq allele 1 | | 0.84 0.86 | G | 0.87 0.85 |
| freq allele 2 | | 0.16 0.14 | T | 0.13 0.15 |
| AMD association | | | | |
| | | X2 P | | X2 P |
| Chi square | | 0.309 0.579 | | 0.155 0.694 |
| | | 1.12 | | 0.893 |
| Count Allele 1 | | 217 691 | | 116 380 |
| Count Allele 2 | | 41 117 | | 18 66 |
| Yates $\chi^2$/P value | | 0.21 0.65 | | 0.64 0.8 |
| OR/95% CI | | 1.12 0.76-1.64 | | 0.89 0.51-1.56 |
| Cohort 2 | | | | |
| | | CON All AMD | | CON All AMD |
| | | 9 8 | TT | 9 10 |
| | | 72 138 | TG | 69 140 |
| | | 184 399 | GG | 186 386 |
| Sum | | 265 545 | | 264 536 |
| freq allele 1 | | 0.17 0.14 | T | 0.16 0.15 |
| freq allele 2 | | 0.83 0.86 | G | 0.84 0.85 |
| | | 2.27 0.322 | | 0.653 0.722 |
| Count allele 1 | | 90 154 | | 87 160 |
| Count allele 2 | | 440 936 | | 441 912 |
| Yates $\chi^2$/P value | | 2.05 0.15 | | 0.53 0.46 |
| OR/95% CI | | 1.24 0.937-1.65 | | 1.12 0.846-1.49 |

TABLE 7

Frequency of the At-risk Allele in Various Ethnic Groups with or without AMD

|  | Rapanui | Columbia Controls | Hispanic | Iowa Controls | African American | Columbia Cases | European American | Iowa Cases | MPGN II |
|---|---|---|---|---|---|---|---|---|---|
| Risk Haplotype | 0.20 | 0.35 | 0.35 | 0.36 | 0.47 | 0.55 | 0.57 | 0.60 | 0.69 |
| N | 52 | 272 | 24 | 131 | 49 | 549 | 56 | 404 | 20 |

The frequency of the at-risk haplotype was estimated in samples from different populations from genotypes of the Y402H variant and/or the IVS10 locus. These include Rapanui natives over the age of 65 (AMD is extremely rare, and most likely absent, in this Easter Island population), controls (>65 years of age) from Columbia University, Hispanics general population, controls (>65 years of age) from the University of Iowa, African Americans general population, AMD cases from Columbia University, European Americans general population, AMD cases from the University of Iowa and individuals with MPGNII.
N = number of individuals.

TABLE 8

Factor H Diplotypes

|  | I62V | IVS2-18 | Y402H | D936E | IVS20 |
|---|---|---|---|---|---|
| Risk | GG | SS | CC | GG | TT |
| Protective | AA | LL | TT | GG | CC |
|  | AA | LL | CT | GG | CC |
| Protective | AA | LL | TT | GG | CC |
|  | AA | LL | TT | GT | TT |
|  | AA | LL | TT | GT | CC |
|  | AA | LS | CT | GG | CC |
|  | AA | SS | CC | GG | TT |
|  | GA | LS | CT | GG | TT |
|  | GA | LS | CT | GG | CT |
|  | GA | LS | CT | GG | CC |
| Protective | GA | LS | CT | GG | CC |
|  | GA | LS | CT | GT | CT |
|  | GA | LS | TT | GG | CT |
|  | GA | LS | TT | GG | CC |
|  | GA | LS | TT | GG | TT |
|  | GA | LS | TT | GT | CC |
|  | GA | LS | TT | TT | CC |
|  | GA | SS | CT | GG | CC |
|  | GG | SS | CT | GT | CC |
|  | GG | SS | TT | GT | TT |
|  | GG | SS | TT | TT | CT |
|  | GG | LL | TT | GG | TT |
| Risk | GG | SS | CC | GG | TT |
| Risk | GG | SS | CT | GG | CT |
|  | GG | SS | CT | GG | CC |
|  | GG | SS | CT | GG | CC |
|  | GG | SS | CT | GT | TT |
|  | GG | SS | CT | GT | CT |
|  | GG | SS | CT | GT | CC |
|  | GG | SS | CT | GT | CC |
|  | GG | SS | CT | GT | CC |
|  | GG | SS | CT | TT | CT |
|  | GG | SS | TT | GG | TT |
|  | GG | SS | TT | GG | CT |
|  | GG | SS | TT | GT | TT |
|  | GG | SS | TT | GT | CT |
|  | GG | SS | TT | GT | GT |
|  | GG | SS | TT | GT | CC |
|  | GG | SS | TT | TT | CT |
|  | GG | SS | TT | TT | CC |
|  | GG | SS | CC | GG | TT |
|  | GG | SS | CT | GG | TT |
|  | GG | SS | CT | GT | CC |

G, A, T, C refer to nucleotides at the indicated polymorphisms.
S, L refer to the short and long (insertion of 2 T nucleotides) alleles of the intron 2 polymorphism.

TABLE 9

Primers Used to Amplify the Factor H Coding Sequence

| Exon | Forward | SEQ ID NO: | Reverse | SEQ ID NO: |
|---|---|---|---|---|
| 1 | TGGGAGTGCAGTGAGAATTG | 140 | GCTAATGATGCTTTTCACAGGA | 141 |
| 2 | CCTGTGACTGTCTAGGCATTTT | 142 | TATGCCTGAATTATATCACTATTGCC | 143 |
| 3 | GCTTTGCTATGTTAATTTTCCTT | 144 | AACTATGATGGAAATAATTAAATCTGG | 145 |
| 4 | TGCATATGCTGTTCATTTTC | 146 | GTCTTACATTAAAATATCTTAAAGTCTC | 147 |
| 5 | TTTCCTCCAATCTTATCCTGAG | 148 | CGTTCATTCTAAGGAATATCAGCA | 149 |
| 6 | CCTGATGGAAACAACATTTCTG | 150 | AACAGGGCCAGAAAAGTTCA | 151 |
| 7 | TGTTCATTTTAATGCCATTTTG | 152 | AGTTTTCGAAGTTGCCGAAA | 153 |
| 8 | CCTAGAAACCCTAATGGAATGTG | 154 | TGTTCAAGCAAAGTGACCAAA | 155 |
| 9 | TGAGCAAATTTATGTTTCTCATTT | 156 | ATGTCACCTTGTTTTACCAATGG | 157 |
| 10 | TGAATGCTTATGGTTATCCAGGT | 158 | AAAACCTGCAGGAACAAAGC | 159 |
| 11 | TCTTAGAATGGGAAATACTCAGATTG | 160 | TGGTTTTTCAGAAATTCATTTTCA | 161 |
| 12 | ATGTAAAATTAACTTTGGCAATGA | 162 | TTGCTGAAATAAGAATTAGAACTTTG | 163 |
| 13 | TGAATAAAAGAAGAAAATCTTTCCA | 164 | ATCTAAAACACATACATCATGTTTTCA | 165 |
| 14 | AAAACACATACATCATGTTTTCACAA | 166 | GATATGCCTCAACATTTCCAGTC | 167 |
| 15 | GTTGGTTTGATTCCTATCATTTG | 168 | TTGGAAAGTAATAGGTATGTGTGTC | 169 |
| 16 | CTATGAGAATACAAGCCAAAAGTTC | 170 | TCTCTTGTGCTTCGTGTAAACAA | 171 |
| 17 | AACCCTTTGATTTTCATTCTTCA | 172 | TCAAAGTGAGGGGAATAATTGA | 173 |
| 18 | AATTTATGAGTTAGTGAAACCTGAAT | 174 | TCTTCATTCAAAGTGTAAGTGGTACC | 175 |
| 19 | ACAAAATGGCTAATATATTTTCTCAAG | 176 | TAATGTGTGGGCCCAGCC | 177 |
| 20 | CAAAATGAACACTAGGTGGAACC | 178 | ATTTTGGGGAGTATAGCAGG | 179 |
| 21 | CTGTGTTTGCGTTTGCCTTA | 180 | TTCACGTGGCTGGAAAAATC | 181 |
| 22 | TTGAAAACCTGAAAGTCTATGAAGA | 182 | TCAATCATAAAGTGCACACCTTT | 183 |

TABLE 10

Primers Used to Amplify the CFHR5 Coding Sequence

| Exon | Forward | SEQ ID NO: | Reverse | SEQ ID NO: |
|---|---|---|---|---|
| 1 | CAGTCCCATTTCTGATTGTTCCA | 184 | GCTGAGGATAATTTGAAGGGG | 185 |
| 2 | GTGATTCATCGATGTAGCTCTTT | 186 | AATGACCAGAGGAGCCTGGAA | 187 |
| 3 | TGATGTCAGTTTTCAAAGTTTTCC | 188 | ACCACTCTCTCAGTTTTGCTAATTAT | 189 |
| 4 | CACATTAAATTTGTTTCTGCAATGA | 190 | AGAAGTGATGAAACAAGAATTTGA | 191 |
| 5 | CCATTTAAGCATTATTTATGGTTTC | 192 | AAACAGGACAGTTACTATTACTTTGCA | 193 |
| 6 | AAATATTTTCAGAGTAAGCACTCATTT | 194 | TTTATCATTTTGATTGGGATTGT | 195 |
| 7 | TGCAGATATTTATTGACATAATTGTT | 196 | GTTGATCTTGTTGCTTCTTTACAAGA | 197 |
| 8 | CCATTTTCCTGAAACACTACCC | 198 | TCTGTTGCACTGTACCCCAA | 199 |
| 9 | AATTATTTGAATTTCCAGACACCTT | 200 | TTTTGGACTAATTTCATAGAATAACCC | 201 |
| 10 | CTTAAATGCAATTTCACTATTCTATGA | 202 | TAGCCATTATGTAGCC | 203 |

TABLE 11

CFH SNPs in 22 Patients Segregating with MPGNII
(Allele Frequencies (f1 and f2) and Number of Patients by Genotype are Shown)

|   |   | EX2 | I62V rs800292 | IVS2 | −18ins TT | EX7 | A307A rs1061147 | IVS7 | −53G > T | EX9 | Y402H rs1061170 | EX10 | A473A rs2274700 |
|---|---|---|---|---|---|---|---|---|---|---|---|---|---|
| 3 |   | GG | 20 | (T)9(T)9 | 20 | CC | 3 | GG | 8 | CC | 9 | GG | 18 |
| 4 |   | GA | 2 | (T)11(T)9 | 2 | CA | 10 | GT | 10 | CT | 10 | GA | 4 |
| 5 |   | AA | 0 | (T)11(T)11 | 0 | AA | 9 | TT | 4 | TT | 3 | AA | 0 |
| 6 | f1 |   | .95G |   | .95 (T)9 |   | .64A |   | .59G |   | .36Y |   | .90G |
| 7 | f2 |   | .05A |   | .05 (T)11 |   | .36C |   | .41T |   | .64H |   | .10A |
| 8 | At-Risk Haplotype |   | G |   | 9 |   | A |   | G |   | C |   | G |
|   | MPGN2-1 |   | G, G |   | 9, 9 |   | A, C |   | G, T |   | C, T |   | G, G |
|   | MPGN2-2 |   | G, G |   | 9, 9 |   | C, C |   | T, T |   | T, T |   | G, G |
|   | MPGN2-7 |   | G, G |   | 9, 9 |   | A, C |   | G, T |   | C, T |   | G, G |
|   | MPGN2-9 |   | G, G |   | 9, 9 |   | A, C |   | G, T |   | C, T |   | G, G |
|   | MPGN2-10 |   | G, G |   | 9, 9 |   | A, C |   | G, T |   | C, T |   | G, G |
|   | MPGN2-11 |   | G, G |   | 9, 9 |   | A, C |   | G, T |   | C, T |   | G, A |
|   | MPGN2-12 |   | G, G |   | 9, 9 |   | A, A |   | T, T |   | C, C |   | G, G |
|   | MPGN2-13 |   | G, G |   | 9, 9 |   | A, C |   | G, T |   | C, T |   | G, G |
|   | MPGN2-14 |   | G, G |   | 9, 9 |   | A, C |   | G, T |   | C, T |   | G, G |
|   | MPGN2-15 |   | G, G |   | 9, 9 |   | A, A |   | G, G |   | C, C |   | G, G |
|   | MPGN2-16 |   | G, G |   | 9, 9 |   | C, C |   | T, T |   | T, T |   | G, A |
|   | MPGN2-17 |   | G.G |   | 9, 9 |   | A, A |   | G, G |   | C, C |   | G, G |
|   | MPGN2-18 |   | G, G |   | 9, 9 |   | A, C |   | G, T |   | C, T |   | G, G |
|   | MPGN2-19 |   | G, G |   | 9, 9 |   | A, A |   | G, G |   | C, C |   | G, G |
|   | MPGN2-20 |   | G, G |   | 9, 9 |   | A, A |   | G, G |   | C, C |   | G, G |
|   | MPGN2-21 |   | G, A |   | 9, 11 |   | C, C |   | T, T |   | T, T |   | G, A |
|   | MPGN2-22 |   | G, G |   | 9, 9 |   | A, A |   | G, G |   | C, C |   | G, G |
|   | MPGN2-23 |   | G, G |   | 9, 9 |   | A, A |   | G, G |   | C, C |   | G, G |
|   | MPGN2-24 |   | G, G |   | 9, 9 |   | A, A |   | G, G |   | C, C |   | G, G |
|   | MPGN2-27-02 |   | G, A |   | 9, 11 |   | A, C |   | G, T |   | C, T |   | G, A |
|   | MPGN2-29 |   | G, G |   | 9, 9 |   | A, A |   | G, G |   | C, C |   | G, G |
|   | MPGN2-30 |   | G, G |   | 9, 9 |   | A, C |   | G, T |   | C, T |   | G, G |

|   |   | EX13 | Q672Q rs3753396 | IVS15 | −30C > A | EX18 | D936E rs1065489 | IVS18 | −89T > C | EX20 | N1050Y |
|---|---|---|---|---|---|---|---|---|---|---|---|
| 3 |   | AA | 13 | CC | 8 | GG | 13 | TT | 19 | AA | 21 |
| 4 |   | AG | 9 | CA | 10 | GT | 9 | TC | 3 | AT | 1 |
| 5 |   | GG | 0 | AA | 4 | TT | 0 | CC | 0 | TT | 0 |
| 6 | f1 |   | .80A |   | .59C |   | .80G |   | .93T |   | .98A |
| 7 | f2 |   | .20G |   | .41A |   | .20T |   | .07C |   | .02T |
| 8 | At-Risk Haplotype |   | A |   | C |   | G |   | T |   | A |
|   | MPGN2-1 |   | G, A |   | C, A |   | G, T |   | T, T |   | A, A |
|   | MPGN2-2 |   | G, A |   | C, A |   | G, T |   | T, T |   | A, A |
|   | MPGN2-7 |   | G, A |   | C, A |   | G, T |   | T, T |   | A, A |
|   | MPGN2-9 |   | G, A |   | C, A |   | G, T |   | T, T |   | A, A |
|   | MPGN2-10 |   | A, A |   | C, A |   | G, T |   | T, T |   | A, A |
|   | MPGN2-11 |   | A, A |   | C, A |   | G, G |   | T, C |   | A, T |
|   | MPGN2-12 |   | A, A |   | C, C |   | G, G |   | T, T |   | A, A |
|   | MPGN2-13 |   | G, A |   | C, A |   | G, T |   | T, T |   | A, A |
|   | MPGN2-14 |   | G, A |   | C, A |   | G, T |   | T, T |   | A, A |
|   | MPGN2-15 |   | A, A |   | C, C |   | G, G |   | T, T |   | A, A |
|   | MPGN2-16 |   | G, A |   | A, A |   | G, T |   | T, C |   | A, A |
|   | MPGN2-17 |   | A, A |   | C, C |   | G, G |   | T, T |   | A, A |
|   | MPGN2-18 |   | G, A |   | C, A |   | G, G |   | T, T |   | A, A |
|   | MPGN2-19 |   | A, A |   | C, C |   | G, G |   | T, T |   | A, A |
|   | MPGN2-20 |   | A, A |   | C, C |   | G, G |   | T, T |   | A, A |
|   | MPGN2-21 |   | G, A |   | A, A |   | G, T |   | T, T |   | A, A |
|   | MPGN2-22 |   | A, A |   | C, C |   | G, G |   | T, T |   | A, A |
|   | MPGN2-23 |   | A, A |   | C, C |   | G, G |   | T, T |   | A, A |
|   | MPGN2-24 |   | A, A |   | C, C |   | G, G |   | T, T |   | A, A |
|   | MPGN2-27-02 |   | A, A |   | C, A |   | G, G |   | T, T |   | A, A |
|   | MPGN2-29 |   | A, A |   | A, A |   | G, G |   | T, T |   | A, A |
|   | MPGN2-30 |   | A, A |   | A, A |   | G, G |   | T, C |   | A, A |

TABLE 12

Comparison of Factor H SNP Frequencies in 22 MPGNII Patients Versus Controls (Allele Frequencies Given as f1 and f2)

| SNP | f1 MPGNII | f2 MPGNII | f1 Controls | f2 Controls | P-value |
|---|---|---|---|---|---|
| Exon 2 I62V | 42 (G) | 2 (A) | 202 (G) | 60 (A) | 0.0051 |
| IVS2 −18insTT | 42 (short) | 2 (long) | 194 (short) | 68 (long) | 0.0018 |
| Exon 7 A307A | 16 (C) | 28 (A) | 88 (A) | 174 (C) | 0.72 |
| Exon 9 Y402H | 28 (H) | 16 (Y) | 88 (H) | 174 (Y) | 0.00014 |
| Exon 10 A473A | 40 (G) | 4 (A) | 74 (G) | 62 (A) | 0.000013 |
| Exon 13 Q672Q | 35 (A) | 9 (G) | 217 (A) | 41 (G) | 0.45 |
| Exon 18 D936E | 35 (D) | 9 (E) | 115 (D) | 19 (E) | 0.32 |

TABLE 13

Coding SNPs Associated with MPGNII and the Related Short Consensus Repeat (SCR) of Factor H

| SNP | SCR | Function of SCR |
|---|---|---|
| Exon 2 I62V | 1 | Interaction with C3b |
| Exon 9 Y402H | 7 | Heparin binding Interaction with C reactive protein |
| Exon 10 A473A | 8 | Interaction with C reactive protein |

TABLE 14

CFHR5 SNPs in 22 Patients Segregating with MPGNII
(Allele Frequencies (f1 and f2) and Number of Patients by Genotype are Shown)

| 1 | | Promoter | −249T > C | Promoter | −20T > C | IVS1 | 75T > A | Exon2 | P46S | IVS2 | 58C > T |
|---|---|---|---|---|---|---|---|---|---|---|---|
| 2 | | | rs9427661 | | rs9427662 | | rs3748557 | | rs12097550 | | rs 12097550 |
| 3 | | TT | 21 | TT | 21 | TT | 16 | CC | 19 | CC | 16 |
| 4 | | TC | 1 | TC | 1 | TA | 5 | CT | 3 | CT | 5 |
| 5 | | CC | 0 | CC | 0 | AA | 1 | TT | 0 | TT | 1 |
| 6 | f1 | | .98T | | .98T | | .84T | | .93P | | .84C |
| 7 | f2 | | .02C | | .02C | | .16A | | .07S | | .16T |
| 8 | At-Risk Haplotype | | T | | T | | T | | C | | C |
| | MPGN2-02 | | T, T | | T, T | | T, T | | C, C | | C, C |
| | MPGN2-03 | | T, T | | T, T | | T, T | | C, C | | C, C |
| | MPGN2-07 | | T, T | | T, T | | T, T | | C, C | | C, C |
| | MPGN2-09 | | T, T | | T, T | | A, T | | C, C | | C, T |
| | MPGN2-10 | | T, T | | T, T | | T, T | | C, C | | C, C |
| | MPGN2-11 | | T, T | | T, T | | A, T | | C, C | | C, T |
| | MPGN2-12 | | T, T | | T, T | | T, T | | C, C | | C, C |
| | MPGN2-13 | | T, T | | T, T | | A, T | | C, T | | C, T |
| | MPGN2-14 | | T, T | | T, T | | A, A | | C, C | | T, T |
| | MPGN2-15 | | T, T | | T, T | | T, T | | C, T | | C, C |
| | MPGN2-16 | | C, T | | C, T | | A, T | | C, C | | C, T |
| | MPGN2-17 | | T, T | | T, T | | T, T | | C, C | | C, C |
| | MPGN2-18 | | T, T | | T, T | | A, T | | C, C | | C, T |
| | MPGN2-19 | | T, T | | T, T | | T, T | | C, C | | C, C |
| | MPGN2-20 | | T, T | | T, T | | T, T | | C, T | | C, C |
| | MPGN2-21 | | T, T | | T, T | | T, T | | C, C | | C, C |
| | MPGN2-22 | | T, T | | T, T | | T, T | | C, C | | C, C |
| | MPGN2-23 | | T, T | | T, T | | T, T | | C, C | | C, C |
| | MPGN2-24 | | T, T | | T, T | | T, T | | C, C | | C, C |
| | MPGN2-27-2 | | T, T | | T, T | | T, T | | C, C | | C, C |
| | MPGN2-29 | | T, T | | T, T | | T, T | | C, C | | C, C |
| | MPGN2-30 | | T, T | | T, T | | T, T | | C, C | | C, C |

TABLE 15

Comparison of CFHR5 SNP Frequencies in 22 MPGNII Patients Versus Controls (Allele Frequencies Given as f1 and f2)

| SNP | f1 MPGN II | f2 MPGN II | f1 Controls | f2 Controls | P-value |
|---|---|---|---|---|---|
| Promoter −249T > C | 43 (T) | 1 (C) | 178 (G) | 28 (A) | 0.033 |
| Promoter −20T > C | 43 (T) | 1 (C) | 178 (G) | 28 (A) | 0.033 |
| IVS1 +75T > A | 37 (T) | 7 (A) | 161 (A) | 41 (C) | 0.38 |
| Exon 2 P46S | 41 (P) | 3 (S) | 205 (P) | 1 (S) | 0.00023 |
| IVS2 +58C > T | 37 (C) | 7 (T) | 158 (C) | 28 (T) | 0.28 |

TABLE 16A

| | | Probes | | | |
|---|---|---|---|---|---|
| SNP Name | Location | Reference Allele | SEQ ID NO: | Variant Allele | SEQ ID NO: |
| | Promoter 1 | 5'-TCTGGGATGTAATAATG-3' | 204 | 5'-TCTGGGATGTAATGATG-3' | 205 |
| | | 5'-GAACATTATTACATCCC-3' | 206 | 5'-GAACATCATTACATCCC-3' | 207 |
| rs3753394 | Promoter 4 | 5'-CAGAGGATATCACCAGC-3' | 208 | 5'-CAGAGGATATTACCAGC-3' | 209 |
| | | 5'-AGCAGCTGGTGATATCC-3' | 210 | 5'-AGCAGCTGGTAATATCC-3' | 211 |
| rs529825 | Intron 1 | 5'-TACACAGTACGATAGAC-3' | 212 | 5'-TACACAGTACAATAGAC-3' | 213 |
| | | 5'-TAAGTCTATCGTACTGT-3' | 214 | 5'-TAAGTCTATTGTACTGT-3' | 215 |
| rs800292 | Exon 2 | 5'-TCTTGGAAATGTAATAA-3' | 216 | 5'-TCTTGGAAATATAATAA-3' | 217 |
| | | 5'-ACCATTATTACATTTCC-3' | 218 | 5'-ACCATTATTATATTTCC-3' | 219 |
| | Intron 2 | 5'-TTTTTTTTTCGTTTTAG-3' | 220 | 5'-TTTTTTTTTTTCGTTTT-3' | 221 |
| | | 5'-CTTTCTAAAACGAAAAA-3' | 222 | 5'-TTCTAAAACGAAAAAAA-3' | 223 |
| rs3766404 | Intron 6 | 5'-TTTAGGACTCATTTGAA-3' | 224 | 5'-TTTAGGACTTATTTGAA-3' | 225 |
| | | 5'-TAACTTCAAATGAGTCC-3' | 226 | 5'-TAACTTCAAATAAGTCC-3' | 227 |
| rs1061147 | Exon 7 | 5'-GAAATACAGCAAAATGC-3' | 228 | 5'-GAAATACAGCCAAATGC-3' | 229 |
| | | 5'-ACTTGTGCATTTTGCTG-3' | 230 | 5'-ACTTGTGCATTTGGCTG-3' | 231 |
| rs1061170 | Exon 9 | 5'-TAATCAAAATTATGGAA-3' | 232 | 5'-TAATCAAAATCATGGAA-3' | 233 |
| | | 5'-TTTCTTCCATAATTTTG-3' | 234 | 5'-TTTCTTCCATGATTTTG-3' | 235 |
| rs2274700 | Exon 10 | 5'-AAGAAAAAGCGAAATAT-3' | 236 | 5'-AAGAAAAAGCAAAATAT-3' | 237 |
| | | 5'-TTGATATTTCGCTTTTT-3' | 238 | 5'-TTGATATTTTGCTTTTT-3' | 239 |
| | Exon 10A | 5'-GGATCAAAGA[-]TGACAA-3' | 240 | 5'-GGATCAAAGA[N]TGACAA-3' | 241 |
| | | 5'-GCCCTTGTCA[-]TCTTTG-3' | 242 | 5'-GCCCTTGTCA[N]TCTTTG-3' | 243 |
| rs203674 | Intron 10 | 5'-TTTATTAGTAGATCTAA-3' | 244 | 5'-TTTATTAGTATATCTAA-3' | 245 |
| | | 5'-TTGATTAGATCTACTAA-3' | 246 | 5'-TTGATTAGATATACTAA-3' | 247 |
| rs3753396 | Exon 13 | 5'-ATAAAATTCAATGTGTT-3' | 248 | 5'-ATAAAATTCAGTGTGTT-3' | 249 |
| | | 5'-CCATCAACACATTGAAT-3' | 250 | 5'-CCATCAACACACTGAAT-3' | 251 |
| rs375046 | Intron 15 | 5'-TTTATTATAACATTAAT-3' | 252 | 5'-TTTATTATAAAATTAAT-3' | 253 |
| | | 5'-TATAATTAATGTTATAA-3' | 254 | 5'-TATAATTAATTTTATAA-3' | 255 |
| rs1065489 | Exon 18 | 5'-CTCCACCTGAGATTTCT-3' | 256 | 5'-CTCCACCTGATATTTCT-3' | 257 |
| | | 5'-CATGAGAAATCTCAGGT-3' | 258 | 5'-CATGAGAAATATCAGGT-3' | 259 |
| | Exon 22 | 5'-TCTTTCATCACGTTCTC-3' | 260 | 5'-TCTTTCATCATGTTCTC-3' | 261 |
| | | 5'-GTGTGAGAACGTGATGA-3' | 262 | 5'-GTGTGAGAACATGATGA-3' | 263 |

TABLE 16B

| | | Primers | | | |
|---|---|---|---|---|---|
| SNP Name | Location | Reference Allele | SEQ ID NO: | Variant Allele | SEQ ID NO: |
| | Promoter 1 | 5'-TTTCTGGGATGTAATA-3' (forward) | 264 | 5'-TTTCTGGGATGTAATG-3' (forward) | 265 |
| | | 5'-CAAAACACTGAACATT-3' (reverse) | 266 | 5'-CAAAACACTGAACATC-3' (reverse) | 267 |

TABLE 16B-continued

| | | Primers | | | |
|---|---|---|---|---|---|
| SNP Name | Location | Reference Allele | SEQ ID NO: | Variant Allele | SEQ ID NO: |
| rs3753394 | Promoter | 5'-AAATCCAGAGGATATC-3' (forward) | 268 | 5'-AAATCCAGAGGATATT-3' (forward) | 269 |
| | | 5'-AAATCAGCAGCTGGTG-3' (reverse) | 270 | 5'-AAATCAGCAGCTGGTA-3' (reverse) | 271 |
| rs529825 | Intron 1 | 5'-AAGTTTACACAGTACG-3' (forward) | 272 | 5'-AAGTTTACACAGTACA-3' (forward) | 273 |
| | | 5'-AATGGGTAAGTCTATC-3' (reverse) | 274 | 5'-AATGGGTAAGTCTATT-3' (reverse) | 275 |
| rs800292 | Exon 2 | 5'-AGATCTCTTGGAAATG-3' (forward) | 276 | 5'-AGATCTCTTGGAAATA-3' (forward) | 277 |
| | | 5'-TGCATACCATTATTAC-3' (reverse) | 278 | 5'-TGCATACCATTATTAT-3' (reverse) | 279 |
| | Intron 2 | 5'-TCATAACTTTTTTTTT-3' (forward) | 280 | 5'-ATAACTTTTTTTTTTT-3' (forward) | 281 |
| | | 5'-GGGCCTTTCTAAAACG-3' (reverse) | 282 | 5'-GCCTTTCTAAAACGAA-3' (reverse) | 283 |
| rs3766404 | Intron 6 | 5'-AATACATTTAGGACTC-3' (forward) | 284 | 5'-AATACATTTAGGACTT-3' (forward) | 285 |
| | | 5'-ACACTAACTTCAAATG-3' (reverse) | 286 | 5'-ACACTAACTTCAAATA-3' (reverse) | 287 |
| rs1061147 | Exon 7 | 5'-CCGGGGAAATACAGCA-3' (forward) | 288 | 5'-CCGGGGAAATACAGCC-3' (forward) | 289 |
| | | 5'-AGTACTTGTGCATTTT-3' (reverse) | 290 | 5'-AGTACTTGTGCATTTG-3' (reverse) | 291 |
| rs1061170 | Exon 9 | 5'-GGATATAATCAAAATT-3' (forward) | 292 | 5'-GGATATAATCAAAATC-3' (forward) | 293 |
| | | 5'-CAAACTTTCTTCCATA-3' (reverse) | 294 | 5'-CAAACTTTCTTCCATG-3' (reverse) | 295 |
| rs2274700 | Exon 10 | 5'-CTTAAAAGAAAAAGCG-3' (forward) | 296 | 5'-CTTAAAAGAAAAAGCA-3' (forward) | 297 |
| | | 5'-TTTGCATTGATATTTC-3' (reverse) | 298 | 5'-TTTGCATTGATATTTT-3' (reverse) | 299 |
| | Exon 10A | 5'-TGAGTGGATCAAAGA[-]-3' (forward) | 300 | 5'-TGAGTGGATCAAAGA[N]-3' (forward) | 301 |
| | | 5'-CATTGGCCCTTGTCA[-]-3' (reverse) | 302 | 5'-CATTGGCCCTTGTCA[N]-3' (reverse) | 303 |
| rs203674 | Intron 10 | 5'-ACCTATTTATTAGTAG-3' (forward) | 304 | 5'-ACCTATTTATTAGTAT-3' (forward) | 305 |
| | | 5'-CTTTATTGATTAGATC-3' (reverse) | 306 | 5'-CTTTATTGATTAGATA-3' (reverse) | 307 |
| rs3753396 | Exon 13 | 5'-ACCTAATAAAATTCAA-3' (forward) | 308 | 5'-ACCTAATAAAATTCAG-3' (forward) | 309 |
| | | 5'-CTCTCCATCAACACAT-3' (reverse) | 310 | 5'-CTCTCCATCAACACAC-3' (reverse) | 311 |
| rs375046 | Intron 15 | 5'-TATTTTTTATTATAAC-3' (forward) | 312 | 5'-TATTTTTTATTATAAA-3' (forward) | 313 |
| | | 5'-AAAAATATAATTAATG-3' (reverse) | 314 | 5'-AAAAATATAATTAATT-3' (reverse) | 315 |
| rs1065489 | Exon 18 | 5'-TAAATCTCCACCTGAG-3' (forward) | 316 | 5'-TAAATCTCCAGCTGAT-3' (forward) | 317 |
| | | 5'-AACACCATGAGAAATC-3' (reverse) | 318 | 5'-AACACCATGAGAAATA-3' (reverse) | 319 |
| | Exon 22 | 5'-TATCGTCTTTCATCAC-3' (forward) | 320 | 5'-TATCGTCTTTCATCAT-3' (forward) | 321 |
| | | 5'-GCAATGTGTGAGAACG-3' (reverse) | 322 | 5'-GCAATGTGTGAGAACG-3' (reverse) | 323 |

XV. References

Full citations are provided below for references cited by by author and date above:

Abecasis et al. "Age-related macular degeneration: a high-resolution genome scan for susceptibility loci in a population enriched for late-stage disease." *American Journal of Human Genetics* 74, 482-94 (2004).

Akiyama et al. "Inflammation and Alzheimer's disease." *Neurobiol. Aging* 2000; 21:383-421.

Allikmets et al. "Mutation of the Stargardt disease gene (ABCR) in age-related macular degeneration." *Science* 1997; 277:1805-1807.

Allikmets. "Further evidence for an association of ABCR alleles with age-related macular degeneration. The International ABCR Screening Consortium." *Am J Hum Genet* 67, 487-91 (2000).

Ambati et al. "Age-related macular degeneration: etiology, pathogenesis, and therapeutic strategies." *Surv Ophthalmol* 2003; 48(3):257-293.

Anderson et al. "A role for local inflammation in the formation of drusen in the aging eye." *Am J Ophthalmol* 2002, 134:411-431.

Anderson et al. "Characterization of βeta-amyloid assemblies in drusen: the deposits associated with aging and age-related macular degeneration." *Exp. Eye Res.* 2004; 78:243-256.

Angaku-. "Complement regulatory proteins in glomerular diseases." *Kidney Int* 1998; 54:1419-1428.

Appel et al. "Membranoproliferative glomerulonephritis type II (Dense Deposit Disease): an update." *J am Soc Nephrol* 2005; 16:1392-1403.

Ault et al. "Human factor H deficiency. Mutations in framework cysteine residues and block in H protein secretion and intracellular catabolism." *J Biol Chem* 1997; 272:25168-25175.

Bao et al. "Decay-accelerating factor expression in the rat kidney is restricted to the apical surface of podocytes." *Kidney Int* 2002; 62:2010-2021.

Barbiano di Belgiojoso et al. "The prognostic value of some clinical and histological parameters in membranoproliferative glomerulonephritis." *Nephron* 1977; 19:250-258.

Barrett et al. "Haploview: analysis and visualization of LD and haplotype maps." *Bioinformatics* 2004; 21:263-5.

Bennett et al. "Mesangiocapillary glomerulonephritis type 2 (dense deposit disease): Clinical features of progressive disease." *Am J Kidney Dis* 1989; 13:469-476.

Bird et al. "An international classification and grading system for age-related maculopathy and age-related macular degeneration. The International ARM Epidemiological Study Group." *Surv Ophthalmol* 1995, 39: 367-374.

Bush R A, Lei B, Tao W, Raz D, Chan C C, Cox T A, Santos-Muffley M, Sieving P A. 2004. Encapsulated cell-based intraocular delivery of ciliary neurotrophic factor in normal rabbit: dose-dependent effects on ERG and retinal histology. Invest Ophthalmol Vis Sci. 45:2420-30.

Cade J R, DeQuesada A M, Shires D L, Levin D M, Hackett R L, Spooner G R, Schlein E M, Pickering M J, Holcomb A. 1971. The Effect of Long Term High Dose Heparin Treatment on the Course of Chronic Proliferative Glomerulonephritis. Nephron. 8:67-80.

Cameron et al. "Idiopathic mesangiocapillary glomerulonephritis. Comparison of types I and II in children and adults and long-term prognosis." *Am J Med* 1983; 74:175-192.

Capecchi. *Science* 1989; 244:1288-1292.

Caprioli et al. "Complement factor H mutations and gene polymorphisms in haemolytic uraemic syndrome: the C-257T, the A2089G and the G2881T polymorphisms are strongly associated with the disease." *Hum Mol Genet* 12, 3385-95 (2003).

Chong et al. "Decreased thickness and integrity of the macular elastic layer of Bruch's membrane correspond to the distribution of lesions associated with age-related macular degeneration" *Am J Pathol* 166, 241-51 (2005).

Colville et al. "Visual impairment caused by retinal abnormalities in mesangiocapillary (membranoprolifeative) glomerulonephritis type II ("dense deposit disease")." *Am J Kidney Dis* 2003; 42:E2-5.

Compton. *Nature* 1991; 350:91-91.

Cousins et al. "Monocyte activation in patients with age-related macular degeneration: a biomarker of risk for choroidal neovascularization?" *Arch Ophthalmol* 122, 1013-8 (2004).

Crabb et al. "Drusen proteome analysis: An approach to the etiology of age-related macular degeneration." *Proc. Natl. Acad. Sci. USA.* 2002; 99:14682-14687.

de Jong. "Risk profiles for ageing macular disease." *Ophthalmologia* 2004; 218 Suppl 1:5-16.

Diamond J R, Karnovsky M J. 1986. Nonanticoagulant Protective Effect of Heparin in Chronic Aminonucleoside Nephrosis. Renal Physiol. Basel 9:366-374.

Dragon-Durey et al. "Heterozygous and homozygous factor H deficiencies associated with hemolytic uremic syndrome or membranoproliferative glomerulonephritis: report and genetic analysis of 16 cases." *J Am Soc Nephrol* 2004; 15:787-795.

Droz et al. "Évolution a long terme des glomérulonéphrites membranoproliferative de l'adulte: remissionspontanée durable chez 13 malades avec étude de biopsies rénales itératives dans 5 cas." *Neprhrologie* 1982; 3:6-11.

Duvall-Young et al. "Fundus changes in (type II) mesangiocapillary glomerulonephritis stimulating drusen: a histopathologiocal report." *Br J Ophthalmol* 1989a; 73(4):297-302.

Duvall-Young et al. "Fundus changes in mesangiocapillary glomerulonephritis type II: clinical and fluorescein angiographic findings." *Br J Ophthalmol* 1989b; 73(11):900-906.

Edwards et al. "Complement factor H Polymorphism and age-related macular degeneration." *Science* 2005; 308:421-424.

Esparza-Gordillo J, Goicoechea de Jorge E, Buil A, Carreras Berges L, Lopez-Trascasa M, Sanchez-Corral P, Rodriguez de Cordoba S. 2005. Predisposition to atypical hemolytic uremic syndrome involves the concurrence of different susceptibility alleles in the regulators of complement activation gene cluster in 1q32. Human Mol. Genetics 14:703-712.

Espinosa-Heidman et al. "Macrophage depletion diminishes lesion size and severity in experimental choroidal neovascularization." *Invest. Ophthalmol. Vis. Sci.* 2003; 44:3586-3592.

Estaller et al. "Cloning of the 1.4-kb mRNA species of human complement factor H reveals a novel member of the short consensus repeat family related to the carboxy terminal of the classical 150-kDa molecule." *J Immunol* 1991; 146(9): 3190-3196.

Floege J, Eng E, Young B A, Couser W G, Johnson R J. 1993. Heparin suppresses mesangial cell proliferation and matrix expansion in experimental mesangioproliferative glomerulonephritis. Kidney International 43:369-380.

Frueh et al. *Clin Chem Lab Med* 2003; 41(4):452-461.

Gibbs. *Nucl Acids Res* 1989; 17:2427-2448.

Girardi G, Redecha P, Salmon J E. 2004. Heparin prevents antiphospholipid antibody-induced fetal loss by inhibiting complement activation. Nature Medicine 10:1222-1226.

Girardi G. 2005. Heparin treatment in pregnancy loss: Potential therapeutic benefits beyond anticoagulation. J. Reproduc. Immunol. 66:45-51.

Gold et al. "Estrogen receptor genotypes and haplotypes associated with breast cancer risk." *Cancer Res* 2004; 64:8891-8900.

Habib et al. "Dense deposit disease. A variant of membranoproliferative glomerulonephritis." *Kidney Int* 1975; 7:204-15.

Habib et al. "Glomerular lesions in the transplanted kidney in children." *Am J Kidney Diseas* 1987; 10:198-207.

Hageman et al. "An integrated hypothesis that considers drusen as biomarkers of immune-mediated processes at the RPE-Bruch's membrane interface in aging and age-related macular degeneration." *Prog Retin Eye Res* 2001; 20: 705-732.

Hageman et al. "Common haplotype in the complement regulatory gene, factor H (HF1/CFH), predisposes individuals to age-related macular degeneration." *Proc Nat Acad Sci* 2005; 102: 7227-32.

Hageman et al. "Vitronectin is a constituent of ocular drusen and the vitronectin gene is expressed in human retinal pigmented epithelial cells." *FASEB Journal* 1999; 13:477-484.

Haines et al. "Complement factor H variant increases the risk of age-related macular degeneration." *Science* 2005; 308: 419-421.

Hayashi et al. "Evaluation of the ARMD1 locus on 1q25-31 in patients with age-related maculopathy: genetic variation in laminin genes and in exon 104 of HEMICENTIN-1." *Ophthalmic Genetics* 25, 111-9 (2004).

Houdebine, 2000, Transgenic animal bioreactors, *Transgenic Res.* 9:305-20

Holers. "The complement system as a therapeutic target in autoimmunity." *Clin Immunol* 2003; 107:140.

Holz. et al. "Pathogenesis of lesions in late age-related macular disease." *Am J Ophthalmol* 2004; 137:504-510.

Huang et al. "Peripheral drusen in membranoproliferative glomerulonephritis." *Retina* 2003; 23(3):429-431.

Iyengar et al. "Model Free Linkage Analysis in Extended Families Confirms a Susceptibility Locus for Age Related Macular Degeneration (ARMD) on 1q31 [ARVO Abstract]." *Invest Ophthalmol Vis Sci* 2003; 44:2113.

Jansen et al. "In situ complement activation in porcine membranoproliferative glomerulonephritis type II." *Kidney Int* 1998; 53(2):331-349.

Johnson et al. "A potential role for immune complex pathogenesis in drusen formation." *Exp Eye Res* 2000; 70:441-449.

Johnson et al. "Complement activation and inflammatory processes in drusen formation and age-related macular degeneration." *Exp. Eye Res.* 2001; 73:887-896.

Johnson et al. "The Alzheimer's A beta-peptide is deposited at sites of complement activation in pathologic deposits associated with aging and age-related macular degeneration." *Proc Natl Acad Sci USA* 99, 11830-5 (2002).

Kinoshita. "Biology of complement: the overture." *Immunol. Today* 1991; 12:291.

Klaver et al. "Genetic risk of age-related maculopathy. Population-based familial aggregation study." *Arch Ophthalmol* 1998a; 116:1646-1651.

Klaver et al. Genetic association of apolipoprotein E with age-related macular degeneration. *Am J Hum Genet* 1998b; 63:200-206.

Klein et al. "Age-related macular degeneration. Clinical features in a large family and linkage to chromosome 1q." *Arch Ophthalmol* 1998; 116:1082-1088.

Klein et al. "Complement factor H polymorphism in age-related macular degeneration." *Science* 2005; 308:385-389.

Klein et al. "Genetics of age-related macular degeneration." *Ophthalmol Clin North Am* 2003; 16(4):575-582.

Klein et al. "Prevalence of age-related maculopathy." *Opthalmol* 1992; 99(6):933-943.

Klein et al. "The epidemiology of age-related macular degeneration." *Am J Ophthalmol* 2004; 137(3):504-510.

Leys et al. "Subretinal neovascular membranes associated with chronic membranoproliferative glomerulonephritis type II." *Graefe's Arch Clin Exper Ophthalmol* 1990; 228: 499-504.

Lillico et al., 2005, Transgenic chickens as bioreactors for protein-based drugs. *Drug Discov Today.* 10:191-6

Liszewski et al. "The role of complement in autoimmunity." *Immunol Ser* 1991; 54:13.

Manuelian et al. "Mutations in factor H reduce binding affinity to C3b and heparin and surface attachment to endothelial cells in hemolytic uremic syndrome." *J Clin Invest* 2003; 111:1181-1190.

McAvoy et al. "Retinal changes associated with type 2 glomerulonephritis." *Eye* 2005 19:985-9

McEnery. "Membranoproliferative glomerulonephritis: The Cincinnati experience cumulative renal survival from 1957 to 1989." *J Pediatr* 1990; 116:S109-S114.

McRae et al. "Human factor H-related protein 5 (FHR-5). A new complement-associated protein." *J Biol Chem* 2001; 276 (9):6747-6754.

Meri et al. "Regulation of alternative pathway complement activation by glycosaminoglycans: specificity of the polyanion binding site on factor H." *Biochem Biophys Res Commun* 1994; 198:52-59.

Miller et al. "The association of prior cytomegalovirus infection with neovascular age-related macular degeneration." *Am J Ophthalmol* 138, 323-8 (2004).

Morgan et al. "Complement deficiency and disease." *Immunol Today* 1991; 12:301.

Morgan. "Regulation of the complement membrane attack pathway." *Crit Rev Immunol* 19, 173-98 (1999).

Mullins et al. "Characterization of drusen-associated glycoconjugates." *Ophthalmology* 104, 288-94 (1997).

Mullins et al. "Drusen associated with aging and age-related macular degeneration contain molecular constituents common to extracellular deposits associated with atherosclerosis, elastosis, amyloidosis and dense deposit disease." *FASEB J.* 2000; 14:835-846.

Mullins et al. "Structure and composition of drusen associated with glomerulonephritis: Implications for the role of complement activation in drusen biogenesis." *Eye* 2001; 15:390-395.

Murphy et al. "Factor H-related protein-5: a novel component of human glomerular immune deposits." *Am J Kid Dis* 2002; 39:24-27.

Neary et al. "Linkage of a gene causing familial membranoproliferative glomerulonephritis type III to chromosome 1." *J Am Soc Nephrol.* 2002; 13(8):2052-2057.

Neri et al. *Adv. Nucl Acid Prot Analysis* 2000; 3826:117-125.

Niculescu et al. "Complement activation and atherosclerosis." *Mol. Immunol.* 1999; 36:949-955.

Nielsen et al. *Science* 1991; 254:1497-1500.

O'Brien et al. "Electrophysiology of type II mesangiocapillary glomerulonephritis with associated fundus abnormalities." *Br J Ophthalmol* 1993; 77:778-80.

Orita et al. *Proc Natl Acad Sci* 1989; 86:2766-2770.

Orth et al. The nephrotic syndrome. *New Engl J Med* 1998; 338:1202-1211.

Pascual et al. "Identification of membrane-bound CR1 (CD35) in human urine: evidence for its release by glomerular podocytes." *J Exp Med* 1994; 79:889-899.

Penfold et al. "Immunological and aetiological aspects of macular degeneration." *Progress in Retinal and Eye Research* 2001; 20:385-414.

Perez-Caballero D, Gonzalez-Rubio C, Gallardo M E, Vera M, Lopez-Trascasa M, Rodriguez de Cordoba S, Sanchez-Corral P. 2001. Clustering of Missense Mutations in the C-Terminal Region of Factor H in Atypical Hemolytic Uremic Syndrome. Am. J. Hum. Genet. 68:478-484.

Piatek et al. *Nat Biotechnol* 1998; 16:359-363.

Pickering et al. "Uncontrolled C3 activation causes membranoproliferative glomerulonephritis in mice deficient in complement factor H." *Nat Genet* 2002; 31:424-428.

Prasad et al. "Pendred syndrome and DFNB4-Mutation screening of SLC26A4 by denaturing high-performance liquid chromatography and the identification of seven novel mutations." *Am J Med Genet* 2004; 124A:1-9.

Raines et al. "Fundus changes in mesangiocapillary glomerulonephritis type II: vitreous fluorophotometry." *Br J Ophthalmol* 1989; 73:907-910.

Richards A, Buddles M R, Donne R L, Kaplan B S, Kirk E, Venning M C, Tielemans C L, Goodship J A, Goodship T H J. 2001. Factor H Mutations in Hemolytic Uremic Syndrome Cluster in Exons 18-20, a Domain Important for Host Cell Recognition. Am. J. Hum. Genet. 68:485-490.

Ripoche et al. "The complete amino acid sequence of human complement factor H." *Biochem J* 1988, 249:593-602.

Rodriguez de Cordoba et al. "The human complement factor H: functional roles, genetic variations and disease associations." *Mol Immunol* 41, 355-67 (2004).

Rops Angelique L. W. M. M., Van Der Vlag J, Lensen Joost F. M., Wijnhoven Tessa J. M., Van Den Heuvel Lambert P. W. J., van Kuppevelt T H, Berden Jo H. M. 2004. Heparan sulfate proteoglycans in glomerular inflammation. Kidney International 65:768-785.

Russell et al. "Location, substructure and composition of basal laminar drusen compared with drusen associated with aging and age-related macular degeneration." *Am. J. Ophthalmol.* 2000; 129:205-214.

Saiki et al. *Nature* 1986; 324:163-166.

Sanchez-Corral P, Perez-Caballero D, Huarte O, Simckes A M, Goicoechea E, Lopez-Trascasa M, Rodriguez de Cordoba S. 2002. Structural and Functional Characterization of Factor H Mutations Associated with Atypical Hemolytic Uremic Syndrome. Am. J. Genet. 71:1285-1295.

Saunders R E, Goodship T H J, Zipfel P F, Perkins S J. An Interactive Web Database of Factor H-Associated Hemolytic Uremic Syndrome Mutations: Insights Into the Structural Consequences of Disease-Associated Mutations. Human Mutation 2006. 27:21-30.

Schultz et al. "Analysis of the ARMD1 locus: evidence that a mutation in HEMICENTIN-1 is associated with age-related macular degeneration in a large family." *Hum Mol Genet* 2003; 12(24):3315-3323.

Schwertz et al. "Complement analysis in children with idiopathic membranoproliferative glomerulonephritis: A long-term follow-up." *Pediatr Allergy Immunol* 2001; 12:166-172.

Seddon et al. "Association between C-reactive protein and age-related macular degeneration." *Jama* 291, 704-10 (2004).

Seddon et al. "The epidemiology of age-related macular degeneration." *Ophthalmol Clin* 2004; 44:17-39.

Sharma et al. "Biologically active recombinant human complement factor H: synthesis and secretion by the baculovirus system." *Gene* 143:301-302.

Sharma et al. "Identification of three physically and functionally distinct binding sites in human complement factor H by deletion mutagenesis." *Proc Natl Acad Sci USA* 1996, 93:10996-11001.

Shen et al. "Ying and Yang: complement activation and regulation of Alzheimer's disease." *Prog Neurobiol* 2003; 70(6):463-472.

Sieving, P. A., R. C. Caruso, W. Tao, D. J. S. Thompson, K. R. Fullmer, H. Rodriquez Coleman and R. A. Bush. 2005. Phase I study of ciliary neurotrophic factor (CNF) delivered by intravitreal implant of encapsulated cell technology (ECT) device in patients with retinitis pigmentosa.

Skerka et al. "The human factor H-related protein 4 (FHR-4). A novel short consensus repeat-containing protein is associated with human triglyceride-rich lipoproteins." *J Biol Cjhem* 1997; 272(9):5627-5634.

Song Y, Zhao L, Tao W, Laties A M, Luo Z, and Wen R. Photoreceptor protection by cardiotrophin-1 in transgenic rats with the rhodopsin mutation s334ter. IOVS, 44(9): 4069-75. 2003.

Souied et al. "The epsilon4 allele of the apolipoprotein E gene as a potential protective factor for exudative age-related macular degeneration." *Am J Ophthalmol.* 1998; 125:353-359.

Strausberg et al. "Generation and initial analysis of more than 15,000 full-length human and mouse cDNA sequences." *Proc Natl Acad Sci USA* 2002; 99(26):16899-16903.

Striker G E. 1999. Therapeutic uses of heparinoids in renal disease patients. Nephrol. Dial. Transplant. 14:540-543.

Swainson et al. "Mesangiocapillary glomerulonephritis: A long-term study of 40 cases." *J Pathol* 1983; 141:449-468.

Tao W, Wen R, Goddard M B, Sherman S, O'Rourke P J, Stabila P F, Bell W J, Dean B J, Kauper K A, Budz V A, Tsiaras W G, Acland G M, Pearce-Kelling S, Laties A M, and Aguirre G D Encapsulated Cell-Based Delivery of CNTF Reduces Photoreceptor Degeneration in Animal Models of Retinitis Pigmentosa. IOVS, Vol. 43 (10) 3292-3298. 2002.

Thelwell et al. *Nucleic Acids Res* 2000; 28:3752-3761.

Timmerman et al. "Differential expression of complement components in human fetal and adult kidneys." *Kidney Int* 1996; 49:730-740.

Torzerski et al. "Processes in atherogenesis complement activation." *Atherosclerosis.* 1997; 132:131-138.

Tuo et al. "Genetic factors in age-related macular degeneration." *Prog Retin Eye Res* 2004; 23(2):229-249.

van den Dobbelsteen et al. "Regulation of C3 and factor H synthesis of human glomerular mesangial cells by IL-1 and interferon-gamma." *Clin Exp Immunol* 1994; 95:173-180.

Van Leeuwen et al. "Epidemiology of age-related macular degeneration." *Eur J Epidemiol* 2003; 18(9):845-854.

Vingerling et al. "Epidemiology of age-related maculopathy." *Epidemiol Rev.* 1995; 17(2):347-360.

Vingerling et al. "The prevalence of age-related maculopathy in the Rotterdam Study." *Ophthalmol* February 1995; 102 (2):205-210.

Walport. "Complement. First of two parts." *N Engl J Med* 2001; 344:1058-1066.

Wang et al. "Systematic identification and analysis of exonic splicing silencers." *Cell* 119, 831-45 (2004).

Weeks et al. "Age-related maculopathy: a genomewide scan with continued evidence of susceptibility loci within the 1q31, 10q26, and 17q25 regions." *Am J Hum Genet* 2004; 75:174.

Weeks et al. "Age-related maculopathy: an expanded genome-wide scan with evidence of susceptibility loci within the 1q31 and 17q25 regions." *Am J Ophthalmol* 2001; 132:682-692.

Weiler J M, Daha M R, Austen K F, Fearon D T. 1976. Control of the amplification convertase of complement by the plasma protein β1H. Proc. Natl. Acad. Sci. USA 73:3268-3272.

Zarbin. "Age Related Macular Degeneration: a review of pathogenesis." *Eur J Ophthalmol* 1998, 8:199-206.

Zarbin. "Current concepts in the pathogenesis of age-related macular degeneration." *Arch Ophthalmol* 2004; 122(4): 598-614.

Zipfel et al. "Complement factor H and hemolytic uremic syndrome." *Int Immunopharmacol* 1, 461-8 (2001).

Zipfel et al. "Factor H family proteins: on complement, microbes and human diseases." *Biochem Soc Trans* 30, 971-8 (2002).

Zipfel et al. "The role of complement in membranoproliferative glomerulonephritis." In *Complement and Kidney Disease* 2005

Zipfel. "Complement factor H: physiology and pathophysiology." *Semin Thromb Hemost* 27, 191-9 (2001).

Zipfel. "Hemolytic uremic syndrome: how do factor H mutants mediate endothelial damage?" *Trends Immunol* 22, 345-8 (2001).

Although the present invention has been described in detail with reference to specific embodiments, those of skill in the art will recognize that modifications and improvements are within the scope and spirit of the invention, as set forth in the claims which follow. All publications and patent documents cited herein are incorporated herein by reference as if each such publication or document was specifically and individually indicated to be incorporated herein by reference. Citation of publications and patent documents (patents, published patent applications, and unpublished patent applications) is not intended as an admission that any such document is pertinent prior art, nor does it constitute any admission as to the contents or date of the same. The invention having now been described by way of written description, those of skill in the art will recognize that the invention can be practiced in a variety of embodiments and that the foregoing description is for purposes of illustration and not limitation of the following claims.

What is claimed is:

1. A method of treating a human patient in need of treatment for age-related macular degeneration (AMD) comprising administering to the patient a composition comprising an inhibitor of the alternative pathway of complement activation, wherein said inhibitor is:
   (a) a naturally occurring human Complement Factor H polypeptide comprising residues 19-1231 of SEQ ID NO:5, or a naturally occurring splice variant thereof, or an allelic variant of said human CFH polypeptide or splice variant, with the proviso that residue 62, numbered relative to SEQ ID NO:5, is isoleucine, residue 402 of said human CFH polypeptide, numbered relative to SEQ ID NO:5, is tyrosine, and residue 1210, numbered relative to SEQ ID NO:5, is arginine, wherein the human CFH polypeptide binds complement component 3b (C3b);
   (b) a recombinant or purified Complement Factor H polypeptide, wherein the complement factor H polypeptide has at least 90% sequence identity to SEQ ID NO:2 and binds to complement component 3b (C3b), with the proviso that at residue 62, numbered relative to SEQ ID NO:2, the complement factor H polypeptide comprises isoleucine, at residue 402, numbered relative to SEQ ID NO:2, the complement factor H polypeptide comprises tyrosine, and at residue 1210, numbered relative to SEQ ID NO:2, the complement factor H polypeptide comprises arginine; or
   (c) a naturally occurring human Complement Factor H polypeptide that binds to complement component 3b (C3b) and has at least 90% amino acid sequence identity to the amino acid sequence of SEQ ID NO:2, with the proviso that residue 62, numbered relative to SEQ ID NO:2, is isoleucine, residue 402, numbered relative to SEQ ID NO:2, is tyrosine, and residue 1210, numbered relative to SEQ ID NO:2, is arginine.

2. The method of claim 1, wherein the inhibitor is a naturally occurring human Complement Factor H (human CFH) polypeptide comprising residues 19-1231 of SEQ ID NO:5, or a naturally occurring splice variant thereof, or an allelic variant of said human CFH polypeptide or splice variant, with the proviso that residue 62 of said human CFH, numbered relative to SEQ ID NO:5, is isoleucine, residue 402, numbered relative to SEQ ID NO:5, is tyrosine and residue 1210, numbered relative to SEQ ID NO:5, is arginine, wherein the human CFH polypeptide protein binds complement component 3b (C3b).

3. The method of claim 1, wherein the Factor H polypeptide is administered to the eye.

4. The method of claim 3, wherein the Factor H polypeptide is administered by intraocular injection.

5. The method of claim 1, wherein the inhibitor is a recombinant or purified Complement Factor H (CFH) polypeptide and wherein the complement factor H polypeptide has at least 90% sequence identity to SEQ ID NO:2 and binds to complement component 3b (C3b), with the proviso that at residue 62, numbered relative to SEQ ID NO:2, the complement factor H polypeptide comprises isoleucine, at residue 402, numbered relative to SEQ ID NO:2, the complement factor H polypeptide comprises tyrosine, and at residue 1210, numbered relative to SEQ ID NO:2, the complement factor H polypeptide comprises arginine.

6. The method of claim 5 wherein the complement factor H polypeptide has at least 95% sequence identity to SEQ ID NO:2.

7. The method of claim 5 wherein the complement factor H polypeptide has a sequence consisting of residues 19-1231 of SEQ ID NO:5.

8. The method of claim 1, wherein the complement factor H polypeptide is a recombinant polypeptide.

9. The method of claim 1, wherein the complement factor H polypeptide is purified from blood.

10. The method of claim 1, wherein the complement factor H polypeptide is administered systemically.

11. The method of claim 1, wherein the composition comprises a pharmaceutically acceptable carrier.

12. The method of claim 1, wherein the composition is a sterile pathogen-free preparation.

13. A method of treating a patient diagnosed with or at risk for developing age-related macular degeneration (AMD) comprising administering a composition comprising a recombinant or purified complement factor H polypeptide to the patient, wherein
   (a) the complement factor H polypeptide has at least 90% sequence identity to SEQ ID NO:2, comprises isoleucine at residue 62 numbered relative to SEQ ID NO:2, comprises tyrosine at residue 402 numbered relative to SEQ ID NO:2, and binds complement component 3b (C3b), or
   (b) is a biologically active fragment of (a) that comprises isoleucine at residue 62 numbered relative to SEQ ID NO:2 and binds C3b.

14. The method of claim 1 or claim 13 wherein the patient has been diagnosed with early stage AMD.

15. The method of claim 14 wherein the patient shows signs of drusen development.

16. The method of claim 1 or claim 13 wherein the patient has signs or symptoms of AMD.

17. The method of claim 1 or claim 13 wherein the patient has been diagnosed as having a propensity to develop AMD.

18. The method of claim 1, wherein said inhibitor is a naturally occurring human Complement Factor H (human CFH) polypeptide that binds to complement component 3b (C3b) and has at least 90% amino acid sequence identity to the amino acid sequence of SEQ ID NO:2, with the proviso that residue 62, numbered relative to SEQ ID NO:2, is isoleucine, residue 402, numbered relative to SEQ ID NO:2, is tyrosine, and residue 1210, numbered relative to SEQ ID NO:2, is arginine.

19. The method of claim 18 wherein the complement factor H polypeptide has at least 95% sequence identity to SEQ ID NO:2.

20. The method of claim 2 wherein the patient's genome comprises a CFH allele encoding a CFH polypeptide having histidine at position 402.

21. The method of claim 5 wherein the patient's genome comprises a CFH allele encoding a CFH protein having histidine at position 402.

22. The method of claim 18 wherein the patient's genome comprises a CFH allele encoding a CFH protein having histidine at position 402.

* * * * *

UNITED STATES PATENT AND TRADEMARK OFFICE
CERTIFICATE OF CORRECTION

PATENT NO.        : 7,745,389 B2
APPLICATION NO.   : 11/354559
DATED             : June 29, 2010
INVENTOR(S)       : Gregory S. Hageman It is certified that error appears in the above-identified patent and that said Letters Patent is hereby corrected as shown below:

On column 259 claim 2, line 62, delete "protein"

Signed and Sealed this

Seventeenth Day of August, 2010

David J. Kappos
*Director of the United States Patent and Trademark Office*

SEQUENCE LISTING

```
<160> NUMBER OF SEQ ID NOS: 337

<210> SEQ ID NO 1
<211> LENGTH: 3926
<212> TYPE: DNA
<213> ORGANISM: Homo sapiens

<400> SEQUENCE: 1
aattcttgga agaggagaac tggacgttgt gaacagagtt agctggtaaa tgtcctctta    60
aaagatccaa aaaatgagac ttctagcaaa gattatttgc cttatgttat gggctatttg   120
tgtagcagaa gattgcaatg aacttcctcc aagaagaaat acagaaattc tgacaggttc   180
ctggtctgac caaacatatc cagaaggcac ccaggctatc tataaatgcc gccctggata   240
tagatctctt ggaaatgtaa taatggtatg caggaaggga gaatgggttg ctcttaatcc   300
attaaggaaa tgtcagaaaa ggccctgtgg acatcctgga gatactcctt ttggtacttt   360 taccctaca ggaggaaatg tgtttgaata tggtgtaaaa gctgtgtata catgtaatga   420
ggggtatcaa ttgctaggtg agattaatta ccgtgaatgt gacacagatg gatggaccaa   480
tgatattcct atatgtgaag ttgtgaagtg tttaccagtg acagcaccag agaatggaaa   540
aattgtcagt agtgcaatgg aaccagatcg ggaataccat tttggacaag cagtacggtt   600
tgtatgtaac tcaggctaca gattgaagg agatgaagaa atgcattgtt cagacgatgg   660
tttttggagt aaagagaaac caaagtgtgt ggaaatttca tgcaaatccc cagatgttat   720
aaatggatct cctatatctc agaagattat ttataaggag aatgaacgat tcaatataa   780 atgtaacatg ggttatgaat acagtgaaag aggagatgct gtatgcactg aatctggatg   840
gcgtccgttg ccttcatgtg aagaaaaatc atgtgataat ccttatattc caaatggtga   900
ctactcacct ttaaggatta aacacagaac tggagatgaa atcacgtacc agtgtagaaa   960 tggttttat cctgcaaccc ggggaaatac agccaaatgc acaagtactg gctggatacc  1020
tgctccgaga tgtaccttga accttgtga ttatccagac attaaacatg gaggtctata  1080
```

```
tcatgagaat atgcgtagac catactttcc agtagctgta ggaaaatatt actcctatta    1140
ctgtgatgaa cattttgaga ctccgtcagg aagttactgg gatcacattc attgcacaca    1200
agatggatgg tcgccagcag taccatgcct cagaaaatgt tattttcctt atttggaaaa    1260
tggatataat caaaatcatg gaagaaagtt tgtacagggt aaatctatag acgttgcctg    1320
ccatcctggc tacgctcttc caaaagcgca gaccacagtt acatgtatgg agaatggctg    1380
gtctcctact cccagatgca tccgtgtcaa acatgttcc aaatcaagta tagatattga    1440
gaatgggttt atttctgaat ctcagtatac atatgcctta aaagaaaaag cgaaatatca    1500
atgcaaacta ggatatgtaa cagcagatgg tgaaacatca ggatcaatta gatgtgggaa    1560
agatggatgg tcagctcaac ccacgtgcat taaatcttgt gatatcccag tatttatgaa    1620
tgccagaact aaaaatgact tcacatggtt taagctgaat gacacattgg actatgaatg    1680
ccatgatggt tatgaaagca atactggaag caccactggt tccatagtgt gtggttacaa    1740
tggttggtct gatttaccca tatgttatga agagaatgc gaacttccta aaatagatgt    1800
acacttagtt cctgatcgca agaaagacca gtataaagtt ggagaggtgt tgaaattctc    1860
ctgcaaacca ggatttacaa tagttggacc taattccgtt cagtgctacc actttggatt    1920
gtctcctgac ctcccaatat gtaaagagca agtacaatca tgtggtccac ctcctgaact    1980
cctcaatggg aatgttaagg aaaaaacgaa agaagaatat ggacacagtg aagtggtgga    2040
atattattgc aatcctagat ttctaatgaa gggacctaat aaaattcaat gtgttgatgg    2100
agagtggaca actttaccag tgtgtattgt ggaggagagt acctgtggag atatacctga    2160
acttgaacat ggctgggccc agcttttcttc ccctccttat tactatggag attcagtgga    2220
attcaattgc tcagaatcat ttacaatgat tggacacaga tcaattacgt gtattcatgg    2280
agtatggacc caacttcccc agtgtgtggc aatagataaa cttaagaagt gcaaatcatc    2340
aaatttaatt atacttgagg aacatttaaa aaacaagaag gaattcgatc ataattctaa    2400
cataaggtac agatgtagag gaaaagaagg atggatacac acagtctgca taaatggaag    2460
atgggatcca gaagtgaact gctcaatggc acaaatacaa ttatgcccac ctccacctca    2520
gattcccaat tctcacaata tgacaaccac actgaattat cgggatggag aaaaagtatc    2580
tgttctttgc caagaaaatt atctaattca ggaaggagaa gaaattacat gcaaagatgg    2640
aagatggcag tcaataccac tctgtgttga aaaaattcca tgttcacaac cacctcagat    2700
agaacacgga accattaatt catccaggtc ttcacaagaa agttatgcac atgggactaa    2760
attgagttat acttgtgagg gtggttttca gatatctgaa gaaaatgaaa caacatgcta    2820
catgggaaaa tggagttctc cacctcagtg tgaaggcctt ccttgtaaat ctccacctga    2880
gatttctcat ggtgttgtag ctcacatgtc agacagttat cagtatggag aagaagttac    2940
gtacaaatgt tttgaaggtt ttggaattga tgggcctgca attgcaaaat gcttaggaga    3000
aaaatggtct caccctccat catgcataaa aacagattgt ctcagtttac ctagctttga    3060
aaatgccata cccatgggag agaagaagga tgtgtataag gcgggtgagc aagtgactta    3120
cacttgtgca acatattaca aaatggatgg agccagtaat gtaacatgca ttaatagcag    3180
atggacagga aggccaacat gcagagacac ctcctgtgtg aatccgccca cagtacaaaa    3240
tgcttatata gtgtcgagac agatgagtaa atatccatct ggtgagagag tacgttatca    3300
atgtaggagc cctatgaaa tgtttgggga tgaagaagtg atgtgtttaa atggaaactg    3360
gacggaacca cctcaatgca aagattctac aggaaaatgt gggccccctc cacctattga    3420
```

```
caatggggac attacttcat tcccgttgtc agtatatgct ccagcttcat cagttgagta    3480
ccaatgccag aacttgtatc aacttgaggg taacaagcga ataacatgta gaaatggaca    3540
atggtcagaa ccaccaaaat gcttacatcc gtgtgtaata tcccgagaaa ttatggaaaa    3600
ttataacata gcattaaggt ggacagccaa acagaagctt tattcgagaa caggtgaatc    3660
agttgaattt gtgtgtaaac ggggatatcg tctttcatca cgttctcaca cattgcgaac    3720
aacatgttgg gatgggaaac tggagtatcc aacttgtgca aaaagataga atcaatcata    3780
aagtgcacac ctttattcag aactttagta ttaaatcagt tctcaatttc attttttatg    3840
tattgtttta ctccttttta ttcatacgta aaattttgga ttaatttgtg aaaatgtaat    3900
tataagctga gaccggtggc tctctt                                        3926
```

<210> SEQ ID NO 2
<211> LENGTH: 1231
<212> TYPE: PRT
<213> ORGANISM: Homo sapiens

<400> SEQUENCE: 2

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285
```

-continued

```
Glu Ile Thr Tyr Gln Cys Arg Asn Gly Phe Tyr Pro Ala Thr Arg Gly
    290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
                325                 330                 335
His Glu Asn Met Arg Arg Pro Tyr Phe Pro Val Ala Val Gly Lys Tyr
            340                 345                 350
Tyr Ser Tyr Tyr Cys Asp Glu His Phe Glu Thr Pro Ser Gly Ser Tyr
        355                 360                 365
Trp Asp His Ile His Cys Thr Gln Asp Gly Trp Ser Pro Ala Val Pro
    370                 375                 380
Cys Leu Arg Lys Cys Tyr Phe Pro Tyr Leu Glu Asn Gly Tyr Asn Gln
385                 390                 395                 400
Asn His Gly Arg Lys Phe Val Gln Gly Lys Ser Ile Asp Val Ala Cys
                405                 410                 415
His Pro Gly Tyr Ala Leu Pro Lys Ala Gln Thr Thr Val Thr Cys Met
            420                 425                 430
Glu Asn Gly Trp Ser Pro Thr Pro Arg Cys Ile Arg Val Lys Thr Cys
        435                 440                 445
Ser Lys Ser Ser Ile Asp Ile Glu Asn Gly Phe Ile Ser Glu Ser Gln
    450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Arg Cys Gly Lys
                485                 490                 495
Asp Gly Trp Ser Ala Gln Pro Thr Cys Ile Lys Ser Cys Asp Ile Pro
            500                 505                 510
Val Phe Met Asn Ala Arg Thr Lys Asn Asp Phe Thr Trp Phe Lys Leu
        515                 520                 525
Asn Asp Thr Leu Asp Tyr Glu Cys His Asp Gly Tyr Glu Ser Asn Thr
    530                 535                 540
Gly Ser Thr Thr Gly Ser Ile Val Cys Gly Tyr Asn Gly Trp Ser Asp
545                 550                 555                 560
Leu Pro Ile Cys Tyr Glu Arg Glu Cys Glu Leu Pro Lys Ile Asp Val
                565                 570                 575
His Leu Val Pro Asp Arg Lys Lys Asp Gln Tyr Lys Val Gly Glu Val
            580                 585                 590
Leu Lys Phe Ser Cys Lys Pro Gly Phe Thr Ile Val Gly Pro Asn Ser
        595                 600                 605
Val Gln Cys Tyr His Phe Gly Leu Ser Pro Asp Leu Pro Ile Cys Lys
    610                 615                 620
Glu Gln Val Gln Ser Cys Gly Pro Pro Glu Leu Leu Asn Gly Asn
625                 630                 635                 640
Val Lys Glu Lys Thr Lys Glu Glu Tyr Gly His Ser Glu Val Val Glu
                645                 650                 655
Tyr Tyr Cys Asn Pro Arg Phe Leu Met Lys Gly Pro Asn Lys Ile Gln
            660                 665                 670
Cys Val Asp Gly Glu Trp Thr Thr Leu Pro Val Cys Ile Val Glu Glu
        675                 680                 685
Ser Thr Cys Gly Asp Ile Pro Glu Leu Glu His Gly Trp Ala Gln Leu
    690                 695                 700
```

-continued

```
Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
            755                 760                 765

Lys Glu Phe Asp His Asn Ser Asn Ile Arg Tyr Arg Cys Arg Gly Lys
        770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
                820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
        850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
            915                 920                 925

Leu Pro Cys Lys Ser Pro Pro Glu Ile Ser His Gly Val Val Ala His
        930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
```

```
                1115                1120                1125
Ala Pro Ala Ser Ser Val Glu Tyr Gln Cys Gln Asn Leu Tyr Gln
        1130                1135                1140

Leu Glu Gly Asn Lys Arg Ile Thr Cys Arg Asn Gly Gln Trp Ser
        1145                1150                1155

Glu Pro Pro Lys Cys Leu His Pro Cys Val Ile Ser Arg Glu Ile
        1160                1165                1170

Met Glu Asn Tyr Asn Ile Ala Leu Arg Trp Thr Ala Lys Gln Lys
        1175                1180                1185

Leu Tyr Ser Arg Thr Gly Glu Ser Val Glu Phe Val Cys Lys Arg
        1190                1195                1200

Gly Tyr Arg Leu Ser Ser Arg Ser His Thr Leu Arg Thr Thr Cys
        1205                1210                1215

Trp Asp Gly Lys Leu Glu Tyr Pro Thr Cys Ala Lys Arg
        1220                1225                1230

<210> SEQ ID NO 3
<211> LENGTH: 1658
<212> TYPE: DNA
<213> ORGANISM: Homo sapiens

<400> SEQUENCE: 3
aattcttgga agaggagaac tggacgttgt gaacagagtt agctggtaaa tgtcctctta      60
aaagatccaa aaaatgagac ttctagcaaa gattatttgc cttatgttat gggctatttg     120
tgtagcagaa gattgcaatg aacttcctcc aagaagaaat acagaaattc tgacaggttc     180
ctggtctgac caaacatatc agaaggcac ccaggctatc tataaatgcc gccctggata      240
tagatctctt ggaaatgtaa taatggtatg caggaaggga aatgggttg ctcttaatcc      300 attaaggaaa tgtcagaaaa ggccctgtgg acatcctgga gatactcctt ttggtacttt     360
tacccttaca ggaggaaatg tgtttgaata tggtgtaaaa gctgtgtata catgtaatga     420
ggggtatcaa ttgctaggtg agattaatta ccgtgaatgt gacacagatg gatggaccaa     480
tgatattcct atatgtgaag ttgtgaagtg tttaccagtg acagcaccag agaatggaaa     540
aattgtcagt agtgcaatgg aaccagatcg ggaataccat tttggacaag cagtacggtt     600
tgtatgtaac tcaggctaca gattgaagg agatgaagaa atgcattgtt cagacgatgg     660
ttttttggag taaagagaaac caaagtgtgt ggaaatttca tgcaaatccc cagatgttat     720
aaatggatct cctatatctc agaagattat ttataaggag aatgaacgat tcaatataa      780 atgtaacatg ggttatgaat acagtgaaag aggagatgct gtatgcactg aatctggatg     840
gcgtccgttg ccttcatgtg aagaaaaatc atgtgataat ccttatattc caaatggtga     900
ctactcacct ttaaggatta aacacagaac tggagatgaa atcacgtacc agtgtagaaa     960 tggttttat cctgcaaccc ggggaaatac agccaaatgc acaagtactg ctggatacc     1020 tgctccgaga tgtaccttga accttgtga ttatccagac attaaacatg gaggtctata     1080
tcatgagaat atgcgtagac catactttcc agtagctgta ggaaaatatt actcctatta     1140
ctgtgatgaa cattttgaga ctccgtcagg aagttactgg gatcacattc attgcacaca     1200
agatggatgg tcgccagcag taccatgcct cagaaaatgt tatttcctt atttggaaaa     1260 tggatataat caaaattatg gaagaaagtt tgtacagggt aaatctatag acgttgcctg     1320
ccatcctggc tacgctcttc caaaagcgca gaccacagtt acatgtatgg agaatggctg     1380
gtctcctact cccagatgca tccgtgtcag ctttaccctc tgaacttctg atcgaaggtc     1440
```

```
atccctctcc agcttgagtg gatcaaagat gacaagggcc aatgaaacca agtttgagtc    1500
ttgccaggtc aatacttggg tcctgagtat ggtgactagt atctgttttg ttatgtgtgt    1560
attattccag ccagaatggg aaatgctaat tcagctcctc caggcagcca atggggctgg    1620
tggctttgag attattaaac tcttctggat cctctacg                            1658
```

<210> SEQ ID NO 4
<211> LENGTH: 449
<212> TYPE: PRT
<213> ORGANISM: Homo sapiens

<400> SEQUENCE: 4

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335
```

```
His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
        370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Ser Phe Thr
                435                 440                 445

Leu

<210> SEQ ID NO 5
<211> LENGTH: 1231
<212> TYPE: PRT
<213> ORGANISM: Artificial
<220> FEATURE:
<223> OTHER INFORMATION: Synthetic Factor H variant

<400> SEQUENCE: 5

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Ile Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
            115                 120                 125

Cys Asp Thr Asp Gly Trp Thr Asn Asp Ile Pro Ile Cys Glu Val Val
        130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
            195                 200                 205

Ser Cys Lys Ser Pro Asp Val Ile Asn Gly Ser Pro Ile Ser Gln Lys
        210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
```

-continued

```
                245                 250                 255
Arg Pro Leu Pro Ser Cys Glu Glu Lys Ser Cys Asp Asn Pro Tyr Ile
                260                 265                 270
Pro Asn Gly Asp Tyr Ser Pro Leu Arg Ile Lys His Arg Thr Gly Asp
                275                 280                 285
Glu Ile Thr Tyr Gln Cys Arg Asn Gly Phe Tyr Pro Ala Thr Arg Gly
                290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
                325                 330                 335
His Glu Asn Met Arg Arg Pro Tyr Phe Pro Val Ala Val Gly Lys Tyr
                340                 345                 350
Tyr Ser Tyr Tyr Cys Asp Glu His Phe Glu Thr Pro Ser Gly Ser Tyr
                355                 360                 365
Trp Asp His Ile His Cys Thr Gln Asp Gly Trp Ser Pro Ala Val Pro
                370                 375                 380
Cys Leu Arg Lys Cys Tyr Phe Pro Tyr Leu Glu Asn Gly Tyr Asn Gln
385                 390                 395                 400
Asn Tyr Gly Arg Lys Phe Val Gln Gly Lys Ser Ile Asp Val Ala Cys
                405                 410                 415
His Pro Gly Tyr Ala Leu Pro Lys Ala Gln Thr Thr Val Thr Cys Met
                420                 425                 430
Glu Asn Gly Trp Ser Pro Thr Pro Arg Cys Ile Arg Val Lys Thr Cys
                435                 440                 445
Ser Lys Ser Ser Ile Asp Ile Glu Asn Gly Phe Ile Ser Glu Ser Gln
                450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Arg Cys Gly Lys
                485                 490                 495
Asp Gly Trp Ser Ala Gln Pro Thr Cys Ile Lys Ser Cys Asp Ile Pro
                500                 505                 510
Val Phe Met Asn Ala Arg Thr Lys Asn Asp Phe Thr Trp Phe Lys Leu
                515                 520                 525
Asn Asp Thr Leu Asp Tyr Glu Cys His Asp Gly Tyr Glu Ser Asn Thr
                530                 535                 540
Gly Ser Thr Thr Gly Ser Ile Val Cys Gly Tyr Asn Gly Trp Ser Asp
545                 550                 555                 560
Leu Pro Ile Cys Tyr Glu Arg Glu Cys Glu Leu Pro Lys Ile Asp Val
                565                 570                 575
His Leu Val Pro Asp Arg Lys Lys Asp Gln Tyr Lys Val Gly Glu Val
                580                 585                 590
Leu Lys Phe Ser Cys Lys Pro Gly Phe Thr Ile Val Gly Pro Asn Ser
                595                 600                 605
Val Gln Cys Tyr His Phe Gly Leu Ser Pro Asp Leu Pro Ile Cys Lys
                610                 615                 620
Glu Gln Val Gln Ser Cys Gly Pro Pro Glu Leu Leu Asn Gly Asn
625                 630                 635                 640
Val Lys Glu Lys Thr Lys Glu Glu Tyr Gly His Ser Glu Val Val Glu
                645                 650                 655
Tyr Tyr Cys Asn Pro Arg Phe Leu Met Lys Gly Pro Asn Lys Ile Gln
                660                 665                 670
```

```
Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
        690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro  Met Gly Glu Lys Lys  Asp Val Tyr
        995                 1000                 1005

Lys Ala  Gly Glu Gln Val Thr  Tyr Thr Cys Ala Thr  Tyr Tyr Lys
     1010                 1015                 1020

Met Asp  Gly Ala Ser Asn Val  Thr Cys Ile Asn Ser  Arg Trp Thr
     1025                 1030                 1035

Gly Arg  Pro Thr Cys Arg Asp  Thr Ser Cys Val Asn  Pro Pro Thr
     1040                 1045                 1050

Val Gln  Asn Ala Tyr Ile Val  Ser Arg Gln Met Ser  Lys Tyr Pro
     1055                 1060                 1065

Ser Gly  Glu Arg Val Arg Tyr  Gln Cys Arg Ser Pro  Tyr Glu Met
     1070                 1075                 1080
```

```
Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 6
<211> LENGTH: 449
<212> TYPE: PRT
<213> ORGANISM: Artificial
<220> FEATURE:
<223> OTHER INFORMATION: Synthetic Truncated Factor H variant

<400> SEQUENCE: 6

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205
```

```
Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Ser Phe Thr
        435                 440                 445

Leu

<210> SEQ ID NO 7
<211> LENGTH: 2823
<212> TYPE: DNA
<213> ORGANISM: Homo sapiens

<400> SEQUENCE: 7
ggcaggtgct tgttactgtt aatgaaagca gatttaaagc aacaccacca tcactggagt      60 attttagtt atatacgatt gagactacca agcatgttgc tcttattcag tgtaatccta     120
atctcatggg tatccactgt tgggggagaa ggaacacttt gtgattttcc aaaaatacac     180
catggatttc tgtatgatga agaagattat aacccttttt cccaagttcc tacagggaa     240 gttttctatt actcctgtga atataatttt gtgtctcctt caaaatcctt ttggactcgc     300
ataacatgca cagaagaagg atggtcacca acaccgaagt gtctcagaat gtgttccttt     360
ccttttgtga aaatggtca ttctgaatct tcaggactaa tacatctgga aggtgatact     420
gtacaaatta tttgcaacac aggatacagc cttcaaaaca atgagaaaaa catttcgtgt     480
gtagaacggg gctggtccac tcctcccata tgcagcttca ctaaaggaga atgtcatgtt     540 ccaatttag aagccaatgt agatgctcag ccaaaaaaag aaagctacaa agttggagac     600
gtgttgaaat tctcctgcag aaaaaatctt ataagagttg gatcagactc agttcaatgt     660
taccaatttg ggtggtcacc taactttcca acatgcaaag gacaagtacg atcatgtggt     720
```

| | | |
|---|---|---|
| ccacctcctc aactctccaa tggtgaagtt aaggagataa gaaaagagga atatggacac | | 780 |
| aatgaagtag tggaatatga ttgcaatcct aattttataa taaacgggcc taagaaaata | | 840 |
| caatgtgtgg atggagaatg gacaacttta cccacttgtg ttgaacaagt gaaaacatgt | | 900 |
| ggatacatac ctgaactcga gtacggttat gttcagccgt ctgtccctcc ctatcaacat | | 960 |
| ggagtttcag tcgaggtgaa ttgcagaaat gaatatgcaa tgattggaaa taacatgatt | | 1020 |
| acctgtatta atggaatatg gacagagctt cctatgtgtg ttgcaacaca ccaacttaag | | 1080 |
| aggtgcaaaa tagcaggagt taatataaaa acattactca agctatctgg gaaagaattt | | 1140 |
| aatcataatt ctagaatacg ttacagatgt tcagacatct tcagatacag gcactcagtc | | 1200 |
| tgtataaacg ggaaatggaa tcctgaagta gactgcacag aaaaaaggga acaattctgc | | 1260 |
| ccaccgccac ctcagatacc taatgctcag aatatgacaa ccacagtgaa ttatcaggat | | 1320 |
| ggagaaaaag tagctgttct ctgtaaagaa aactatctac ttccagaagc aaaagaaatt | | 1380 |
| gtatgtaaag atggacgatg gcaatcatta ccacgctgtg ttgagtctac tgcatattgt | | 1440 |
| gggccccctc catctattaa caatggagat accacctcat tcccattatc agtatatcct | | 1500 |
| ccagggtcaa cagtgacgta ccgttgccag tccttctata aactccaggg ctctgtaact | | 1560 |
| gtaacatgca gaaataaaca gtggtcagaa ccaccaagat gcctagatcc atgtgtggta | | 1620 |
| tctgaagaaa acatgaacaa aaataacata cagttaaaat ggagaaacga tggaaaactc | | 1680 |
| tatgcaaaaa caggggatgc tgttgaattc cagtgtaaat tcccacataa agcgatgata | | 1740 |
| tcatcaccac catttcgagc aatctgtcag gaagggaaat ttgaatatcc tatatgtgaa | | 1800 |
| tgaagcaagc ataattttcc tgaatatatt cttcaaacat ccatctacgc taaaagtagc | | 1860 |
| cattatgtag ccaattctgt agttacttct tttattcttt caggtgttgt ttaactcagt | | 1920 |
| tttatttaga actctggatt tttagagctt tagaaatttg taagctgaga gaacaatgtt | | 1980 |
| tcacttaata ggagggtgtc ttagtccata ttacattgtt ataacagagt atcacagact | | 2040 |
| ggataacttc taaccaatag tttatttgtt tcataaatct aaaagctgag aagtccaaga | | 2100 |
| tggtggggct gcctctggtg agggtcttct cgaagcatca taatatgctg gaaggcatca | | 2160 |
| caacatggtg aagggatca cgtggcaaaa gagcatgtac atgggagtga gagaaaaga | | 2220 |
| gagagagaga cagagtggcg ggggccgggg aggagcgcaa actcatcctt tataaagaca | | 2280 |
| ccactcctga gataacaatc caatcccatg ataatgacat taatccattc aagaagatag | | 2340 |
| agctctcgtg acttaatcac cttctaaaga tctcacctga caacactgtt gcattggcag | | 2400 |
| ttaagtttcc acgtaaactt tcggggacac attcaaacca caggagaaac tcaaattgtt | | 2460 |
| cctgggcaaa tcacaacatg gggaattta ttcataaatg tccacagaaa cagtaaatgt | | 2520 |
| tctcgcttca gaacttaatt catctaatcc ctcctgtttg tctcaaatta taggataact | | 2580 |
| ttgaaacttt ctgaattaac gttatttaaa aggaaatgta gatgttattt tagtctctat | | 2640 |
| cttcaggtta ttatcactta aaaacctgcg aaagctgtca acttttgtgg ttgtagcaag | | 2700 |
| tattaataaa tatttataaa tcctctaatg taagtctagc tacctatcca atactaaata | | 2760 |
| ccccttaaag tattaaatgc actatctgct gtaaacggaa aaaaaaaaa aaaaaaaaa | | 2820 |
| aaa | | 2823 |

<210> SEQ ID NO 8
<211> LENGTH: 569
<212> TYPE: PRT
<213> ORGANISM: Homo sapiens

<400> SEQUENCE: 8

-continued

```
Met Leu Leu Leu Phe Ser Val Ile Leu Ile Ser Trp Val Ser Thr Val
1               5                   10                  15

Gly Gly Glu Gly Thr Leu Cys Asp Phe Pro Lys Ile His His Gly Phe
            20                  25                  30

Leu Tyr Asp Glu Glu Asp Tyr Asn Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Thr Glu Glu Gly Trp Ser Pro Thr
65                  70                  75                  80

Pro Lys Cys Leu Arg Met Cys Ser Phe Pro Phe Val Lys Asn Gly His
                85                  90                  95

Ser Glu Ser Ser Gly Leu Ile His Leu Glu Gly Asp Thr Val Gln Ile
            100                 105                 110

Ile Cys Asn Thr Gly Tyr Ser Leu Gln Asn Asn Glu Lys Asn Ile Ser
        115                 120                 125

Cys Val Glu Arg Gly Trp Ser Thr Pro Pro Ile Cys Ser Phe Thr Lys
    130                 135                 140

Gly Glu Cys His Val Pro Ile Leu Glu Ala Asn Val Asp Ala Gln Pro
145                 150                 155                 160

Lys Lys Glu Ser Tyr Lys Val Gly Asp Val Leu Lys Phe Ser Cys Arg
                165                 170                 175

Lys Asn Leu Ile Arg Val Gly Ser Asp Ser Val Gln Cys Tyr Gln Phe
            180                 185                 190

Gly Trp Ser Pro Asn Phe Pro Thr Cys Lys Gly Gln Val Arg Ser Cys
        195                 200                 205

Gly Pro Pro Pro Gln Leu Ser Asn Gly Glu Val Lys Glu Ile Arg Lys
    210                 215                 220

Glu Glu Tyr Gly His Asn Glu Val Val Glu Tyr Asp Cys Asn Pro Asn
225                 230                 235                 240

Phe Ile Ile Asn Gly Pro Lys Lys Ile Gln Cys Val Asp Gly Glu Trp
                245                 250                 255

Thr Thr Leu Pro Thr Cys Val Glu Gln Val Lys Thr Cys Gly Tyr Ile
            260                 265                 270

Pro Glu Leu Glu Tyr Gly Tyr Val Gln Pro Ser Val Pro Pro Tyr Gln
        275                 280                 285

His Gly Val Ser Val Glu Val Asn Cys Arg Asn Glu Tyr Ala Met Ile
    290                 295                 300

Gly Asn Asn Met Ile Thr Cys Ile Asn Gly Ile Trp Thr Glu Leu Pro
305                 310                 315                 320

Met Cys Val Ala Thr His Gln Leu Lys Arg Cys Lys Ile Ala Gly Val
                325                 330                 335

Asn Ile Lys Thr Leu Leu Lys Leu Ser Gly Lys Glu Phe Asn His Asn
            340                 345                 350

Ser Arg Ile Arg Tyr Arg Cys Ser Asp Ile Phe Arg Tyr Arg His Ser
        355                 360                 365

Val Cys Ile Asn Gly Lys Trp Asn Pro Glu Val Asp Cys Thr Glu Lys
    370                 375                 380

Arg Glu Gln Phe Cys Pro Pro Pro Gln Ile Pro Asn Ala Gln Asn
385                 390                 395                 400

Met Thr Thr Thr Val Asn Tyr Gln Asp Gly Glu Lys Val Ala Val Leu
                405                 410                 415
```

-continued

```
Cys Lys Glu Asn Tyr Leu Leu Pro Glu Ala Lys Glu Ile Val Cys Lys
                420                 425                 430
Asp Gly Arg Trp Gln Ser Leu Pro Arg Cys Val Glu Ser Thr Ala Tyr
            435                 440                 445
Cys Gly Pro Pro Pro Ser Ile Asn Asn Gly Asp Thr Thr Ser Phe Pro
        450                 455                 460
Leu Ser Val Tyr Pro Pro Gly Ser Thr Val Thr Tyr Arg Cys Gln Ser
465                 470                 475                 480
Phe Tyr Lys Leu Gln Gly Ser Val Thr Val Thr Cys Arg Asn Lys Gln
                485                 490                 495
Trp Ser Glu Pro Pro Arg Cys Leu Asp Pro Cys Val Val Ser Glu Glu
            500                 505                 510
Asn Met Asn Lys Asn Asn Ile Gln Leu Lys Trp Arg Asn Asp Gly Lys
        515                 520                 525
Leu Tyr Ala Lys Thr Gly Asp Ala Val Glu Phe Gln Cys Lys Phe Pro
530                 535                 540
His Lys Ala Met Ile Ser Ser Pro Pro Phe Arg Ala Ile Cys Gln Glu
545                 550                 555                 560
Gly Lys Phe Glu Tyr Pro Ile Cys Glu
                565

<210> SEQ ID NO 9
<211> LENGTH: 41
<212> TYPE: DNA
<213> ORGANISM: Artificial
<220> FEATURE:
<223> OTHER INFORMATION: Factor H gene polymorphism

<400> SEQUENCE: 9 ggggtttttct gggatgtaat ratgttcagt gttttgacct t                   41

<210> SEQ ID NO 10
<211> LENGTH: 41
<212> TYPE: DNA
<213> ORGANISM: Artificial
<220> FEATURE:
<223> OTHER INFORMATION: Polymorphism

<400> SEQUENCE: 10
ttatgaaatc cagaggatat yaccagctgc tgatttgcac a                    41

<210> SEQ ID NO 11
<211> LENGTH: 41
<212> TYPE: DNA
<213> ORGANISM: Artificial
<220> FEATURE:
<223> OTHER INFORMATION: Polymorphism

<400> SEQUENCE: 11
agtccaagtt tacacagtac ratagactta cccattgcca a                    41

<210> SEQ ID NO 12
<211> LENGTH: 41
<212> TYPE: DNA
<213> ORGANISM: Artificial
<220> FEATURE:
<223> OTHER INFORMATION: Factor H gene polymorphism

<400> SEQUENCE: 12
gatatagatc tcttggaaat rtaataatgg tatgcaggaa g                    41
```

<210> SEQ ID NO 13
<211> LENGTH: 42
<212> TYPE: DNA
<213> ORGANISM: Artificial
<220> FEATURE:
<223> OTHER INFORMATION: Factor H gene polymorphism
<220> FEATURE:
<221> NAME/KEY: misc_feature
<222> LOCATION: (21)..(22)
<223> OTHER INFORMATION: Residues 21-22 may be absent

<400> SEQUENCE: 13
taattcataa cttttttttt ttcgttttag aaaggccctg tg                42

<210> SEQ ID NO 14
<211> LENGTH: 41
<212> TYPE: DNA
<213> ORGANISM: Artificial
<220> FEATURE:
<223> OTHER INFORMATION: Factor H gene polymorphism

<400> SEQUENCE: 14
aaaggaatac atttaggact yatttgaagt tagtgtcaac a                 41

<210> SEQ ID NO 15
<211> LENGTH: 40
<212> TYPE: DNA
<213> ORGANISM: Artificial
<220> FEATURE:
<223> OTHER INFORMATION: Factor H gene polymorphism

<400> SEQUENCE: 15
caacccgggg aaatacagcm aaatgcacaa gtactggctg                   40

<210> SEQ ID NO 16
<211> LENGTH: 41
<212> TYPE: DNA
<213> ORGANISM: Artificial
<220> FEATURE:
<223> OTHER INFORMATION: Factor H gene polymorphism

<400> SEQUENCE: 16
aaaatggata taatcaaaat yatggaagaa agtttgtaca g                 41

<210> SEQ ID NO 17
<211> LENGTH: 41
<212> TYPE: DNA
<213> ORGANISM: Artificial
<220> FEATURE:
<223> OTHER INFORMATION: Factor H gene polymorphism

<400> SEQUENCE: 17
tatgccttaa aagaaaaagc raaatatcaa tgcaaactag g                 41

<210> SEQ ID NO 18
<211> LENGTH: 41
<212> TYPE: DNA
<213> ORGANISM: Artificial
<220> FEATURE:
<223> OTHER INFORMATION: Factor H gene polymorphism
<220> FEATURE:
<221> NAME/KEY: misc_feature
<222> LOCATION: (21)..(21)
<223> OTHER INFORMATION: Residue 21 is optionally absent

<400> SEQUENCE: 18
cagcttgagt ggatcaaaga ntgacaaggg ccaatggaac c                 41

```
<210> SEQ ID NO 19
<211> LENGTH: 41
<212> TYPE: DNA
<213> ORGANISM: Artificial
<220> FEATURE:
<223> OTHER INFORMATION: Factor H gene polymorphism

<400> SEQUENCE: 19
acggtaccta tttattagta katctaatca ataaagcttt t                              41

<210> SEQ ID NO 20
<211> LENGTH: 41
<212> TYPE: DNA
<213> ORGANISM: Artificial
<220> FEATURE:
<223> OTHER INFORMATION: Factor H gene polymorphism

<400> SEQUENCE: 20
aagggaccta ataaaattca rtgtgttgat ggagagtgga c                              41

<210> SEQ ID NO 21
<211> LENGTH: 41
<212> TYPE: DNA
<213> ORGANISM: Artificial
<220> FEATURE:
<223> OTHER INFORMATION: Factor H gene polymorphism

<400> SEQUENCE: 21 tttttattt tttattataa mattaattat atttttaata t                               41

<210> SEQ ID NO 22
<211> LENGTH: 41
<212> TYPE: DNA
<213> ORGANISM: Artificial
<220> FEATURE:
<223> OTHER INFORMATION: Factor H gene polymorphism

<400> SEQUENCE: 22
ccttgtaaat ctccacctga katttctcat ggtgttgtag c                              41

<210> SEQ ID NO 23
<211> LENGTH: 41
<212> TYPE: DNA
<213> ORGANISM: Artificial
<220> FEATURE:
<223> OTHER INFORMATION: Factor H gene polymorphism

<400> SEQUENCE: 23
ggggatatcg tctttcatca ygttctcaca cattgcgaac a                              41

<210> SEQ ID NO 24
<211> LENGTH: 31
<212> TYPE: DNA
<213> ORGANISM: Artificial
<220> FEATURE:
<223> OTHER INFORMATION: Factor H gene polymorphism

<400> SEQUENCE: 24
aaatccagag gatatyacca gctgctgatt t                                         31

<210> SEQ ID NO 25
<211> LENGTH: 31
<212> TYPE: DNA
<213> ORGANISM: Artificial
<220> FEATURE:
<223> OTHER INFORMATION: Factor H gene polymorphism
```

```
<400> SEQUENCE: 25
aatgggtaag tctatygtac tgtgtaaact t                               31

<210> SEQ ID NO 26
<211> LENGTH: 31
<212> TYPE: DNA
<213> ORGANISM: Artificial
<220> FEATURE:
<223> OTHER INFORMATION: Factor H gene polymorphism

<400> SEQUENCE: 26
tgcataccat tattayattt ccaagagatc t                               31

<210> SEQ ID NO 27
<211> LENGTH: 36
<212> TYPE: DNA
<213> ORGANISM: Artificial
<220> FEATURE:
<223> OTHER INFORMATION: Factor H gene polymorphism
<220> FEATURE:
<221> NAME/KEY: misc_feature
<222> LOCATION: (18)..(19)
<223> OTHER INFORMATION: Residues 18-19 may be optionally absent

<400> SEQUENCE: 27
acatactaat tcataacttt tttttttcg ttttag                           36

<210> SEQ ID NO 28
<211> LENGTH: 31
<212> TYPE: DNA
<213> ORGANISM: Artificial
<220> FEATURE:
<223> OTHER INFORMATION: Factor H gene polymorphism

<400> SEQUENCE: 28
aatacattta ggactyattt gaagttagtg t                               31

<210> SEQ ID NO 29
<211> LENGTH: 31
<212> TYPE: DNA
<213> ORGANISM: Artificial
<220> FEATURE:
<223> OTHER INFORMATION: Factor H gene polymorphism

<400> SEQUENCE: 29
ccggggaaat acagcmaaat gcacaagtac t                               31

<210> SEQ ID NO 30
<211> LENGTH: 31
<212> TYPE: DNA
<213> ORGANISM: Artificial
<220> FEATURE:
<223> OTHER INFORMATION: Factor H gene polymorphism

<400> SEQUENCE: 30
ggatataatc aaaatyatgg aagaaagttt g                               31

<210> SEQ ID NO 31
<211> LENGTH: 31
<212> TYPE: DNA
<213> ORGANISM: Artificial
<220> FEATURE:
<223> OTHER INFORMATION: Factor H gene polymorphism

<400> SEQUENCE: 31
```

```
cttaaaagaa aaagcraaat atcaatgcaa a                              31
```

<210> SEQ ID NO 32
<211> LENGTH: 31
<212> TYPE: DNA
<213> ORGANISM: Artificial
<220> FEATURE:
<223> OTHER INFORMATION: Factor H gene polymorphism

<400> SEQUENCE: 32

```
ctttattgat tagatmtact aataaatagg t                              31
```

<210> SEQ ID NO 33
<211> LENGTH: 31
<212> TYPE: DNA
<213> ORGANISM: Artificial
<220> FEATURE:
<223> OTHER INFORMATION: Factor H gene polymorphism

<400> SEQUENCE: 33

```
acctaataaa attcartgtg ttgatggaga g                              31
```

<210> SEQ ID NO 34
<211> LENGTH: 31
<212> TYPE: DNA
<213> ORGANISM: Artificial
<220> FEATURE:
<223> OTHER INFORMATION: Factor H gene polymorphism

<400> SEQUENCE: 34

```
taaatctcca cctgakattt ctcatggtgt t                              31
```

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35

```
acttgttccc ccactcctac                                           20
```

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36

```
cctcttttcg tatggactac                                           20
```

<210> SEQ ID NO 37
<211> LENGTH: 27
<212> TYPE: DNA
<213> ORGANISM: Artificial
<220> FEATURE:
<223> OTHER INFORMATION: Primer

<400> SEQUENCE: 37

```
tgaaatcacg taccagtgta gaaatgg                                   27
```

<210> SEQ ID NO 38
<211> LENGTH: 22
<212> TYPE: DNA
<213> ORGANISM: Artificial

<220> FEATURE:
<223> OTHER INFORMATION: Primer

<400> SEQUENCE: 38
caggtatcca gccagtactt gt                                    22

<210> SEQ ID NO 39
<211> LENGTH: 45
<212> TYPE: DNA
<213> ORGANISM: Artificial
<220> FEATURE:
<223> OTHER INFORMATION: Primer

<400> SEQUENCE: 39
ctttatttat ttatcattgt tatggtcctt aggaaaatgt tattt           45

<210> SEQ ID NO 40
<211> LENGTH: 25
<212> TYPE: DNA
<213> ORGANISM: Artificial
<220> FEATURE:
<223> OTHER INFORMATION: Primer

<400> SEQUENCE: 40
ggcaggcaac gtctatagat ttacc                                 25

<210> SEQ ID NO 41
<211> LENGTH: 27
<212> TYPE: DNA
<213> ORGANISM: Artificial
<220> FEATURE:
<223> OTHER INFORMATION: Primer

<400> SEQUENCE: 41
tcaccatctg ctgttacata tcctagt                               27

<210> SEQ ID NO 42
<211> LENGTH: 33
<212> TYPE: DNA
<213> ORGANISM: Artificial
<220> FEATURE:
<223> OTHER INFORMATION: Primer

<400> SEQUENCE: 42
tgggtttatt tctgaatctc agtatacata tgc                        33

<210> SEQ ID NO 43
<211> LENGTH: 15
<212> TYPE: DNA
<213> ORGANISM: Artificial
<220> FEATURE:
<223> OTHER INFORMATION: Probe

<400> SEQUENCE: 43
aatacagcaa aatgc                                            15

<210> SEQ ID NO 44
<211> LENGTH: 17
<212> TYPE: DNA
<213> ORGANISM: Artificial
<220> FEATURE:
<223> OTHER INFORMATION: Probe

<400> SEQUENCE: 44
tttcttccat gattttg                                          17

```
<210> SEQ ID NO 45
<211> LENGTH: 17
<212> TYPE: DNA
<213> ORGANISM: Artificial
<220> FEATURE:
<223> OTHER INFORMATION: Probe

<400> SEQUENCE: 45
aagaaaaagc gaaatat                                                17

<210> SEQ ID NO 46
<211> LENGTH: 14
<212> TYPE: DNA
<213> ORGANISM: Artificial
<220> FEATURE:
<223> OTHER INFORMATION: Probe

<400> SEQUENCE: 46
atacagccaa atgc                                                   14

<210> SEQ ID NO 47
<211> LENGTH: 16
<212> TYPE: DNA
<213> ORGANISM: Artificial
<220> FEATURE:
<223> OTHER INFORMATION: Probe

<400> SEQUENCE: 47
ttcttccata attttg                                                 16

<210> SEQ ID NO 48
<211> LENGTH: 17
<212> TYPE: DNA
<213> ORGANISM: Artificial
<220> FEATURE:
<223> OTHER INFORMATION: Probe

<400> SEQUENCE: 48
aagaaaaagc aaaatat                                                17

<210> SEQ ID NO 49
<211> LENGTH: 41
<212> TYPE: DNA
<213> ORGANISM: Artificial
<220> FEATURE:
<223> OTHER INFORMATION: Polymorphism

<400> SEQUENCE: 49
ccaggctatc tataaatgcc rccctggata tagatctctt g                     41

<210> SEQ ID NO 50
<211> LENGTH: 41
<212> TYPE: DNA
<213> ORGANISM: Artificial
<220> FEATURE:
<223> OTHER INFORMATION: Polymorphism

<400> SEQUENCE: 50
ttggtacttt taccctaca kgaggaaatg tgtttgaata t                      41

<210> SEQ ID NO 51
<211> LENGTH: 41
<212> TYPE: DNA
<213> ORGANISM: Artificial
<220> FEATURE:
<223> OTHER INFORMATION: Polymorphism
```

```
<220> FEATURE:
<221> NAME/KEY: misc_feature
<222> LOCATION: (21)..(21)
<223> OTHER INFORMATION: Residue 21 is G or H

<400> SEQUENCE: 51
acgatggttt ttggagtaaa nagaaaccaa agtgtgtggg t                 41

<210> SEQ ID NO 52
<211> LENGTH: 41
<212> TYPE: DNA
<213> ORGANISM: Artificial
<220> FEATURE:
<223> OTHER INFORMATION: Polymorphism
<220> FEATURE:
<221> NAME/KEY: misc_feature
<222> LOCATION: (21)..(21)
<223> OTHER INFORMATION: Residue is C or D

<400> SEQUENCE: 52
ttatttataa ggagaatgaa ngatttcaat ataaatgtaa c                 41

<210> SEQ ID NO 53
<211> LENGTH: 38
<212> TYPE: DNA
<213> ORGANISM: Artificial
<220> FEATURE:
<223> OTHER INFORMATION: Polymorphism
<220> FEATURE:
<221> NAME/KEY: misc_feature
<222> LOCATION: (21)..(21)
<223> OTHER INFORMATION: Residue is C or D

<400> SEQUENCE: 53
cactgaatct ggatggcgtc ngttgccttc atgtgaag                     38

<210> SEQ ID NO 54
<211> LENGTH: 33
<212> TYPE: DNA
<213> ORGANISM: Artificial
<220> FEATURE:
<223> OTHER INFORMATION: Polymorphism
<220> FEATURE:
<221> NAME/KEY: misc_feature
<222> LOCATION: (21)..(21)
<223> OTHER INFORMATION: Residue 21 is optionally absent

<400> SEQUENCE: 54
aagatggatg gtcgccagca staccatgcc tca                          33

<210> SEQ ID NO 55
<211> LENGTH: 41
<212> TYPE: DNA
<213> ORGANISM: Artificial
<220> FEATURE:
<223> OTHER INFORMATION: Polymorphism

<400> SEQUENCE: 55
acaattatgc ccacctccac stcagattcc caattctcac a                 41

<210> SEQ ID NO 56
<211> LENGTH: 41
<212> TYPE: DNA
<213> ORGANISM: Artificial
<220> FEATURE:
<223> OTHER INFORMATION: Polymorphism

<400> SEQUENCE: 56
```

-continued caaccacctc agatagaaca yggaaccatt aattcatcca g         41

<210> SEQ ID NO 57
<211> LENGTH: 41
<212> TYPE: DNA
<213> ORGANISM: Artificial
<220> FEATURE:
<223> OTHER INFORMATION: Polymorphism

<400> SEQUENCE: 57
gtcttcacaa gaaagttatg yacatgggac taaattgagt t         41

<210> SEQ ID NO 58
<211> LENGTH: 41
<212> TYPE: DNA
<213> ORGANISM: Artificial
<220> FEATURE:
<223> OTHER INFORMATION: Polymorphism

<400> SEQUENCE: 58
cacatgtcag acagttatca ktatggagaa gaagttacgt a         41

<210> SEQ ID NO 59
<211> LENGTH: 41
<212> TYPE: DNA
<213> ORGANISM: Artificial
<220> FEATURE:
<223> OTHER INFORMATION: Polymorphism

<400> SEQUENCE: 59
tcagtatgga gaagaagtta ygtacaaatg ttttgaaggt t         41

<210> SEQ ID NO 60
<211> LENGTH: 27
<212> TYPE: DNA
<213> ORGANISM: Artificial
<220> FEATURE:
<223> OTHER INFORMATION: Polymorphism

<400> SEQUENCE: 60
gtatggkgca ttgaatttta ttatatg         27

<210> SEQ ID NO 61
<211> LENGTH: 35
<212> TYPE: DNA
<213> ORGANISM: Artificial
<220> FEATURE:
<223> OTHER INFORMATION: Polymorphism

<400> SEQUENCE: 61
acacctcctg tgtgwatccg cccacagtac aaaat         35

<210> SEQ ID NO 62
<211> LENGTH: 44
<212> TYPE: DNA
<213> ORGANISM: Artificial
<220> FEATURE:
<223> OTHER INFORMATION: Polymorphism
<220> FEATURE:
<221> NAME/KEY: misc_feature
<222> LOCATION: (21)..(21)
<223> OTHER INFORMATION: Residue 21 may be optionally absent
<220> FEATURE:
<221> NAME/KEY: misc_feature
<222> LOCATION: (23)..(23)
<223> OTHER INFORMATION: Residue 23 may be optionally absent

<400> SEQUENCE: 62

-continued cttgtatcaa cttgagggta nancaagcga ataacatgta gaaa         44

<210> SEQ ID NO 63
<211> LENGTH: 41
<212> TYPE: DNA
<213> ORGANISM: Artificial
<220> FEATURE:
<223> OTHER INFORMATION: Polymorphism

<400> SEQUENCE: 63
aaaagcttta ttgattagat mtactaataa ataggtaccg t           41

<210> SEQ ID NO 64
<211> LENGTH: 19
<212> TYPE: DNA
<213> ORGANISM: Artificial
<220> FEATURE:
<223> OTHER INFORMATION: Primer

<400> SEQUENCE: 64
gcaaaagttt ctgataggc                                     19

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
aatcttacct tctgctacac                                    20

<210> SEQ ID NO 66
<211> LENGTH: 19
<212> TYPE: DNA
<213> ORGANISM: Artificial
<220> FEATURE:
<223> OTHER INFORMATION: Primer

<400> SEQUENCE: 66
ttagatagac ctgtgactg                                     19

<210> SEQ ID NO 67
<211> LENGTH: 17
<212> TYPE: DNA
<213> ORGANISM: Artificial
<220> FEATURE:
<223> OTHER INFORMATION: Primer

<400> SEQUENCE: 67
tcaggcataa ttgctac                                       17

<210> SEQ ID NO 68
<211> LENGTH: 16
<212> TYPE: DNA
<213> ORGANISM: Artificial
<220> FEATURE:
<223> OTHER INFORMATION: Primer

<400> SEQUENCE: 68
acttgttccc ccactc                                        16

<210> SEQ ID NO 69
<211> LENGTH: 20
<212> TYPE: DNA

```
<213> ORGANISM: Artificial
<220> FEATURE:
<223> OTHER INFORMATION: Primer

<400> SEQUENCE: 69
cctcttttcg tatggactac                                          20

<210> SEQ ID NO 70
<211> LENGTH: 18
<212> TYPE: DNA
<213> ORGANISM: Artificial
<220> FEATURE:
<223> OTHER INFORMATION: Primer

<400> SEQUENCE: 70
ttgttccccc actcctac                                            18

<210> SEQ ID NO 71
<211> LENGTH: 20
<212> TYPE: DNA
<213> ORGANISM: Artificial
<220> FEATURE:
<223> OTHER INFORMATION: Primer

<400> SEQUENCE: 71
acacatttcc tcctgtaagg                                          20

<210> SEQ ID NO 72
<211> LENGTH: 17
<212> TYPE: DNA
<213> ORGANISM: Artificial
<220> FEATURE:
<223> OTHER INFORMATION: Primer

<400> SEQUENCE: 72
ccctgtggac atcctgg                                             17

<210> SEQ ID NO 73
<211> LENGTH: 22
<212> TYPE: DNA
<213> ORGANISM: Artificial
<220> FEATURE:
<223> OTHER INFORMATION: Primer

<400> SEQUENCE: 73
aacctctttt cgtatggact ac                                       22

<210> SEQ ID NO 74
<211> LENGTH: 16
<212> TYPE: DNA
<213> ORGANISM: Artificial
<220> FEATURE:
<223> OTHER INFORMATION: Primer

<400> SEQUENCE: 74
atgctgttca ttttcc                                              16

<210> SEQ ID NO 75
<211> LENGTH: 17
<212> TYPE: DNA
<213> ORGANISM: Artificial
<220> FEATURE:
<223> OTHER INFORMATION: Primer

<400> SEQUENCE: 75
ccatccatct gtgtcac                                             17
```

```
<210> SEQ ID NO 76
<211> LENGTH: 17
<212> TYPE: DNA
<213> ORGANISM: Artificial
<220> FEATURE:
<223> OTHER INFORMATION: Primer

<400> SEQUENCE: 76
attaccgtga atgtgac                                                    17

<210> SEQ ID NO 77
<211> LENGTH: 19
<212> TYPE: DNA
<213> ORGANISM: Artificial
<220> FEATURE:
<223> OTHER INFORMATION: Primer

<400> SEQUENCE: 77
ttgtatgaga aaaaaaaac                                                  19

<210> SEQ ID NO 78
<211> LENGTH: 18
<212> TYPE: DNA
<213> ORGANISM: Artificial
<220> FEATURE:
<223> OTHER INFORMATION: Primer

<400> SEQUENCE: 78
tccaatctta tcctgagg                                                   18

<210> SEQ ID NO 79
<211> LENGTH: 18
<212> TYPE: DNA
<213> ORGANISM: Artificial
<220> FEATURE:
<223> OTHER INFORMATION: Primer

<400> SEQUENCE: 79
tcttacccac acactttg                                                   18

<210> SEQ ID NO 80
<211> LENGTH: 16
<212> TYPE: DNA
<213> ORGANISM: Artificial
<220> FEATURE:
<223> OTHER INFORMATION: Primer

<400> SEQUENCE: 80
gtcctggtca cagtcc                                                     16

<210> SEQ ID NO 81
<211> LENGTH: 17
<212> TYPE: DNA
<213> ORGANISM: Artificial
<220> FEATURE:
<223> OTHER INFORMATION: Primer

<400> SEQUENCE: 81
gcatacagca tctcctc                                                    17

<210> SEQ ID NO 82
<211> LENGTH: 16
<212> TYPE: DNA
<213> ORGANISM: Artificial
<220> FEATURE:
```

```
<223> OTHER INFORMATION: Primer

<400> SEQUENCE: 82
gcactgaatc tggatg                                                      16

<210> SEQ ID NO 83
<211> LENGTH: 17
<212> TYPE: DNA
<213> ORGANISM: Artificial
<220> FEATURE:
<223> OTHER INFORMATION: Primer

<400> SEQUENCE: 83
atgaaccttg aacacag                                                     17

<210> SEQ ID NO 84
<211> LENGTH: 17
<212> TYPE: DNA
<213> ORGANISM: Artificial
<220> FEATURE:
<223> OTHER INFORMATION: Primer

<400> SEQUENCE: 84
cggatactta tttctgc                                                     17

<210> SEQ ID NO 85
<211> LENGTH: 17
<212> TYPE: DNA
<213> ORGANISM: Artificial
<220> FEATURE:
<223> OTHER INFORMATION: Primer

<400> SEQUENCE: 85
cgtgatttca tctccag                                                     17

<210> SEQ ID NO 86
<211> LENGTH: 18
<212> TYPE: DNA
<213> ORGANISM: Artificial
<220> FEATURE:
<223> OTHER INFORMATION: Primer

<400> SEQUENCE: 86
agaactggag atgaaatc                                                    18

<210> SEQ ID NO 87
<211> LENGTH: 17
<212> TYPE: DNA
<213> ORGANISM: Artificial
<220> FEATURE:
<223> OTHER INFORMATION: Primer

<400> SEQUENCE: 87
tgaatggaac ttacagg                                                     17

<210> SEQ ID NO 88
<211> LENGTH: 19
<212> TYPE: DNA
<213> ORGANISM: Artificial
<220> FEATURE:
<223> OTHER INFORMATION: Primer

<400> SEQUENCE: 88
gtgaaacctt gtgattatc                                                   19
```

```
<210> SEQ ID NO 89
<211> LENGTH: 16
<212> TYPE: DNA
<213> ORGANISM: Artificial
<220> FEATURE:
<223> OTHER INFORMATION: Primer

<400> SEQUENCE: 89
tcccagtaac ttcctg                                                     16

<210> SEQ ID NO 90
<211> LENGTH: 19
<212> TYPE: DNA
<213> ORGANISM: Artificial
<220> FEATURE:
<223> OTHER INFORMATION: Primer

<400> SEQUENCE: 90
ctgtgatgaa cattttgag                                                  19

<210> SEQ ID NO 91
<211> LENGTH: 16
<212> TYPE: DNA
<213> ORGANISM: Artificial
<220> FEATURE:
<223> OTHER INFORMATION: Primer

<400> SEQUENCE: 91
tgctctcctt tcttcg                                                     16

<210> SEQ ID NO 92
<211> LENGTH: 19
<212> TYPE: DNA
<213> ORGANISM: Artificial
<220> FEATURE:
<223> OTHER INFORMATION: Primer

<400> SEQUENCE: 92
cattgttatg gtccttagg                                                  19

<210> SEQ ID NO 93
<211> LENGTH: 19
<212> TYPE: DNA
<213> ORGANISM: Artificial
<220> FEATURE:
<223> OTHER INFORMATION: Primer

<400> SEQUENCE: 93
acatgctagg atttcagag                                                  19

<210> SEQ ID NO 94
<211> LENGTH: 20
<212> TYPE: DNA
<213> ORGANISM: Artificial
<220> FEATURE:
<223> OTHER INFORMATION: Primer

<400> SEQUENCE: 94 cttttttctta ttctcttccc                                                20

<210> SEQ ID NO 95
<211> LENGTH: 17
<212> TYPE: DNA
<213> ORGANISM: Artificial
<220> FEATURE:
<223> OTHER INFORMATION: Primer
```

```
<400> SEQUENCE: 95
tcaccatctg ctgttac                                                 17

<210> SEQ ID NO 96
<211> LENGTH: 17
<212> TYPE: DNA
<213> ORGANISM: Artificial
<220> FEATURE:
<223> OTHER INFORMATION: Primer

<400> SEQUENCE: 96
tgtaacagca gatggtg                                                 17

<210> SEQ ID NO 97
<211> LENGTH: 18
<212> TYPE: DNA
<213> ORGANISM: Artificial
<220> FEATURE:
<223> OTHER INFORMATION: Primer

<400> SEQUENCE: 97
cccacaaaaa gactaaag                                                18

<210> SEQ ID NO 98
<211> LENGTH: 17
<212> TYPE: DNA
<213> ORGANISM: Artificial
<220> FEATURE:
<223> OTHER INFORMATION: Primer

<400> SEQUENCE: 98
gggaaatact cagattg                                                 17

<210> SEQ ID NO 99
<211> LENGTH: 16
<212> TYPE: DNA
<213> ORGANISM: Artificial
<220> FEATURE:
<223> OTHER INFORMATION: Primer

<400> SEQUENCE: 99
atggcattca tagtcc                                                  16

<210> SEQ ID NO 100
<211> LENGTH: 20
<212> TYPE: DNA
<213> ORGANISM: Artificial
<220> FEATURE:
<223> OTHER INFORMATION: Primer

<400> SEQUENCE: 100
ccagaactaa aaatgacttc                                              20

<210> SEQ ID NO 101
<211> LENGTH: 17
<212> TYPE: DNA
<213> ORGANISM: Artificial
<220> FEATURE:
<223> OTHER INFORMATION: Primer

<400> SEQUENCE: 101
ggtaaatcag accaacc                                                 17

<210> SEQ ID NO 102
<211> LENGTH: 19
```

-continued

<212> TYPE: DNA
<213> ORGANISM: Artificial
<220> FEATURE:
<223> OTHER INFORMATION: Primer

<400> SEQUENCE: 102
atagtgtgtg gttacaatg					19

<210> SEQ ID NO 103
<211> LENGTH: 19
<212> TYPE: DNA
<213> ORGANISM: Artificial
<220> FEATURE:
<223> OTHER INFORMATION: Primer

<400> SEQUENCE: 103
gtttatgtca aatcaggag					19

<210> SEQ ID NO 104
<211> LENGTH: 19
<212> TYPE: DNA
<213> ORGANISM: Artificial
<220> FEATURE:
<223> OTHER INFORMATION: Primer

<400> SEQUENCE: 104
caagaaagag aatgcgaac					19

<210> SEQ ID NO 105
<211> LENGTH: 17
<212> TYPE: DNA
<213> ORGANISM: Artificial
<220> FEATURE:
<223> OTHER INFORMATION: Primer

<400> SEQUENCE: 105
agattacagg caatggg					17

<210> SEQ ID NO 106
<211> LENGTH: 17
<212> TYPE: DNA
<213> ORGANISM: Artificial
<220> FEATURE:
<223> OTHER INFORMATION: Primer

<400> SEQUENCE: 106
ttgattgttt aggatgc					17

<210> SEQ ID NO 107
<211> LENGTH: 20
<212> TYPE: DNA
<213> ORGANISM: Artificial
<220> FEATURE:
<223> OTHER INFORMATION: Primer

<400> SEQUENCE: 107
ttgaggagtt caggaggtgg					20

<210> SEQ ID NO 108
<211> LENGTH: 16
<212> TYPE: DNA
<213> ORGANISM: Artificial
<220> FEATURE:
<223> OTHER INFORMATION: Primer

<400> SEQUENCE: 108
ctgaactcct caatgg                                              16

<210> SEQ ID NO 109
<211> LENGTH: 18
<212> TYPE: DNA
<213> ORGANISM: Artificial
<220> FEATURE:
<223> OTHER INFORMATION: Primer

<400> SEQUENCE: 109
attaccaata cacactgg                                            18

<210> SEQ ID NO 110
<211> LENGTH: 18
<212> TYPE: DNA
<213> ORGANISM: Artificial
<220> FEATURE:
<223> OTHER INFORMATION: Primer

<400> SEQUENCE: 110
ttacatagtg gaggagag                                            18

<210> SEQ ID NO 111
<211> LENGTH: 15
<212> TYPE: DNA
<213> ORGANISM: Artificial
<220> FEATURE:
<223> OTHER INFORMATION: Primer

<400> SEQUENCE: 111
tggaaatgtt gaggc                                               15

<210> SEQ ID NO 112
<211> LENGTH: 19
<212> TYPE: DNA
<213> ORGANISM: Artificial
<220> FEATURE:
<223> OTHER INFORMATION: Primer

<400> SEQUENCE: 112
agttggtttg attcctatc                                           19

<210> SEQ ID NO 113
<211> LENGTH: 18
<212> TYPE: DNA
<213> ORGANISM: Artificial
<220> FEATURE:
<223> OTHER INFORMATION: Primer

<400> SEQUENCE: 113
ttgagcagtt cacttctg                                            18

<210> SEQ ID NO 114
<211> LENGTH: 16
<212> TYPE: DNA
<213> ORGANISM: Artificial
<220> FEATURE:
<223> OTHER INFORMATION: Primer

<400> SEQUENCE: 114
ttatgcccac ctccac                                              16

<210> SEQ ID NO 115
<211> LENGTH: 19
<212> TYPE: DNA
<213> ORGANISM: Artificial

```
<220> FEATURE:
<223> OTHER INFORMATION: Primer

<400> SEQUENCE: 115
atacactact gaccaacac                                              19

<210> SEQ ID NO 116
<211> LENGTH: 19
<212> TYPE: DNA
<213> ORGANISM: Artificial
<220> FEATURE:
<223> OTHER INFORMATION: Primer

<400> SEQUENCE: 116
gtctatgaga atacaagcc                                              19

<210> SEQ ID NO 117
<211> LENGTH: 16
<212> TYPE: DNA
<213> ORGANISM: Artificial
<220> FEATURE:
<223> OTHER INFORMATION: Primer

<400> SEQUENCE: 117
gaatctgagg tggagg                                                 16

<210> SEQ ID NO 118
<211> LENGTH: 17
<212> TYPE: DNA
<213> ORGANISM: Artificial
<220> FEATURE:
<223> OTHER INFORMATION: Primer

<400> SEQUENCE: 118
ccctttgatt ttcattc                                                17

<210> SEQ ID NO 119
<211> LENGTH: 16
<212> TYPE: DNA
<213> ORGANISM: Artificial
<220> FEATURE:
<223> OTHER INFORMATION: Primer

<400> SEQUENCE: 119
agaactccat tttccc                                                 16

<210> SEQ ID NO 120
<211> LENGTH: 18
<212> TYPE: DNA
<213> ORGANISM: Artificial
<220> FEATURE:
<223> OTHER INFORMATION: Primer

<400> SEQUENCE: 120
cacaaccacc tcagatag                                               18

<210> SEQ ID NO 121
<211> LENGTH: 17
<212> TYPE: DNA
<213> ORGANISM: Artificial
<220> FEATURE:
<223> OTHER INFORMATION: Primer

<400> SEQUENCE: 121
gcctaacctt cacactg                                                17
```

<210> SEQ ID NO 122
<211> LENGTH: 21
<212> TYPE: DNA
<213> ORGANISM: Artificial
<220> FEATURE:
<223> OTHER INFORMATION: Primer

<400> SEQUENCE: 122
gtcatagtag ctcctgtatt g                                             21

<210> SEQ ID NO 123
<211> LENGTH: 20
<212> TYPE: DNA
<213> ORGANISM: Artificial
<220> FEATURE:
<223> OTHER INFORMATION: Primer

<400> SEQUENCE: 123
acgtaacttc ttctccatac                                               20

<210> SEQ ID NO 124
<211> LENGTH: 19
<212> TYPE: DNA
<213> ORGANISM: Artificial
<220> FEATURE:
<223> OTHER INFORMATION: Primer

<400> SEQUENCE: 124
cttccttgta aatctccac                                                19

<210> SEQ ID NO 125
<211> LENGTH: 19
<212> TYPE: DNA
<213> ORGANISM: Artificial
<220> FEATURE:
<223> OTHER INFORMATION: Primer

<400> SEQUENCE: 125
caatgcacca tacttatgc                                                19

<210> SEQ ID NO 126
<211> LENGTH: 16
<212> TYPE: DNA
<213> ORGANISM: Artificial
<220> FEATURE:
<223> OTHER INFORMATION: Primer

<400> SEQUENCE: 126
taaagatttg cggaac                                                   16

<210> SEQ ID NO 127
<211> LENGTH: 16
<212> TYPE: DNA
<213> ORGANISM: Artificial
<220> FEATURE:
<223> OTHER INFORMATION: Primer

<400> SEQUENCE: 127
ggctccatcc attttg                                                   16

<210> SEQ ID NO 128
<211> LENGTH: 17
<212> TYPE: DNA
<213> ORGANISM: Artificial
<220> FEATURE:
<223> OTHER INFORMATION: Primer

```
<400> SEQUENCE: 128
ttacaaaatg gatggag                                                17

<210> SEQ ID NO 129
<211> LENGTH: 20
<212> TYPE: DNA
<213> ORGANISM: Artificial
<220> FEATURE:
<223> OTHER INFORMATION: Primer

<400> SEQUENCE: 129
aagtgctggg attacaggcg                                             20

<210> SEQ ID NO 130
<211> LENGTH: 21
<212> TYPE: DNA
<213> ORGANISM: Artificial
<220> FEATURE:
<223> OTHER INFORMATION: Primer

<400> SEQUENCE: 130
ctactcaaaa tgaacactag g                                           21

<210> SEQ ID NO 131
<211> LENGTH: 19
<212> TYPE: DNA
<213> ORGANISM: Artificial
<220> FEATURE:
<223> OTHER INFORMATION: Primer

<400> SEQUENCE: 131
tttaaccctg ctatactcc                                              19

<210> SEQ ID NO 132
<211> LENGTH: 17
<212> TYPE: DNA
<213> ORGANISM: Artificial
<220> FEATURE:
<223> OTHER INFORMATION: Primer

<400> SEQUENCE: 132
taaatggaaa ctggacg                                                17

<210> SEQ ID NO 133
<211> LENGTH: 20
<212> TYPE: DNA
<213> ORGANISM: Artificial
<220> FEATURE:
<223> OTHER INFORMATION: Primer

<400> SEQUENCE: 133
accctattac ttgtgttctg                                             20

<210> SEQ ID NO 134
<211> LENGTH: 15
<212> TYPE: DNA
<213> ORGANISM: Artificial
<220> FEATURE:
<223> OTHER INFORMATION: Primer

<400> SEQUENCE: 134
gtgtttgcgt ttgcc                                                  15

<210> SEQ ID NO 135
```

```
<211> LENGTH: 17
<212> TYPE: DNA
<213> ORGANISM: Artificial
<220> FEATURE:
<223> OTHER INFORMATION: Primer

<400> SEQUENCE: 135 gagattttc cagccac                                                     17

<210> SEQ ID NO 136
<211> LENGTH: 17
<212> TYPE: DNA
<213> ORGANISM: Artificial
<220> FEATURE:
<223> OTHER INFORMATION: Primer

<400> SEQUENCE: 136
tctcacacat tgcgaac                                                    17

<210> SEQ ID NO 137
<211> LENGTH: 17
<212> TYPE: DNA
<213> ORGANISM: Artificial
<220> FEATURE:
<223> OTHER INFORMATION: Primer

<400> SEQUENCE: 137
accgttagtt ttccagg                                                    17

<210> SEQ ID NO 138
<211> LENGTH: 20
<212> TYPE: DNA
<213> ORGANISM: Artificial
<220> FEATURE:
<223> OTHER INFORMATION: Primer

<400> SEQUENCE: 138
ggtttggata gtgttttgag                                                 20

<210> SEQ ID NO 139
<211> LENGTH: 17
<212> TYPE: DNA
<213> ORGANISM: Artificial
<220> FEATURE:
<223> OTHER INFORMATION: Primer

<400> SEQUENCE: 139
atgttgttcg caatgtg                                                    17

<210> SEQ ID NO 140
<211> LENGTH: 20
<212> TYPE: DNA
<213> ORGANISM: Artificial
<220> FEATURE:
<223> OTHER INFORMATION: Primer

<400> SEQUENCE: 140
tgggagtgca gtgagaattg                                                 20

<210> SEQ ID NO 141
<211> LENGTH: 22
<212> TYPE: DNA
<213> ORGANISM: Artificial
<220> FEATURE:
<223> OTHER INFORMATION: Primer

<400> SEQUENCE: 141
```

```
gctaatgatg cttttcacag ga                                             22

<210> SEQ ID NO 142
<211> LENGTH: 22
<212> TYPE: DNA
<213> ORGANISM: Artificial
<220> FEATURE:
<223> OTHER INFORMATION: Primer

<400> SEQUENCE: 142
cctgtgactg tctaggcatt tt                                             22

<210> SEQ ID NO 143
<211> LENGTH: 26
<212> TYPE: DNA
<213> ORGANISM: Artificial
<220> FEATURE:
<223> OTHER INFORMATION: Primer

<400> SEQUENCE: 143
tatgcctgaa ttatatcact attgcc                                         26

<210> SEQ ID NO 144
<211> LENGTH: 24
<212> TYPE: DNA
<213> ORGANISM: Artificial
<220> FEATURE:
<223> OTHER INFORMATION: Primer

<400> SEQUENCE: 144
gctttgctat gtttaatttt cctt                                           24

<210> SEQ ID NO 145
<211> LENGTH: 27
<212> TYPE: DNA
<213> ORGANISM: Artificial
<220> FEATURE:
<223> OTHER INFORMATION: Primer

<400> SEQUENCE: 145
aactatgatg gaaataatta aatctgg                                        27

<210> SEQ ID NO 146
<211> LENGTH: 20
<212> TYPE: DNA
<213> ORGANISM: Artificial
<220> FEATURE:
<223> OTHER INFORMATION: Primer

<400> SEQUENCE: 146
tgcatatgct gttcattttc                                                20

<210> SEQ ID NO 147
<211> LENGTH: 28
<212> TYPE: DNA
<213> ORGANISM: Artificial
<220> FEATURE:
<223> OTHER INFORMATION: Primer

<400> SEQUENCE: 147
gtcttacatt aaaatatctt aaagtctc                                       28

<210> SEQ ID NO 148
<211> LENGTH: 22
<212> TYPE: DNA
```

```
<213> ORGANISM: Artificial
<220> FEATURE:
<223> OTHER INFORMATION: Primer

<400> SEQUENCE: 148
tttcctccaa tcttatcctg ag                                              22

<210> SEQ ID NO 149
<211> LENGTH: 24
<212> TYPE: DNA
<213> ORGANISM: Artificial
<220> FEATURE:
<223> OTHER INFORMATION: Primer

<400> SEQUENCE: 149
cgttcattct aaggaatatc agca                                            24

<210> SEQ ID NO 150
<211> LENGTH: 22
<212> TYPE: DNA
<213> ORGANISM: Artificial
<220> FEATURE:
<223> OTHER INFORMATION: Primer

<400> SEQUENCE: 150
cctgatggaa acaacatttc tg                                              22

<210> SEQ ID NO 151
<211> LENGTH: 20
<212> TYPE: DNA
<213> ORGANISM: Artificial
<220> FEATURE:
<223> OTHER INFORMATION: Primer

<400> SEQUENCE: 151
aacagggcca gaaaagttca                                                 20

<210> SEQ ID NO 152
<211> LENGTH: 22
<212> TYPE: DNA
<213> ORGANISM: Artificial
<220> FEATURE:
<223> OTHER INFORMATION: Primer

<400> SEQUENCE: 152
tgttcatttt aatgccattt tg                                              22

<210> SEQ ID NO 153
<211> LENGTH: 20
<212> TYPE: DNA
<213> ORGANISM: Artificial
<220> FEATURE:
<223> OTHER INFORMATION: Primer

<400> SEQUENCE: 153
agttttcgaa gttgccgaaa                                                 20

<210> SEQ ID NO 154
<211> LENGTH: 23
<212> TYPE: DNA
<213> ORGANISM: Artificial
<220> FEATURE:
<223> OTHER INFORMATION: Primer

<400> SEQUENCE: 154
cctagaaacc ctaatggaat gtg                                             23
```

<210> SEQ ID NO 155
<211> LENGTH: 21
<212> TYPE: DNA
<213> ORGANISM: Artificial
<220> FEATURE:
<223> OTHER INFORMATION: Primer

<400> SEQUENCE: 155
tgttcaagca aagtgaccaa a                                              21

<210> SEQ ID NO 156
<211> LENGTH: 24
<212> TYPE: DNA
<213> ORGANISM: Artificial
<220> FEATURE:
<223> OTHER INFORMATION: Primer

<400> SEQUENCE: 156
tgagcaaatt tatgtttctc attt                                           24

<210> SEQ ID NO 157
<211> LENGTH: 23
<212> TYPE: DNA
<213> ORGANISM: Artificial
<220> FEATURE:
<223> OTHER INFORMATION: Primer

<400> SEQUENCE: 157
atgtcacctt gttttaccaa tgg                                            23

<210> SEQ ID NO 158
<211> LENGTH: 23
<212> TYPE: DNA
<213> ORGANISM: Artificial
<220> FEATURE:
<223> OTHER INFORMATION: Primer

<400> SEQUENCE: 158
tgaatgctta tggttatcca ggt                                            23

<210> SEQ ID NO 159
<211> LENGTH: 20
<212> TYPE: DNA
<213> ORGANISM: Artificial
<220> FEATURE:
<223> OTHER INFORMATION: Primer

<400> SEQUENCE: 159
aaaacctgca ggaacaaagc                                                20

<210> SEQ ID NO 160
<211> LENGTH: 26
<212> TYPE: DNA
<213> ORGANISM: Artificial
<220> FEATURE:
<223> OTHER INFORMATION: Primer

<400> SEQUENCE: 160
tcttagaatg ggaaatactc agattg                                         26

<210> SEQ ID NO 161
<211> LENGTH: 24
<212> TYPE: DNA
<213> ORGANISM: Artificial
<220> FEATURE:

<223> OTHER INFORMATION: Primer

<400> SEQUENCE: 161
tggtttttca gaaattcatt ttca                                              24

<210> SEQ ID NO 162
<211> LENGTH: 24
<212> TYPE: DNA
<213> ORGANISM: Artificial
<220> FEATURE:
<223> OTHER INFORMATION: Primer

<400> SEQUENCE: 162
atgtaaaatt aactttggca atga                                              24

<210> SEQ ID NO 163
<211> LENGTH: 26
<212> TYPE: DNA
<213> ORGANISM: Artificial
<220> FEATURE:
<223> OTHER INFORMATION: Primer

<400> SEQUENCE: 163
ttgctgaaat aagaattaga actttg                                            26

<210> SEQ ID NO 164
<211> LENGTH: 25
<212> TYPE: DNA
<213> ORGANISM: Artificial
<220> FEATURE:
<223> OTHER INFORMATION: Primer

<400> SEQUENCE: 164
tgaataaaag aagaaaatct ttcca                                             25

<210> SEQ ID NO 165
<211> LENGTH: 27
<212> TYPE: DNA
<213> ORGANISM: Artificial
<220> FEATURE:
<223> OTHER INFORMATION: Primer

<400> SEQUENCE: 165
atctaaaaca catacatcat gttttca                                           27

<210> SEQ ID NO 166
<211> LENGTH: 26
<212> TYPE: DNA
<213> ORGANISM: Artificial
<220> FEATURE:
<223> OTHER INFORMATION: Primer

<400> SEQUENCE: 166
aaaacacata catcatgttt tcacaa                                            26

<210> SEQ ID NO 167
<211> LENGTH: 23
<212> TYPE: DNA
<213> ORGANISM: Artificial
<220> FEATURE:
<223> OTHER INFORMATION: Primer

<400> SEQUENCE: 167
gatatgcctc aacatttcca gtc                                               23

```
<210> SEQ ID NO 168
<211> LENGTH: 23
<212> TYPE: DNA
<213> ORGANISM: Artificial
<220> FEATURE:
<223> OTHER INFORMATION: Primer

<400> SEQUENCE: 168
gttggtttga ttcctatcat ttg                                          23

<210> SEQ ID NO 169
<211> LENGTH: 26
<212> TYPE: DNA
<213> ORGANISM: Artificial
<220> FEATURE:
<223> OTHER INFORMATION: Primer

<400> SEQUENCE: 169
ttggaaaagt aataggtatg tgtgtc                                       26

<210> SEQ ID NO 170
<211> LENGTH: 25
<212> TYPE: DNA
<213> ORGANISM: Artificial
<220> FEATURE:
<223> OTHER INFORMATION: Primer

<400> SEQUENCE: 170
ctatgagaat acaagccaaa agttc                                        25

<210> SEQ ID NO 171
<211> LENGTH: 23
<212> TYPE: DNA
<213> ORGANISM: Artificial
<220> FEATURE:
<223> OTHER INFORMATION: Primer

<400> SEQUENCE: 171
tctcttgtgc ttcgtgtaaa caa                                          23

<210> SEQ ID NO 172
<211> LENGTH: 23
<212> TYPE: DNA
<213> ORGANISM: Artificial
<220> FEATURE:
<223> OTHER INFORMATION: Primer

<400> SEQUENCE: 172
aaccctttga ttttcattct tca                                          23

<210> SEQ ID NO 173
<211> LENGTH: 22
<212> TYPE: DNA
<213> ORGANISM: Artificial
<220> FEATURE:
<223> OTHER INFORMATION: Primer

<400> SEQUENCE: 173
tcaaagtgag gggaataatt ga                                           22

<210> SEQ ID NO 174
<211> LENGTH: 26
<212> TYPE: DNA
<213> ORGANISM: Artificial
<220> FEATURE:
<223> OTHER INFORMATION: Primer
```

```
<400> SEQUENCE: 174
aatttatgag ttagtgaaac ctgaat                                    26

<210> SEQ ID NO 175
<211> LENGTH: 26
<212> TYPE: DNA
<213> ORGANISM: Artificial
<220> FEATURE:
<223> OTHER INFORMATION: Primer

<400> SEQUENCE: 175
tcttcattca aagtgtaagt ggtacc                                    26

<210> SEQ ID NO 176
<211> LENGTH: 27
<212> TYPE: DNA
<213> ORGANISM: Artificial
<220> FEATURE:
<223> OTHER INFORMATION: Primer

<400> SEQUENCE: 176
acaaaatggc taatatattt tctcaag                                   27

<210> SEQ ID NO 177
<211> LENGTH: 18
<212> TYPE: DNA
<213> ORGANISM: Artificial
<220> FEATURE:
<223> OTHER INFORMATION: Primer

<400> SEQUENCE: 177
taatgtgtgg gcccagcc                                             18

<210> SEQ ID NO 178
<211> LENGTH: 23
<212> TYPE: DNA
<213> ORGANISM: Artificial
<220> FEATURE:
<223> OTHER INFORMATION: Primer

<400> SEQUENCE: 178
caaaatgaac actaggtgga acc                                       23

<210> SEQ ID NO 179
<211> LENGTH: 21
<212> TYPE: DNA
<213> ORGANISM: Artificial
<220> FEATURE:
<223> OTHER INFORMATION: Primer

<400> SEQUENCE: 179
attttggggg agtatagcag g                                         21

<210> SEQ ID NO 180
<211> LENGTH: 20
<212> TYPE: DNA
<213> ORGANISM: Artificial
<220> FEATURE:
<223> OTHER INFORMATION: Primer

<400> SEQUENCE: 180
ctgtgtttgc gtttgcctta                                           20

<210> SEQ ID NO 181
<211> LENGTH: 20
```

```
<212> TYPE: DNA
<213> ORGANISM: Artificial
<220> FEATURE:
<223> OTHER INFORMATION: Primer

<400> SEQUENCE: 181
ttcacgtggc tggaaaaatc                                              20

<210> SEQ ID NO 182
<211> LENGTH: 25
<212> TYPE: DNA
<213> ORGANISM: Artificial
<220> FEATURE:
<223> OTHER INFORMATION: Primer

<400> SEQUENCE: 182
ttgaaaacct gaaagtctat gaaga                                        25

<210> SEQ ID NO 183
<211> LENGTH: 23
<212> TYPE: DNA
<213> ORGANISM: Artificial
<220> FEATURE:
<223> OTHER INFORMATION: Primer

<400> SEQUENCE: 183
tcaatcataa agtgcacacc ttt                                          23

<210> SEQ ID NO 184
<211> LENGTH: 23
<212> TYPE: DNA
<213> ORGANISM: Artificial
<220> FEATURE:
<223> OTHER INFORMATION: Primer

<400> SEQUENCE: 184
cagtcccatt tctgattgtt cca                                          23

<210> SEQ ID NO 185
<211> LENGTH: 21
<212> TYPE: DNA
<213> ORGANISM: Artificial
<220> FEATURE:
<223> OTHER INFORMATION: Primer

<400> SEQUENCE: 185
gctgaggata atttgaaggg g                                            21

<210> SEQ ID NO 186
<211> LENGTH: 23
<212> TYPE: DNA
<213> ORGANISM: Artificial
<220> FEATURE:
<223> OTHER INFORMATION: Primer

<400> SEQUENCE: 186
gtgattcatc gatgtagctc ttt                                          23

<210> SEQ ID NO 187
<211> LENGTH: 21
<212> TYPE: DNA
<213> ORGANISM: Artificial
<220> FEATURE:
<223> OTHER INFORMATION: Primer

<400> SEQUENCE: 187
```

-continued

```
aatgaccaga ggagcctgga a                                         21
```

<210> SEQ ID NO 188
<211> LENGTH: 24
<212> TYPE: DNA
<213> ORGANISM: Artificial
<220> FEATURE:
<223> OTHER INFORMATION: Primer

<400> SEQUENCE: 188

```
tgatgtcagt tttcaaagtt ttcc                                      24
```

<210> SEQ ID NO 189
<211> LENGTH: 26
<212> TYPE: DNA
<213> ORGANISM: Artificial
<220> FEATURE:
<223> OTHER INFORMATION: Primer

<400> SEQUENCE: 189

```
accactctct cagttttgct aattat                                    26
```

<210> SEQ ID NO 190
<211> LENGTH: 25
<212> TYPE: DNA
<213> ORGANISM: Artificial
<220> FEATURE:
<223> OTHER INFORMATION: Primer

<400> SEQUENCE: 190

```
cacattaaat ttgtttctgc aatga                                     25
```

<210> SEQ ID NO 191
<211> LENGTH: 24
<212> TYPE: DNA
<213> ORGANISM: Artificial
<220> FEATURE:
<223> OTHER INFORMATION: Primer

<400> SEQUENCE: 191

```
agaagtgatg aaacaagaat ttga                                      24
```

<210> SEQ ID NO 192
<211> LENGTH: 25
<212> TYPE: DNA
<213> ORGANISM: Artificial
<220> FEATURE:
<223> OTHER INFORMATION: Primer

<400> SEQUENCE: 192

```
ccatttaagc attatttatg gtttc                                     25
```

<210> SEQ ID NO 193
<211> LENGTH: 27
<212> TYPE: DNA
<213> ORGANISM: Artificial
<220> FEATURE:
<223> OTHER INFORMATION: Primer

<400> SEQUENCE: 193

```
aaacaggaca gttactatta ctttgca                                   27
```

<210> SEQ ID NO 194
<211> LENGTH: 27
<212> TYPE: DNA
<213> ORGANISM: Artificial

```
<220> FEATURE:
<223> OTHER INFORMATION: Primer

<400> SEQUENCE: 194
aaatattttc agagtaagca ctcattt                                27

<210> SEQ ID NO 195
<211> LENGTH: 23
<212> TYPE: DNA
<213> ORGANISM: Artificial
<220> FEATURE:
<223> OTHER INFORMATION: Primer

<400> SEQUENCE: 195
tttatcattt tgattgggat tgt                                   23

<210> SEQ ID NO 196
<211> LENGTH: 27
<212> TYPE: DNA
<213> ORGANISM: Artificial
<220> FEATURE:
<223> OTHER INFORMATION: Primer

<400> SEQUENCE: 196
tgcagatatt ttattgacat aattgtt                               27

<210> SEQ ID NO 197
<211> LENGTH: 26
<212> TYPE: DNA
<213> ORGANISM: Artificial
<220> FEATURE:
<223> OTHER INFORMATION: Primer

<400> SEQUENCE: 197
gttgatcttg ttgcttcttt acaaga                                26

<210> SEQ ID NO 198
<211> LENGTH: 22
<212> TYPE: DNA
<213> ORGANISM: Artificial
<220> FEATURE:
<223> OTHER INFORMATION: Primer

<400> SEQUENCE: 198
ccattttcct gaaacactac cc                                    22

<210> SEQ ID NO 199
<211> LENGTH: 25
<212> TYPE: DNA
<213> ORGANISM: Artificial
<220> FEATURE:
<223> OTHER INFORMATION: Primer

<400> SEQUENCE: 199
aattatttga atttccagac acctt                                 25

<210> SEQ ID NO 200
<211> LENGTH: 25
<212> TYPE: DNA
<213> ORGANISM: Artificial
<220> FEATURE:
<223> OTHER INFORMATION: Primer

<400> SEQUENCE: 200
aattatttga atttccagac acctt                                 25
```

```
<210> SEQ ID NO 201
<211> LENGTH: 27
<212> TYPE: DNA
<213> ORGANISM: Artificial
<220> FEATURE:
<223> OTHER INFORMATION: Primer

<400> SEQUENCE: 201
ttttggacta atttcataga ataaccc                                              27

<210> SEQ ID NO 202
<211> LENGTH: 27
<212> TYPE: DNA
<213> ORGANISM: Artificial
<220> FEATURE:
<223> OTHER INFORMATION: Primer

<400> SEQUENCE: 202
cttaaatgca atttcactat tctatga                                              27

<210> SEQ ID NO 203
<211> LENGTH: 16
<212> TYPE: DNA
<213> ORGANISM: Artificial
<220> FEATURE:
<223> OTHER INFORMATION: Primer

<400> SEQUENCE: 203
tagccattat gtagcc                                                          16

<210> SEQ ID NO 204
<211> LENGTH: 17
<212> TYPE: DNA
<213> ORGANISM: Artificial
<220> FEATURE:
<223> OTHER INFORMATION: Probe

<400> SEQUENCE: 204
tctgggatgt aataatg                                                         17

<210> SEQ ID NO 205
<211> LENGTH: 17
<212> TYPE: DNA
<213> ORGANISM: Artificial
<220> FEATURE:
<223> OTHER INFORMATION: Probe

<400> SEQUENCE: 205
tctgggatgt aatgatg                                                         17

<210> SEQ ID NO 206
<211> LENGTH: 17
<212> TYPE: DNA
<213> ORGANISM: Artificial
<220> FEATURE:
<223> OTHER INFORMATION: Probe

<400> SEQUENCE: 206
gaacattatt acatccc                                                         17

<210> SEQ ID NO 207
<211> LENGTH: 17
<212> TYPE: DNA
<213> ORGANISM: Artificial
<220> FEATURE:
<223> OTHER INFORMATION: Probe
```

```
<400> SEQUENCE: 207
gaacatcatt acatccc                                                17

<210> SEQ ID NO 208
<211> LENGTH: 17
<212> TYPE: DNA
<213> ORGANISM: Artificial
<220> FEATURE:
<223> OTHER INFORMATION: Probe

<400> SEQUENCE: 208
cagaggatat caccagc                                                17

<210> SEQ ID NO 209
<211> LENGTH: 17
<212> TYPE: DNA
<213> ORGANISM: Artificial
<220> FEATURE:
<223> OTHER INFORMATION: Probe

<400> SEQUENCE: 209
cagaggatat taccagc                                                17

<210> SEQ ID NO 210
<211> LENGTH: 17
<212> TYPE: DNA
<213> ORGANISM: Artificial
<220> FEATURE:
<223> OTHER INFORMATION: Probe

<400> SEQUENCE: 210
agcagctggt gatatcc                                                17

<210> SEQ ID NO 211
<211> LENGTH: 17
<212> TYPE: DNA
<213> ORGANISM: Artificial
<220> FEATURE:
<223> OTHER INFORMATION: Probe

<400> SEQUENCE: 211
agcagctggt aatatcc                                                17

<210> SEQ ID NO 212
<211> LENGTH: 17
<212> TYPE: DNA
<213> ORGANISM: Artificial
<220> FEATURE:
<223> OTHER INFORMATION: Probe

<400> SEQUENCE: 212
tacacagtac gatagac                                                17

<210> SEQ ID NO 213
<211> LENGTH: 17
<212> TYPE: DNA
<213> ORGANISM: Artificial
<220> FEATURE:
<223> OTHER INFORMATION: Probe

<400> SEQUENCE: 213
tacacagtac aatagac                                                17

<210> SEQ ID NO 214
```

```
<211> LENGTH: 17
<212> TYPE: DNA
<213> ORGANISM: Artificial
<220> FEATURE:
<223> OTHER INFORMATION: Probe

<400> SEQUENCE: 214
taagtctatc gtactgt                                                  17

<210> SEQ ID NO 215
<211> LENGTH: 17
<212> TYPE: DNA
<213> ORGANISM: Artificial
<220> FEATURE:
<223> OTHER INFORMATION: Probe

<400> SEQUENCE: 215
taagtctatt gtactgt                                                  17

<210> SEQ ID NO 216
<211> LENGTH: 17
<212> TYPE: DNA
<213> ORGANISM: Artificial
<220> FEATURE:
<223> OTHER INFORMATION: Probe

<400> SEQUENCE: 216
tcttggaaat gtaataa                                                  17

<210> SEQ ID NO 217
<211> LENGTH: 17
<212> TYPE: DNA
<213> ORGANISM: Artificial
<220> FEATURE:
<223> OTHER INFORMATION: Probe

<400> SEQUENCE: 217
tcttggaaat ataataa                                                  17

<210> SEQ ID NO 218
<211> LENGTH: 17
<212> TYPE: DNA
<213> ORGANISM: Artificial
<220> FEATURE:
<223> OTHER INFORMATION: Probe

<400> SEQUENCE: 218
accattatta catttcc                                                  17

<210> SEQ ID NO 219
<211> LENGTH: 17
<212> TYPE: DNA
<213> ORGANISM: Artificial
<220> FEATURE:
<223> OTHER INFORMATION: Probe

<400> SEQUENCE: 219
accattatta tatttcc                                                  17

<210> SEQ ID NO 220
<211> LENGTH: 17
<212> TYPE: DNA
<213> ORGANISM: Artificial
<220> FEATURE:
<223> OTHER INFORMATION: Probe

<400> SEQUENCE: 220
```
tttttttttc gttttag 17

<210> SEQ ID NO 221
<211> LENGTH: 17
<212> TYPE: DNA
<213> ORGANISM: Artificial
<220> FEATURE:
<223> OTHER INFORMATION: Probe

<400> SEQUENCE: 221
tttttttttt tcgtttt 17

<210> SEQ ID NO 222
<211> LENGTH: 17
<212> TYPE: DNA
<213> ORGANISM: Artificial
<220> FEATURE:
<223> OTHER INFORMATION: Probe

<400> SEQUENCE: 222
ctttctaaaa cgaaaaa 17

<210> SEQ ID NO 223
<211> LENGTH: 17
<212> TYPE: DNA
<213> ORGANISM: Artificial
<220> FEATURE:
<223> OTHER INFORMATION: Probe

<400> SEQUENCE: 223
ttctaaaacg aaaaaaa 17

<210> SEQ ID NO 224
<211> LENGTH: 17
<212> TYPE: DNA
<213> ORGANISM: Artificial
<220> FEATURE:
<223> OTHER INFORMATION: Probe

<400> SEQUENCE: 224
tttaggactc atttgaa 17

<210> SEQ ID NO 225
<211> LENGTH: 17
<212> TYPE: DNA
<213> ORGANISM: Artificial
<220> FEATURE:
<223> OTHER INFORMATION: Probe

<400> SEQUENCE: 225
tttaggactt atttgaa 17

<210> SEQ ID NO 226
<211> LENGTH: 17
<212> TYPE: DNA
<213> ORGANISM: Artificial
<220> FEATURE:
<223> OTHER INFORMATION: Probe

<400> SEQUENCE: 226
taacttcaaa tgagtcc 17

<210> SEQ ID NO 227
<211> LENGTH: 17
<212> TYPE: DNA

```
<213> ORGANISM: Artificial
<220> FEATURE:
<223> OTHER INFORMATION: Probe

<400> SEQUENCE: 227
taacttcaaa taagtcc                                                   17

<210> SEQ ID NO 228
<211> LENGTH: 17
<212> TYPE: DNA
<213> ORGANISM: Artificial
<220> FEATURE:
<223> OTHER INFORMATION: Probe

<400> SEQUENCE: 228
gaaatacagc aaaatgc                                                   17

<210> SEQ ID NO 229
<211> LENGTH: 17
<212> TYPE: DNA
<213> ORGANISM: Artificial
<220> FEATURE:
<223> OTHER INFORMATION: Probe

<400> SEQUENCE: 229
gaaatacagc caaatgc                                                   17

<210> SEQ ID NO 230
<211> LENGTH: 17
<212> TYPE: DNA
<213> ORGANISM: Artificial
<220> FEATURE:
<223> OTHER INFORMATION: Probe

<400> SEQUENCE: 230
acttgtgcat tttgctg                                                   17

<210> SEQ ID NO 231
<211> LENGTH: 17
<212> TYPE: DNA
<213> ORGANISM: Artificial
<220> FEATURE:
<223> OTHER INFORMATION: Probe

<400> SEQUENCE: 231
acttgtgcat ttggctg                                                   17

<210> SEQ ID NO 232
<211> LENGTH: 17
<212> TYPE: DNA
<213> ORGANISM: Artificial
<220> FEATURE:
<223> OTHER INFORMATION: Probe

<400> SEQUENCE: 232
taatcaaaat tatggaa                                                   17

<210> SEQ ID NO 233
<211> LENGTH: 17
<212> TYPE: DNA
<213> ORGANISM: Artificial
<220> FEATURE:
<223> OTHER INFORMATION: Probe

<400> SEQUENCE: 233
taatcaaaat catggaa                                                   17
```

```
<210> SEQ ID NO 234
<211> LENGTH: 17
<212> TYPE: DNA
<213> ORGANISM: Artificial
<220> FEATURE:
<223> OTHER INFORMATION: Probe

<400> SEQUENCE: 234
tttcttccat aattttg                                                    17

<210> SEQ ID NO 235
<211> LENGTH: 17
<212> TYPE: DNA
<213> ORGANISM: Artificial
<220> FEATURE:
<223> OTHER INFORMATION: Probe

<400> SEQUENCE: 235
tttcttccat gattttg                                                    17

<210> SEQ ID NO 236
<211> LENGTH: 17
<212> TYPE: DNA
<213> ORGANISM: Artificial
<220> FEATURE:
<223> OTHER INFORMATION: Probe

<400> SEQUENCE: 236
aagaaaaagc gaaatat                                                    17

<210> SEQ ID NO 237
<211> LENGTH: 17
<212> TYPE: DNA
<213> ORGANISM: Artificial
<220> FEATURE:
<223> OTHER INFORMATION: Probe

<400> SEQUENCE: 237
aagaaaaagc aaaatat                                                    17

<210> SEQ ID NO 238
<211> LENGTH: 17
<212> TYPE: DNA
<213> ORGANISM: Artificial
<220> FEATURE:
<223> OTHER INFORMATION: Probe

<400> SEQUENCE: 238
ttgatatttc gcttttt                                                    17

<210> SEQ ID NO 239
<211> LENGTH: 17
<212> TYPE: DNA
<213> ORGANISM: Artificial
<220> FEATURE:
<223> OTHER INFORMATION: Probe

<400> SEQUENCE: 239
ttgatatttt gcttttt                                                    17

<210> SEQ ID NO 240
<211> LENGTH: 16
<212> TYPE: DNA
<213> ORGANISM: Artificial
<220> FEATURE:
```

<223> OTHER INFORMATION: Probe

<400> SEQUENCE: 240
ggatcaaaga tgacaa                                                  16

<210> SEQ ID NO 241
<211> LENGTH: 17
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (11)..(11)
<223> OTHER INFORMATION: n is a, c, g, or t

<400> SEQUENCE: 241
ggatcaaaga ntgacaa                                                 17

<210> SEQ ID NO 242
<211> LENGTH: 16
<212> TYPE: DNA
<213> ORGANISM: Artificial
<220> FEATURE:
<223> OTHER INFORMATION: Probe

<400> SEQUENCE: 242
gcccttgtca tctttg                                                  16

<210> SEQ ID NO 243
<211> LENGTH: 17
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (11)..(11)
<223> OTHER INFORMATION: n is a, c, g, or t

<400> SEQUENCE: 243
gcccttgtca ntctttg                                                 17

<210> SEQ ID NO 244
<211> LENGTH: 17
<212> TYPE: DNA
<213> ORGANISM: Artificial
<220> FEATURE:
<223> OTHER INFORMATION: Probe

<400> SEQUENCE: 244
tttattagta gatctaa                                                 17

<210> SEQ ID NO 245
<211> LENGTH: 17
<212> TYPE: DNA
<213> ORGANISM: Artificial
<220> FEATURE:
<223> OTHER INFORMATION: Probe

<400> SEQUENCE: 245
tttattagta tatctaa                                                 17

<210> SEQ ID NO 246
<211> LENGTH: 17
<212> TYPE: DNA
<213> ORGANISM: Artificial

```
<220> FEATURE:
<223> OTHER INFORMATION: Probe

<400> SEQUENCE: 246
ttgattagat ctactaa                                                17

<210> SEQ ID NO 247
<211> LENGTH: 17
<212> TYPE: DNA
<213> ORGANISM: Artificial
<220> FEATURE:
<223> OTHER INFORMATION: Probe

<400> SEQUENCE: 247
ttgattagat atactaa                                                17

<210> SEQ ID NO 248
<211> LENGTH: 17
<212> TYPE: DNA
<213> ORGANISM: Artificial
<220> FEATURE:
<223> OTHER INFORMATION: Probe

<400> SEQUENCE: 248
ataaaattca atgtgtt                                                17

<210> SEQ ID NO 249
<211> LENGTH: 17
<212> TYPE: DNA
<213> ORGANISM: Artificial
<220> FEATURE:
<223> OTHER INFORMATION: Probe

<400> SEQUENCE: 249
ataaaattca gtgtgtt                                                17

<210> SEQ ID NO 250
<211> LENGTH: 17
<212> TYPE: DNA
<213> ORGANISM: Artificial
<220> FEATURE:
<223> OTHER INFORMATION: Probe

<400> SEQUENCE: 250
ccatcaacac attgaat                                                17

<210> SEQ ID NO 251
<211> LENGTH: 17
<212> TYPE: DNA
<213> ORGANISM: Artificial
<220> FEATURE:
<223> OTHER INFORMATION: Probe

<400> SEQUENCE: 251
ccatcaacac actgaat                                                17

<210> SEQ ID NO 252
<211> LENGTH: 17
<212> TYPE: DNA
<213> ORGANISM: Artificial
<220> FEATURE:
<223> OTHER INFORMATION: Probe

<400> SEQUENCE: 252
tttattataa cattaat                                                17
```

```
<210> SEQ ID NO 253
<211> LENGTH: 17
<212> TYPE: DNA
<213> ORGANISM: Artificial
<220> FEATURE:
<223> OTHER INFORMATION: Probe

<400> SEQUENCE: 253
tttattataa aattaat                                                    17

<210> SEQ ID NO 254
<211> LENGTH: 17
<212> TYPE: DNA
<213> ORGANISM: Artificial
<220> FEATURE:
<223> OTHER INFORMATION: Probe

<400> SEQUENCE: 254
tataattaat gttataa                                                    17

<210> SEQ ID NO 255
<211> LENGTH: 17
<212> TYPE: DNA
<213> ORGANISM: Artificial
<220> FEATURE:
<223> OTHER INFORMATION: Probe

<400> SEQUENCE: 255
tataattaat tttataa                                                    17

<210> SEQ ID NO 256
<211> LENGTH: 17
<212> TYPE: DNA
<213> ORGANISM: Artificial
<220> FEATURE:
<223> OTHER INFORMATION: Probe

<400> SEQUENCE: 256
ctccacctga gatttct                                                    17

<210> SEQ ID NO 257
<211> LENGTH: 17
<212> TYPE: DNA
<213> ORGANISM: Artificial
<220> FEATURE:
<223> OTHER INFORMATION: Probe

<400> SEQUENCE: 257
ctccacctga tatttct                                                    17

<210> SEQ ID NO 258
<211> LENGTH: 17
<212> TYPE: DNA
<213> ORGANISM: Artificial
<220> FEATURE:
<223> OTHER INFORMATION: Probe

<400> SEQUENCE: 258
catgagaaat ctcaggt                                                    17

<210> SEQ ID NO 259
<211> LENGTH: 17
<212> TYPE: DNA
<213> ORGANISM: Artificial
<220> FEATURE:
<223> OTHER INFORMATION: Probe
```

```
<400> SEQUENCE: 259
catgagaaat atcaggt                                                    17

<210> SEQ ID NO 260
<211> LENGTH: 17
<212> TYPE: DNA
<213> ORGANISM: Artificial
<220> FEATURE:
<223> OTHER INFORMATION: Probe

<400> SEQUENCE: 260
tctttcatca cgttctc                                                    17

<210> SEQ ID NO 261
<211> LENGTH: 17
<212> TYPE: DNA
<213> ORGANISM: Artificial
<220> FEATURE:
<223> OTHER INFORMATION: Probe

<400> SEQUENCE: 261
tctttcatca tgttctc                                                    17

<210> SEQ ID NO 262
<211> LENGTH: 17
<212> TYPE: DNA
<213> ORGANISM: Artificial
<220> FEATURE:
<223> OTHER INFORMATION: Probe

<400> SEQUENCE: 262
gtgtgagaac gtgatga                                                    17

<210> SEQ ID NO 263
<211> LENGTH: 17
<212> TYPE: DNA
<213> ORGANISM: Artificial
<220> FEATURE:
<223> OTHER INFORMATION: Probe

<400> SEQUENCE: 263
gtgtgagaac atgatga                                                    17

<210> SEQ ID NO 264
<211> LENGTH: 16
<212> TYPE: DNA
<213> ORGANISM: Artificial
<220> FEATURE:
<223> OTHER INFORMATION: Primer

<400> SEQUENCE: 264
tttctgggat gtaata                                                     16

<210> SEQ ID NO 265
<211> LENGTH: 16
<212> TYPE: DNA
<213> ORGANISM: Artificial
<220> FEATURE:
<223> OTHER INFORMATION: Primer

<400> SEQUENCE: 265
tttctgggat gtaatg                                                     16

<210> SEQ ID NO 266
```

```
<211> LENGTH: 16
<212> TYPE: DNA
<213> ORGANISM: Artificial
<220> FEATURE:
<223> OTHER INFORMATION: Primer

<400> SEQUENCE: 266
caaaacactg aacatt                                                         16

<210> SEQ ID NO 267
<211> LENGTH: 16
<212> TYPE: DNA
<213> ORGANISM: Artificial
<220> FEATURE:
<223> OTHER INFORMATION: Primer

<400> SEQUENCE: 267
caaaacactg aacatc                                                         16

<210> SEQ ID NO 268
<211> LENGTH: 16
<212> TYPE: DNA
<213> ORGANISM: Artificial
<220> FEATURE:
<223> OTHER INFORMATION: Primer

<400> SEQUENCE: 268
aaatccagag gatatc                                                         16

<210> SEQ ID NO 269
<211> LENGTH: 16
<212> TYPE: DNA
<213> ORGANISM: Artificial
<220> FEATURE:
<223> OTHER INFORMATION: Primer

<400> SEQUENCE: 269
aaatccagag gatatt                                                         16

<210> SEQ ID NO 270
<211> LENGTH: 16
<212> TYPE: DNA
<213> ORGANISM: Artificial
<220> FEATURE:
<223> OTHER INFORMATION: Primer

<400> SEQUENCE: 270
aaatcagcag ctggtg                                                         16

<210> SEQ ID NO 271
<211> LENGTH: 16
<212> TYPE: DNA
<213> ORGANISM: Artificial
<220> FEATURE:
<223> OTHER INFORMATION: Primer

<400> SEQUENCE: 271
aaatcagcag ctggta                                                         16

<210> SEQ ID NO 272
<211> LENGTH: 16
<212> TYPE: DNA
<213> ORGANISM: Artificial
<220> FEATURE:
<223> OTHER INFORMATION: Primer

<400> SEQUENCE: 272
```
aagtttacac agtacg                                                  16

<210> SEQ ID NO 273
<211> LENGTH: 16
<212> TYPE: DNA
<213> ORGANISM: Artificial
<220> FEATURE:
<223> OTHER INFORMATION: Primer

<400> SEQUENCE: 273
aagtttacac agtaca                                                  16

<210> SEQ ID NO 274
<211> LENGTH: 16
<212> TYPE: DNA
<213> ORGANISM: Artificial
<220> FEATURE:
<223> OTHER INFORMATION: Primer

<400> SEQUENCE: 274
aatgggtaag tctatc                                                  16

<210> SEQ ID NO 275
<211> LENGTH: 16
<212> TYPE: DNA
<213> ORGANISM: Artificial
<220> FEATURE:
<223> OTHER INFORMATION: Primer

<400> SEQUENCE: 275
aatgggtaag tctatt                                                  16

<210> SEQ ID NO 276
<211> LENGTH: 16
<212> TYPE: DNA
<213> ORGANISM: Artificial
<220> FEATURE:
<223> OTHER INFORMATION: Primer

<400> SEQUENCE: 276
agatctcttg gaaatg                                                  16

<210> SEQ ID NO 277
<211> LENGTH: 16
<212> TYPE: DNA
<213> ORGANISM: Artificial
<220> FEATURE:
<223> OTHER INFORMATION: Primer

<400> SEQUENCE: 277
agatctcttg gaaata                                                  16

<210> SEQ ID NO 278
<211> LENGTH: 16
<212> TYPE: DNA
<213> ORGANISM: Artificial
<220> FEATURE:
<223> OTHER INFORMATION: Primer

<400> SEQUENCE: 278
tgcataccat tattac                                                  16

<210> SEQ ID NO 279
<211> LENGTH: 16
<212> TYPE: DNA

```
<213> ORGANISM: Artificial
<220> FEATURE:
<223> OTHER INFORMATION: Primer

<400> SEQUENCE: 279
tgcataccat tattat                                                16

<210> SEQ ID NO 280
<211> LENGTH: 16
<212> TYPE: DNA
<213> ORGANISM: Artificial
<220> FEATURE:
<223> OTHER INFORMATION: Primer

<400> SEQUENCE: 280
tcataacttt tttttt                                                16

<210> SEQ ID NO 281
<211> LENGTH: 16
<212> TYPE: DNA
<213> ORGANISM: Artificial
<220> FEATURE:
<223> OTHER INFORMATION: Primer

<400> SEQUENCE: 281 ataactttt tttttt                                                 16

<210> SEQ ID NO 282
<211> LENGTH: 16
<212> TYPE: DNA
<213> ORGANISM: Artificial
<220> FEATURE:
<223> OTHER INFORMATION: Primer

<400> SEQUENCE: 282
gggcctttct aaaacg                                                16

<210> SEQ ID NO 283
<211> LENGTH: 16
<212> TYPE: DNA
<213> ORGANISM: Artificial
<220> FEATURE:
<223> OTHER INFORMATION: Primer

<400> SEQUENCE: 283
gcctttctaa aacgaa                                                16

<210> SEQ ID NO 284
<211> LENGTH: 16
<212> TYPE: DNA
<213> ORGANISM: Artificial
<220> FEATURE:
<223> OTHER INFORMATION: Primer

<400> SEQUENCE: 284
aatacattta ggactc                                                16

<210> SEQ ID NO 285
<211> LENGTH: 16
<212> TYPE: DNA
<213> ORGANISM: Artificial
<220> FEATURE:
<223> OTHER INFORMATION: Primer

<400> SEQUENCE: 285
aatacattta ggactt                                                16
```

```
<210> SEQ ID NO 286
<211> LENGTH: 16
<212> TYPE: DNA
<213> ORGANISM: Artificial
<220> FEATURE:
<223> OTHER INFORMATION: Primer

<400> SEQUENCE: 286
acactaactt caaatg                                                    16

<210> SEQ ID NO 287
<211> LENGTH: 16
<212> TYPE: DNA
<213> ORGANISM: Artificial
<220> FEATURE:
<223> OTHER INFORMATION: Primer

<400> SEQUENCE: 287
acactaactt caaata                                                    16

<210> SEQ ID NO 288
<211> LENGTH: 16
<212> TYPE: DNA
<213> ORGANISM: Artificial
<220> FEATURE:
<223> OTHER INFORMATION: Primer

<400> SEQUENCE: 288
ccggggaaat acagca                                                    16

<210> SEQ ID NO 289
<211> LENGTH: 16
<212> TYPE: DNA
<213> ORGANISM: Artificial
<220> FEATURE:
<223> OTHER INFORMATION: Primer

<400> SEQUENCE: 289
ccggggaaat acagcc                                                    16

<210> SEQ ID NO 290
<211> LENGTH: 16
<212> TYPE: DNA
<213> ORGANISM: Artificial
<220> FEATURE:
<223> OTHER INFORMATION: Primer

<400> SEQUENCE: 290
agtacttgtg catttt                                                    16

<210> SEQ ID NO 291
<211> LENGTH: 16
<212> TYPE: DNA
<213> ORGANISM: Artificial
<220> FEATURE:
<223> OTHER INFORMATION: Primer

<400> SEQUENCE: 291
agtacttgtg catttg                                                    16

<210> SEQ ID NO 292
<211> LENGTH: 16
<212> TYPE: DNA
<213> ORGANISM: Artificial
<220> FEATURE:
```

```
<223> OTHER INFORMATION: Primer

<400> SEQUENCE: 292
ggatataatc aaaatt                                                      16

<210> SEQ ID NO 293
<211> LENGTH: 16
<212> TYPE: DNA
<213> ORGANISM: Artificial
<220> FEATURE:
<223> OTHER INFORMATION: Primer

<400> SEQUENCE: 293
ggatataatc aaaatc                                                      16

<210> SEQ ID NO 294
<211> LENGTH: 16
<212> TYPE: DNA
<213> ORGANISM: Artificial
<220> FEATURE:
<223> OTHER INFORMATION: Primer

<400> SEQUENCE: 294
caaactttct tccata                                                      16

<210> SEQ ID NO 295
<211> LENGTH: 16
<212> TYPE: DNA
<213> ORGANISM: Artificial
<220> FEATURE:
<223> OTHER INFORMATION: Primer

<400> SEQUENCE: 295
caaactttct tccatg                                                      16

<210> SEQ ID NO 296
<211> LENGTH: 16
<212> TYPE: DNA
<213> ORGANISM: Artificial
<220> FEATURE:
<223> OTHER INFORMATION: Primer

<400> SEQUENCE: 296
cttaaaagaa aaagcg                                                      16

<210> SEQ ID NO 297
<211> LENGTH: 16
<212> TYPE: DNA
<213> ORGANISM: Artificial
<220> FEATURE:
<223> OTHER INFORMATION: Primer

<400> SEQUENCE: 297
cttaaaagaa aaagca                                                      16

<210> SEQ ID NO 298
<211> LENGTH: 16
<212> TYPE: DNA
<213> ORGANISM: Artificial
<220> FEATURE:
<223> OTHER INFORMATION: Primer

<400> SEQUENCE: 298
tttgcattga tatttc                                                      16
```

```
<210> SEQ ID NO 299
<211> LENGTH: 16
<212> TYPE: DNA
<213> ORGANISM: Artificial
<220> FEATURE:
<223> OTHER INFORMATION: Primer

<400> SEQUENCE: 299
tttgcattga tatttt                                                       16

<210> SEQ ID NO 300
<211> LENGTH: 15
<212> TYPE: DNA
<213> ORGANISM: Artificial
<220> FEATURE:
<223> OTHER INFORMATION: Primer

<400> SEQUENCE: 300
tgagtggatc aaaga                                                        15

<210> SEQ ID NO 301
<211> LENGTH: 16
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: n is a, c, g, or t

<400> SEQUENCE: 301
tgagtggatc aaagan                                                       16

<210> SEQ ID NO 302
<211> LENGTH: 15
<212> TYPE: DNA
<213> ORGANISM: Artificial
<220> FEATURE:
<223> OTHER INFORMATION: Primer

<400> SEQUENCE: 302
cattggccct tgtca                                                        15

<210> SEQ ID NO 303
<211> LENGTH: 16
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: n is a, c, g, or t

<400> SEQUENCE: 303
cattggccct tgtcan                                                       16

<210> SEQ ID NO 304
<211> LENGTH: 16
<212> TYPE: DNA
<213> ORGANISM: Artificial
<220> FEATURE:
<223> OTHER INFORMATION: Primer

<400> SEQUENCE: 304
acctatttat tagtag                                                       16
```

```
<210> SEQ ID NO 305
<211> LENGTH: 16
<212> TYPE: DNA
<213> ORGANISM: Artificial
<220> FEATURE:
<223> OTHER INFORMATION: Primer

<400> SEQUENCE: 305
acctatttat tagtat                                                         16

<210> SEQ ID NO 306
<211> LENGTH: 16
<212> TYPE: DNA
<213> ORGANISM: Artificial
<220> FEATURE:
<223> OTHER INFORMATION: Primer

<400> SEQUENCE: 306
ctttattgat tagatc                                                         16

<210> SEQ ID NO 307
<211> LENGTH: 16
<212> TYPE: DNA
<213> ORGANISM: Artificial
<220> FEATURE:
<223> OTHER INFORMATION: Primer

<400> SEQUENCE: 307
ctttattgat tagata                                                         16

<210> SEQ ID NO 308
<211> LENGTH: 16
<212> TYPE: DNA
<213> ORGANISM: Artificial
<220> FEATURE:
<223> OTHER INFORMATION: Primer

<400> SEQUENCE: 308
acctaataaa attcaa                                                         16

<210> SEQ ID NO 309
<211> LENGTH: 16
<212> TYPE: DNA
<213> ORGANISM: Artificial
<220> FEATURE:
<223> OTHER INFORMATION: Primer

<400> SEQUENCE: 309
acctaataaa attcag                                                         16

<210> SEQ ID NO 310
<211> LENGTH: 16
<212> TYPE: DNA
<213> ORGANISM: Artificial
<220> FEATURE:
<223> OTHER INFORMATION: Primer

<400> SEQUENCE: 310
ctctccatca acacat                                                         16

<210> SEQ ID NO 311
<211> LENGTH: 16
<212> TYPE: DNA
<213> ORGANISM: Artificial
<220> FEATURE:
<223> OTHER INFORMATION: Primer
```

```
<400> SEQUENCE: 311
ctctccatca acacac                                                       16

<210> SEQ ID NO 312
<211> LENGTH: 16
<212> TYPE: DNA
<213> ORGANISM: Artificial
<220> FEATURE:
<223> OTHER INFORMATION: Primer

<400> SEQUENCE: 312 tatttttat tataac                                                        16

<210> SEQ ID NO 313
<211> LENGTH: 16
<212> TYPE: DNA
<213> ORGANISM: Artificial
<220> FEATURE:
<223> OTHER INFORMATION: Primer

<400> SEQUENCE: 313 tatttttat tataaa                                                        16

<210> SEQ ID NO 314
<211> LENGTH: 16
<212> TYPE: DNA
<213> ORGANISM: Artificial
<220> FEATURE:
<223> OTHER INFORMATION: Primer

<400> SEQUENCE: 314
aaaaatataa ttaatg                                                       16

<210> SEQ ID NO 315
<211> LENGTH: 16
<212> TYPE: DNA
<213> ORGANISM: Artificial
<220> FEATURE:
<223> OTHER INFORMATION: Primer

<400> SEQUENCE: 315
aaaaatataa ttaatt                                                       16

<210> SEQ ID NO 316
<211> LENGTH: 16
<212> TYPE: DNA
<213> ORGANISM: Artificial
<220> FEATURE:
<223> OTHER INFORMATION: Primer

<400> SEQUENCE: 316
taaatctcca cctgag                                                       16

<210> SEQ ID NO 317
<211> LENGTH: 16
<212> TYPE: DNA
<213> ORGANISM: Artificial
<220> FEATURE:
<223> OTHER INFORMATION: Primer

<400> SEQUENCE: 317
taaatctcca cctgat                                                       16

<210> SEQ ID NO 318
```

```
<211> LENGTH: 16
<212> TYPE: DNA
<213> ORGANISM: Artificial
<220> FEATURE:
<223> OTHER INFORMATION: Primer

<400> SEQUENCE: 318
aacaccatga gaaatc                                                   16

<210> SEQ ID NO 319
<211> LENGTH: 16
<212> TYPE: DNA
<213> ORGANISM: Artificial
<220> FEATURE:
<223> OTHER INFORMATION: Primer

<400> SEQUENCE: 319
aacaccatga gaaata                                                   16

<210> SEQ ID NO 320
<211> LENGTH: 16
<212> TYPE: DNA
<213> ORGANISM: Artificial
<220> FEATURE:
<223> OTHER INFORMATION: Primer

<400> SEQUENCE: 320
tatcgtcttt catcac                                                   16

<210> SEQ ID NO 321
<211> LENGTH: 16
<212> TYPE: DNA
<213> ORGANISM: Artificial
<220> FEATURE:
<223> OTHER INFORMATION: Primer

<400> SEQUENCE: 321
tatcgtcttt catcat                                                   16

<210> SEQ ID NO 322
<211> LENGTH: 16
<212> TYPE: DNA
<213> ORGANISM: Artificial
<220> FEATURE:
<223> OTHER INFORMATION: Primer

<400> SEQUENCE: 322
gcaatgtgtg agaacg                                                   16

<210> SEQ ID NO 323
<211> LENGTH: 16
<212> TYPE: DNA
<213> ORGANISM: Artificial
<220> FEATURE:
<223> OTHER INFORMATION: Primer

<400> SEQUENCE: 323
gcaatgtgtg agaacg                                                   16

<210> SEQ ID NO 324
<211> LENGTH: 20
<212> TYPE: DNA
<213> ORGANISM: Artificial
<220> FEATURE:
<223> OTHER INFORMATION: Primer

<400> SEQUENCE: 324
```

```
gaacattttg agactccgtc                                              20

<210> SEQ ID NO 325
<211> LENGTH: 18
<212> TYPE: DNA
<213> ORGANISM: Artificial
<220> FEATURE:
<223> OTHER INFORMATION: Primer

<400> SEQUENCE: 325
accatccatc tttcccac                                                18

<210> SEQ ID NO 326
<211> LENGTH: 17
<212> TYPE: DNA
<213> ORGANISM: Artificial
<220> FEATURE:
<223> OTHER INFORMATION: Primer

<400> SEQUENCE: 326
tcctggctac gctcttc                                                 17

<210> SEQ ID NO 327
<211> LENGTH: 19
<212> TYPE: DNA
<213> ORGANISM: Artificial
<220> FEATURE:
<223> OTHER INFORMATION: Primer

<400> SEQUENCE: 327
tccgtcagga agttactgg                                               19

<210> SEQ ID NO 328
<211> LENGTH: 20
<212> TYPE: DNA
<213> ORGANISM: Artificial
<220> FEATURE:
<223> OTHER INFORMATION: Primer

<400> SEQUENCE: 328
agtcaccata ctcaggaccc                                              20

<210> SEQ ID NO 329
<211> LENGTH: 19
<212> TYPE: DNA
<213> ORGANISM: Artificial
<220> FEATURE:
<223> OTHER INFORMATION: Primer

<400> SEQUENCE: 329
ggctacgctc ttccaaaag                                               19

<210> SEQ ID NO 330
<211> LENGTH: 20
<212> TYPE: DNA
<213> ORGANISM: Artificial
<220> FEATURE:
<223> OTHER INFORMATION: Primer

<400> SEQUENCE: 330
agtcaccata ctcaggaccc                                              20

<210> SEQ ID NO 331
<211> LENGTH: 26
<212> TYPE: DNA
```

```
<213> ORGANISM: Artificial
<220> FEATURE:
<223> OTHER INFORMATION: Primer

<400> SEQUENCE: 331
gaagattgca atgaacttcc tccaag                                          26

<210> SEQ ID NO 332
<211> LENGTH: 21
<212> TYPE: DNA
<213> ORGANISM: Artificial
<220> FEATURE:
<223> OTHER INFORMATION: Primer

<400> SEQUENCE: 332
aagttctgaa taaaggtgtg c                                               21

<210> SEQ ID NO 333
<211> LENGTH: 36
<212> TYPE: DNA
<213> ORGANISM: Artificial
<220> FEATURE:
<223> OTHER INFORMATION: Primer

<400> SEQUENCE: 333
tatagatctc ttggaaatat aataatggta tgcagg                               36

<210> SEQ ID NO 334
<211> LENGTH: 36
<212> TYPE: DNA
<213> ORGANISM: Artificial
<220> FEATURE:
<223> OTHER INFORMATION: Primer

<400> SEQUENCE: 334
atggatataa tcaaaattat ggaagaaagt ttgtac                               36

<210> SEQ ID NO 335
<211> LENGTH: 3769
<212> TYPE: DNA
<213> ORGANISM: Artificial
<220> FEATURE:
<223> OTHER INFORMATION: Synthetic human CFH variant

<400> SEQUENCE: 335
agttagctgg taaatgtcct cttaaaagat ccaaaaaatg agacttctag caaagattat      60
ttgccttatg ttatgggcta tttgtgtagc agaagattgc aatgaacttc ctccaagaag     120
aaatacagaa attctgacag gttcctggtc tgaccaaaca tatccagaag gcacccaggc     180
tatctataaa tgccgccctg gatatagatc tcttggaaat ataataatgg tatgcaggaa     240
gggagaatgg gttgctctta atccattaag gaaatgtcag aaaaggccct gtggacatcc     300
tggagatact cctttggta cttttaccct acaggagga aatgtgtttg aatatggtgt       360
aaaagctgtg tatacatgta atgaggggta tcaattgcta ggtgagatta ttaccgtga      420 atgtgacaca gatggatgga ccaatgatat tcctatatgt gaagttgtga gtgttttacc    480
agtgacagca ccagagaatg gaaaaattgt cagtagtgca atggaaccag atcgggaata    540
ccatttggga caagcagtac ggtttgtatg taactcaggc tacaagattg aaggagatga    600
agaaatgcat tgttcagacg atggtttttg gagtaaagag aaaccaaagt gtgtggaaat    660
ttcatgcaaa tccccagatg ttataaatgg atctccata tctcagaaga ttatttataa     720
ggagaatgaa cgatttcaat ataaatgtaa catgggttat gaatacagtg aaagaggaga    780
```

```
tgctgtatgc actgaatctg gatggcgtcc gttgccttca tgtgaagaaa aatcatgtga    840
taatccttat attccaaatg gtgactactc acctttaagg attaaacaca gaactggaga    900
tgaaatcacg taccagtgta gaaatggttt ttatcctgca acccgggaaa atacagcaaa    960
atgcacaagt actggctgga tacctgctcc gagatgtacc ttgaaacctt gtgattatcc   1020
agacattaaa catggaggtc tatatcatga gaatatgcgt agaccatact ttccagtagc   1080
tgtaggaaaa tattactcct attactgtga tgaacatttt gagactccgt caggaagtta   1140
ctgggatcac attcattgca cacaagatgg atggtcgcca gcagtaccat gcctcagaaa   1200
atgttatttt ccttatttgg aaaatggata taatcaaaat tatggaagaa gtttgtaca    1260
gggtaaatct atagacgttg cctgccatcc tggctacgct cttccaaaag cgcagaccac   1320
agttacatgt atggagaatg gctggtctcc tactcccaga tgcatccgtg tcaaaacatg   1380
ttccaaatca agtatagata ttgagaatgg gtttatttct gaatctcagt atacatatgc   1440
cttaaaagaa aaagcgaaat atcaatgcaa actaggatat gtaacagcag atggtgaaac   1500
atcaggatca attacatgtg ggaaagatgg atggtcagct caacccacgt gcattaaatc   1560
ttgtgatatc ccagtatttta tgaatgccag aactaaaaat gacttcacat ggtttaagct   1620
gaatgacaca ttggactatg aatgccatga tggttatgaa agcaatactg gaagcaccac   1680
tggttccata gtgtgtggtt acaatggttg gtctgattta cccatatgtt atgaaagaga   1740
atgcgaactt cctaaaatag atgtacactt agttcctgat cgcaagaaag accagtataa   1800
agttggagag gtgttgaaat tctcctgcaa accaggattt acaatagttg gacctaattc   1860
cgttcagtgc taccactttg gattgtctcc tgacctccca atatgtaaag agcaagtaca   1920
atcatgtggt ccacctcctg aactcctcaa tgggaatgtt aaggaaaaaa cgaaagaaga   1980
atatggacac agtgaagtgg tggaatatta ttgcaatcct agatttctaa tgaagggacc   2040
taataaaatt caatgtgttg atggagagtg gacaactttta ccagtgtgta ttgtggagga   2100
gagtacctgt ggagatatac ctgaacttga acatggctgg gcccagcttt cttcccctcc   2160
ttattactat ggagattcag tggaattcaa ttgctcagaa tcatttacaa tgattggaca   2220
cagatcaatt acgtgtattc atggagtatg gacccaactt ccccagtgtg tggcaataga   2280
taaacttaag aagtgcaaat catcaaattt aattatactt gaggaacatt taaaaaacaa   2340
gaaggaattc gatcataatt ctaacataag gtacagatgt agaggaaaag aaggatggat   2400
acacacagtc tgcataaatg gaagatggga tccagaagtg aactgctcaa tggcacaaat   2460
acaattatgc ccacctccac ctcagattcc caattctcac aatatgacaa ccacactgaa   2520
ttatcgggat ggagaaaaag tatctgttct ttgccaagaa aattatctaa ttcaggaagg   2580
agaagaaatt acatgcaaag atggaagatg gcagtcaata ccactctgtg ttgaaaaaat   2640
tccatgttca caaccacctc agatagaaca cggaaccatt aattcatcca gtcttcaca   2700
agaaagttat gcacatggga ctaaattgag ttatacttgt gagggtggtt tcaggatatc   2760
tgaagaaaat gaaacaacat gctacatggg aaaatggagt tctccacctc agtgtgaagg   2820
ccttccttgt aaatctccac ctgagatttc tcatggtgtt gtagctcaca tgtcagacag   2880
ttatcagtat ggagaagaag ttcgtacaaa atgttttgaa ggttttggaa ttgatgggcc   2940
tgcaattgca aaatgcttag gagaaaaatg gtctcaccct ccatcatgca taaaaacaga   3000
ttgtctcagt ttacctagct ttgaaaatgc catacccatg ggagagaaga aggatgtgta   3060
taaggcgggt gagcaagtga cttacacttg tgcaacatat tacaaaatgg atggagccag   3120
```

| | | | | |
|---|---|---|---|---|
| taatgtaaca | tgcattaata | gcagatggac | aggaaggcca | acatgcagag acacctcctg 3180 |
| tgtgaatccg | cccacagtac | aaaatgctta | tatagtgtcg | agacagatga gtaaatatcc 3240 |
| atctggtgag | agagtacgtt | atcaatgtag | gagcccttat | gaaatgtttg gggatgaaga 3300 |
| agtgatgtgt | ttaaatggaa | actggacgga | accacctcaa | tgcaaagatt ctacaggaaa 3360 |
| atgtgggccc | cctccaccta | ttgacaatgg | ggacattact | tcattcccgt tgtcagtata 3420 |
| tgctccagct | tcatcagttg | agtatcaatg | ccagaacttg | tatcaacttg agggtaacaa 3480 |
| gcgaataaca | tgtagaaatg | gacaatggtc | agaaccacca | aaatgcttac atccgtgtgt 3540 |
| aatatcccga | gaaattatgg | aaaattataa | catagcatta | aggtggacag ccaaacagaa 3600 |
| gctttattcg | agaacaggtg | aatcagttga | atttgtgtgt | aaacggggat atcgtctttc 3660 |
| atcacgttct | cacacattgc | gaacaacatg | ttgggatggg | aaactggagt atccaacttg 3720 |
| tgcaaaaaga | tagaatcaat | cataaagtgc | acacctttat | tcagaactt 3769 |

<210> SEQ ID NO 336
<211> LENGTH: 3926
<212> TYPE: DNA
<213> ORGANISM: Homo sapiens

<400> SEQUENCE: 336

| | | | | |
|---|---|---|---|---|
| aattcttgga | agaggagaac | tggacgttgt | gaacagagtt | agctggtaaa tgtcctctta 60 |
| aaagatccaa | aaaatgagac | ttctagcaaa | gattatttgc | cttatgttat gggctatttg 120 |
| tgtagcagaa | gattgcaatg | aacttcctcc | aagaagaaat | acagaaattc tgacaggttc 180 |
| ctggtctgac | caaacatatc | cagaaggcac | ccaggctatc | tataaatgcc gccctggata 240 |
| tagatctctt | ggaaatgtaa | taatggtatg | caggaaggga | gaatgggttg ctcttaatcc 300 |
| attaaggaaa | tgtcagaaaa | ggccctgtgg | acatcctgga | gatactcctt ttggtacttt 360 |
| taccccttaca | ggaggaaatg | tgtttgaata | tggtgtaaaa | gctgtgtata catgtaatga 420 |
| ggggtatcaa | ttgctaggtg | agattaatta | ccgtgaatgt | gacacagatg gatggaccaa 480 |
| tgatattcct | atatgtgaag | ttgtgaagtg | tttaccagtg | acagcaccag agaatggaaa 540 |
| aattgtcagt | agtgcaatgg | aaccagatcg | ggaataccat | tttggacaag cagtacggtt 600 |
| tgtatgtaac | tcaggctaca | agattgaagg | agatgaagaa | atgcattgtt cagacgatgg 660 |
| tttttggagt | aaagagaaac | caaagtgtgt | ggaaatttca | tgcaaatccc cagatgttat 720 |
| aaatggatct | cctatatctc | agaagattat | ttataaggag | aatgaacgat tcaatataa 780 |
| atgtaacatg | ggttatgaat | acagtgaaag | aggagatgct | gtatgcactg aatctggatg 840 |
| gcgtccgttg | ccttcatgtg | aagaaaaatc | atgtgataat | ccttatattc caaatggtga 900 |
| ctactcacct | ttaaggatta | acacagaac | tggagatgaa | atcacgtacc agtgtagaaa 960 |
| tggttttttat | cctgcaaccc | ggggaaatac | agccaaatgc | acaagtactg gctggatacc 1020 |
| tgctccgaga | tgtaccttga | aaccttgtga | ttatccagac | attaaacatg gaggtctata 1080 |
| tcatgagaat | atgcgtagac | catactttcc | agtagctgta | ggaaaatatt actcctatta 1140 |
| ctgtgatgaa | catttgaga | ctccgtcagg | aagttactgg | gatcacattc attgcacaca 1200 |
| agatggatgg | tcgccagcag | taccatgcct | cagaaaatgt | tattttcctt atttggaaaa 1260 |
| tggatataat | caaaattatg | gaagaaagtt | tgtacagggt | aaatctatag acgttgcctg 1320 |
| ccatcctggc | tacgctcttc | caaaagcgca | gaccacagtt | acatgtatgg agaatggctg 1380 |
| gtctcctact | cccagatgca | tccgtgtcaa | aacatgttcc | aaatcaagta tagatattga 1440 |
| gaatgggttt | atttctgaat | ctcagtatac | atatgcctta | aaagaaaaag cgaaatatca 1500 |

```
atgcaaacta ggatatgtaa cagcagatgg tgaaacatca ggatcaatta gatgtgggaa    1560
agatggatgg tcagctcaac ccacgtgcat taaatcttgt gatatcccag tatttatgaa    1620
tgccagaact aaaaatgact tcacatggtt taagctgaat gacacattgg actatgaatg    1680
ccatgatggt tatgaaagca atactggaag caccactggt tccatagtgt gtggttacaa    1740
tggttggtct gatttaccca tatgttatga aagagaatgc gaacttccta aaatagatgt    1800
acacttagtt cctgatcgca agaaagacca gtataaagtt ggagaggtgt tgaaattctc    1860
ctgcaaacca ggatttacaa tagttggacc taattccgtt cagtgctacc actttggatt    1920
gtctcctgac ctcccaatat gtaaagagca agtacaatca tgtggtccac ctcctgaact    1980
cctcaatggg aatgttaagg aaaaaacgaa agaagaatat ggacacagtg aagtggtgga    2040
atattattgc aatcctagat ttctaatgaa gggacctaat aaaattcaat gtgttgatgg    2100
agagtggaca actttaccag tgtgtattgt ggaggagagt acctgtggag atatacctga    2160
acttgaacat ggctgggccc agcttttcttc ccctccttat tactatggag attcagtgga    2220
attcaattgc tcagaatcat ttacaatgat tggacacaga tcaattacgt gtattcatgg    2280
agtatggacc caacttcccc agtgtgtggc aatagataaa cttaagaagt gcaaatcatc    2340
aaatttaatt atacttgagg aacatttaaa aaacaagaag gaattcgatc ataattctaa    2400
cataaggtac agatgtagag gaaagaagg atggatacac acagtctgca taaatggaag    2460
atgggatcca gaagtgaact gctcaatggc acaaatacaa ttatgcccac ctccacctca    2520
gattcccaat tctcacaata tgacaaccac actgaattat cgggatggag aaaaagtatc    2580
tgttctttgc caagaaaatt atctaattca ggaaggagaa gaaattacat gcaaagatgg    2640
aagatggcag tcaataccac tctgtgttga aaaaattcca tgttcacaac cacctcagat    2700
agaacacgga accattaatt catccaggtc ttcacaagaa agttatgcac atgggactaa    2760
attgagttat acttgtgagg gtggtttcag gatatctgaa gaaaatgaaa caacatgcta    2820
catgggaaaa tggagttctc cacctcagtg tgaaggcctt ccttgtaaat ctccacctga    2880
gatttctcat ggtgttgtag ctcacatgtc agacagttat cagtatggag aagaagttac    2940
gtacaaatgt tttgaaggtt ttggaattga tgggcctgca attgcaaaat gcttaggaga    3000
aaaatggtct caccctccat catgcataaa aacagattgt ctcagtttac ctagctttga    3060
aaatgccata cccatgggag agaagaagga tgtgtataag gcgggtgagc aagtgactta    3120
cacttgtgca acatattaca aaatggatgg agccagtaat gtaacatgca ttaatagcag    3180
atggacagga aggccaacat gcagagacac ctcctgtgtg aatccgccca cagtacaaaa    3240
tgcttatata gtgtcgagac agatgagtaa atatccatct ggtgagagag tacgttatca    3300
atgtaggagc ccttatgaaa tgtttgggga tgaagaagtg atgtgtttaa atggaaactg    3360
gacggaacca cctcaatgca aagattctac aggaaaatgt gggccccctc cacctattga    3420 caatgggac attacttcat tcccgttgtc agtatatgct ccagcttcat cagttgagta    3480
ccaatgccag aacttgtatc aacttgaggg taacaagcga ataacatgta gaaatggaca    3540
atggtcagaa ccaccaaaat gcttacatcc gtgtgtaata tcccgagaaa ttatggaaaa    3600
ttataacata gcattaaggt ggacagccaa acagaagctt tattcgagaa caggtgaatc    3660
agttgaattt gtgtgtaaac ggggatatcg tctttcatca cgttctcaca cattgcgaac    3720
aacatgttgg gatgggaaac tggagtatcc aacttgtgca aaaagataga atcaatcata    3780
aagtgcacac ctttattcag aactttagta ttaaatcagt tctcaatttc atttttatg    3840
```

-continued

```
tattgtttta ctccttttta ttcatacgta aaattttgga ttaatttgtg aaaatgtaat    3900
tataagctga gaccggtggc tctctt                                         3926
```

<210> SEQ ID NO 337
<211> LENGTH: 1231
<212> TYPE: PRT
<213> ORGANISM: Homo sapiens

<400> SEQUENCE: 337

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
```

-continued

```
              355                 360                 365
Trp Asp His Ile His Cys Thr Gln Asp Gly Trp Ser Pro Ala Val Pro
    370                 375                 380
Cys Leu Arg Lys Cys Tyr Phe Pro Tyr Leu Glu Asn Gly Tyr Asn Gln
385                 390                 395                 400
Asn Tyr Gly Arg Lys Phe Val Gln Gly Lys Ser Ile Asp Val Ala Cys
                405                 410                 415
His Pro Gly Tyr Ala Leu Pro Lys Ala Gln Thr Val Thr Cys Met
            420                 425                 430
Glu Asn Gly Trp Ser Pro Thr Pro Arg Cys Ile Arg Val Lys Thr Cys
            435                 440                 445
Ser Lys Ser Ser Ile Asp Ile Glu Asn Gly Phe Ile Ser Glu Ser Gln
        450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Arg Cys Gly Lys
                485                 490                 495
Asp Gly Trp Ser Ala Gln Pro Thr Cys Ile Lys Ser Cys Asp Ile Pro
            500                 505                 510
Val Phe Met Asn Ala Arg Thr Lys Asn Asp Phe Thr Trp Phe Lys Leu
        515                 520                 525
Asn Asp Thr Leu Asp Tyr Glu Cys His Asp Gly Tyr Glu Ser Asn Thr
    530                 535                 540
Gly Ser Thr Thr Gly Ser Ile Val Cys Gly Tyr Asn Gly Trp Ser Asp
545                 550                 555                 560
Leu Pro Ile Cys Tyr Glu Arg Glu Cys Glu Leu Pro Lys Ile Asp Val
                565                 570                 575
His Leu Val Pro Asp Arg Lys Lys Asp Gln Tyr Lys Val Gly Glu Val
            580                 585                 590
Leu Lys Phe Ser Cys Lys Pro Gly Phe Thr Ile Val Gly Pro Asn Ser
        595                 600                 605
Val Gln Cys Tyr His Phe Gly Leu Ser Pro Asp Leu Pro Ile Cys Lys
    610                 615                 620
Glu Gln Val Gln Ser Cys Gly Pro Pro Glu Leu Leu Asn Gly Asn
625                 630                 635                 640
Val Lys Glu Lys Thr Lys Glu Tyr Gly His Ser Glu Val Val Glu
                645                 650                 655
Tyr Tyr Cys Asn Pro Arg Phe Leu Met Lys Gly Pro Asn Lys Ile Gln
            660                 665                 670
Cys Val Asp Gly Glu Trp Thr Thr Leu Pro Val Cys Ile Val Glu Glu
            675                 680                 685
Ser Thr Cys Gly Asp Ile Pro Glu Leu Glu His Gly Trp Ala Gln Leu
        690                 695                 700
Ser Ser Pro Pro Tyr Tyr Tyr Gly Asp Ser Val Glu Phe Asn Cys Ser
705                 710                 715                 720
Glu Ser Phe Thr Met Ile Gly His Arg Ser Ile Thr Cys Ile His Gly
                725                 730                 735
Val Trp Thr Gln Leu Pro Gln Cys Val Ala Ile Asp Lys Leu Lys Lys
            740                 745                 750
Cys Lys Ser Ser Asn Leu Ile Ile Leu Glu Glu His Leu Lys Asn Lys
        755                 760                 765
Lys Glu Phe Asp His Asn Ser Asn Ile Arg Tyr Arg Cys Arg Gly Lys
    770                 775                 780
```

```
Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
            805                 810                 815

Ile Pro Asn Ser His Asn Met Thr Thr Thr Leu Asn Tyr Arg Asp Gly
                820                 825                 830

Glu Lys Val Ser Val Leu Cys Gln Glu Asn Tyr Leu Ile Gln Glu Gly
            835                 840                 845

Glu Glu Ile Thr Cys Lys Asp Gly Arg Trp Gln Ser Ile Pro Leu Cys
            850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
            915                 920                 925

Leu Pro Cys Lys Ser Pro Pro Glu Ile Ser His Gly Val Val Ala His
            930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
                980                 985                 990

Pro Ser Phe Glu Asn Ala Ile Pro Met Gly Glu Lys Lys Asp Val Tyr
            995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170
```

```
-continued

Met Glu Asn Tyr Asn Ile Ala Leu Arg Trp Thr Ala Lys Gln Lys
    1175            1180                1185

Leu Tyr Ser Arg Thr Gly Glu Ser Val Glu Phe Val Cys Lys Arg
    1190            1195                1200

Gly Tyr Arg Leu Ser Ser Arg Ser His Thr Leu Arg Thr Thr Cys
    1205            1210                1215

Trp Asp Gly Lys Leu Glu Tyr Pro Thr Cys Ala Lys Arg
    1220            1225                1230
```